US010538777B2

(12) United States Patent
Lee et al.

(10) Patent No.: US 10,538,777 B2
(45) Date of Patent: Jan. 21, 2020

(54) PLANT REGULATORY SEQUENCE

(71) Applicant: Syngenta Participations AG, Basel (CH)

(72) Inventors: Mikyong Lee, Research Triangle Park, NC (US); Michael L. Nuccio, Research Triangle Park, NC (US); Joseph Clarke, Research Triangle Park, NC (US)

(73) Assignee: Syngenta Participations AG, Basel (CH)

(*) Notice: Subject to any disclaimer, the term of this patent is extended or adjusted under 35 U.S.C. 154(b) by 0 days.

(21) Appl. No.: 15/725,979

(22) Filed: Oct. 5, 2017

(65) Prior Publication Data

US 2018/0044691 A1 Feb. 15, 2018

Related U.S. Application Data

(62) Division of application No. 14/820,702, filed on Aug. 7, 2015, now Pat. No. 9,809,826, which is a division of application No. 13/682,982, filed on Nov. 21, 2012, now abandoned, which is a division of application No. 12/172,535, filed on Jul. 14, 2008, now Pat. No. 8,344,209.

(51) Int. Cl.
*C12N 15/00* (2006.01)
*C12N 15/82* (2006.01)

(52) U.S. Cl.
CPC ......... *C12N 15/8222* (2013.01); *C12N 15/00* (2013.01); *C12N 15/8225* (2013.01)

(58) Field of Classification Search
None
See application file for complete search history.

(56) References Cited

U.S. PATENT DOCUMENTS

| | | | |
|---|---|---|---|
| 6,320,100 B1 | 11/2001 | Koziel et al. | |
| 6,321,000 B1 | 11/2001 | King | |
| 2004/0034888 A1 | 2/2004 | Liu et al. | |
| 2004/0214272 A1 | 10/2004 | La Rosa et al. | |
| 2006/0141495 A1* | 6/2006 | Wu | C12Q 1/6895 435/6.11 |
| 2006/0168695 A1 | 7/2006 | Klebsattel et al. | |
| 2007/0174935 A1 | 7/2007 | Abbitt et al. | |
| 2007/0250959 A1 | 10/2007 | Crane et al. | |

OTHER PUBLICATIONS

Lu et al., GenEmbl Database, Acc. No. AX540744, WO02053717, Jul. 11, 2002, SEQ ID No. 27.
Lindsey et al.,"Tagging genomic sequences that direct transgene expression by activation of a promoter trap in plants", Transgenic Research, vol. 2, pp. 33-47, 1993.
Gaxiola et al.,"Drought- and salt-tolerant plants result from overexpression of the AVP1 H+ pump", PNAS, vol. 98, No. 20, pp. 11444-11449, Sep. 25, 2001.
Gutherie, W.D., "Advances in Rearing the European Corn Borer on a Meridic Diet", Proceedings of the Int Sym on Methodologies for Developing Host Pant Resistance to Maize Insects, Mar. 1987.
Park et al., PNAS, "Up-regulation of a H+-pyrophosphatase (H+-PPase) as a strategy to engineer drought-resistant crop plants", vol. 102, No. 52, pp. 18830-18835, Dec. 27, 2005.
GenBank AC211477, Jun. 7, 2008, Retrived from the Internet Sep. 6, 2009: <http://www.ncbi.nlm.nih.gov/nuccore/166158565>.
Lopez et al., "Pollen specific expression of maize genes encoding actin depolymerizing factor-like proteins", Proc. Natl. Acad. Sci., vol. 93, pp. 7415-7420, Jul. 1996.
Whitelaw et al., EST Database, Direct Submission, Accession No. CG295599, Aug. 25, 2003.
Kausch et al.,"Mesophyll1specific, light and metabolic regulation of the C4 PPCZml promoter in trnasgenic maize" Plant Molecular Biology, 2001, vol. 41, No. 1, pp. 1-15.
Taniguchi et al.,"The Promoter for the Maize C4 Pyruvate, Orthophosphate Dikinase Gene Directs Cell- and Tissue-Specific Transcription in Transgenic Maize Plants", Plant Cell Physiol., 2000, vol. 41, No. 1, pp. 42-48.

* cited by examiner

*Primary Examiner* — Phuong T Bui
(74) *Attorney, Agent, or Firm* — Amy Krom

(57) ABSTRACT

The present invention relates to regulatory sequences. In particular, the invention relates to a regulatory nucleic acid molecule, at least part of which has a transcription initiation function directing expression of an operably associated protein encoding polynucleotide of interest to non-tassel tissue in maize, but not or substantially not to tassel.
The invention further relates to chimeric genes and expression cassettes comprising the regulatory nucleic acid molecule and to transgenic plants comprising the chimeric genes and expression cassettes.

7 Claims, No Drawings

Specification includes a Sequence Listing.

PLANT REGULATORY SEQUENCE

This application is a divisional of U.S. application Ser. No. 14/820,702, filed Aug. 7, 2015, now U.S. Pat. No. 9,809,826, which is a divisional of U.S. application Ser. No. 13/682,982, filed Nov. 21, 2012, now abandoned, which is a divisional of U.S. application Ser. No. 12/172,535, filed Jul. 14, 2008, now U.S. Pat. No. 8,344,209, all of which are incorporated herein by reference in their entirety.

STATEMENT REGARDING ELECTRONIC SUBMISSION OF A SEQUENCE LISTING

A Sequence Listing file in ASCII text format, submitted herewith electronically via EFS web under 37 C.F.R. § 1.821, entitled "71760-US-REG-D-NAT-4_Sequence_Listing_ST25" which is 250 kilobytes in size was created Oct. 5, 2017 and is herein incorporated by reference in its entirety.

The present invention is in the field of plant biotechnology and relates to regulatory sequences. In particular, the invention relates to a regulatory nucleotide sequence, at least part of which has a transcription initiation function directing expression of an operably associated protein encoding polynucleotide of interest to basically all plant tissues, but essentially excluding expression in the tissues of the reproductive structures of the plant, particularly in the tissues of the pollen and/or the tassel so that no expression product is present in said tissues to any significant extent. The invention further relates to chimeric genes and expression cassettes comprising said regulatory sequence in association with an expressible protein encoding polynucleotide of interest and to transgenic plants comprising said chimeric genes and expression cassettes, respectively, expressing the protein encoding polynucleotide of interest in basically all plant tissues, but essentially excluding expression in the tissues of the reproductive structures of the plant, particularly in the tissues of the pollen and/or the tassel so that no expression product is present in said tissues to any significant extent.

BACKGROUND OF THE INVENTION

In many agricultural crops such as corn, devastating pests tend to feed on vegetative tissues such as the leaf, stalk and root and also reproductive tissues such as the ear. One technique used to protect plants from pests is the application of chemical compounds. An alternative technique involves genetic recombination, wherein a gene or genes are introduced into the plant to express protein products that are directly or indirectly involved in the control of the pest organisms. Current protein products produced by genetic recombination are expressed constitutively, i.e., throughout the plant at all times and in most tissues and organs. Such protein products are also expressed specifically, either in response to particular stimuli or confined to specific cells or tissues. In contrast, the present invention includes expression of the protein or polynucleotide of interest in basically all plant tissues, but essentially excludes expression in the tissues of the reproductive structures of the plant, particularly in the tissues of the pollen and/or the tassel so that no expression product is present in said tissues to any significant extent.

Several insect control trait genes target the larval stage of development. Under certain circumstances, these proteins also affect unintended insects, which are not corn pests, but do occasionally feed on corn pollen. These insects may be harmed by insecticidal proteins expressed in pollen tissue. This was seen as a problem in early BT-corn events which had high insecticidal protein expression in pollen. This issue was addressed in later BT-corn events through the development of alternative transgene expression systems. These newer events remained effective against target pests and accumulated less insecticidal protein in pollen, but are still viewed as potentially harmful to non-target pests due to the presence of insecticidal protein in pollen.

In some instances, useful insect control trait genes may also compromise the development of reproductive structures of the plant such as, for example, the tassel.

It is, therefore, desirable to provide plants, particularly corn plants that exclude expression of the transgene in the tissues of the reproductive structures of the plant such as the tissues of the pollen and/or the tassel. This could be achieved within the scope of the present invention by providing a regulatory nucleotide sequence, at least part of which has a transcription initiation function directing expression of an operably associated protein encoding a polynucleotide of interest to basically all plant tissues, but essentially excluding expression in the tissues of the male reproductive structures of the plant, particularly in the tissues of the pollen and/or the tassel so that no expression product is present in said tissues to any significant extent. This regulatory nucleotide sequence can then be used to develop expression systems that enable effective accumulation of the polypeptide or protein of interest such as, for example, an insecticidal protein, in tissues that target pests normally feed on, and eliminate or reduce accumulation of the insecticidal protein in non-target tissues or organs and/or in those tissues that may be compromised by the polypeptide or protein of interest.

SUMMARY OF THE INVENTION

In one embodiment, the invention relates to a transgenic plant comprising stably integrated in its genome a chimeric polynucleotide construct, particularly a chimeric construct, comprising a polynucleotide of interest, particularly a polypeptide or protein encoding polynucleotide of interest, associated with and/or under control of a regulatory nucleotide sequence, at least part of which has a transcription initiation function directing expression of said protein encoding polynucleotide of interest to basically all tissues of said plant, particularly the tissues target insects normally feed on, but essentially excluding the tissues of the reproductive plant structures, particularly the tissues of the pollen and/or the tassel so that no expression product is present in said tissues to any significant extent.

In one embodiment, the polynucleotide of interest, particularly a polypeptide or protein encoding polynucleotide of interest, is not transcribed to any significant extent in the tissues of the reproductive plant structures, particularly in pollen and/or tassel tissue of the transgenic plant according to the invention. Therefore, essentially no expression of the polynucleotide of interest, particularly a polypeptide or protein encoding polynucleotide of interest, occurs in the tissues of the male reproductive plant structures, particularly in the tissues of the pollen and/or the tassel, and only residual amounts of the expression product, if any, can be detected in said tissues, which is not sufficient for the expression product to fulfil its envisaged biological function in said tissues, particularly in the tissues of the pollen and/or the tassel, and therefore also does not exhibit any toxic effects on insects feeding on said tissues or on the plant reproductive structures.

In one embodiment of the invention, a transgenic plant is provided as described herein, wherein a chimeric polynucleotide construct, particularly a chimeric DNA construct, comprises a polynucleotide of interest, particularly a polypeptide or protein encoding polynucleotide of interest, operably associated with and/or under operable control of a regulatory nucleotide sequence, at least part of which has a transcription initiation function and is obtainable from a gene encoding an actin depolymerizing factor 3 (ABP3), which polypeptide or protein is highly expressed in most tissues of the plant but essentially excluding the tissues of the pollen so that no expression product is present in said tissues to any significant extent.

In one embodiment, said actin depolymerizing factor 3 (ABP3) gene is obtainable from maize.

In one embodiment of the invention, a transgenic plant is provided as described herein, wherein a chimeric polynucleotide construct, particularly a chimeric DNA construct, comprises a polynucleotide of interest, particularly a polypeptide or protein encoding polynucleotide of interest, operably associated with and/or under operable control of a regulatory nucleotide sequence, at least part of which has a transcription initiation function and is obtainable from a gene represented by a DNA probe, particularly a DNA probe exhibiting a DNA sequence as depicted in SEQ ID NOs: 47 to 56, which DNA probe shows a signal pattern in tissue samples, which is indicative of expression of said gene in all tissues and of no or substantially no expression in pollen.

In one embodiment, a transgenic plant according to the invention and as described herein is provided comprising a regulatory nucleotide sequence or a polynucleotide construct, particularly a chimeric polynucleotide construct, comprising said regulatory sequence as described herein, at least part of which has a transcription initiation function and mediates expression of an operably associated protein encoding polynucleotide of interest in most tissues of the plant but essentially excluding the tissues of the pollen so that no expression product is present in said tissues to any significant extent, which regulatory sequence can be obtained in a PCR reaction from a genomic *Zea mays* DNA template using i) a first primer which has at least 90%, particularly at least 91%, particularly at least 92%, 93%, 94%, 95%, 96%, 97%, 98% or 99% sequence identity with a nucleotide sequence as depicted in SEQ ID NO: 1, particularly a first primer of SEQ ID NO: 1; or
ii) second primer which has at least 90%, particularly at least 91%, particularly at least 92%, 93%, 94%, 95%, 96%, 97%, 98% or 99% sequence identity with a nucleotide sequence as depicted in SEQ ID NO: 2, particularly a second primer of; SEQ ID NO: 2; or
iii) a first primer as a forward primer which has at least 90%, particularly at least 91%, particularly at least 92%, 93%, 94%, 95%, 96%, 97%, 98% or 99% sequence identity with a nucleotide sequence as depicted in SEQ ID NO: 1 and a second primer as a reverse primer which has at least 90%, particularly at least 91%, particularly at least 92%, 93%, 94%, 95%, 96%, 97%, 98% or 99% sequence identity with a nucleotide sequence as depicted in SEQ ID NO: 2, particularly the forward primer of SEQ ID NO: 1 and the reverse primer of SEQ ID NO: 2.

In one embodiment, the invention relates to a transgenic plant as described herein, wherein the nucleotide sequence providing the transcription initiation function has at least between 80% and 85% sequence identity with a nucleotide sequence depicted in SEQ ID NO: 13, with all integers falling within this range also being comprised herewith, particularly at least between 85% and 90% sequence identity with a nucleotide sequence depicted in SEQ ID NO: 13, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 13, or a fragment thereof, and wherein said regulatory nucleotide sequence or fragment thereof mediates transcription of an operably associated polynucleotide molecule, particularly of an operably associated protein encoding polynucleotide of interest such that said polynucleotide of interest is transcribed in most of the plant tissues but essentially excluding the tissues of the pollen so that no expression product is present in said tissues to any significant extent.

In one embodiment, the invention relates to a transgenic plant as described herein, wherein the complementary strand of the nucleotide sequence providing the transcription initiation function is capable of hybridizing with a nucleotide sequence depicted in SEQ ID NO: 13, particularly under moderate hybridization conditions, more particularly under stringent hybridization conditions, and wherein said regulatory nucleotide sequence mediates transcription of an operably associated polynucleotide molecule, particularly of an operably associated protein encoding polynucleotide of interest such that said polynucleotide of interest is transcribed in most of the plant tissues but essentially excluding the tissues of the pollen so that no expression product is present in said tissues to any significant extent.

In one embodiment, the invention relates to a transgenic plant as described herein, wherein the nucleotide sequence providing the transcription initiation function is the sequence depicted in SEQ ID NO: 13 or a fragment thereof, which still exhibits the full functionality as a transcription initiation sequence.

In one embodiment the invention relates to a transgenic plant according to the invention and as described herein comprising a regulatory nucleotide sequence or an expression cassette comprising said regulatory nucleotide sequence or a polynucleotide construct, particularly a chimeric polynucleotide construct, comprising said regulatory sequence at least part of which has a transcription termination function obtainable from a gene encoding an actin depolymerizing factor 3 (ABP3), which regulatory sequence mediates transcription of an operably associated polynucleotide molecule, particularly of an operably associated protein encoding polynucleotide molecule of interest such that said polynucleotide of interest is transcribed in most of the plant tissues excluding the tissues of the pollen but essentially excluding the tissues of the pollen so that no expression product is present in said tissues to any significant extent, particularly from a maize actin depolymerizing factor 3 (ABP3) gene, wherein i) said regulatory nucleotide sequence comprises a transcription termination sequence which has at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 14; or a fragment thereof, which still exhibits the functionality of a termination sequence; or
ii) the complementary strand of said regulatory nucleotide sequence hybridizes to a nucleotide sequence depicted in SEQ ID NO: 14, particularly under moderate hybridization conditions, more particularly under moderate-stringent hybridization conditions, particularly under stringent hybridization conditions and mediates termination of transcription of an operably associated protein encoding polynucleotide of interest; or.

iii) said regulatory nucleotide sequence has a sequence as depicted in SEQ ID NO: 14, including complements thereof.

In one embodiment the invention relates to a transgenic plant according to the invention and as described herein comprising a regulatory nucleotide sequence or an expression cassette comprising said regulatory nucleotide sequence or a polynucleotide construct, particularly a chimeric polynucleotide construct, comprising said regulatory sequence at least part of which has a transcription initiation function and a termination function, respectively, which regulatory nucleotide sequence is obtainable from a gene encoding an actin depolymerizing factor 3 (ABP3), which is expressed in most plant tissues but essentially excluding the tissues of the pollen so that no expression product is present in said tissues to any significant extent, particularly from a maize actin depolymerizing factor 3 (ABP3) gene, and which regulatory nucleotide sequence comprises a transcription initiation sequence and a transcription termination sequence, respectively, which have at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 13 and SEQ ID NO:14, respectively, or a fragment thereof which still exhibits the full functionality as a transcription initiation and a termination sequence, respectively.

In one embodiment the invention relates to a transgenic plant according to the invention and as described herein comprising a regulatory nucleotide sequence or an expression cassette comprising said regulatory nucleotide sequence or a polynucleotide construct, particularly a chimeric polynucleotide construct, comprising said regulatory sequence at least part of which has a transcription initiation function and a termination function, respectively, which regulatory nucleotide sequence is obtainable from a gene encoding an actin depolymerizing factor 3 (ABP3), which is expressed in most tissues of the plant but essentially excluding the tissues of the pollen so that no expression product is present in said tissues to any significant extent, particularly from a maize actin depolymerizing factor 3 (ABP3) gene, and which regulatory nucleotide sequence comprises a transcription initiation sequence as depicted in SEQ ID NO: 13 and a transcription termination sequence as depicted in SEQ ID NO:14.

In one embodiment the invention relates to a transgenic plant according to the invention and as described herein comprising a regulatory nucleotide sequence or an expression cassette comprising said regulatory nucleotide sequence or a polynucleotide construct, particularly a chimeric polynucleotide construct, comprising said regulatory sequence at least part of which has a transcription initiation function and a termination function, respectively, which regulatory nucleotide sequence is obtainable from a gene represented by a DNA probe, particularly a DNA probe exhibiting a DNA sequence as depicted in SEQ ID NOs: 47 to 56, which DNA probe shows a signal pattern in tissue samples, which is indicative of expression of said gene in all tissues and of no or substantially no expression in pollen.

In one embodiment of the invention, a transgenic plant is provided as described herein, wherein the chimeric polynucleotide construct, particularly the chimeric DNA construct, comprises a polynucleotide of interest, particularly a polypeptide or protein encoding polynucleotide of interest, operably associated with and/or under operable control of a regulatory nucleotide sequence, at least part of which has a transcription initiation function and is obtainable from plant genomic DNA, particularly from maize genomic DNA, which polypeptide or protein is expressed in most tissues of the plant but essentially excluding tissues of the tassel so that no expression product is present in said tissues to any significant extent.

In one embodiment of the invention, a transgenic plant is provided as described herein, wherein the chimeric polynucleotide construct, particularly the chimeric DNA construct, comprises a polynucleotide of interest, particularly a polypeptide or protein encoding polynucleotide of interest, operably associated with and/or under operable control of a regulatory nucleotide sequence, at least part of which has a transcription initiation function and is obtainable from a gene represented by a DNA probe, particularly a DNA probe exhibiting a DNA sequence as depicted in SEQ ID NOs: 57 to 79, which DNA probe shows a signal pattern in tissue samples, which is indicative of expression of said gene in all tissues and of no or substantially no expression in the tissues of the tassel.

In one embodiment, a transgenic plant according to the invention and as described herein is provided comprising a regulatory nucleotide sequence or an expression cassette comprising said regulatory nucleotide sequence or a polynucleotide construct, particularly a chimeric polynucleotide construct, comprising said regulatory sequence as described herein, which regulatory sequence can be obtained in a PCR reaction from a genomic *Zea mays* DNA template using i) a first primer which has at least 90%, particularly at least 91%, particularly at least 92%, 93%, 94%, 95%, 96%, 97%, 98% or 99% sequence identity with a nucleotide sequence as depicted in SEQ ID NO: 19, particularly the primer of SEQ ID NO: 19; or ii) a second primer which has at least 90%, particularly at least 91%, particularly at least 92%, 93%, 94%, 95%, 96%, 97%, 98% or 99% sequence identity with a nucleotide sequence as depicted in SEQ ID NO: 20, particularly the reverse primer of SEQ ID NO: 20; or iii) a first primer as a forward primer which has at least 90%, particularly at least 91%, particularly at least 92%, 93%, 94%, 95%, 96%, 97%, 98% or 99% sequence identity with a nucleotide sequence as depicted in SEQ ID NO: 19 and a second primer as a reverse primer which has at least 90%, particularly at least 91%, particularly at least 92%, 93%, 94%, 95%, 96%, 97%, 98% or 99% sequence identity with a nucleotide sequence as depicted in SEQ ID NO: 20, particularly the forward primer of SEQ ID NO: 19 and the reverse primer of SEQ ID NO: 20.

In one embodiment, the invention relates to a transgenic plant as described herein, wherein the nucleotide sequence providing the transcription initiation function has at least between 80% and 85% sequence identity with a nucleotide sequence depicted in SEQ ID NO: 35, with all integers falling within this range also being comprised herewith, particularly at least between 85% and 90% sequence identity with a nucleotide sequence depicted in SEQ ID NO: 35, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 35, or a fragment thereof, and wherein said regulatory nucleotide sequence or fragment thereof mediates transcription of an operably associated polynucleotide molecule, particularly of an operably associated protein encoding polynucleotide of interest such that said polynucleotide of interest is transcribed in most tissues of the plant but essentially excluding the tissues of the tassel so that no expression product is present in said tissues to any significant extent.

In one embodiment, the invention relates to a transgenic plant as described herein, wherein the complementary strand of the nucleotide sequence providing the transcription initiation function is capable of hybridizing with a nucleotide sequence depicted in SEQ ID NO: 35, particularly under moderate hybridization conditions, more particularly under stringent hybridization conditions and wherein said regulatory nucleotide sequence mediates transcription of an operably associated polynucleotide molecule, particularly of an operably associated protein encoding polynucleotide of interest such that said polynucleotide of interest is transcribed in most tissues of the plant but essentially excluding the tissues of the tassel so that no expression product is present in said tissues to any significant extent.

In one embodiment, the invention relates to a transgenic plant as described herein, wherein the nucleotide sequence providing the transcription initiation function is the sequence depicted in SEQ ID NO: 35 or a fragment thereof, which still exhibits the full functionality as a transcription initiation sequence.

In one embodiment the invention relates to a transgenic plant according to the invention and as described herein comprising a regulatory nucleotide sequence or an expression cassette comprising said regulatory nucleotide sequence or a polynucleotide construct, particularly a chimeric polynucleotide construct, comprising said regulatory sequence at least part of which has a transcription termination function obtainable from a plant genomic DNA, particularly a maize genomic DNA and mediates transcription of an operably associated polynucleotide molecule, particularly of an operably associated protein encoding polynucleotide of interest such that said polynucleotide of interest is transcribed in most tissues of the plant but essentially excluding the tissues of the tassel so that no expression product is present in said tissues to any significant extent, wherein i) said regulatory nucleotide sequence comprises a transcription termination sequence which has at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 36; or a fragment thereof which still exhibits the full functionality as a transcription initiation sequence; or
ii) the complementary strand of said regulatory nucleotide sequence hybridizes to a nucleotide sequence depicted in SEQ ID NO: 36, particularly under moderate hybridization conditions, particularly under moderate-stringent hybridization conditions, particularly under stringent hybridization conditions and mediates termination of transcription of an operably associated protein encoding polynucleotide of interest; or
iii) said regulatory sequence has a sequence as depicted in SEQ ID NO: 36, or a fragment thereof, which still exhibits the full functionality as a transcription initiation sequence including complements thereof.

In one embodiment the invention relates to a transgenic plant according to the invention and as described herein comprising a regulatory nucleotide sequence or an expression cassette comprising said regulatory nucleotide sequence or a polynucleotide construct, particularly a chimeric polynucleotide construct, comprising said regulatory sequence at least part of which has a transcription initiation function and a termination function, respectively, which regulatory nucleotide sequence is obtainable from a genomic plant DNA, particularly from a genomic maize DNA and is expressed in most tissues of the plant but essentially excluding tissues of the tassel so that no expression product is present in said tissues to any significant extent, which regulatory nucleotide sequence comprises a transcription initiation sequence and a transcription termination sequence, respectively, which sequences have at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 35 and SEQ ID NO:36, respectively, including a fragment thereof, which still exhibits the full functionality as a transcription initiation sequence and a termination sequence, respectively.

In one embodiment the invention relates to a transgenic plant according to the invention and as described herein comprising a regulatory nucleotide sequence or an expression cassette comprising said regulatory nucleotide sequence or a polynucleotide construct, particularly a chimeric polynucleotide construct, comprising said regulatory sequence at least part of which has a transcription initiation function and a termination function, respectively, which regulatory nucleotide sequence is obtainable from a genomic plant DNA, particularly a genomic maize DNA and is expressed in most tissues of the plant but essentially excluding tissues of the tassel so that no expression product is present in said tissues to any significant extent, which regulatory nucleotide sequence comprises a transcription initiation sequence as depicted in SEQ ID NO: 35 and a transcription termination sequence as depicted in and SEQ ID NO:36 respectively, including a fragment thereof, which still exhibits the full functionality as a transcription initiation sequence and a termination sequence, respectively.

In one embodiment, a transgenic plant according to the invention and as described herein is provided, wherein the polypeptide or protein encoding polynucleotide of interest encodes a polypeptide product exhibiting an insecticidal activity, particularly an endotoxin of *Bacillus thuringiensis*.

In one embodiment, the concentration of the polypeptide product expressed from the protein encoding polynucleotide of interest in the tissues of the plant reproductive structures, particularly in the tissues of the pollen and/or the tassel is such that no insecticidal activity can be detected in a standard insect feeding assay. In particular, the concentration of the expression product in the tassel is below a basic level of not more than 10 ng/mg soluble protein, particularly of not more than 5 ng/mg soluble protein, more particularly of not more than 3 ng/mg soluble protein, but especially of not more than 2 ng/mg soluble protein or less.

In one embodiment, a transgenic plant according to the invention and as described herein is provided, wherein the polypeptide or protein encoding polynucleotide of interest encodes an endotoxin of *Bacillus thuringiensis* which has at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence as depicted in SEQ ID NO:15.

In one embodiment, a transgenic plant according to the invention and as described herein is provided, wherein the polypeptide or protein encoding polynucleotide of interest encodes an endotoxin of *Bacillus thuringiensis* which has the nucleotide sequence as depicted in SEQ ID NO: 15.

In one embodiment, a transgenic plant according to the invention and as described herein is provided, wherein the polypeptide or protein encoding polynucleotide of interest encodes a polypeptide product contributing to the enhancement of drought tolerance, particularly a deregulated form of a $H^+$-pyrophosphatase, wherein said polypeptide or protein is under control of a regulatory sequence according to the invention at least part of which has a transcription initiation function which mediates expression of an operably associated protein encoding polynucleotide of interest in most plant tissues but essentially excluding expression in the tissues of the pollen and/or the tissues of the tassel so that no expression product is present in said tissues to any significant extent.

In one embodiment, the transgenic plant according to the invention and as described herein is a *Zea mays* plant.

In one embodiment, the invention relates to a regulatory nucleotide sequence or an expression cassette comprising said regulatory nucleotide sequence or a polynucleotide construct, particularly a chimeric polynucleotide construct, comprising said regulatory sequence, at least part of which has a transcription initiation function which mediates expression of an operably associated protein encoding a polynucleotide of interest in most plant tissues but essentially excluding expression in the tissues of the male reproductive structures, particularly the tissues of the pollen and/or the tassel so that no expression product is present in said tissues to any significant extent.

In one embodiment of the invention, the regulatory nucleotide sequence is obtainable from a gene represented by a DNA probe, particularly a DNA probe exhibiting a DNA sequence as depicted in SEQ ID NOs: 47 to 56, which DNA probe shows a signal pattern in tissue samples which is indicative of expression of said gene in all tissues and of no or substantially no expression in pollen.

In one embodiment of the invention, the regulatory nucleotide sequence is obtainable from a gene encoding an actin depolymerizing factor 3, which is expressed in most tissues of the plant but essentially excluding the tissues of the pollen so that no expression product is present in said tissues to any significant extent, particularly an actin depolymerizing factor 3 gene from maize.

In one embodiment of the invention, the regulatory nucleotide sequence is obtainable from a gene represented by a DNA probe, particularly a DNA probe exhibiting a DNA sequence as depicted in SEQ ID NOs: 57 to 79, which DNA probe shows a signal pattern in tissue samples, which is indicative of expression of said gene in all tissues and of no or substantially no expression in the tissues of the tassel . . . .

In one embodiment, the invention provides a regulatory nucleotide sequence or an expression cassette comprising said regulatory nucleotide sequence or a polynucleotide construct, particularly a chimeric polynucleotide construct, comprising said regulatory sequence as described herein, which sequence is obtainable from a genomic *Zea mays* DNA template using i) a first primer which has at least 90%, particularly at least 91%, particularly at least 92%, 93%, 94%, 95%, 96%, 97%, 98% or 99% sequence identity with a nucleotide sequence as depicted in SEQ ID NO: 1, particularly a first primer of SEQ ID NO: 1; or ii) second primer which has at least 90%, particularly at least 91%, particularly at least 92%, 93%, 94%, 95%, 96%, 97%, 98% or 99% sequence identity with a nucleotide sequence as depicted in SEQ ID NO: 2, particularly a second primer of; SEQ ID NO: 2; or iii) a first primer as a forward primer which has at least 90%, particularly at least 91%, particularly at least 92%, 93%, 94%, 95%, 96%, 97%, 98% or 99% sequence identity with a nucleotide sequence as depicted in SEQ ID NO: 1 and a second primer as a reverse primer which has at least 90%, particularly at least 91%, particularly at least 92%, 93%, 94%, 95%, 96%, 97%, 98% or 99% sequence identity with a nucleotide sequence as depicted in SEQ ID NO: 2, particularly the forward primer of SEQ ID NO: 1 and the reverse primer of SEQ ID NO: 2.

In one embodiment, the regulatory nucleotide sequence according to the invention and as described herein is modified using one or more oligonucleotides selected from the group of oligonucleotides depicted in SEQ ID NO: 3, SEQ ID NO: 4, SEQ ID NO: 5, SEQ ID NO: 6, SEQ ID NO: 7 and SEQ ID NO: 8.

In one embodiment the invention relates to a regulatory nucleotide sequence or an expression cassette comprising said regulatory nucleotide sequence or a polynucleotide construct, particularly a chimeric polynucleotide construct, comprising said regulatory sequence as described herein, which regulatory nucleotide sequence provides a transcription initiation function, wherein the nucleotide sequence providing said function has at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 13 and wherein said regulatory nucleotide sequence mediates transcription of an operably associated protein encoding polynucleotide of interest in most tissues of the plant but essentially excluding the tissues of the pollen so that no expression product is present in said tissues to any significant extent.

In one embodiment, the invention relates to a regulatory nucleotide sequence or an expression cassette comprising said regulatory nucleotide sequence or a polynucleotide construct, particularly a chimeric polynucleotide construct, comprising said regulatory sequence as described herein, which regulatory nucleotide sequence provides a transcription initiation function, wherein the complementary strand of the nucleotide sequence providing said function hybridizes to a nucleotide sequence depicted in SEQ ID NO: 13, particularly under moderate hybridization conditions, more particularly under moderately stringent hybridization conditions and wherein said regulatory nucleotide sequence mediates transcription of an operably associated protein encoding polynucleotide of interest in most tissues of the plant but essentially excluding the tissues of the pollen so that no expression product is present in said tissues to any significant extent. In particular, said hybridization occurs under stringent hybridization conditions.

In one embodiment of the invention, the nucleotide sequence providing the transcription initiation function is the sequence depicted in SEQ ID NO: 13, or a fragment thereof which still exhibits full functionality as a transcription initiation sequence, and complements thereof.

In one embodiment, a regulatory nucleotide sequence or an expression cassette comprising said regulatory nucleotide sequence or a polynucleotide construct, particularly a chimeric polynucleotide construct, comprising said regulatory sequence according to the invention and as described herein is provided comprising approximately 1 kb of the nucleotide sequence upstream of the ZmABP3 transcription start site of a ZmABP3 gene, particularly upstream of the ZmABP3 transcription start site of the ZmABP3 gene as depicted in SEQ ID NO: 17.

In one embodiment of the invention, said regulatory nucleotide sequence comprises in addition the ZmABP3 5'-untranslated sequence, the ZmABP3 first exon, the ZmABP3 first intron and a portion of the ZmABP3 second exon, particularly a portion of the ZmABP3 second exon terminating at the translation initiation codon, particularly a portion of the ZmABP3 second exon comprising between about 10 to about 20 nucleotides, particularly between about 12 and about 16 nucleotides, particularly about 14 nucleotides, of the second exon.

In one embodiment, a regulatory nucleotide sequence or an expression cassette comprising said regulatory nucleotide sequence or a polynucleotide construct, particularly a chimeric polynucleotide construct, comprising said regulatory sequence is provided at least part of which has a transcription termination function, which sequence is obtainable in a PCR amplification reaction from a gDNA template, particularly a maize gDNA template, using a forward primer (P3 (5'-tatatagagctcgcatcatgatcatgcatcatggact-3') which has at least 90%, particularly at least 91%, particularly at least 92%, 93%, 94%, 95%, 96%, 97%, 98% or 99% sequence identity with a nucleotide sequence as depicted in SEQ ID NO: 9 and a reverse primer (P4 (5'-atatatactagtggcgcgcca-cactttctgtcgcatgtgatttgca-3') which has at least 90%, particularly at least 91%, particularly at least 92%, 93%, 94%, 95%, 96%, 97%, 98% or 99% sequence identity with a nucleotide sequence as depicted in SEQ ID NO: 10. In particular, said regulatory nucleotide sequence comprises a transcriptional terminator and poly-adenylation signal. In particular, a forward primer (P3 (5'-tatatagagctcgcatcatgatcatgcatcatggact-3')) which has a nucleotide sequence as depicted in SEQ ID NO: 9 and a reverse primer (P4 (5'-atatatactagtggcgcgcca-cactttctgtcgcatgtgatttgca-3') which has a nucleotide sequence as depicted in SEQ ID NO: 10 are used.

In one embodiment of the invention, a regulatory nucleotide sequence or an expression cassette comprising said regulatory nucleotide sequence or a polynucleotide construct, particularly a chimeric polynucleotide construct, comprising said regulatory sequence is provided which comprises a transcription termination sequence obtainable from a gene encoding an actin depolymerizing factor 3 (ABP3), which regulatory sequence mediates transcription of an operably associated polynucleotide molecule, particularly of an operably associated protein encoding polynucleotide molecule of interest such that said polynucleotide of interest is transcribed in most of the plant tissues but not or substantially not in the tissues of the pollen so that no expression product is present in said tissues to any significant extent, particularly from a maize actin depolymerizing factor 3 (ABP3) gene, wherein i) said regulatory nucleotide sequence comprises a transcription termination sequence which regulatory sequence has at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 14; or
ii) the complementary strand of said regulatory nucleotide sequence hybridizes to a nucleotide sequence depicted in SEQ ID NO: 14, particularly under moderate hybridization conditions, more particularly under moderate-stringent hybridization conditions, particularly under stringent hybridization conditions and mediates termination of transcription of an operably associated protein encoding polynucleotide of interest; or
iii) said regulatory nucleotide sequence has a sequence as depicted in SEQ ID NO: 14, or a fragment thereof which still exhibits full functionality as a termination sequence, including complements thereof.

In one embodiment of the invention, a regulatory nucleotide sequence is provided or an expression cassette comprising said regulatory nucleotide sequence or a polynucleotide construct, particularly a chimeric polynucleotide construct, comprising said regulatory sequence at least part of which has a transcription initiation function and a termination function, respectively, which regulatory nucleotide sequence is obtainable from a gene encoding an actin depolymerizing factor 3 (ABP3), which is expressed in most tissues of the plant but not or substantially not in the tissues of the pollen so that no expression product is present in said tissues to any significant extent, particularly from a maize actin depolymerizing factor 3 (ABP3) gene, and which regulatory nucleotide sequence comprises a transcription initiation sequence as depicted in SEQ ID NO: 13 and a transcription termination sequence as depicted in SEQ ID NO:14.

In one embodiment of the invention, the regulatory nucleotide sequence is obtainable from maize genomic DNA, particularly from a putative gene on the maize genome, which is highly expressed in most tissues of the plant but not or substantially not in the tissues of the tassel so that no expression product is present in said tissues to any significant extent.

In one embodiment, a regulatory nucleotide sequence or an expression cassette comprising said regulatory nucleotide sequence or a polynucleotide construct, particularly a chimeric polynucleotide construct, comprising said regulatory sequence according to the invention and as described herein is provided comprising approximately 2.6 kb of the 5'-sequence including approximately 2 kb of 5'-non-transcribed sequence, a 5'-UTR, and exon 1 and part of exon 2 and intron 1, particularly approximately 0.6 kb representing exon 1, intron 1 and about 16 bp of exon 2.

In one embodiment, the invention provides a regulatory nucleotide sequence or an expression cassette comprising said regulatory nucleotide sequence or a polynucleotide construct, particularly a chimeric polynucleotide construct, comprising said regulatory sequence at least part of which has a transcription initiation function as described herein, which regulatory sequence is obtainable from a genomic *Zea mays* DNA template using i) a first primer which has at least 90%, particularly at least 91%, particularly at least 92%, 93%, 94%, 95%, 96%, 97%, 98% or 99% sequence identity with a nucleotide sequence as depicted in SEQ ID NO: 19, particularly the primer of SEQ ID NO: 19; or ii) a second primer which has at least 90%, particularly at least 91%, particularly at least 92%, 93%, 94%, 95%, 96%, 97%, 98% or 99% sequence identity with a nucleotide sequence as depicted in SEQ ID NO: 20, particularly the reverse primer of SEQ ID NO: 20; or iii) a first primer as a forward primer which has at least 90%, particularly at least 91%, particularly at least 92%, 93%, 94%, 95%, 96%, 97%, 98% or 99% sequence identity with a nucleotide sequence as depicted in SEQ ID NO: 19 and a second primer as a reverse primer which has at least 90%, particularly at least 91%, particularly at least 92%, 93%, 94%, 95%, 96%, 0.97%, 98% or 99% sequence identity with a nucleotide sequence as depicted in SEQ ID NO: 20, particularly the forward primer of SEQ ID NO: 19 and the reverse primer of SEQ ID NO: 20.

In one embodiment, the regulatory nucleotide sequence according to the invention and as described herein is modified using one or more oligonucleotides selected from the group of oligonucleotides depicted in SEQ ID NO: 21, SEQ ID NO: 22, SEQ ID NO: 23, SEQ ID NO: 24, SEQ ID NO: 25 and SEQ ID NO: 26.

In one embodiment, the invention relates to a regulatory nucleotide sequence or an expression cassette comprising said regulatory nucleotide sequence or a polynucleotide construct, particularly a chimeric polynucleotide construct, comprising said regulatory sequence as described herein, which regulatory nucleotide sequence provides a transcription initiation function, wherein the nucleotide sequence providing said function has at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 35 and wherein said regulatory nucleotide sequence mediates transcription of an operably associated protein encoding polynucleotide of interest in most tissues of the plant but essentially excluding the tissues of the tassel so that no expression product is present in said tissues to any significant extent.

In one embodiment, the invention relates to a regulatory nucleotide sequence or an expression cassette comprising said regulatory nucleotide sequence or a polynucleotide construct, particularly a chimeric polynucleotide construct, comprising said regulatory sequence as described herein, which regulatory nucleotide sequence provides a transcription initiation function, wherein the complementary strand of the nucleotide sequence providing said function hybridizes to a nucleotide sequence depicted in SEQ ID NO: 35, particularly under moderate hybridization conditions, more particularly under moderately stringent hybridization conditions and wherein said regulatory nucleotide sequence mediates transcription of an operably associated protein encoding polynucleotide of interest in most tissues of the plant but essentially excluding the tissues of the pollen so that no expression product is present in said tissues to any significant extent. In particular, said hybridization occurs under stringent hybridization conditions.

In one embodiment of the invention, the nucleotide sequence providing the transcription initiation function is the sequence depicted in SEQ ID NO: 35, or a fragment thereof, which still exhibits the full functionality as a transcription initiation sequence and complements thereof.

In one embodiment, a regulatory nucleotide sequence or an expression cassette comprising said regulatory nucleotide sequence or a polynucleotide construct, particularly a chimeric polynucleotide construct, comprising said regulatory sequence is provided at least part of which has a transcription termination function which sequence is obtainable in a PCR amplification reaction from a gDNA template, particularly a maize gDNA template, using a forward primer which has at least 90%, particularly at least 91%, particularly at least 92%, 93%, 94%, 95%, 96%, 97%, 98% or 99% sequence identity with a nucleotide sequence as depicted in SEQ ID NO: 29 and a reverse primer, which has at least 90%, particularly at least 91%, particularly at least 92%, 93%, 94%, 95%, 96%, 97%, 98% or 99% sequence identity with a nucleotide sequence as depicted in SEQ ID NO: 30. In particular, said regulatory nucleotide sequence comprises a transcriptional terminator and poly-adenylation signal. In particular, a forward primer, which has a nucleotide sequence as depicted in SEQ ID NO: 29 and a reverse primer, which has a nucleotide sequence as depicted in SEQ ID NO: 30 are used.

In one embodiment of the invention, a regulatory nucleotide sequence or an expression cassette comprising said regulatory nucleotide sequence or a polynucleotide construct, particularly a chimeric polynucleotide construct, comprising said regulatory sequence is provided wherein i) said regulatory nucleotide sequence comprises a transcription termination sequence which has at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 36; or ii) the complementary strand of said regulatory nucleotide sequence hybridizes to a nucleotide sequence depicted in SEQ ID NO: 36, particularly under moderate hybridization conditions, particularly under moderate-stringent hybridization conditions, particularly under stringent hybridization conditions and mediates termination of transcription of an operably associated protein encoding polynucleotide of interest; or iii) said regulatory sequence has a sequence as depicted in SEQ ID NO: 36, or a fragment thereof, which still exhibits the full functionality as a termination sequence, including complements thereof.

In one embodiment of the invention, a regulatory nucleotide sequence or an expression cassette comprising said regulatory nucleotide sequence or a polynucleotide construct, particularly a chimeric polynucleotide construct, comprising said regulatory sequence, is provided at least part of which has a transcription initiation function and a termination function, respectively, which regulatory nucleotide sequence is obtainable from a maize genomic DNA, which is expressed in most tissues of the plant but not or substantially not in the tissues of the tassel so that no expression product is present in said tissues to any significant extent, and which regulatory nucleotide sequence comprises a transcription initiation sequence and a transcription termination sequence, respectively, which have at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 35 and SEQ ID NO:36, respectively.

In one embodiment of the invention, a regulatory nucleotide sequence or an expression cassette comprising said regulatory nucleotide sequence or a polynucleotide construct, particularly a chimeric polynucleotide construct, comprising said regulatory sequence, is provided at least part of which has a transcription initiation function and a termination function, respectively, which regulatory nucleotide sequence is obtainable from a maize genomic DNA, which is expressed in most tissues of the plant but not or substantially not in the tissues of the tassel so that no expression product is present in said tissues to any significant extent, and which regulatory nucleotide sequence comprises a transcription initiation sequence as depicted in SEQ ID NO: 35 and a transcription termination sequence as depicted in SEQ ID NO: 36.

It is apparent to the skilled artisan that, based on the nucleotide sequences shown in SEQ ID NO: 13, SEQ ID NO 14, SEQ ID NO: 35 and SEQ ID NO: 36, fragments of various length can be obtained from said sequences, for example by using any primer combinations of interest to generate fragments that still exhibit the specific regulatory function according to the invention that is driving expression of an operably associated polynucleotide of interest in most plant tissues but tissues of the pollen and the tassel, respectively. The invention thus includes fragments derived from a full-length transcript promoter and a full-length terminator of the invention and as described herein, respectively that function according to the invention, i.e. are capable of conferring expression and termination of an operably associated nucleotide sequence in most plant tissues but essentially excluding the tissues of the pollen so that no expression product is present in said tissues to any significant extent and/or the tassel.

The function of the promoter and terminator fragments, once obtained, can be easily tested by fusing them to a selectable or screenable marker gene and assaying the fusion constructs for retention of the specific promoter activity. Such assays are within the ordinary skill of the person skilled in the art.

In one embodiment, the invention relates to nucleotide fragments, particularly to nucleotide fragments obtainable from the regulatory sequences of an action depolymerizing factor 3 (ABP3) gene, which nucleotide fragments are of at least about 50 bases, preferably of between about 400 bases and about 650 bases, more preferably of between about 200 bases and about 400 bases and most preferably of about 350 bases in length and still exhibit the specific regulatory function according to the invention that is driving expression of an operably associated polynucleotide of interest in most plant tissues but essentially excluding the tissues of the pollen and/or the tassel so that no expression product is present in said tissues to any significant extent.

In one embodiment, the invention relates to nucleotide fragment comprising a nucleotide sequence comprising a consecutive stretch of at least 50 nt, particularly of between about 400 nt and about 650 nt, particularly of between about 200 nt and about 400 nt, particularly of about 350 nt in length of the nucleotide sequence depicted in SEQ ID NO:13 and SEQ ID NO: 35, respectively, wherein said nucleotide sequences still exhibit the specific regulatory function according to the invention that is driving expression of an operably associated polynucleotide of interest in most plant tissues but essentially excluding the tissues of the pollen and/or the tassel so that no expression product is present in said tissues to any significant extent.

It is also clear to the skilled artisan that variant sequences may be obtained without affecting the specific properties of the regulatory sequences according to the invention by introducing mutations, i.e. insertions, deletions and/or substitutions of one or more nucleotides, into the DNA sequences of SEQ ID NO: 13, SEQ ID NO 14, SEQ ID NO: 35 and SEQ ID NO: 36, respectively, using methods known in the art. In addition, an unmodified or modified nucleotide sequence of the present invention may be further varied by shuffling the sequence of the invention. To test for a function of variant DNA sequences according to the invention, the sequence of interest is operably linked to a selectable or screenable marker gene and expression of the marker gene is tested in transient expression assays with protoplasts or in whole plant tissues or in stably transformed plants. It is known to the skilled artisan that DNA sequences capable of driving expression of an operably associated nucleotide sequence are build in a modular way. Accordingly, expression levels from shorter DNA fragments may be different than the one from the longest fragment and may be different from each other. For example, deletion of a down-regulating upstream element will lead to an increase in the expression levels of the associated nucleotide sequence while deletion of an up-regulating element will decrease the expression levels of the associated nucleotide sequence.

In one embodiment, the invention relates to an expression cassette comprising a regulatory nucleotide sequence or an expression cassette comprising said regulatory nucleotide sequence or a polynucleotide construct, particularly a chimeric polynucleotide construct, comprising said regulatory sequence according to the invention and as described herein.

In one embodiment, the expression cassette according to the invention comprises about 2.3 kb of the 5'-sequence of ZmABP3 which consists of about 1.1 kb of 5'-non-transcribed sequence, about 0.25 kb of 5'-UTR and about 0.98 kb representing ZmABP3-intron 1, about 1.013 kb of the 3'-sequence starting just past the ABP3 translation stop codon including about 0.3 kb of 3'-UTR and about 0.7 kb of non-transcribed sequence, which functions as the transcriptional terminator and poly-adenylation signal.

In one embodiment, an expression cassette according to the invention is provided wherein the natural translation start codon is silenced and moved to the second exon, particularly moved within 15 nucleotides of the 5'-end of ZmABP3 exon 2.

In one embodiment, an expression cassette according to the invention is provided wherein the start codon is preceded by the Kozak sequence 5'- . . . CCACC . . . -3'.

In one embodiment, the expression cassette according to the invention comprises a regulatory nucleotide sequence comprising approximately 2.6 kb of the 5'-sequence, which consists of approximately 2 kb of 5'-non-transcribed sequence, and about 12 bp of 5'-UTR, approximately 0.6 kb representing exon 1, intron 1 and about 16 bp of exon 2; and approximately 1 kb of the 3'-sequence that begins just past the translation stop codon and includes approximately 0.6 kb of 3'-UTR and about 0.4 kb of non-transcribed sequence, and functions as the transcriptional terminator and polyadenylation signal.

In one embodiment, an expression cassette according to the invention is provided wherein the natural translation start codon is silenced and moved to the second exon.

In one embodiment, a polypeptide or protein encoding nucleotide sequence is provided encoding an endotoxin of *Bacillus thuringiensis* which has at least 80% sequence identity, particularly at least 85% sequence identity, particularly at least 90%, 91%, 92%, 93%, 94%, 95%, 96%, 97%, 98% or 99% sequence identity with a nucleotide sequence as depicted in SEQ ID NO:15.

In one embodiment, a polypeptide or protein encoding nucleotide sequence is provided encoding an endotoxin of *Bacillus thuringiensis* which has the nucleotide sequence as depicted in SEQ ID NO: 15.

In one embodiment, the invention relates to a transgenic plant comprising an expression cassette according to the invention and as described herein.

In one embodiment, the invention provides a transgenic plant, particularly a transgenic maize plant comprising a regulatory sequence according to the invention and as described herein.

In one embodiment, the invention provides a transgenic plant, particularly a transgenic maize plant comprising a regulatory sequence according to the invention and as described herein in association with a polynucleotide of interest, particularly a polypeptide or protein encoding polynucleotide of interest.

In one embodiment, the invention provides a transgenic plant, particularly a transgenic maize plant comprising an expression cassette according to the invention and as described herein.

In one embodiment, a transgenic plant according to the invention and as described herein is provided, wherein the polypeptide or protein encoding nucleotide sequence encodes an endotoxin of *Bacillus thuringiensis* which has at least 80% sequence identity, particularly at least 85% sequence identity, particularly at least 90%, 91%, 92%, 93%, 94%, 95%, 96%, 97%, 98% or 99% sequence identity with a nucleotide sequence as depicted in SEQ ID NO:15 and is under the control of a regulatory sequences operable in said plant.

In one embodiment, a transgenic plant according to the invention and as described herein is provided, wherein the polypeptide or protein encoding nucleotide sequence encodes an endotoxin of *Bacillus thuringiensis* which has the nucleotide sequence as depicted in SEQ ID NO: 15 and is under the control of a regulatory sequences operable in said plant.

The invention also provides methods for preparing expression cassettes comprising the regulatory sequence according to the invention comprising linking an expressible polynucleotide encoding a polypeptide or a protein of interest with the regulatory sequence according to the invention and as described herein to obtain an expression construct, wherein the polynucleotide of interest is operably linked or associated with the regulatory sequence such that expression of the polypeptide or a protein of interest is mediated by the regulatory sequence according to the invention and results in the expression of said polypeptide or a protein of interest in essentially all plant tissues, but essentially excludes expression in the tissues of the reproductive structures of the plant, particularly in the tissues of the pollen and/or the tassel so that no expression product is present in said tissues to any significant extent.

In one embodiment, the invention relates to a method of producing a transgenic plant expressing a DNA sequence of interest in non-pollen tissue but not or substantially not in the tissues of the pollen and/or the tassel, comprising a. transforming an expression cassette according to the invention and as described herein into a plant cell which comprises a regulatory nucleotide sequence, at least part of which has a transcription initiation function which mediates expression of an operably associated protein encoding polynucleotide of interest in most plant tissues but essentially excluding the tissues of the pollen and/or the tassel so that no expression product is present in said tissues to any significant extent; and
b. regenerating the plant cell transformed in step a) into a plant.

In one embodiment, the invention relates to a method of controlling insect target-pests feeding on vegetative plant tissues such as the leaf, stalk and root and/or on reproductive tissues such as the ear, but protecting non-target pests feeding on pollen comprising a. growing a plant according to the invention and as described herein in an area that is infested with the target pest;
b. expressing a polypeptide or protein that is capable of controlling said target pest under the control of a regulatory sequence according to the invention and as described herein.

In one embodiment, the invention relates to a method of protecting the reproductive tissues of a plant, particularly the tissues of the pollen and/or the tassel against damage caused by expression in said tissues of a polypeptide or protein of interest comprising a. growing a plant according to the invention and as described herein;
b. expressing in said plant a polypeptide or protein of interest under the control of a regulatory sequence according to the invention and as described herein.

In one embodiment the present invention relates to the use of a regulatory sequence according to the present invention and as disclosed herein for protecting the reproductive tissues of a plant, particularly the tissues of the pollen and/or the tassel against damage caused by expression in said tissues of a polypeptide or protein of interest comprising expressing in said plant said polypeptide or protein of interest under the control of a regulatory sequence according to the invention and as described herein.

BRIEF DESCRIPTION OF THE SEQUENCES

SEQ ID NO: 1 depicts the nucleotide sequence of forward primer P1

SEQ ID NO: 2 depicts the nucleotide sequence of reverse primer P2

SEQ ID NO: 3 depicts the nucleotide sequence of oligonucleotide Patg

SEQ ID NO: 4 depicts the nucleotide sequence of oligonucleotide Pnco

SEQ ID NO: 5 depicts the nucleotide sequence of oligonucleotide ADPc-1

SEQ ID NO: 6 depicts the nucleotide sequence of oligonucleotide ADPc-2

SEQ ID NO: 7 depicts the nucleotide sequence of oligonucleotide ADPc-4

SEQ ID NO: 8 depicts the nucleotide sequence of oligonucleotide adp3-a

SEQ ID NO: 9 depicts the nucleotide sequence of forward primer P3

SEQ ID NO: 10 depicts the nucleotide sequence of reverse primer P4

SEQ ID NO: 11 depicts the nucleotide sequence of forward primer Tnco

SEQ ID NO: 12 depicts the nucleotide sequence of forward primer T2

SEQ ID NO: 13 depicts the nucleotide sequence of modified ZmABP3 regulatory sequence including the transcription initiation sequence SEQ ID NO: 14 depicts the nucleotide sequence of ZmABP3 terminal sequence SEQ ID NO: 15 depicts the nucleotide sequence of Cry1AbG6

SEQ ID NO: 16 depicts the nucleotide sequence of maize-optimized AtAVP1 D coding sequence SEQ ID NO: 17 depicts the nucleotide sequence of the ZmABP3 gene SEQ ID NO: 18 depicts the nucleotide sequence of the pNOV1321 plasmid SEQ ID NO: 19 depicts the nucleotide sequence of forward primer ABT P1 forw SEQ ID NO: 20 depicts the nucleotide sequence of reverse primer ABT P2 rev SEQ ID NO: 21 depicts the nucleotide sequence of oligonucleotide pABT mut1

SEQ ID NO: 22 depicts the nucleotide sequence of oligonucleotide pABT mut2

SEQ ID NO: 23 depicts the nucleotide sequence of oligonucleotide pABT mut3

SEQ ID NO: 24 depicts the nucleotide sequence of oligonucleotide pABT mut4

SEQ ID NO: 25 depicts the nucleotide sequence of oligonucleotide pABT mut5

SEQ ID NO: 26 depicts the nucleotide sequence of oligonucleotide pABT mut6

SEQ ID NO: 27 depicts the nucleotide sequence of forward primer pABT amp1

SEQ ID NO: 28 depicts the nucleotide sequence of reverse primer pABT amp2

SEQ ID NO: 29 depicts the nucleotide sequence of forward primer ABT P4

SEQ ID NO: 30 depicts the nucleotide sequence of reverse primer ABT P5

SEQ ID NO: 31 depicts the nucleotide sequence of oligonucleotide ABTt m1

SEQ ID NO: 32 depicts the nucleotide sequence of oligonucleotide ABTt m2

SEQ ID NO: 33 depicts the nucleotide sequence of ZmABT1 cDNA

SEQ ID NO: 34 depicts the nucleotide sequence of ZmABT2 cDNA

SEQ ID NO: 35 depicts the nucleotide sequence of the ZmABT promoter

SEQ ID NO: 36 depicts the nucleotide sequence of the ZmABT terminal sequence.

SEQ ID NO: 37 depicts the nucleotide sequence of the ZmABP3-Cry1AbG6 Assembly construct.

SEQ ID NO: 38 depicts the nucleotide sequence of the ZmABP3-Cry1AbG6 binary construct.

SEQ ID NO: 39 depicts the nucleotide sequence of the enhanced ZmABP3-Cry1AbG6 binary construct.

SEQ ID NO: 40 depicts the nucleotide sequence of the ZmABP3-AmCyan assembly construct.

SEQ ID NO: 41 depicts the nucleotide sequence of the ZmABP3-AmCyan binary construct.

SEQ ID NO: 42 depicts the nucleotide sequence of the ZmABP3-AtAVP1 D assembly construct.

SEQ ID NO: 43 depicts the nucleotide sequence of the ZmABP3-AtAVP1 D binary construct.

SEQ ID NO: 44 depicts the nucleotide sequence of plasmid 15772 (ZmABT Assembly)

SEQ ID NO: 45 depicts the nucleotide sequence of plasmid 15773

SEQ ID NO: 46 depicts the nucleotide sequence of ZmABT gDNA

SEQ ID NO: 47 depicts the nucleotide sequence of Ctrl-_ZMU45855-3_at

SEQ ID NO: 48 depicts the nucleotide sequence of AF032370_at

SEQ ID NO: 49 depicts the nucleotide sequence of Zm001747_s_at

SEQ ID NO: 50 depicts the nucleotide sequence of Zm005803_s_at

SEQ ID NO: 51 depicts the nucleotide sequence of Zm007728_s_at

SEQ ID NO: 52 depicts the nucleotide sequence of Zm009722_s_at

SEQ ID NO: 53 depicts the nucleotide sequence of Zm015335_s_at

SEQ ID NO: 54 depicts the nucleotide sequence of Zm021004_s_at

SEQ ID NO: 55 depicts the nucleotide sequence of Zm058948_s_at

SEQ ID NO: 56 depicts the nucleotide sequence of Zm061393_s_at

SEQ ID NO: 57 depicts the nucleotide sequence of Zm016864_s_at

SEQ ID NO: 58 depicts the nucleotide sequence of Zm018791_at

SEQ ID NO: 59 depicts the nucleotide sequence of ZMMETALL_x_at

SEQ ID NO: 60 depicts the nucleotide sequence of Zm000019_at

SEQ ID NO: 61 depicts the nucleotide sequence of Zm002987_at

SEQ ID NO: 62 depicts the nucleotide sequence of Zm002990_s_at

SEQ ID NO: 63 depicts the nucleotide sequence of Zm002990_x_at

SEQ ID NO: 64 depicts the nucleotide sequence of Zm004433_at

SEQ ID NO: 65 depicts the nucleotide sequence of Zm005761_at

SEQ ID NO: 66 depicts the nucleotide sequence of Zm006285_at

SEQ ID NO: 67 depicts the nucleotide sequence of Zm006481_s_at

SEQ ID NO: 68 depicts the nucleotide sequence of Zm010323_s_at

SEQ ID NO: 69 depicts the nucleotide sequence of Zm011554_at

SEQ ID NO: 70 depicts the nucleotide sequence of Zm011554_x_at

SEQ ID NO: 71 depicts the nucleotide sequence of Zm021403_at

SEQ ID NO: 72 depicts the nucleotide sequence of Zm028405_s_at

SEQ ID NO: 73 depicts the nucleotide sequence of Zm032921_s_at

SEQ ID NO: 74 depicts the nucleotide sequence of Zm033444_s_at

SEQ ID NO: 75 depicts the nucleotide sequence of Zm035082_s_at

SEQ ID NO: 76 depicts the nucleotide sequence of Zm040564_x_at

SEQ ID NO: 77 depicts the nucleotide sequence of Zm054116_s_at

SEQ ID NO: 78 depicts the nucleotide sequence of Zm066342_at

SEQ ID NO: 79 depicts the nucleotide sequence of Zm051284_at

SEQ ID NO: 80 depicts the nucleotide sequence of Vector 15289

SEQ ID NO: 81 depicts the nucleotide sequence of ZmABP-948-binary

SEQ ID NO: 82 depicts the nucleotide sequence of ZmABT-990-binary

SEQ ID NO: 83 depicts the nucleotide sequence of 5' Bfr1 primer

SEQ ID NO: 84 depicts the nucleotide sequence of 3' Xba1 primer

SEQ ID NO: 85 depicts the nucleotide sequence of 5'Gfix primer

SEQ ID NO: 86 depicts the nucleotide sequence of 3'Gfix primer

SEQ ID NO: 87 depicts the nucleotide sequence of 5'1Ab5XbaI primer

SEQ ID NO: 88 depicts the nucleotide sequence of 3'1Ab3d6 primer

SEQ ID NO: 89 depicts the nucleotide sequence of cy2'

SEQ ID NO: 90 depicts the nucleotide sequence of cy1

SEQ ID NO: 91 depicts the nucleotide sequence of cy2

DETAILED DESCRIPTION OF THE INVENTION

Definitions

The technical terms and expressions used within the scope of this application are generally to be given the meaning commonly applied to them in the pertinent art of plant molecular biology if not otherwise indicated herein below.

As used in this specification and the appended claims, the singular forms “a”, “an”, and “the” include plural referents unless the context clearly dictates otherwise. Thus, for example, reference to “a plant” includes one or more plants, and reference to “a cell” includes mixtures of cells, tissues, and the like.

As used in this specification and the appended claims, the plural form “tissues”, includes also the singular form unless the context clearly dictates otherwise. Thus, for example, reference to “tissues of the tassel” includes one or more tissues present in the tassel.

As used in this specification and the appended claims, the phrase “most tissues of the plant” or “essentially all tissues of the plant” is used interchangeably and refers to the majority to the tissues present in the plant with the exception of the tissues of the reproductive structures, particularly the tissues of the pollen and the tassel. In particular, “most tissues” refer to those tissues of the plant where target insects mainly feed on, with the exception of the tissues of the male reproductive structures, such as the tissues of the stalk, the roots, the leaves, the ear, the ear sheath, the silks and the developing kernels.

The term “polynucleotide” is understood herein to refer to polymeric molecule of high molecular weight which can be single-stranded or double-stranded, composed of monomers (nucleotides) containing a sugar, phosphate and a base which is either a purine or pyrimidine. A “polynucleotide fragment” is a fraction of a given polynucleotide molecule. In higher plants, deoxyribonucleic acid (DNA) is the genetic material while ribonucleic acid (RNA) is involved in the transfer of information contained within DNA into proteins. A “genome” is the entire body of genetic material contained in each cell of an organism, including the genomes of the mitochondria and the plastids. The term “polynucleotide” thus refers to a polymer of DNA or RNA which can be single- or double-stranded, optionally containing synthetic, non-natural or altered nucleotide bases capable of incorporation into DNA or RNA polymers. Unless otherwise indicated, a particular nucleic acid sequence of this invention also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer, et al., Nucleic Acid Res. 19:5081 (1991); Ohtsuka, et al., J. Biol. Chem. 260:2605-2608 (1985); and Rossolini, et al., Mol. Cell. Probes 8:91-98 (1994)). The term polynucleotide is used interchangeably with nucleic acid, nucleotide sequence and may include genes, cDNAs, and mRNAs encoded by a gene, etc.

A “regulatory nucleotide sequence at least part of which has a transcription initiation function” is understood herein to refer to a nucleotide sequence, which controls the expression of an operably associated coding sequence by providing the recognition for RNA polymerase and other factors required for proper transcription and is located usually upstream (5') to its coding sequence. “Regulatory nucleotide sequences” include 5' regulatory sequences located proximal and more distal elements upstream of the associated coding region, which influence the transcription, RNA processing or stability, or translation of the associated coding sequence. “Regulatory nucleotide sequences” may further include 3' sequences, including 3' non-translated and/or 3' non-transcribed sequences, located downstream of the associated coding region, and can include a transcription termination site. “Regulatory nucleotide sequences” may include enhancers, promoters, untranslated leader sequences, introns, and polyadenylation signal sequences. They include natural and synthetic sequences as well as sequences that may be a combination of synthetic and natural sequences. An “enhancer” is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. The meaning of the term “regulatory nucleotide sequences” includes “transcription initiation” or “promoter” sequences and “promoter regulatory sequences.” These terms are used interchangeably herein after.

For purposes of this invention, the definition of the term “3'-nontranscribed sequence” includes modifications to the nucleotide sequence of a 3'-nontranscribed sequence derived from a target gene, provided the modified 3'-nontranscribed sequence does not significantly reduce the activity of its associated 3' regulatory sequence. The 3'-nontranscribed sequence extends approximately 0.5 to 1.5 kb downstream of the transcription termination site.

The polynucleotide of the invention is understood to be provided in isolated form. The term “isolated” means that the polynucleotide disclosed and claimed herein is not a polynucleotide as it occurs in its natural context, if it indeed has a naturally occurring counterpart. Accordingly, the other compounds of the invention described further below are understood to be isolated. If claimed in the context of a plant genome, the polynucleotide of the invention is distinguished over naturally occurring counterparts by i.e. modifications introduced into the naturally occurring counterpart sequence and/or the insertion side in the genome and the flanking sequences at the insertion side.

"Operably associated" and "operably-linked" are used interchangeably and refer to the association of nucleic acid sequences on a single nucleic acid fragment so that the function of one is affected by the other. For example, a promoter is associated or operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

The term "present to any significant extent" as used within the context of the present invention refers to the fact that only negligible expression occurs in pollen resulting in only minor amounts of the expression product in pollen tissue at concentrations that may be detectable by high-resolution detection methods such as HPLC, ELISA-based assays, Western analysis, insect feeding assays, enzyme activity assays etc., but stay below a certain threshold level that would be needed to effect the envisaged biological function of the expression product. For example, in case of the Cry1AbG6 endotoxin of *Bacillus thuringiensis* the threshold level is in the range of between 5 ng/mg soluble protein and 60 ng/mg soluble protein, particularly in the range of between 20 ng/mg soluble protein and 50 ng/mg soluble protein.

The term "chimeric gene" refers to any gene that contains 1) DNA sequences, including regulatory and coding sequences that are not found together in nature in this specific combination or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

The terms "heterologous DNA sequence," "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling or mutation. These terms also include non-naturally occurring multiple copies of a naturally occurring DNA sequence. Thus, the terms refer to a DNA segment that is foreign or heterologous to the cell, or homologous to the cell but in a position within the host cell genome in which the element is not ordinarily found. Exogenous DNA segments are expressed to yield exogenous polypeptides. A "homologous" DNA sequence is a DNA sequence that is naturally associated with a host cell into which it is introduced.

A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

"Expression cassette" as used herein means a DNA sequence capable of directing expression of a particular nucleotide sequence in an appropriate host cell, comprising a promoter operably linked to the protein encoding polynucleotide of interest which is operably linked to a terminator. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the protein encoding polynucleotide of interest may be chimeric.

"Intron" refers to an intervening section of DNA which occurs almost exclusively within a eukaryotic gene, but which is not translated to amino acid sequences in the gene product. The introns are removed from the pre-mature mRNA through a process called splicing, which leaves the exons untouched, to form an mRNA. For purposes of the present invention, the definition of the term "intron" includes modifications to the nucleotide sequence of an intron derived from a target gene, provided the modified intron does not significantly reduce the activity of its associated 5' regulatory sequence.

"Exon" refers to a section of DNA which carries the coding sequence for a protein or part of it. Exons are separated by intervening, non-coding sequences (introns). For purposes of the present invention, the definition of the term "exon" includes modifications to the nucleotide sequence of an exon derived from a target gene, provided the modified exon does not significantly reduce the activity of its associated 5' regulatory sequence.

The terms "protein," "peptide" and "polypeptide" are used interchangeably herein.

A "probe" as used herein refers to a defined nucleic acid (DNA or RNA) fragment of variable length which may be used to detect in a DNA or RNA containing sample nucleotide sequences that are complementary to the sequence represented by the probe molecule.

The probe molecules may be used in a microarray set up, where they are covalently attached to a chemical matrix on an inert surface, such as coated glass slides or silicon based gene chips. Hybridization of the probe molecules to a target nucleic acid in the sample usually occurs under high stringency conditions. Probe-target hybridization is usually detected and quantified by fluorescence-based detection of fluorophore-labeled targets to determine relative transcript abundance of nucleic acid sequences in the target. DNA microarrays may be used in expression profiling experiments to quantify transcript abundance for a target molecule in tissue samples such as the tissues of the pollen and/or the tassel, calculated based on the strength of the signal detected in the respective samples.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardts solution see Sambrook et al. loc. cit.). High stringency hybridization conditions as for instance described in Sambrook et al, supra, are particularly preferred. Particularly preferred stringent hybridization conditions are for instance present if hybridization and washing occur at 65° C. as indicated above.

Non-stringent hybridization conditions for instance with hybridization and washing carried out at 45° C. are less preferred and at 35° C. even less.

"Sequence Homology or Sequence Identity" is used herein interchangeably. The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestf it program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and workbench.sdsc.edu/). For this purpose, the "default" parameter settings may be used.

Another indication that two nucleic acid sequences are substantially identical is that the two molecules hybridize to each other under stringent conditions. The phrase: "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 0.1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M $Na^+$ ion, typically about 0.01 to 1.0 M $Na^+$ ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. "Plant tissue" includes differentiated and undifferentiated tissues or plants, including but not limited to roots, stems, shoots, leaves, pollen, seeds, tumor tissue and various forms of cells and culture such as single cells, protoplasts, embryos, and callus tissue. The plant tissue may be in plants or in organ, tissue or cell culture.

The use of this term in conjunction with, or in the absence of, any specific type of plant tissue as listed above or otherwise embraced by this definition is not intended to be exclusive of any other type of plant tissue.

The terms “maize”, “corn” and “*Zea mays*” are used herein interchangeably and refer to plants belonging to the genus *Zea* including, for example, different strains, races or varieties, commercial and non-commercial, of the species *Zea mays.*

The present invention relates to a transgenic plant comprising stably integrated in its genome a chimeric polynucleotide construct, particularly a chimeric DNA construct, comprising a protein encoding polynucleotide of interest, particularly a polypeptide or protein encoding polynucleotide of interest, under control of a regulatory nucleotide sequence, at least part of which has a transcription initiation function directing expression of said protein encoding polynucleotide of interest to essentially all tissues of the plant with the exception of the tissues of the male reproductive structures, particularly the tissues of the pollen and/or the tassel so that no expression product is present in said tissues to any significant extent.

A regulatory nucleotide sequence according to the present invention at least part of which has a transcription initiation function which mediates expression of an operably associated protein encoding polynucleotide of interest in most plant tissues but the tissues of the male reproductive structures, particularly the tissues of the pollen and/or the tassel, may be obtained in an expression profiling experiment to screen for probes that give strong signals in all samples, but only a weak or no signal in the pollen and/or the tassel sample, which is indicative of expression of the respective polynucleotides represented by said probes in most plant tissues and of no or substantially no expression in the tissues of the pollen and/or the tassel. In particular, maize plant tissues and tissues of the reproductive structures, particularly tissues of the pollen and/or the tassel may be screened to identify and obtain a regulatory sequence according to the present invention.

In particular, samples of all plant tissues, particularly samples of the green tissues and the root of a maize plant, may be directly compared to tissue samples from the male reproductive structures, particularly tissue samples of the pollen and/or the tassel. Probes representing polynucleotides that do not meet the target expression profile are eliminated. Only those probes with the strongest signal across all non-pollen/non-tassel tissues and weak of no signal in pollen and/or the tassel are selected for further analysis that is probes representing polynucleotides that are highly expressed in all tissue samples, but show substantially no expression in pollen and/or the tassel. Said probes may then be aligned with plant cDNA assembly datasets to detect bona fide plant genes, particularly maize genes or putative maize genes.

The DNA sequence representing probes on the maize chip identified as representing genes that are highly expressed in all tissue samples but essentially not expressed in pollen, particularly probes represented by the DNA sequence as given in SEQ ID NOs: 47 to 56 and those representing genes that are highly expressed in all tissue samples and have essentially no or reduced expression in tassel samples, particularly probes represented by the DNA sequence a given in SEQ ID NOs: 57-79, can easily be extended to designed expression cassettes following the steps outlined in the Examples.

Probe candidate sequences from the expression profiling analysis for each expression category may be selected and progressed to a finished binary vector with the designed expression cassette linked to a gene of interest such as, for example, a reported gene, i.e., the GUS reporter gene.

In a first step, each expression cassette is flanked with one or more suitable restriction sites such as, for example, SanDI/RsrII sites and cloned into the vector molecule. The regulatory region including the transcription initiation function typically resides within a fragment of about 1000-1500 bp upstream of the transcription start site and extends into the second exon, or to the natural translation start codon if it is not on the first exon. It typically terminates with the maize optimized Kozak sequence ‘gtaaaccatgg’. The engineered translation start codon is then embedded in a suitable restriction site such as the NcoI restriction endonuclease site ‘ccatgg’. All translation start codons in the theoretical transcript that are upstream of the engineered restriction site are eliminated. At least one stop codon should be present in each reading frame upstream of the engineered restriction site. The regulatory region including the transcription initiation function is designed to be flanked by suitable restriction sites such as, for example, XhoI/SanDI sites at the 5'-end and a NcoI site at the 3'-end.

The Gene Of Interest (G01) such as the GUS reporter gene is provided as a suitable restriction fragment, in the example given here as a NcoI/SacI fragment. The terminus extends from just after the translation stop codon for about 1 kb downstream. The terminus is designed to be flanked by suitable restriction sites such as, for example, SacI at the 5'-end and RsrII/XmaI at the 3'-end.

The complete expression cassette is designed to be mobilized as a suitable restriction fragment, such as a SanDI/RsrII fragment, which can be ligated into the corresponding site located on an *Agrobacterium* binary vector such as the vector given in SEQ ID NO: 80.

All internal restriction sites used in the cloning steps identified above are mutated by single base substitutions to silence them.

Through application of these basic steps a plant expression cassette can be designed that corresponds to the respective probe molecules, particularly probe molecules on the maize chip identified as representing genes that are highly expressed in all tissue samples but essentially not expressed in pollen, particularly probes represented by the DNA sequence as given in SEQ ID NOs: 47 to 56 and those identified as representing genes that are highly expressed in all tissue samples and have essentially no or reduced expression in tassel samples, particularly probes represented by the DNA sequence a given in SEQ ID NOs: 57-79. The former is an expression cassette that should be transcribed in all maize tissues and not in pollen. The latter is an expression cassette that should be transcribed in all maize tissues but not or only moderately transcribed in tassels. This design strategy can be applied to all probes identified in an expression profiling experiment.

In a specific embodiment of the invention, applying the above criteria results in the identification of genes which exhibit the desired expression profile. In particular, a gene is identified which encodes an actin binding protein 3 (ABP3), particularly a actin binding protein 3 of maize (ZmABP3), which is a member of a small gene family that had been previously characterized (Lopez et al., 1996). The gene product has also been called actin depolymerizing factor 3.

It was shown by southern analysis that there are two ABP3 genes in the maize genome (Lopez et al., 1996), designated herein as ZmABP3-A and ZmABP3-B, respectively. The ZmABP3-A and ZmABP3-B cDNAs encode a protein of 139 amino acids that are identical at all residues, except one. The expression profiling data indicate that ZmABP3-B is highly expressed in most tissues of the plant, but essentially excluding the tissues of the pollen so that no expression product is present in said tissues to any significant extent, whereas. ZmABP3-A is not as highly expressed.

A structural analysis of the ZmABP3-B gene reveals that the ZmABP3-B protein coding region is encoded on 3 exons, which are interrupted by two intervening sequences (introns) flanked by the expected GT . . . AG border nucleotides.

The regulatory sequence is located in the 5'-region of the ABP3 gene immediately upstream of the coding sequence. The size of the regulatory region is in a range of between about 2 kb to 3 kb, particularly between about 2.3 kb and 2.5 kb, and comprises a 5'-non-transcribed sequence, particularly a 5'-non-transcribed sequence of between about 0.9 kb and 1.3 kb, but especial of about 1.1 kb, and a 5'-UTR, particularly between about of 0.1 kb and 0.3 kb, but especially 0.25 kb of the 5'-UTR and all or part of a nucleotide sequence representing ZmABP3-intron 1, particularly a nucleotide sequence of between about 0.7 kb and 1.2 kb, but especially of about 0.98 kb.

The regulatory sequence according to the invention further comprises part of 3'-sequence that begins just past the ABP3 translation stop codon including transcribed but not translated sequence (UTR) and non-transcribed sequence that functions as the transcriptional terminator and a polyadenylation signal. In particular, the 3'-sequence is in a range of between about 0.8 kb and about 1.2 kb, particularly between about 0.9 kb and about 1.1 kb, but especially about 1.013 kb. The size of the 3'-UTR is in a range of between about 0.2 kb and about 0.4 kb, but especially about 0.3 kb, and that of the non-transcribed sequence in a range of between about 0.5 kb and about 0.8 kb, but specifically about 0.7 kb.

In a specific embodiment of the invention, the regulatory sequence is modified such that the natural translation start codon is silenced in order to move it to the second exon.

In another embodiment of the invention, candidate probes can be identified on a DNA chip or gene array, particularly a maize DNA chip or gene array such as, for example, the maize Affymetrix™ Chip applying the above criteria, which can be used in the identification of genes or putative genes on the maize genome which exhibit the desired expression profile. Two candidate probes were identified which demonstrate virtually no signal in tassel but a high signal in other tissues. This indicates that the gene represented by said candidate probes is not expressed in tassel, but is highly expressed throughout the rest of the plant. The greatest expression differential, 60-fold higher in non-tassel tissue, was observed in candidate probe Zm033444_S_AT. The other candidate probe (Zm040564_X_AT) showed signal variation depending on the development status of the probed plant material, i.e. a low signal in young tassel that gradually increases to a high or strong signal when the plant becomes older. The signal strength between tassel and non-tassel samples differed by less than 10-fold, but the signal strength in non-tassel samples was nearly 10-fold higher as compared to the other candidate probe. The sequence data indicate that neither probe corresponds to a characterized gene. Both probes identify good candidate genes for development of promoters that deliver high expression in non-tassel tissue and little or no expression in tassels. Given the high signal differential between tassel and non-tassel samples, an expression cassette based on probe Zm033444_S_AT was developed.

Public and proprietary databases can be queried by BLASTN with the candidate probe Zm033444_S_AT sequence to obtain DNA sequence evidence for both transcripts and gDNA corresponding to Zm033444_S_AT. cDNA hits with precise matches to the query sequence fell into two similar contigs. ZmABT1 corresponds to Maize.1482.c47 and Maize.1908.c31, and ZmABT2 corresponds to Maize.1482.c32, Maize.1482.c28, Maize.1482.c53, Maize.1908.c17, Maize.1908.c20, Maize.1908.c37 and A1947567.

The Zm033444_S_AT, ZmABT1 and ZmABT2 sequences can then be used to query maize genomic DNA sequence databases to identify the regulatory sequence(s) that give high expression in non-tassel tissue and little or no expression in tassels. These queries identified three entries, AZM4_12, ZmGSStuc11-12-04.4740.1 and MAGI_88845, that assemble into a single contig. The ZmABT gDNA sequence is shown in SEQ ID NO: 46. It encodes both the ZmABT1 and ZmABT2 transcript, which suggests that they are alternatively spliced variants of the same transcript.

ZmABT1 is encoded on 5 exons, and ZmABT2 is encoded on 6 exons. The additional exon lies between exon 1 and exon 2 of ZmABT1. The largest open reading frame on ZmABT1 and ZmABT2 can be used to define their translation start and stop codons and further to define the location of each translation start and stop codon. By this analysis both cDNAs use the same translation start and stop codon.

In one important aspect of the present invention the regulatory sequence according to the invention can be used in the development of robust expression cassettes that express recombinant genes in most tissues of the plant but not or substantially not in the tissues of the male reproductive structures, particularly the tissues of the pollen and/or the tassel so that no expression product is present in said tissues to any significant extent.

In a specific embodiment of the invention a regulatory sequence obtainable from a ABP3 gene, more particularly of regulatory sequence obtainable form a *Zea mays* ABP3 gene, can be used in the development of robust expression cassettes that express recombinant genes in most tissues of the plant but essentially excluding the tissues of the pollen so that no expression product is present in said tissues to any significant extent.

The transcription initiation region of the regulatory sequence according to the invention, particularly of regulatory sequence obtainable from a ABP3 gene, more particularly of regulatory sequence obtainable from a *Zea mays* ABP3 gene can be obtained in a PCR reaction containing a primer pair involving forward primer P1 (5'-atatatgcatgcg-gcgcgccgaaagtagcaaacaacaggttcatgtgcac-3') as depicted in SEQ ID NO: 1 and reverse primer P2 (5'-tatataccatggtgggttt-gcctgcgaccacaagttca-3') as depicted in SEQ ID NO: 2 through amplification from a gDNA template, particularly a maize gDNA template. In a specific embodiment of the invention a thermocycling program is applied involving amplification at about 95° C. for about 15 minutes followed by about 45 cycles at about 94° C. for about 1 minute, at about 64° C. for about 1 minute and at about 72° C. for about 5 minutes. The final extension step is carried out at about 72° C. for about 15 minutes. The reaction product, particularly an about 2.3 kb reaction product, is purified and the DNA extracted using a DNA extraction method known in the art. The DNA is precipitated, recovered and finally cloned into a suitable vector.

The transcription initiation region according to the invention, particularly a transcription initiation region obtainable from an ABP3 gene, more particularly obtainable from a ZmABP3, may be modified in a series of reactions using at least one of the oligonucleotides selected from the group of oligonucleotides depicted in SEQ ID NO: 3
(Patg (5'-cagctcgcccgagttggtaaggccccct-3')), SEQ ID NO: 4
(Pnco (5'-acagattagtccatcgcccacggt-3')), SEQ ID NO: 5
(ADPc-1 (5'-agccctgtccatgacggcccaagcaac-3')), SEQ ID NO: 6
(ADPc-2 (5'-agtagcaattcggtaggcacaggcac-3')), SEQ ID NO: 7
(ADPc-4 (5'-tctatggtctgcgaggtgcggtggc-3')),
and SEQ ID NO: 8
(adp3-a (5'-gtccccttcttcgccgcgccagctcgc-3')).

The terminus of the regulatory sequence according to the invention, particularly a terminal sequence obtainable from an ABP3 gene, more particularly a terminal sequence obtainable from a ZmABP3, can be amplified from a gDNA template, particularly a maize gDNA template, in a DNA polymerase reaction using a forward primer (P3 (5'-tatatagagctcgcatcatgatcatgcatcatggact-3')) as depicted in SEQ ID NO: 9 and a reverse primer (P4 (5'-atatatactagtggcgcgccacactttctgtcgcatgtgatttgca-3')) as depicted in SEQ ID NO: 10. A thermocycling program may be applied comprising a first cycle of about 95° C. for about 5 minutes followed by about 45 cycles of about 94° C. for about 30 seconds, about 50° C. for about 1 minute and about 72° C. for about 4 minutes. The final extension step may be carried out at about 72° C. for about 15 minutes. The about 1 kb reaction product is then purified and the DNA extracted using standard extraction methods. The DNA is precipitated, recovered and cloned into a suitable vector.

The terminus of the regulatory sequence according to the invention, particularly a terminal sequence obtainable from a ABP3 gene, more particularly a terminal sequence obtainable from a ZmABP3, may be modified to remove an internal restriction site, particularly a NcoI restriction site using a suitable primer pair, particularly primer pair Tnco (5'-Pgtaaaaaaaggtcccttggctcccagaaga-3')/T2 (5'-Pcaatgtgttagactgacgtg-3') as depicted in SEQ ID NO: 11 and SEQ ID NO: 12, respectively, in a DNA polymerase reaction. The thermocycling program employed may comprise a first cycle at about 95° C. for about 5 minutes followed by about 30 cycles of about 95° C. for about 1 minute, about 50° C. for about 1 minute and about 65° C. for about 15 minutes. The product may then be processed and sequenced. The present invention is also directed to expression cassettes that incorporate the regulatory mechanisms of a target gene of interest that shows the desired expression profile, that is high expression in most plant tissues but no expression in pollen tissue, particularly an ABP target gene, more particularly of a ZmABP3 target gene, to control in plants the expression of products of nucleic acid molecules of interest in a manner that mimics the expression profile of the original target gene.

The present invention further includes expression cassettes that incorporate regulatory sequences obtainable from the 5'-region of the target gene, particularly an ABP target gene, more particularly of a ZmABP3 target gene, to express the products of nucleic acid hb molecules of interest in plant tissues but not or substantially not in pollen tissue, The present invention is also directed to expression cassettes incorporating both regulatory sequences obtainable from the 5'-region and the 3'-region of the target gene, particularly an ABP3 target gene, more particularly of a ZmABP3 target gene.

In another specific embodiment of the invention a regulatory sequence obtainable from maize genomic DNA can be used in the development of robust expression cassettes that transcribe polynucleotides in most tissues of the plant but essentially excluding the tissues of the tassel so that no expression product is present in said tissues to any significant extent.

An inclusive gene structure-based design strategy may be used to construct such an expression cassette. To incorporate the known alternative splicing of the putative maize gene identified in a method as described above into the expression cassette, the design strategy can be based on the structure of ZmABT1 transcript as shown in SEQ ID NO: 33.

The transcription initiation region of the regulatory sequence according to the invention, particularly of the ZmABT promoter region can be amplified from a maize gDNA template in a DNA polymerase reaction containing gDNA and a primer pair involving forward primer ABT P1 forw (5'-CGACCAGCGCGACATGCATGGCA-3') as depicted in SEQ ID NO: 19 and ABT P2 rev (5'-ACCCCAGGGCGTACGACAAGGCC-3') as depicted in SEQ ID NO: 20. In a specific embodiment of the invention a thermocycling program is applied involving amplification at about 95° C. for about 5 minutes followed by about 40 cycles of 94° C. for about 30 seconds, about 67° C. for about 30 seconds and about 72° C. for about 2.5 minutes. The final extension step was done at about 72° C. for about 10 minutes.

This amplification reaction leads to an amplification product of about 2.6 kb, which can be purified and the DNA extracted using a standard DNA extraction method. The DNA can than be cloned into a suitable vector such as, for example, the pCR-BluntII-TOPO vector.

The ZmABT promoter can be modified in a series of mutagenesis reactions to silence the endogenous translation start codon, silence a SanDI restriction site and correct point mutations created during amplification. This can be done in a series of reactions using at least one of the oligonucleotides selected from the group of oligonucleotides depicted in pABT mut1
SEQ ID NO: 21
(5'-GATGGCCGGATTGGGCTCCCGGGGTGGAG-3')

pABT mut2
SEQ ID NO: 22
(5'-CTGGGAGGCGCGCAAGGGGCAGTTCCTCG-3')

pABT mut3
SEQ ID NO: 23
(5'-CCCACCGCCGGAGCACCGAAAGGCCCCGCG-3')

pABT mut4
SEQ ID NO: 24
(5'-GTCACCCGGGAGCACTTCCCGGCGCCG-3')

pABT mut5
SEQ ID NO: 25
(5'-CATTGGGCCGAGCACGGCTTCTTCCGC-3')

pABT mut6
SEQ ID NO: 26
(5'-GGGGTACGGTGTTCTTGAGTCGTGAAGCGAC-3')

The modified ZmABT promoter can the be amplified in another PCR reaction using primers pABT amp1 (5'-GCGTCTAGAGGGACCCCGACCAGCGCGACATG-CATGGCA-3') as depicted in SEQ ID NO: 27 and pABT amp2 (5'-ACCCCAGGG-CGTACGACAAGGCCCCAC-CATGGGCGC-3') as depicted in SEQ ID NO: 28. The PCR product can then be purified and the DNA extracted using standard a DNA extraction method. The DNA can be cloned into a suitable vector such as, for example, the pCR-BluntII-TOPO vector, transformed and sequenced. The ZmABT promoter can then be excised, particularly as an XbaI/NcoI fragment and ligated to a suitable expression vector such as, for example, pNOV6901.

In one embodiment of the invention, an expression cassette is provided comprising a termination sequence which can be obtained form the ZmABT gene identified and described herein above. The ZmABT terminus can be amplified from maize gDNA template in a DNA polymerase reaction containing gDNA and a primer pair involving forward primer ABT P4 (5'-TATATAGAGCTCGAATC-GAAGAAGCCACACTGTAAATCTGCCGGG-3') as depicted in SEQ ID NO: 29 and reverse primer ABT P5 (5'-AGCAAGGCATATGCAGCAGCTGCTGGTCGGAC-CGGGCCCTATATA-3') as depicted in SEQ ID NO: 30 resulting in an amplification product of about 1 kb. This reaction product can be purified and the DNA extracted using a standard DNA extraction method. The purified DNA can then be cloned into a suitable vector such as, for example, the pCR4-TOPO-Blunt vector.

In one embodiment of the invention, the ZmABP3 terminus is modified to remove internal NcoI and XhoI restriction sites. This can be done in a series of reactions using at least one of the oligonucleotides selected from the group of oligonucleotides depicted in.

```
ABTt m1
                                    SEQ ID NO: 31
(5'-GTCATGCATGGGCATGTGAAGGAGGAGCC-3')

ABTt m2
                                    SEQ ID NO: 32
(5'-GTTGCATGCATGCTGCATGGCGTCGAGAT-3')
```

The amplification product can then be processed and sequenced to result in a terminator sequence as shown in SEQ ID NO: 36.

In one embodiment of the invention, an expression cassette is provided that express recombinant genes in most tissues of the plant but essentially excluding the tissues of the tassel so that no expression product is present in said tissues to any significant extent, comprising both a regulatory sequence at least part of which has a transcription initiation function and a regulatory sequence at least part of which has a termination function, which regulatory sequences can be obtained form the ZmABT gene identified and described herein above.

In one embodiment of the invention such an expression cassette can be obtained by excising the ZmABT terminus excised and ligating it into a suitable vector already comprising a regulatory sequence at least part of which has a transcription initiation function, particularly the sequence of the ZmABT promoter such as, for example, the pNOV6901-prABT vector as described above.

In one embodiment, the expression cassette according to the invention comprises a regulatory nucleotide sequence comprising approximately 2.6 kb of the 5'-sequence, which consists of approximately 2 kb of 5'-non-transcribed sequence, and about 12 bp of 5'-UTR, approximately 0.6 kb representing exon 1, intron 1 and about 16 bp of exon 2; and approximately 1 kb of the 3'-sequence that begins just past the translation stop codon and includes approximately 0.6 kb of 3'-UTR and about 0.4 kb of non-transcribed sequence, and functions as the transcriptional terminator and poly-adenylation signal.

In one embodiment, an expression cassette according to the invention is provided wherein the natural translation start codon is silenced and moved to the second exon The complete expression cassette can then be mobilized into a suitable vector for plant transformation and expression such as, for example, an *Agrobacterium* binary vector, particularly *Agrobacterium* binary vector 15289.

The nucleic acid segment of interest can, for example, code for a ribosomal RNA, an antisense RNA or any other type of RNA that is not translated into protein. In another preferred embodiment of the invention, the nucleic acid segment of interest is translated into a protein product. The nucleotide sequence which directs transcription and/or the nucleic acid segment may be of homologous or heterologous origin with respect to the plant to be transformed. A recombinant DNA molecule useful for introduction into plant cells includes that which has been derived or isolated from any source that may be subsequently characterized as to structure size and/or function, chemically altered, and later introduced into plants. Therefore a useful nucleotide sequence, segment or fragment of interest includes completely synthetic DNA, semi-synthetic DNA, DNA isolated from biological sources, etc. Generally, the introduced DNA is not originally resident in the plant genotype which is the recipient of the DNA, but it is within the scope of the invention to isolate a gene from a given plant genotype, and to subsequently introduce multiple copies of the gene into the same genotype, e.g., to enhance production of a given gene product such as a storage protein or a protein that is involved in carbohydrate metabolism or any other gene of interest as provided in the SEQ ID NOs of the sequence listing.

The introduced recombinant DNA molecule includes but is not limited to, DNA from plant genes, and non-plant genes such as those from bacteria, yeasts, animals or viruses. The introduced DNA can include modified genes, portions of genes, or chimeric genes, including genes from the same or different genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of untransformed plant.

The introduced recombinant DNA molecule used for transformation herein may be circular or linear, double-stranded or single-stranded. Generally, the DNA is in the form of chimeric DNA, such as plasmid DNA, In one embodiment, the regulatory sequences may be operably associated with an expressible polynucleotide of interest. The expressible polynucleotide may encode a polypeptide or protein of interest.

Such a polypeptide or protein of interest may be one exhibiting a certain biological activity such as, for example, an insecticidal, herbicidal or fungicidal activity or may contribute of an improved performance of a crop plant of agronomic interest in form of improved yield, quality, lodging, biotic and abiotic stress resistance, flowering control, etc.

In one embodiment, the concentration of the polypeptide product expressed from the protein encoding polynucleotide of interest in the tissues of the reproductive structures, particularly in the tissues of the pollen and/or the tassel, is such that no insecticidal activity can be detected in a standard insect feeding assay. In particular, the concentration of the expression product in the tissues of the male reproductive structures, particularly in the tissues of the pollen and/or the tassel, is below a basic level of about 10 ng/mg soluble protein, particularly of about 5 ng/mg soluble protein, more particularly of about 3 ng/mg soluble protein, but especially of about 2 ng/mg soluble protein or below.

In one specific embodiment of the invention, the polypeptide or protein of interest is an insecticidally active protein or polypeptide, particularly an insecticidally active protein or polypeptide obtainable from *Bacillus thuringiensis*, more particularly a *Bacillus thuringiensis* endotoxin such as, for example, cryIA(b) endotoxin. Other endotoxins known to occur in *Bacillus thuringiensis* may likewise be used in association with the regulatory sequence according to the invention to obtain toxin expression in most plant tissues except pollen and/or the tassel so that no expression product is present in said tissues to any significant extent.

In one embodiment, a transgenic plant according to the invention and as described herein is provided, wherein the polypeptide or protein encoding polynucleotide of interest encodes an endotoxin of *Bacillus thuringiensis* which has at least 80% sequence identity, particularly at least 85% sequence identity, particularly at least 90%, 91%, 92%, 93%, 94%, 95%, 96%, 97%, 98% or 99% sequence identity with a nucleotide sequence as depicted in SEQ ID NO:15.

In one embodiment, a transgenic plant according to the invention and as described herein is provided, wherein the polypeptide or protein encoding polynucleotide of interest encodes an endotoxin of *Bacillus thuringiensis* which has the nucleotide sequence as depicted in SEQ ID NO: 15.

Once completed, the expression cassette may be mobilized into a suitable vector for plant transformation, such as, for example, a binary vector, which may then be mobilized to maize via *Agrobacterium*-mediated transformation.

Transgenic plants (or plant cells, or plant explants, or plant tissues) incorporating the polynucleotides of the invention and/or expressing a polypeptide of interest such as, for example, a toxin protein of *B. thuringiensis*, can be produced by a variety of well established techniques. Following construction of an expression cassette and a vector incorporating the regulatory polynucleotide sequence according to the invention and as described herein, standard techniques can be used to introduce the polynucleotide into a plant, a plant cell, a plant explant or a plant tissue of interest. Optionally, the plant cell, explant or tissue can be regenerated to produce a transgenic plant. The plant can be any higher plant, including gymnosperms, monocotyledonous and dicotyledonous plants. Suitable protocols are available for Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops. See protocols described in Ammirato et al., eds., (1984) Handbook of Plant Cell Culture—Crop Species, Macmillan Publ. Co., New York, N.Y.; Shimamoto et al. (1989) Nature 338: 274 276; Fromm et al. (1990) Bio/Technol. 8: 833 839; and Vasil et al. (1990) Bio/Technol. 8: 429 434. Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* mediated transformation.

Transformation of plants can be undertaken with a single DNA molecule or multiple DNA molecules (i.e., co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

A variety of techniques are available and known to those skilled in the art for introduction of constructs into a plant cell host. These techniques generally include transformation with DNA employing *A. tumefaciens* or *A. rhizogenes* as the transforming agent, liposomes, PEG precipitation, electroporation, DNA injection, direct DNA uptake, microprojectile bombardment, particle acceleration, and the like (See, for example, EP 295959 and EP 138341) (see below). However, cells other than plant cells may be transformed with the expression cassettes of the invention. The general descriptions of plant expression vectors and reporter genes, and *Agrobacterium* and *Agrobacterium*-mediated gene transfer, can be found in Gruber et al. (1993).

Expression vectors containing the regulatory polynucleotide sequence according to the invention can be introduced into protoplasts or into intact tissues or isolated cells. Preferably expression vectors are introduced into intact tissue. General methods of culturing plant tissues are provided for example by Maki et al., (1993); and by Phillips et al. (1988). Preferably, expression vectors are introduced into maize or other plant tissues using a direct gene transfer method such as microprojectile-mediated delivery, DNA injection, electroporation and the like. More preferably expression vectors are introduced into plant tissues using the microprojectile media delivery with the biolistic device. See, for example, Tomes et al. (1995). The vectors of the invention can not only be used for expression of structural genes but may also be used in exon-trap cloning, or promoter trap procedures to detect differential gene expression in varieties of tissues, (Lindsey et al., 1993; Auch & Reth et al.).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti et al., 1985: Byrne et al., 1987; Sukhapinda et al., 1987; Lorz et al., 1985; Potrykus, 1985; Park et al., 1985: Hiei et al., 1994). The use of T-DNA to transform plant cells has received extensive study and is amply described (EP 120516; Hoekema, 1985; Knauf, et al., 1983; and An et al., 1985). For introduction into plants, the chimeric genes of the invention can be inserted into binary vectors as described in the examples.

Those skilled in the art will appreciate that the choice of method might depend on the type of plant, i.e., monocotyledonous or dicotyledonous, targeted for transformation. Suitable methods of transforming plant cells include, but are not limited to, microinjection (Crossway et al., 1986), electroporation (Riggs et al., 1986), *Agrobacterium*-mediated transformation (Hinchee et al., 1988), direct gene transfer (Paszkowski et al., 1984), and ballistic particle acceleration using devices available from Agracetus, Inc., Madison, Wis. and BioRad, Hercules, Calif. (see, for example, Sanford et al., U.S. Pat. No. 4,945,050; and McCabe et al., 1988). Also see, Weissinger et al., 1988; Sanford et al., 1987 (onion); Christou et al., 1988 (soybean); McCabe et al., 1988 (soybean); Datta et al., 1990 (rice); Klein et al., 1988 (maize); Klein et al., 1988 (maize); Klein et al., 1988 (maize); Fromm et al., 1990 (maize); and Gordon-Kamm et al., 1990 (maize); Svab et al., 1990 (tobacco chloroplast); Koziel et al., 1993 (maize); Shimamoto et al., 1989 (rice); Christou et al., 1991 (rice); European Patent Application EP 0 332 581 (orchardgrass and other Pooideae); Vasil et al., 1993 (wheat); Weeks et al., 1993 (wheat). In one embodiment, the protoplast transformation method for maize is employed (European Patent Application EP 0 292 435, U.S. Pat. No. 5,350,689).

In another embodiment, a nucleotide sequence of the present invention is directly transformed into the plastid genome. Plastid transformation technology is extensively described in U.S. Pat. Nos. 5,451,513, 5,545,817, and 5,545,818, in PCT application no. WO 95/16783, and in McBride et al., 1994. Following transformation, plants are preferably selected using a dominant selectable marker incorporated into the transformation vector. Typically, such a marker will confer antibiotic or herbicide resistance on the transformed plants and selection of transformants can be accomplished by exposing the plants to appropriate concentrations of the antibiotic or herbicide.

After transformed plant cells or plants are selected and grown to maturity, those plants showing the trait of interest are identified. The trait can be any of those traits described above. Additionally, to confirm that the trait of interest is due to the expression of the introduced polynucleotide of interest under control of the regulatory nucleotide according to the invention, expression levels or activity of the polypeptide or polynucleotide of interest can be determined by analyzing mRNA expression using Northern blots, RT-PCR or microarrays, or protein expression using immunoblots or Western blots or enzyme activity assays.

The invention thus relates to plant cells and tissues, to plants derived from such cells and tissues, respectively, to plant material, to the progeny and to seeds derived from such plants, and to agricultural products including processed plant products with improved properties obtainable by, for example, any one of the transformation methods described below.

Once an expression cassette according the present invention and as described herein comprising a regulatory sequence according to the invention in association with a polynucleotide of interest has been transformed into a particular plant species, it may be propagated in that species or moved into other varieties of the same species, particularly including commercial varieties, using traditional breeding techniques. Preferred plants of the invention include gymnosperms, monocots, and dicots, especially agronomically important crop plants, such as rice, wheat, barley, rye, rape, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

The genetic properties engineered into the transgenic plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. Use of the advantageous genetic properties of the transgenic plants according to the invention can further be made in plant breeding that aims at the development of plants with improved properties such as tolerance to pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic plants according to the invention can be used for the breeding of improved plant lines that for example increase the effectiveness of conventional methods such as herbicide or pesticide treatment or allow to dispense with said methods due to their modified genetic properties. Alternatively new crops with improved stress tolerance can be obtained that, due to their optimized genetic "equipment", yield harvested product of better quality than products that were not able to tolerate comparable adverse developmental conditions.

In one embodiment of the invention, the plant has been transformed with and expresses a polypeptide or protein encoding nucleotide sequence encoding a polypeptide product exhibiting an insecticidal activity, particularly an endotoxin of *Bacillus thuringiensis* in most tissues of the plant but essentially excluding the tissues of the pollen and/or the tassel so that no expression product is present in said tissues to any significant extent, where the nucleotide sequence is not transcribed to any significant extent. Therefore, essentially no expression occurs in the pollen and/or the tassel tissue and only residual amounts of the expression product, if any, can be detected in said tissues, which is not sufficient for the expression product to fulfil its envisaged biological function in said tissues or to exhibit any toxic effects either towards insects feeding on these tissues or the plant itself.

In particular, the concentration of the polypeptide product expressed from the protein encoding polynucleotide of interest in the tissues of the pollen and/or the tassel is such that no insecticidal activity can be detected in a standard insect feeding assay. In one embodiment of the invention, the concentration of the expression product in pollen is below a basic level of about 10 ng/mg soluble protein, particularly of about 5 ng/mg soluble protein, more particularly of about 3 ng/mg soluble protein, but especially of about 2 ng/mg soluble protein or below.

The invention also provides methods for preparing expression cassettes comprising the regulatory sequence according to the invention comprising linking an expressible polynucleotide encoding a polypeptide or a protein of interest with the regulatory sequence according to the invention and as described herein to obtain an expression construct, wherein the polynucleotide of interest is operably linked or associated with the regulatory sequence such that expression of the polypeptide or a protein of interest is mediated by the regulatory sequence according to the invention and results in the expression of said polypeptide or a protein of interest in essentially all plant tissues, but essentially excludes expression in the tissues of the reproductive structures of the plant, particularly in the tissues of the pollen and/or the tassel so that no expression product is present in said tissues to any significant extent.

In one embodiment, the invention relates to a method of producing a transgenic plant expressing a DNA sequence of interest in non-pollen tissue but not or substantially not in the tissues of the pollen and/or the tassel, comprising a) transforming an expression cassette according to the invention and as described herein into a plant cell which comprises a regulatory nucleotide sequence, at least part of which has a transcription initiation function which mediates expression of an operably associated protein encoding polynucleotide of interest in most plant tissues but essentially excluding the tissues of the pollen and/or the tassel so that no expression product is present in said tissues to any significant extent; and b) regenerating the plant cell transformed in step a) into a plant.

In one embodiment, the invention relates to a method of controlling insect target-pests feeding on vegetative plant tissues such as the leaf, stalk and root and/or on reproductive tissues such as the ear, but protecting non-target pests feeding on pollen comprising a) growing a plant according to the invention and as described herein in an area that is infested with the target pest;

b) expressing a polypeptide or protein that is capable of controlling said target pest under the control of a regulatory sequence according to the invention and as described herein.

In one embodiment, the invention relates to a method of protecting the reproductive tissues of a plant, particularly the tissues of the pollen and/or the tassel against damage caused by expression in said tissues of a polypeptide or protein of interest comprising a) growing a plant according to the invention and as described herein;

b) expressing a polypeptide or protein of interest under the control of a regulatory sequence according to the invention and as described herein.

In one embodiment the present invention relates to the use of a regulatory sequence according to the present invention and as disclosed herein for controlling insect target-pests feeding on vegetative plant tissues such as the leaf, stalk and root and/or on reproductive tissues such as the ear, but protecting non-target pests feeding on pollen comprising a) growing a plant according to the invention and as described herein in an area that is infested with the target pest;

b) expressing a polypeptide or protein that is capable of controlling said target pest under the control of a regulatory sequence according to the invention and as described herein.

In one embodiment the present invention relates to the use of a regulatory sequence according to the present invention and as disclosed herein for protecting the reproductive tissues of a plant, particularly the tissues of the pollen and/or the tassel against damage caused by expression in said tissues of a polypeptide or protein of interest comprising expressing said polypeptide or protein of interest under the control of a regulatory sequence according to the invention and as described herein.

EXAMPLE

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

All manipulations and techniques necessary to construct and propagate strains described in this invention are known to those skilled in the art. Technical details are described e.g. in Ausubel et al 1995; Sambrook, J, 2001 and Miller, J. H. 1992 and in relevant publications cited within this invention.

Example 1: Non-Pollen Expression

Example 1.1 Identification of ZmABP3

In an expression profiling experiment a maize developmental series was queried on a *Zea mays* (Zm80K) Affymetrix chip for probes that gave strong signals in all samples, but not or substantially not in the pollen sample. All the green tissue and root samples were directly compared to pollen, and probes representing polynucleotides that did not meet the target expression profile were eliminated. The analysis produced two sets of results. The first set contains 36 probes representing polynucleotides that were highly expressed in all the tissue samples, but very low in pollen. The second set contains 10 probes represented polynucleotides that are highly expressed in all tissue samples, but gave no signal in pollen. Alignment of probe sequence with maize cDNA assembly datasets showed that all 46 probes represent bona fide maize genes. The top 10 probes are those with the strongest signal across all non-pollen tissues and no signal in pollen (see Table A).

Applying further criteria including determination of the availability of genomic DNA (gDNA) and cDNA sequence for each lead produced Zm07728_s_at as the top candidate that met all promoter development requirements. Literature analysis revealed that this probe represents the gene encoding actin binding protein 3 (ZmABP3) which is a member of a small gene family that had been previously characterized (Lopez et al., 1996). The gene product has also been called actin depolymerizing factor 3. Lopez et al (1996) confirms in FIG. 3 that ZmABP3 is highly expressed in most tissues of the plant examined, except pollen samples.

Lopez et al (1996) also show by southern analysis that there are two ABP3 genes in the maize genome. The ZmABP3 cDNA they report is GenBank Accession X97726, and it corresponds to the TIGR Accession TC248585. This gene was designated ZmABP3-A. Both ZmABP3 genes are represented on the maize (Zm80K) Affymetrix Chip: ZmABP3-A corresponds to probe Zm007595_at and ZmABP3-B corresponds to Zm07728_s_at. The 'Zm07728_s_at' sequence was used to identify the TC248588 in the TIGR database, and MAIZE.974.CB1 in a maize cDNA assembly database. It also identified the MAGI_93606, MAGI_93607, AZM4_39177, ZmGSStuc11-12-04.2725.1, ZmGSStuc11-12-04.2725.2 and CC463190 gDNA sequences. The ZmABP3-A and ZmABP3-B cDNAs encode proteins that are identical at all residues, except one. The expression profiling data indicate that ZmABP3-B is highly expressed in most tissues of the plant, but essentially excluding the tissues of the pollen so that no expression product is present in said tissues to any significant extent. ZmABP3-A is not as highly expressed.

SEQ ID NO: 16 show that the ZmABP3-B mRNA is encoded on 3 exons. The two intervening sequences (introns) are bracketed by the expected GT . . . AG border nucleotides.

More specifically, SEQ ID NO: 16 discloses the design of the ZmABP3 expression cassette. The ZmABP3 regulatory components to be included in the construct are 2.3 kb of 5'-sequence (prZmABP3-01) which contains 1.1 kb of 5'-non-transcribed sequence, 0.25 kb of 5'-UTR and 0.98 kb representing ZmABP3-B-intron 1; and 1.013 kb of 3'-sequence (tZmZBP3-01) that begins just past the ABP3-B translation stop codon. This includes about 0.3 kb of 3'-UTR and 0.7 kb of non-transcribed sequence.

```
5' Bfr1
                                        (SEQ ID NO: 83)
(5'-cctggtggagtgcttaagcgacgagttctgcctgg-3'),

3' Xba1
                                        (SEQ ID NO: 84)
(5'-gggcttctcctccaggaactctagattgcccaggcg-3'),

5'Gfix
                                        (SEQ ID NO: 85)
(5'-catcggcaagtgccaccacagccaccacttcagcctg-3')
and

3'Gfix
                                        (SEQ ID NO: 86)
(5'-gctgtggtggcacttgccgatggggctggg-3').
```

PCR product A was made using high-fidelity PCR with Michigan-pTrcHisB as a template, and the 5' Bfr1 and 3' Gfix primers. PCR product B was made using high-fidelity PCR with Michigan-pTrcHisB as a template, and the 5'Gfix and 3'Xba1 primers. The final PCR used products A and B as templates, and the 5'Bfr1 and 3'Xba1 primers. The final PCR band was digested with AflII/XbaI and gel-purified. This fragment was ligated to Michigan-pTrcHisB that had also been digested with XbaI/AflII. The correct recombinant DNA product was identified by AflII/XbaI digestion analysis. This construct was named as Cry1Ab-G.

TABLE A shows a summary of the top 10 candidate probes representing polynucleotides with a high expression level in all maize tissues and no expression signal in pollen

| Probe Name | Description of Reference Gene | Pollen Expression | Average Expression (all tissues) | *Zea mays* TIGR Hit |
|---|---|---|---|---|
| AF032370_at | "*Zea mays* profilin (PRO4) mRNA, complete cds." | absent | 4208 | TC269677 |
| Ctrl_ZmU45855-3_at | From 808 to 1307 of glyceraldehyde-3-phosphate dehydrogenase GAPC2 (gpc2) mRNA, complete cds. | absent | 4275 | TC269361 |
| Zm001747_s_at | Similar to CAA63903.1 *Pennisetum glaucum*; heat shock protein 17.9; *P. glaucum* mRNA for heat shock protein, HSP 17.9 | absent | 4945 | TC268849 |
| Zm005803_s_at | "Similar to AAB99745.1 *Triticum aestivum*; HSP70; *Triticum aestivum* 70 kDa heat shock protein (TaHSP70d) mRNA, complete cds; 70 kDa heat shock protein, molecular chaperone" | absent | 4091 | TC247918 |
| Zm007728_s_at | Similar to SW:ADF3_MAIZE Q41764 *zea mays* (maize), actin-depolymerizing factor 3 (adf 3) (zmabp3) (zmadf3). | absent | 4805 | TC248588 |
| Zm009722_s_at | "Similar to BAC22420.1 *Oryza sativa* (japonica cultivar-group);; *Oryza sativa* (japonica cultivar-group) genomic DNA, chromosome 7, PAC clone: P0453E03; contains ESTs C96778(C10671), D22278(C10671) unknown | absent | 3306 | TC248975 |
| Zm015335_s_at | Similar to SW:RS5A_ARATH Q9zut9 *arabidopsis thaliana* (mouse-ear cress). 40s ribosomal protein s5-1. February 2003 | absent | 3598 | TC269022 |
| Zm021004_s_at | "Similar to AAD39835.1 *Arabidopsis thaliana*; Ran-binding protein siRanBP; *Arabidopsis thaliana* Ran-binding protein (siRanBP) mRNA, complete cds; atranbp1a homolog" | absent | 3092 | TC259986 |
| Zm058948_s_at | No Description | absent | 4337 | TC270333 |
| Zm061393_s_a | No Description = sucrose synthase | absent | 6509 | TC258905 |

Example 1.2 Cry1AbG6 Construction

Cry1AbG6 (2814 bp) is a modified version of the full-length Cry1Ab (pNOV1321, 3546 bp) gene. The Geiser sequence (81 bp from 4398-4478 in pNOV1321) and the 3'-end (651 bp from 4908-5558 in pNOV1321) were deleted.

The Cry1AbG6 sequence was constructed from pNOV1321 (source vector for the Cry1Ab full-length gene) as follows: pNOV1321 plasmid DNA was cut with BamHI/SacI. The Cry1Ab full-length gene (3546 bp, named Michigan) was gel purified and ligated to pTrcHisB expression vector (In vitrogen life technologies, Cat# V36020), which was cut with BamHI/SacI. This construct was named as Michigan-pTrcHisB. The Geiser sequence (81 bp) was deleted from Michigan-pTrcHisB by overlapping PCR with the following primers:

A second PCR product was made by high-fidelity PCR using pNOV1321 as a template, the 5'1Ab5XbaI (5'-gcccgcctgggcaatctagagttcctggaggag-3') primer depicted in SEQ ID NO: 87, and the 3'1Ab3d6 (5'-gcgagctcctagatgcggccctcgagttcctcgaaga-3') primer depicted in SEQ ID NO: 88. The PCR product was digested with XbaI/SacI then ligated to Cry1Ab-G that was also digested with XbaI/SacI. The correct recombinant DNA product was identified using BamHI/SacI restriction analysis. This construct was named as Cry1AbG6.

The Cry1AbG6 sequence was subjected to QuikChange mutagenesis to remove an internal NcoI site. The 25 μL reaction contained 1 µL Cry1AbG6 template,
2.5 µL 10× QuikChange buffer,
1 µL QuikChange dNTP mix,
1 µL of 20 µM cy2' (5'-Pccctgtacggcacgatgggcaacgctgca-3'; SEQ ID NO: 89),
0.75 µL Quik solution and
1 µL QuikChange DNA polymerase.

The thermocycling program was 95° C. for 5 minutes followed by 30 cycles of 95° C. for 1 minute, 55° C. for 1 minute and 65° C. for 20 minutes. The product was processed as described by the manufacturer (Stratagene) and completely sequenced.

The Cry1AbG6 coding sequence was amplified from the mutagenized plasmid template, above, in a 50 µL Pfu turbo (Stratagene) DNA polymerase reaction containing
5 µL template,
5 µL 10×Pfu buffer,
1 µL 10 mM dNTP mix,
1 µL of 20 µM cy1 (5'-atatatccaccatggacaacaaccccaaca-3'; SEQ ID NO: 90),
1 µL of 20 µM cy2 (5'-tatatagagctcctagatgcggccctcgagt-3'; SEQ ID NO: 91) and
1 µL Pfu turbo DNA polymerase.

The thermocycling program was 95° C. for 2 minutes followed by 40 cycles of 95° C. for 1 minute, 50° C. for 1 minute and 72° C. for 7 minutes. The final extension step was 72° C. for 15 minutes. The 2.8 kb reaction product was gel-purified on 1% TAE agarose, and the DNA was extracted using Qiaprep DNA extraction method. The recovered DNA was digested with NcoI/SacI, then ligated to pNOV6901 vector that was also digested with NcoI/SacI. This operation replaced the GUS coding sequence in pNOV6901 with Cry1AbG6. The Cry1AbG6 sequence is given in SEQ ID NO: 15.

Example 1.3 Construction of the ZmABP3 Expression Cassette

An inclusive design strategy was used to develop the ZmABP3 expression cassette. The cassette contains 2.3 kb of 5'-sequence which consists of 1.1 kb of 5'-non-transcribed sequence, 0.25 kb of 5'-UTR and 0.98 kb representing ZmABP3-intron 1. The natural translation start codon was silenced in order to move it to the second exon. The expression cassette also contains 1.013 kb of 3'-sequence that begins just past the ABP3 translation stop codon. This includes about 0.3 kb of 3'-UTR and 0.7 kb of non-transcribed sequence, and functions as the transcriptional terminator and poly-adenylation signal.

The ZmABP3 terminus was amplified from maize gDNA template in a 50 µL Proofstart (Qiagen) DNA polymerase reaction containing
10 µg gDNA,
5 µL 10× Proofstart buffer,
1.5 µL 10 mM dNTP mix,
2.5 µL of 20 µM P3 (5'-tatatagagctcgcatcatgatcatgcatcatggact-3'; SEQ ID NO: 9),
2.5 µL of 20 µM P4 (5'-atatatactagtggcgcgccacactttctgtcgcatgtgatttgca-3'; SEQ ID NO: 10),
10 µL Q solution and
2 µL Proofstart DNA polymerase.

The thermocycling program was 95° C. for 5 minutes followed by 45 cycles of 94° C. for 30 seconds, 50° C. for 1 minute and 72° C. for 4 minutes. The final extension step was 72° C. for 15 minutes. The 1 kb reaction product was gel-purified on 1% TAE agarose, and the DNA was extracted using Qiaprep DNA extraction method. The DNA was ethanol precipitated and recovered in 4 µL $ddH_2O$, then cloned into the pCR4-TOPO-Blunt vector.

The ZmABP3 terminus was modified to remove an internal NcoI restriction site using the Stratagene QuikChange Multi-site mutagenesis kit. The 25 µL reaction contained
1 µL pCR4-TOPO-ZmABP3-terminus,
2.5 µL 10× QuikChange buffer,
1 µL QuikChange dNTP mix,
1 µL of 20 µM Tnco (5'-Pgtaaaaaaaggtcccttggctcccagaaga-3'; SEQ ID NO: 11),
1 µL of 20 µM T2 (5'-Pcaatgtgttagactgacgtg-3'; SEQ ID NO: 12),
0.75 µL Quik solution and
1 µL QuikChange DNA polymerase.

The thermocycling program was 95° C. for 5 minutes followed by 30 cycles of 95° C. for 1 minute, 50° C. for 1 minute and 65° C. for 15 minutes. The product was processed as described by the manufacturer (Stratagene) and completely sequenced. The ZmABP3-terminus sequence is shown in SEQ ID NO: 14.

The ZmABP3 promoter was amplified from maize gDNA template in a 50 µL Hotstart (Qiagen) DNA polymerase reaction containing
10 µg gDNA,
25 µL 2× Hotstart Master Mix,
1.25 µL of 20 µM P1 (5'-atatatgcatgcggcgcgccgaaagtagcaaacaacaggttcatgtgcac-3'; SEQ ID NO: 1),
1.25 µL of 20 µM P2 (5'-tatataccatggtgggtttgcctgcgaccacaagttca-3'; SEQ ID NO: 2),
10.5 µL Q solution and
2 µL 25 mM $MgCl_2$.

The thermocycling program was 95° C. for 15 minutes followed by 45 cycles of 94° C. for 1 minute, 64° C. for 1 minute and 72° C. for 5 minutes. The final extension step was 72° C. for 15 minutes. The 2.3 kb reaction product was gel-purified on 1% TAE agarose, and the DNA was extracted using Qiaprep DNA extraction method. The DNA was ethanol precipitated and recovered in 4 µL $ddH_2O$, then cloned into the pCR4-TOPO vector.

The ZmABP3 promoter was modified in a series of QuikChange reactions as outlined above using the following oligonucleotides:

```
Patg
(5'-cagctcgcccgagttggtaaggccccct-3'; SEQ ID NO: 3),

Pnco
(5'-acagattagtccatcgcccacggt-3'; SEQ ID NO: 4),

ADPc-1
(5'-agccctgtccatgacggcccaagcaac-3'; SEQ ID NO: 5),

ADPc-2
(5'-agtagcaattcggtaggcacaggcac-3'; SEQ ID NO: 6),

ADPc-4
(5'-tctatggtctgcgaggtgcggtggc-3'; SEQ ID NO: 7),
and

adp3-a
(5'-gtccccttcttcgccgcgccagctcgc-3'; SEQ ID NO: 8).
```

The ZmABP3 promoter sequence is shown in SEQ ID NO: 13.

The ZmABP3 terminus was ligated to the pNOV6901-Cry1AbG6 vector (from Example 2) as a SacI/SpeI fragment. The ZmABP3 Promoter was subsequently ligated to the vector as a SphI/NcoI fragment. This produced ZmABP3-Cry1AbG6-assembly, shown in SEQ ID NO: 37. The complete ZmABP3-Cry1AbG6 expression cassette was mobilized into a binary vector, pNOV6900, as an AscI fragment. These constructs, ZmABP3-Cry1AbG6-6900 and enhanced ZmABP3-Cry1AbG6-binary, are shown in SEQ ID NOS: 38 and 39, respectively. The only difference between these vectors is the presence of the CaMV-FMV dual enhancer in enhanced ZmABP3-Cry1AbG6-binary. Both were mobilized to maize via *Agrobacterium*-mediated transformation.

Example 1.4 Construction of ZmABP3-AmCyan

The Cry1AbG6 coding sequence was excised from ZmABP3-Cry1AbG6-assembly as an NcoI/SacI fragment. It was replaced with the AmCyan reporter gene coding sequence that was excised from plasmid 13718 as an NcoI/SacI fragment. This produced the ZmABP3-AmCyan-assembly construct shown in SEQ ID NO: 40. The ZmABP3-AmCyan expression cassette was mobilized into a binary vector, pNOV6900, as an AscI fragment. This construct, ZmABP3-AmCyan-binary, is shown in SEQ ID NO: 41. It was mobilized to maize via *Agrobacterium*-mediated transformation.

Example 1.5 Expression from ZmABP3-AmCyan in Transgenic Maize

Several transgenic maize events containing the ZmABP3-AmCyan expression cassette were produced. Those containing a single-copy of the transgene and no unintended vector sequence were analyzed. All transgenic events accumulated AmCyan transcript in leaf tissue (data not shown). Several tissues from a representative event were examined for AmCyan transcript accumulation. Total RNA was prepared using the Plant RNAeasy total RNA isolation system (Qiagen). Pollen total RNA was prepared using the method described by Shirzadegan et al (1991). Preparation quality was assessed by UV spectrophotometry, and 10 μg of total RNA per sample was resolved on a 1% formaldehyde gel then transferred to Nytran SuPerCharge membrane following the recommended protocol (Schleicher & Schuell). The blot was hybridized to a random-primed $^{32}P$-labeled AmCyan DNA probe using high stringency conditions. The results clearly show that ZmABP3 promotes transcription in tassel, leaf, silk, ear and root tissue, but does not promote transcription in pollen.

Example 1.6 Expression from ZmABP3-Cry1AbG6 in Transgenic Maize

Several transgenic maize events containing the ZmABP3-Cry1AbG6 expression cassette were produced. Those containing a single-copy of the transgene and no unintended vector sequence were analyzed. The T0 events were tested for insecticidal activity against corn earworm twice during the course of development. The first samples were taken at V2-V4, and the second samples were taken at V7-V9. Leaf discs from lower leaf tips were excised and placed on water-moistened Whatman paper in 47×10 mm petri dishes. Ten-to-twenty L1 corn earworm or European corn borer larvae were added to each dish, and they were incubated for 48 hours at 28° C. Leaf discs were then scored for insect damage. Samples with no visible leaf damage and absolute mortality were scored as positive, and those with visible damage were negative. The data obtained show that several transgenic events with activity against both insects were identified.

Cry1AbG6 protein accumulation was also measured in T0 plants using the enzyme-linked immunosorbent assay (ELISA) with a fully-truncated Cry1Ab standard. The first assay was done on seedling leaf tissue, sampled 1-2 weeks after transfer to soil. The second assay was done on leaf tissue from maturing plants, sampled just prior to the transition to reproductive development. The data in TABLE B show the range of Cry1AbG6 protein accumulated in plants with insecticidal activity. The data indicate that plants require nearly 50 ng (or more) Cry1AbG6 protein/mg extractable protein to have insecticidal activity.

TABLE B shows the insect control characteristics of greenhouse grown plants.

| Event | Cassette | Cry1AbG6 (ng/mg extractable protein) | | Corn Earworm Activity | | ECB Activity |
|---|---|---|---|---|---|---|
| Number | Description | seedling | adult | V2-V4 | V7-V9 | V7-V9 |
| 1 | ABP3-Cry1Abg6 | 63 | 79 | + | + | + |
| 2 | ABP3-Cry1Abg6 | 54 | 56 | + | + | + |
| 3 | ABP3-Cry1Abg6 | 85 | 108 | + | + | + |
| 4 | ABP3-Cry1Abg6 | 67 | 94 | + | + | + |
| 5 | ABP3-Cry1Abg6 | 45 | 83 | + | +/− | +/− |
| 6 | ABP3-Cry1Abg6 | 68 | 120 | + | + | + |
| 7 | ABP3-Cry1Abg6 | 133 | 159 | + | + | + |
| 8 | ABP3-Cry1Abg6 | 96 | 46 | + | + | + |
| 9 | ABP3-Cry1Abg6 | 138 | 101 | + | + | + |
| 10 | ABP3-Cry1Abg6 | 131 | 100 | + | + | + |
| 11 | ABP3-Cry1Abg6 | 94 | 65 | + | + | + |
| 12 | ABP3-Cry1Abg6 | 111 | 59 | + | + | + |
| 13 | ABP3-Cry1Abg6 | 139 | 60 | + | + | + |
| 14 | ABP3-Cry1Abg6 | 121 | 81 | | | |
| 15 | ABP3-Cry1Abg6 | 66 | 55 | + | + | + |
| 16 | ABP3-Cry1Abg6 | 130 | 95 | + | + | + |

Leaf tissue from T0 plants was assayed for Cry1AbG6 protein by ELISA using truncated Cry1Ab protein as standard, Corn Earworm activity and European Corn Borer (ECB) activity. The plant developmental stage when sampled is indicated at the top of each column. The older (lower) leaf tissue was sampled. For insect assays a (+) indicates no visible leaf damage and complete and absolute insect mortality. Visible leaf damage produced a (−) score.

Example 1.7 European Cornborer Efficacy of ZmABP3-Cry1AbG6 Events in the Field

The ECB (European corn borer) field efficacy studies were conducted in Stanton, Minn. (SMN) and Bloomington, Ill. (BIL) during the 2006 growing season. Near-isogenic hybrids, comprising the ABP3-Cry1AbG6 events listed in TABLE C, Bt11, and a nontransgenic control hybrid were tested. The experimental design was randomized complete block with three replications in each location. A plot consisted of one 5.31 m long row containing 25 plants, with 0.76 m spacing between rows.

TABLE C shows the performance of ZmABP3-Cry1AbG6 maize in field studies.

| | | Trial | | | | | | | |
|---|---|---|---|---|---|---|---|---|---|
| | | MG371 | | | | MG331 | | | |
| | | Location | | | | | | | |
| | | BIL | | | | SMN | | | |
| | | Trial Type | | | | | | | |
| | | ECB | | | | ECB | | | |
| Event Number | Cassette Description | ECBLR Leaf Feeding Rating | CEBSN Shank (cm) | ECBKN Ear Feeding (cm) | ECBSN Stalk Feeding (cm) | ECBLR Leaf Feeding Rating | CEBSN Shank (cm) | ECBKN Ear Feeding (cm) | ECBSN Stalk Feeding (cm) |
| 1 | ABP3-Cry1Abg6 | 1.0 | 0.00 | 1.42 | 0.00 | 1.1 | 0.00 | 0.00 | 0.30 |
| 2 | ABP3-Cry1Abg6 | 1.0 | 0.00 | 1.42 | 0.08 | 1.0 | 0.00 | 0.15 | 0.10 |
| 3 | ABP3-Cry1Abg6 | 1.0 | 0.00 | 1.25 | 0.08 | 1.0 | 0.00 | 0.00 | 0.80 |
| 4 | ABP3-Cry1Abg6 | 1.0 | 0.00 | 1.57 | 0.00 | 1.0 | 0.10 | 0.51 | 1.10 |
| 5 | ABP3-Cry1Abg6 | 1.0 | 0.00 | 1.25 | 0.04 | 1.0 | 0.00 | 0.07 | 0.20 |
| 6 | ABP3-Cry1Abg6 | 1.0 | 0.00 | 1.08 | 0.00 | | | | |
| 7 | ABP3-Cry1Abg6 | 1.0 | 0.00 | 1.31 | 0.00 | 1.1 | 0.10 | 0.45 | 0.80 |
| 8 | ABP3-Cry1Abg6 | 1.0 | 0.04 | 2.00 | 0.08 | 1.1 | 0.00 | 0.00 | 0.30 |
| 9 | ABP3-Cry1Abg6 | 1.0 | 0.00 | 0.92 | 0.00 | 1.3 | 0.00 | 0.00 | 0.10 |
| 10 | ABP3-Cry1Abg6 | 1.0 | 0.00 | 1.42 | 0.04 | 1.2 | 0.00 | 0.00 | 0.40 |
| 11 | ABP3-Cry1Abg6 | 1.0 | 0.13 | 1.17 | 0.00 | 1.0 | 0.00 | 0.00 | 0.10 |
| 12 | ABP3-Cry1Abg6 | 1.0 | 0.00 | 1.62 | 0.08 | 1.1 | 0.00 | 0.17 | 0.30 |
| 13 | ABP3-Cry1Abg6 | 1.0 | 0.00 | 1.29 | 0.00 | 1.2 | 0.00 | 0.00 | 0.20 |
| 14 | ABP3-Cry1Abg6 | 1.0 | 0.00 | 1.10 | 0.13 | 1.0 | 0.00 | 0.07 | 0.10 |
| 15 | ABP3-Cry1Abg6 | 1.0 | 0.08 | 1.33 | 0.04 | 1.1 | 0.00 | 0.24 | 0.20 |
| 16 | ABP3-Cry1Abg6 | 1.0 | 0.00 | 1.33 | 0.21 | 1.0 | 0.00 | 0.00 | 0.10 |
| Bt11 | | 1.0 | 0.00 | 2.75 | 0.00 | 1.3 | 0.00 | 0.00 | 0.00 |
| Negative Check | | 7.0 | 0.21 | 3.00 | 4.67 | 4.3 | 0.40 | 5.80 | 13.50 |
| Rep with data | | 3 | 3 | 3 | 3 | 3 | 3 | 3 | 3 |
| Loc with data | | 1 | 1 | 1 | 1 | 1 | 1 | 1 | 1 |
| Design Used | | RCB | RCB | RCB | RCB | RCB | RCB | RCB | RCB |
| LSD (5%) General EE | | | 0.149 | 0.923 | 0.257 | 0.399 | 0.200 | 1.988 | 0.650 |
| LSD (5%) Excluded Negatives | | | 0.158 | 0.936 | 0.255 | 0.397 | 0.181 | 0.505 | 1.391 |
| CV % | | | 242.21 | 38.47 | 72.14 | 20.10 | 292.75 | 138.76 | 120.87 |
| Probablitiy % | | | 0.90 | 0.09 | 0.00 | 0.00 | 4.10 | 0.00 | 0.00 |

Two studies were undertaken in Bloomington, Ill. (BIL) and Stanton, Minn. (SMN) in 2006. Several ZmABP3-Cry1AG6 events were compared to positive and negative benchmarks represented by Bt11 and Negative Check, respectively.

First-instar ECB larvae were produced from a laboratory colony following procedures outlined in Guthrie (1989) at the Syngenta Seeds, Inc. entomology laboratory in Slater, Iowa. Eggs were incubated at about 28° C. and approximately 80% relative humidity, and neonates were collected from hatching containers approximately 6 hours after hatch. Larvae were healthy and vigorous when placed on the plants as indicated by movement.

Two ECB application types were performed: ECB1, applied at approximately leaf stage V6-V8 and ECB2, applied at pollen shed. The applications were made with the BioServe Davis Inoculator using 1 ml corn cob grits per application. For ECB1 (first-generation ECB infestation) a total of about 150 larvae were placed into the whorl of each plant, in corn cob grits. Two to four applications were made, with one to six days between each application. The first plant in the row was not treated, and then up to 10 consecutive plants were infested.

For ECB2 (second-generation ECB infestation) a total of about 200 larvae were applied per plant, placed into the ear leaf axil and leaf axils directly above or below the ear, in corn cob grits. Four applications were made, with one to six days between each application. Up to ten consecutive plants on the opposite end of the row from the ECB1 treatment were infested. The last plant in the row was not treated.

The following observations were recorded. For ECB1, up to eight consecutive infested plants in the row were evaluated for foliar ECB damage (ECBLR in TABLE C) at least 14 days after the first infestation. The Guthrie scale of 1-9 (Guthrie et al. (1960) was used and one rating, the average for the evaluated plants, was recorded for each plot. For ECB2, approximately 45 days after the plants were infested, up to eight consecutively infested plants on the opposite end of the row from the ECB1 evaluations were dissected to assess ear shank, ear kernel, and stalk feeding, by measuring feeding tunnel lengths (cm).

ECB2 data were subjected to analyses of variance appropriate for a randomized complete block design. Replications were considered random while all other effects were considered fixed. Mean separation was done using the least significant difference (LSD) procedure, but only if the F-test for entries was significant at the customary 5% significance level. Because there was no variability among the events in the ECB1 data, an analysis of variance was not done for this trait. The data and analysis are summarized in TABLE D. In general, the data show that ZmABP3-Cry1ABG6 affords protection against ECB similar to that observed in Bt11 material.

TABLE D shows the amount of Cry1AbG6 protein in transgenic maize tissue. The youngest developing leaf was tested for Cry1AbG6 by ELISA at 5 developmental stages (V5-V6, V8, V10, R1, R3-R4) for each plant. Cry1AbG6 was also measured in pollen. Events 5, 12, 15 and 16 express the ABP3-Cry1AbG6 construct, and Events A-D express the enhanced ABP3-Cry1Ab construct. Data shown are the mean±SD (n=8–10).

| | Developmental Stage | | | | | |
|---|---|---|---|---|---|---|
| | V5-V6 | V8 | V10 | R1 | R3-R4 | Pollen |
| Event 5 | 39 (3.8) | 38 (2.7) | 61 (8.2) | 75 (5.3) | 60 (3.5) | 1.5 (0.14) |
| Event 12 | 61 (5.2) | 32 (1.9) | 50 (6.1) | 44 (5.1) | 49 (4.4) | 1.4 (0.39) |
| Event 15 | 45 (4.5) | 45 (4.8) | 46 (4.8) | 38 (7.4) | 55 (5.4) | 1.0 (0.14) |
| Event 16 | 58 (5.4) | 30 (2.9) | 47 (5.3) | 53 (7.2) | 44 (4.6) | 1.2 (0.17) |
| Event A | 260 (24) | 190 (22) | 250 (18) | 200 (21) | 150 (14) | 1.3 (0.19) |
| Event B | 260 (22) | 227 (29) | 240 (30) | 200 (23) | 150 (76) | 1.6 (0.30) |
| Event C | 310 (31) | 210 (26) | 270 (26) | 150 (15) | 160 (16) | 1.9 (0.31) |
| Event D | 310 (30) | 180 (23) | 240 (15) | 170 (26) | 150 (18) | 1.4 (0.19) |

Example 1.8 Use of ZmABP3 Expression Cassette to Improve Drought Tolerance in Maize A deregulated form of an *Arabidopsis* $H^+$-pyrophosphatase (AtAVP1 D) has been shown to improve drought tolerance when over-expressed in several plants (Gaxiola et al., 2001; Park et al., 2005). The improved performance is enabled by high expression throughout the plant. To demonstrate the utility of AtAVP1 D to improve drought tolerance in maize, a maize-optimized coding sequence was synthesized. The sequence of the AtAVP1D synthetic gene is shown in SEQ ID NO: 16. It was ligated to the ZmABP3 expression cassette as an NcoI/SacI fragment. The vector map shown in SEQ ID: 42 illustrates the ZmABP3-AtAVP1D expression cassette. The complete ZmABP3-AVP1D expression cassette was excised from the Assembly vector as a SanDI/RsrII fragment and ligated to the RsrII site of the *Agrobacterium* binary vector, 15289. A map of the construct is shown in SEQ ID NO: 43.

Example 1.9 Measurement of Cry1AbG6 in Maize Tissue

Hybrid T1 seed (in the ID5829/AX5707 background) for several ZmABP3-Cry1ABG6 events were produced at a Syngenta field station in Bloomington, Ill. Several seed were germinated in 2 inch pots. Seedlings were tested for transgene zygosity, and only hemizygotes were retained. A minimum of 8 plants per event were transplanted to 3 gallon pots and grown in a temperature controlled greenhouse. Leaf tissue from each plant was sampled and assayed for Cry1AbG6 protein at 5 stages of development, V5-V6, V8, V10, R1, and R3-R4 (Ritchie et al., 1997). Pollen was also collected and assayed for Cry1AbG6 protein.

At each stage, leaf tissue (minus the collar, midrib and sheath) was sampled from the youngest expanding leaf. Duplicate samples were pulverized in 96-well blocks. The powder was suspended in 500 μL-1 mL extraction buffer (0.1 M Sodium Borate, 0.5% Tween 20, 0.2% Polyvinylpyrrolidone, 0.05% Sodium Azide, and 1× protease inhibitor cocktail tablets (Roche)). The mixture was clarified by centrifugation and soluble protein quantified using the BCA assay. Fresh pollen was collected in 1.5 mL Eppendorf tubes. Three 3 mm glass beads were added to each tube and the samples were frozen at −80° C. Samples were then pulverized in a horizontal oscillator at 600 rpm. Protein was extracted by adding 500 μL-1 mL extraction buffer and incubating at 4° C. for 30 minutes. The samples were clarified by centrifugation at 4° C., and the soluble protein in each sample was quantified by BCA Assay.

Samples were normalized for protein content and Cry1AbG6 was quantified by ELISA using fully-truncated Cry1Ab as a standard. Each data point is the mean of duplicate measurements, taken at a different dilution of total protein. Data for each event are reported as the mean±SD for all siblings.

Results in TABLE D show that the ZmABP3-Cry1AbG6 cassette produces steady Cry1AbG6 protein in leaf tissue throughout development. Some reduction in CryAbG6 protein is evident as the vegetative tissue begins to senesce (R3-R4). Also evident is the 3-5 fold increase in Cry1AbG6 accumulation in events that also have the CaMV-FMV dual-enhancer complex. Finally, the data show virtually no detectable Cry1AbG6 protein in pollen. In all events CryAbG6, on average, accumulates to less than 1.5 ng/mg total soluble protein. Furthermore, the dual-enhancer complex does not influence Cry1AbG6 accumulation in pollen; it is identical between all events. This is consistent with our data showing that ZmABP3 is not transcribed in pollen (Example 1.5). We conclude that detectable Cry1AbG6 in pollen was likely produced in the microspore mother cells or their progenitors, and carried to pollen through cell division.

Example 2 Non-Tassel Expression

Example 2.1 Identification of ZmABT 2.1.1 Expression Profiling Experiment:

A maize developmental series on the Zm80K Affymetrix chip, was queried for probes that gave strong signals in all samples, and a low or no signal in the tassel samples. Twenty-three (23) probes were identified representing polynucleotides that met the expression criteria. To better represent the differential expression signal between the tassel samples and other tissue samples, the ratio of mean signal for other samples and tassel was calculated for each probe. This indicates the expression differential between tassel and other samples. Any signal below 50 is in the experimental noise, which means the gene may not be transcribed or is transcribed at a very low level. To understand the expression level of each gene represented by candidate probes, a second expression profiling study was queried. In this experiment tissues from two maize genotypes were hybridized to the Zm80K Affymetrix chip. In general signals over 1000 indicate high expression and signals over 10,000 indicate very high expression.

2.1.2 Identification of Candidate Probes:

Two top candidate probes were identified. Probe Zm033444_S_AT demonstrates virtually no signal in tassel and a high signal in other tissues. This indicates that the gene represented by Zm033444_S_AT is not expressed in tassel and is highly expressed throughout the rest of the plant. It also demonstrates the greatest expression differential, 60-fold higher in non-tassel tissue. Probe Zm040564_X_AT has a low signal in young tassel that gradually increases to a high or strong signal. The signal strength between tassel and non-tassel samples differs by less than 10-fold. However the signal strength in non-tassel samples is nearly 10-fold higher than Zm033444_S_AT. The sequence data indicate that neither probe corresponds to a characterized gene. Both probes identify good candidate genes for development of promoters that deliver high expression in non-tassel tissue and little or no expression in tassels. Given the high signal differential between tassel and non-tassel samples, an expression cassette based on probe Zm033444_S_AT was developed.

Table E: shows a summary of the top candidate probes representing polynucleotides with a high expression level in all maize tissues and low expression signal in tassel

| Probe | P-Value | BH Q-Value | Mean induction in non-tassel samples | V9 tassel | V12 tassel | V15 tassel |
|---|---|---|---|---|---|---|
| Zm033444_s_at | 0.00 | 0.00 | 60 | 16.2 | 10.2 | 132 |
| Zm002990_s_at | 0.00 | 0.00 | 45 | 32.8 | 68.7 | 47.8 |
| Zm006285_at | 0.00 | 0.00 | 20 | 37.9 | 44.1 | 35.8 |
| Zm000019_at | 0.00 | 0.00 | 16 | 117 | 200 | 242 |
| Zm006481_s_at | 0.00 | 0.00 | 14 | 26.9 | 32.1 | 31.5 |
| Zm002987_at | 0.00 | 0.00 | 14 | 83.7 | 80.8 | 119 |
| Zm004433_at | 0.00 | 0.00 | 12 | 53.8 | 35.3 | 127 |
| Zm010323_s_at | 0.00 | 0.00 | 11 | 45.4 | 63 | 71.5 |
| Zm016864_s_at | 0.01 | 0.01 | 11 | 89.5 | 55.6 | 1280 |
| Zm018791_at | 0.01 | 0.01 | 11 | 41.4 | 34.7 | 252 |
| Zm028405_s_at | 0.00 | 0.00 | 10 | 69 | 65.1 | 89 |
| Zm021403_at | 0.00 | 0.00 | 10 | 42.2 | 41.4 | 71 |
| Zm054116_s_at | 0.00 | 0.00 | 10 | 93.3 | 62.4 | 219 |
| Zm002990_x_at | 0.00 | 0.00 | 10 | 13.6 | 29.5 | 29.2 |
| Zm005761_at | 0.00 | 0.00 | 9.6 | 33.2 | 40 | 46.7 |
| Zm035082_s_at | 0.00 | 0.00 | 8.5 | 83 | 84 | 143 |
| Zm066342_at | 0.00 | 0.00 | 8.2 | 52.9 | 59.2 | 199 |
| Zm032921_s_at | 0.00 | 0.00 | 8.1 | 57.5 | 29.8 | 90.5 |
| Zm040564_x_at | 0.01 | 0.01 | 7.5 | 277 | 143 | 3710 |
| Zm051284_at | 0.01 | 0.01 | 6.5 | 53.2 | 40 | 194 |
| Zm011554_at | 0.03 | 0.04 | 5.4 | 72.5 | 64.2 | 895 |
| Zmmetall_x_at | 0.01 | 0.01 | 5.3 | 325 | 199 | 2330 |
| Zm011554_x_at | 0.04 | 0.04 | 4.9 | 63.5 | 62.6 | 664 |

Example 2.2 Development of an Expression Cassette

DNA sequence evidence to identify cDNAs corresponding to Zm033444_S_AT was collected. Public and proprietary databases were queried by BLASTN with Zm033444_S_AT sequence. cDNA hits with precise matches to the query sequence fell into two similar contigs. ZmABT1 corresponds to Maize.1482.c47 and Maize.1908.c31, and ZmABT2 corresponds to Maize.1482.c32, Maize.1482.c28, Maize.1482.c53, Maize.1908.c17, Maize.1908.c20, Maize.1908.c37 and A1947567. The Zm033444_S_AT, ZmABT1 and ZmABT2 sequences were used to query maize genomic DNA sequence databases to identify the regulatory sequence(s) that give high expression in non-tassel tissue and little or no expression in tassels. The queries identified three entries, AZM4_12, ZmGSStuc11-12-04.4740.1 and MAGI_88845, that assemble into a single contig. The ZmABT gDNA sequence is shown in SEQ ID NO: 46. It encodes both ZmABT1 and ZmABT2 (SEQ ID NO: 33 and 34, respectively). They are alternatively spliced variants of the same transcript.

ZmABT1 is encoded on 5 exons, and ZmABT2 is encoded on 6 exons. The additional exon lies between exon 1 and exon 2 of ZmABT1. The largest open reading frame on ZmABT1 and ZmABT2 was used to define their translation start and stop codons. Both cDNAs used the same translation start and stop codon. This information enabled the design of a ZmABT-based expression cassette.

Example 3: Construction of a ZmABT-GUS Expression Cassette

An inclusive, gene structure-based design strategy was used to construct the ZmABT expression cassette. To incorporate the known alternative splicing of this gene into the expression cassette, the design strategy was based on the structure of ZmABT1. The cassette contains 2.615 kb of 5'-sequence, which consists of 2.020 kb of 5'-non-transcribed sequence, 12 bp of 5'-UTR and 0.58 kb representing exon 1, intron 1 and 16 bp of exon 2. The natural translation start codon was silenced in order to move it to the second exon. The expression cassette also contains 1.039 kb of 3'-sequence that begins just past the translation stop codon. This includes 0.603 kb of 3'-UTR and 0.436 kb of non-transcribed sequence, and functions as the transcriptional terminator and poly-adenylation signal.

The ZmABT promoter was amplified from maize gDNA template in a 50 μL Proofstart (Qiagen) DNA polymerase reaction containing 10 μg gDNA, 5 μL 10× Proofstart Buffer, 1.0 μL 10 mM dNTP mix, 1.0 μL of 20 μM ABT P1 forw (5'-CGACCAGCGCGACATGCATGGCA-3'; SEQ ID NO: 19), 1.0 μL of 20 μM ABT P2 rev (5'-ACCCCAGGGCG-TACGACAAGGCC-3'; SEQ ID NO: 20), and 10.0 μL 5×Q solution. The thermocycling program was 95° C. for 5 minutes followed by 40 cycles of 94° C. for 30 seconds, 67° C. for 30 seconds and 72° C. for 2.5 minutes. The final extension step was 72° C. for 10 minutes. The 2.6 kb reaction product was gel-purified on 1% TBE agarose and the DNA was extracted using Qiaprep DNA extraction method. The DNA was cloned into the pCR-BluntII-TOPO vector.

The ZmABT promoter was modified in a series of mutagenesis reactions to silence the endogenous START codon, silence a SanDI restriction site and correct point mutations created during amplification. This was done using the Stratagene QuikChange Multi-site mutagenesis kit. The 25 μL reaction contained 1 μL pCR4-TOPO-ZmABT-promoter, 2.5 μL 10× QuikChange buffer, 1 μL QuikChange dNTP mix, 0.75 μL Quik solution, 1 μL QuikChange DNA polymerase and 1 μL of 20 μM of at least one of the following oligonucleotides:

```
pABT mut1
                                (SEQ ID NO: 21)
(5'-GATGGCCGGATTGGGCTCCCGGGGTGGAG-3')

pABT mut2
                                (SEQ ID NO: 22)
(5'-CTGGGAGGCGCGCAAGGGGCAGTTCCTCG-3')

pABT mut3
                                (SEQ ID NO: 23)
(5'-CCCACCGCCGGAGCACCGAAAGGCCCCGCG-3')

pABT mut4
                                (SEQ ID NO: 24)
(5'-GTCACCCGGGAGCACTTCCCGGCGCCG-3')

pABT mut5
                                (SEQ ID NO: 25)
(5'-CATTGGGCCGAGCACGGCTTCTTCCGC-3')

pABT mut6
                                (SEQ ID NO: 26)
(5'-GGGGTACGGTGTTCTTGAGTCGTGAAGCGAC-3')
```

The thermocycling program was 95° C. for 1 minute followed by 35 cycles of 95° C. for 1 minute, 50° C. for 1 minute and 65° C. for 12 minutes. The product was processed as described by the manufacturer (Stratagene) and completely sequenced. The ZmABT promoter sequence is shown in SEQ ID NO: 35.

The corrected ZmABT promoter was PCR amplified from the TOPO vector in a 50 μL Proofstart (Qiagen) DNA polymerase reaction as above using primers pABT amp1 (5'-GCGTCTAGAGGGACCCCGACCAGCGCGACATG-CATGGCA-3'), depicted in SEQ ID NO: 27 and pABT amp2 (5'-ACCCCAGGGCGTACGACAA-GGCCCCAC-CATGGGCGC-3'), depicted in SEQ ID NO: 28. The PCR product was gel-purified on 1% TBE agarose and the DNA was extracted using Qiaprep DNA extraction method. The DNA was cloned into the pCR-BluntII-TOPO vector, transformed and sequenced. The ZmABT promoter was excised as an XbaI/NcoI fragment and ligated to pNOV6901.

The ZmABT terminus was amplified from maize gDNA template in a 50 μL Extensor (ABgene) DNA polymerase reaction containing 10 μg gDNA, 5 μL 10× Extensor buffer #1, 2.0 μL 10 mM dNTP mix, 2.0 μL of 20 μM ABT P4 (5'-TATATAGAGCTCGAATCGAAGAAGCCACACTG-TAAATCTGCCGGG-3'; SEQ ID NO: 29), 2.0 μL of 20 μM ABT P5 (5'-AGCAAGGCATATGCAGCAGCTGCTG-GTCGGACCGGGCCCTATATA-3'; SEQ ID NO: 30), 10 μL 5×Q solution, 0.5 μL Extensor DNA polymerase and 0.5 μL Amplitaq DNA polymerase. The reactions were overlaid with mineral oil and the thermocycling program was 95° C. for 2 minutes followed by 40 cycles of 98° C. for 2 seconds, 63° C. for 1 minute and 68° C. for 4 minutes. The final extension step was 68° C. for 7 minutes. The 1 kb reaction product was gel-purified on 1% TAE agarose, and the DNA was extracted using Qiaprep DNA extraction method. The DNA was ethanol precipitated and recovered in 4 μL $ddH_2O$, then cloned into the pCR4-TOPO-Blunt vector.

The ZmABT terminus was modified to remove internal NcoI and XhoI restriction sites using the Stratagene QuikChange Multi-site mutagenesis kit, as above. The 25 μL reaction contained 1 μL pCR4-TOPO-ZmABT-promoter, 2.5 μL 10× QuikChange buffer, 1 μL QuikChange dNTP mix, 0.75 μL Quik solution, 1 μL QuikChange DNA polymerase and 1 μL of 20 μM of at least one of the following oligonucleotides:

```
ABTt m1
                                   (SEQ ID NO: 31)
(5'-GTCATGCATGGGCATGTGAAGGAGGAGCC-3')

ABTt m2
                                   (SEQ ID NO: 32)
(5'-GTTGCATGCATGCTGCATGGCGTCGAGAT-3')
```

The thermocycling program was 95° C. for 1 minute followed by 35 cycles of 95° C. for 1 minute, 50° C. for 1 minute and 65° C. for 13 minutes. The product was processed as described by the manufacturer (Stratagene) and completely sequenced. The ZmABT terminator sequence is shown in SEQ ID NO: 36.

The ZmABT terminus was excised as a SacI/ApaI fragment and ligated to pNOV6901-prABT vector (above). This produced plasmid 15772 (ZmABT Assembly), and a plasmid map is shown in SEQ ID NO: 44. The complete ZmABT expression cassette was mobilized as a SanDI/RsrII fragment into the RsrII site of the *Agrobacterium* binary vector 15289. A plasmid map of this construct, 15773, is shown in SEQ ID NO: 45.

Example 4: Extension of DNA Probe Sequences to Designed Expression Cassettes

DNA sequence representing probes on the maize chip can easily be extended to designed expression cassettes following the steps outlined above. The DNA sequence for probes identified as representing genes that are highly expressed in all tissue samples and not expressed in pollen (Table A) and those that are highly expressed in all tissue samples and have reduced expression in tassel samples (Table E) is reported as SEQ ID NOs: 47-79.

An additional probe candidate from the expression profiling analysis for each expression category was selected to demonstrate progression from this DNA sequence to a finished binary vector with the designed expression cassette linked to the GUS reporter gene. The method used is identical to that for ZmABP3 and ZmABT. In summary the process steps to be applied are as follows:

1. Flank each expression cassette with SanDI/RsrII sites and report as cloned into the RsrII site of 15289 (SEQ ID NO: 80).

2. Promoter consists of 1000-1500 bp of sequence upstream of the transcription start site and extends 10 bases into the second exon, or to the natural translation start codon if it is not on the first exon. It terminates with the maize optimized Kozak sequence 'gtaaaccatgg'. The engineered translation start codon is now embedded in the NcoI restriction endonuclease site 'ccatgg'. Mutate all translation start codons in the theoretical transcript that are upstream of the engineered NcoI site. Ensure at least one stop codon is in each reading frame upstream of the engineered NcoI site. The promoter is designed to be flanked by XhoI/SanDI at the 5'-end and NcoI at the 3'-end.

3. The Gene Of Interest (G01) is represented by the GUS reporter gene as an NcoI/SacI fragment.

4. The terminus extends from just after the translation stop codon for 1 kb downstream. The terminus is designed to be flanked by SacI at the 5'-end and RsrII/XmaI at the 3'-end.

5. The complete expression cassette is designed to be mobilized as a SanDI/RsrII fragment, which can be ligated into an RsrII site located on an *Agrobacterium* binary vector such as 15289 (SEQ ID NO: 80).

6. Mutate all internal SanDI, RsrII, NcoI, SacI, XhoI and XmaI sites by single base substitution to silence them.

Through application of these basic steps a plant expression cassette (SEQ ID NO: 81) can be designed that corresponds to probe Zm058948_s_at (SEQ ID NO: 55) and a plant expression cassette (SEQ ID NO: 82) that corresponds to probe Zm002990_s_at (SEQ ID NO: 62). The former is an expression cassette that should be transcribed in all maize tissues and not in pollen. The latter is an expression cassette that should be transcribed in all maize tissues and have reduced transcription in tassels. This design strategy applies to all probes identified in Tables A and E.

Further details of how to make such expression cassettes are described in US2005235311, which is incorporated herein by reference in its entirety.

REFERENCES

Ammirato et al., eds., (1984) Handbook of Plant Cell Culture—Crop Species, Macmillan Publ. Co., New York, N.Y.

An et al., (1985) EMBO J. 4, 277 287

Auch & Reth et al.

Batzer, et al., Nucleic Acid Res. 19:5081 (1991)

Byrne, M. C., McDonnell, R. E., Wright, M. S. and Carnes, M. G., 1987. "Strain and Cultivar Specificity in the *Agrobacterium*-soybean Interaction." Plant Cell Tissue and Organ Culture 8:3-15

Christou et al., *Plant Physiol.* 87:671-674 (1988)

Christou et al., *Biotechnology* 9: 957-962 (1991)

Crossway et al., *BioTechniques* 4:320-334 (1986)

Datta et al., *Bio/Technology* 8:736-740 (1990)

Fromm et al., *Bio/Technology* 8:833-839 (1990)

Gaxiola, R. A., Li, J., Undurraga, S., Dang, L. M., Allen, G. J. Alper, S. L., Fink, G. R. (2001). Drought- and salt-tolerant plants result from over-expression of the AVP1 $H^+$-pump. Proc. Natl. Acad. Sci. USA 98: 11444-11449.

Gordon-Kamm et al., *Plant Cell* 2:603-618 (1990)

Gruber, et al., "Vectors for Plant Transformation, in Methods in Plant Molecular Biology & Biotechnology" in Glich, et al., (Eds. pp. 89-119, CRC Press, 1993).

Guthrie, W. D., F. F. Dicke, and C. R. Neiswander (1960) Leaf and sheath feeding resistance to the Eur. corn borer in eight inbred lines of dent corn. Ohio Agric. Exp. Stn. Res. Bull. 860.

Guthrie, W. D. (1989) Advances in Rearing the European Corn Borer on a Meridic Diet, In: *Toward Insect Resistant Maize for the Third World; Proceedings of the International Symposium on Methodologies for Developing Host Plant Resistance to Maize Insects*. Mexico, D. F.:CIMMYT Hiei et al., (1994) Plant J. 6, 271-282

Hinchee et al., *Biotechnology* 6:915-921 (1988)

Hoekema (1985) The Binary Plant Vector System, Offset-drukkerij Kanters B. V., Alblasserdam, Chap. V Klein et al., *Proc. Natl. Acad. Sci. USA,* 85:4305-4309 (1988)

Klein et al., *Bio/Technology* 6:559-563 (1988)(maize); Klein et al., *Plant Physiol.* 91:440-444 (1988)

Knauf, et al., 1983

Koziel et al., *Biotechnology* 11: 194-200 (1993)

Lindsey K, Wei W, Clarke M C, McArdle H F, Rooke L M, Topping J F. Tagging genomic sequences that direct transgene expression by activation of a promoter trap in plants. Transgenic Res. 1993 January; 2(1):33-47.

Lopez, I, Anthony, R. G., Maciver, S. K., Jiang, C.-J., Khan, S., Weeds, A. G., Hussey, P. J. (1996) Pollen specific expression of maize genes encoding actin depolymerizing factor-like proteins. Proc. Natl. Acad. Sci. USA. 93: 7415-7420.

Lörz et al. (Mol. Gen. Genet. 199, 178, (1985))

McBride, et al. (1994) Proc. Natl. Acad. Sci. USA 91:7301-7305

McCabe et al., *Biotechnology* 6:923-926 (1988)

Ohtsuka, et al., J. Biol. Chem. 260:2605-2608 (1985)

Pacciotti et al. (1985) Bio/Technology 3:241

Park et al., 1985

Park, S., Li, J., Pittman, J. K., Berkowitz, G. A., Yang, H., Undurrago, S., Morris, J., Hirschi, K. D., Gaxiola, R. A. (2005). Up-regulation of a $H^+$-pyrophosphatase ($H^+$-PPase) as a strategy to engineer drought-resistant crop plants. Proc. Natl. Acad. Sci. USA 102: 18830-18835.

Paszkowski et al., *EMBO J.* 3:2717-2722 (1984)

Pearson, W. R. (1990), Methods in Enzymology 183, 63-98

Potrykus, I., Paszkowski, J. P., Saul, M. W., Petruska, P. and Shillito, R. D. 1985. Molecular and general genetics of a hybrid foreign gene introduced into tobacco by direct gene transfer. *Mol. Gen. Genet.* 199:169-177.

Ritchie, S. W., Hanway, J. J., Benson, G. O. (1997). How a corn plant develops: Special Report No. 48. Iowa State University of Science and Technology Cooperative Extension service: Ames, Iowa.

Riggs et al., *Proc. Natl. Acad. Sci. USA* 83:5602-5606 (1986)

Rossolini, et al., Mol. Cell. Probes 8:91-98 (1994)

Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis et al. (eds.) Cold Spring Harbor Laboratory, Cold Spring Harbor, N.Y. (1980)

Sanford et al., *Particulate Science and Technology* 5:27-37 (1987)

Shimamoto et al., *Nature* 338: 274-277 (1989)

Shirzadegan, M., Christie, P., Seemann, J. (1991) An efficient method for isolation of RNA from tissue-cultured plant cells. Nucleic Acids Res. 19(21): 6055.

Smith and Waterman, Advances in Applied Mathematics 2 (1981), 482-489

Sukhapinda et al., Plant Mol. Biol., vol. 8:209-216, 1987

Svab et al., *Proc. Natl. Acad. Sci. USA* 87: 8526-8530 (1990)

Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York., Vasil et al., *Biotechnology* 11: 1553-1558 (1993)

Weeks et al., *Plant Physiol.* 102: 1077-1084 (1993)

Weissinger et al., *Annual Rev. Genet.* 22:421-477 (1988)

PATENT LITERATURE

EP 0 332 581

EP 0 292 435

EP 0 295959

EP 0 138341

EP 0 120516

U.S. Pat. No. 5,451,513

U.S. Pat. No. 5,545,817

U.S. Pat. No. 5,545,818

U.S. Pat. No. 5,350,689

U.S. Pat. No. 5,451,513,

U.S. Pat. No. 4,945,050

WO 95/16783

The invention claimed is:

1. An isolated polynucleotide comprising SEQ ID NO: 36 operably linked to a heterologous nucleotide sequence of interest in maize, wherein the heterologous nucleotide sequence is transcribed in maize leaf tissue and not in tassel.

2. An expression cassette comprising the isolated polynucleotide of claim 1.

3. A vector molecule comprising the expression cassette according to claim 2.

4. A transgenic plant comprising the expression cassette of claim 2.

5. A transgenic plant comprising the vector of claim 3.

6. The transgenic plant of claim 4 wherein the plant is *Zea mays*.

7. A seed of the transgenic plant of claim 6, wherein the seed comprises a polynucleotide comprising SEQ ID NO: 36 operably linked to a heterologous nucleotide sequence of interest in maize.

* * * * *

SEQUENCE LISTING

```
<160> NUMBER OF SEQ ID NOS: 91

<210> SEQ ID NO 1
<211> LENGTH: 50
<212> TYPE: DNA
<213> ORGANISM: Artificial Sequence
<220> FEATURE:
<223> OTHER INFORMATION: forward primer P1

<400> SEQUENCE: 1

atatatgcat gcggcgcgcc gaaagtagca aacaacaggt tcatgtgcac           50
```

```
<210> SEQ ID NO 2
<211> LENGTH: 38
<212> TYPE: DNA
<213> ORGANISM: Artificial Sequence
<220> FEATURE:
<223> OTHER INFORMATION: reverse primer P2

<400> SEQUENCE: 2

tatataccat ggtgggtttg cctgcgacca caagttca                              38

<210> SEQ ID NO 3
<211> LENGTH: 28
<212> TYPE: DNA
<213> ORGANISM: Artificial Sequence
<220> FEATURE:
<223> OTHER INFORMATION: oligonucleotide Patg

<400> SEQUENCE: 3

cagctcgccc gagttggtaa ggccccct                                        28

<210> SEQ ID NO 4
<211> LENGTH: 24
<212> TYPE: DNA
<213> ORGANISM: Artificial Sequence
<220> FEATURE:
<223> OTHER INFORMATION: oligonucleotide Pnco

<400> SEQUENCE: 4

acagattagt ccatcgccca cggt                                            24

<210> SEQ ID NO 5
<211> LENGTH: 27
<212> TYPE: DNA
<213> ORGANISM: Artificial Sequence
<220> FEATURE:
<223> OTHER INFORMATION: oligonucleotide ADPc-1

<400> SEQUENCE: 5

agccctgtcc atgacggccc aagcaac                                         27

<210> SEQ ID NO 6
<211> LENGTH: 26
<212> TYPE: DNA
<213> ORGANISM: Artificial Sequence
<220> FEATURE:
<223> OTHER INFORMATION: oligonucleotide ADPc-2

<400> SEQUENCE: 6

agtagcaatt cggtaggcac aggcac                                          26

<210> SEQ ID NO 7
<211> LENGTH: 25
<212> TYPE: DNA
<213> ORGANISM: Artificial Sequence
<220> FEATURE:
<223> OTHER INFORMATION: oligonucleotide ADPc-4

<400> SEQUENCE: 7

tctatggtct gcgaggtgcg gtggc                                           25

<210> SEQ ID NO 8
<211> LENGTH: 27
<212> TYPE: DNA
<213> ORGANISM: Artificial Sequence
<220> FEATURE:
<223> OTHER INFORMATION: oligonucleotide adp3-a
```

<400> SEQUENCE: 8
gtccccttct tcgccgcgcc agctcgc 27

<210> SEQ ID NO 9
<211> LENGTH: 37
<212> TYPE: DNA
<213> ORGANISM: Artificial Sequence
<220> FEATURE:
<223> OTHER INFORMATION: forward primer P3

<400> SEQUENCE: 9
tatatagagc tcgcatcatg atcatgcatc atggact 37

<210> SEQ ID NO 10
<211> LENGTH: 46
<212> TYPE: DNA
<213> ORGANISM: Artificial Sequence
<220> FEATURE:
<223> OTHER INFORMATION: reverse primer P4

<400> SEQUENCE: 10
atatatacta gtggcgcgcc acactttctg tcgcatgtga tttgca 46

<210> SEQ ID NO 11
<211> LENGTH: 30
<212> TYPE: DNA
<213> ORGANISM: Artificial Sequence
<220> FEATURE:
<223> OTHER INFORMATION: forward primer Tnco

<400> SEQUENCE: 11
gtaaaaaaag gtcccttggc tcccagaaga 30

<210> SEQ ID NO 12
<211> LENGTH: 20
<212> TYPE: DNA
<213> ORGANISM: Artificial Sequence
<220> FEATURE:
<223> OTHER INFORMATION: forward primer T2

<400> SEQUENCE: 12
caatgtgtta gactgacgtg 20

<210> SEQ ID NO 13
<211> LENGTH: 2333
<212> TYPE: DNA
<213> ORGANISM: Zea mays

<400> SEQUENCE: 13
gcatgcggcg cgccgaaagt agcaaacaac aggttcatgt gcactataaa aagacaaaat 60
tctcgagttt catcttttat tccacataag ccttatattt tccattttca tatgattttt 120
agtttaagtt tgtgtcttaa ctttttcgtt aatacgtaat tctatgcatt atggatgcgt 180
gaagtatttt tgtttaaaaa aatgaaatgt caaaatacgt tttgtgatct atttccatgt 240
tttcacctaa caggtggttt ttactatata ttctgccata actctagcct tagatgtaaa 300
tcgaaaaaaa atgagagatg agctggagat agccttagat gaagcgtctg aaatataaaa 360
gaaagagtaa tgttgaacgc agtaggtgta gcagctgtag ttccatctct aggaaaggga 420
actgcaatcc gggctccggg cctcgcgcaa tctggcctgt cgtgtagatg cagccctgtc 480
catgacggcc caagcaacgc ccgcggctct cgatccacca cggaacccac tccgacacac 540
actgacacac acatgctgga tgtggatgtg ctgtccaatt attagtagca attcggtagg 600

-continued

```
cacaggcacg tactggccgg tgttttagct gtaagtaccg aaccaatcac ggttaagaac    660
cgattaatcc gtgcccagcc gccgagtgcg ttcgtacgtg catcggatgc actgcatgaa    720
ttgagagcat catcatatca tacgcaggag tagtacgacg ccgctgctgt cttgtccggc    780
taatgctttg ctcacagatt agtccatcgc ccacggtcgg tgtggtgtgg atcgctgatg    840
ccactgcttt ttgtttggtt tttattcccc tgataatcct ccgcgtccct gaatgtatct    900
atttattttc attccgaaat ccctttcacg aaaaagaaaa cgaataaaaa gagagttacg    960
aatacgcttc cggcggccca catcaccttc cagcgaacat cgcgccgcgc tgacgtgtcg   1020
cccatcgcgg ccgtccatat cgccatccga cgaccgtgga agctggcagc ggccgctccg   1080
ttccgtcgaa ggggcaggtc agtcaggtca cccacacggc cacacccgcg cgggggatac   1140
gcggtggaaa acccggcgac cacatcaaaa cacgaggcgt ctcccgcagg actggtcact   1200
cggcacgcag gcagaggcag cacagcagca gccagctcca tccatcctct ttcccctcct   1260
cgcttcgctt cctcggcgga ttcctcctcc ctcggccgtc cccgtcccct tcttcgccgc   1320
gccagctcgc ccgagttggt aaggccccct ccacccctcc gcttcccctc ccccgggcgc   1380
gctctggctt cctccccgga tcggcgcggg gcgtgctggc tccgcgcctg atttcgggcc   1440
ttttgtttcc ttctcgcgga gcgctcgtgt aacgcttcgg atctagctgg attcaggcgg   1500
gatcgcggcc gctcggcttc ctcgtggcct gattcgtggt tttcctcggg gagggaatcc   1560
tgatcggatc atcgggattc ctcgtgcggc cgggacacgc ttgcgagcca gaaacatagt   1620
ctgcgtggcc gggattccac gatctgtgat ctagacgtcg ggcgcttcgt ctatgtgctc   1680
gctgcaggct gtggcgtact ggcgtggtgc gcggccgcta tggatccgtg cttgtttgtt   1740
cgccctgtag cgtgtgaaat cgagctgtgt agatctatgg tctgcgaggt gcggtggcgg   1800
tggaatctcg gttgatcttt acctcagcgg cgccagtgta gctcgtgtgg ctgcagttca   1860
tctgcgaatt tggctctcgg cggcttaggt cgcggagctt ggattatgga gcaccagctg   1920
cagcgtgacc ctgttggttc tcatgtggat ctgttggctg aggttgcaga cttcaagtgc   1980
cactgccatt gaccggagct gctgcacgat tatactggaa tatctagcgg tagtatactc   2040
tgctagtact caatacgggt ctcctgacaa atgtctttcg tgtttaggga cctagcactc   2100
tagtgtcaag actatttgct ggaatatcta atattagcag tttctgtagt ggctcagttg   2160
cagcctggtt tagaatgatg gggacagttg gctgtgccat gcaaaataaa gtgtgtgaaa   2220
gcaactgcct cttaaactat gggtggtgca agcaggttat ttgaagggac tctccacact   2280
gtatctccag ttaactatga ctgaacttgt ggtcgcaggc aaacccacca tgg          2333
```

<210> SEQ ID NO 14
<211> LENGTH: 1031
<212> TYPE: DNA
<213> ORGANISM: Zea mays

<400> SEQUENCE: 14

```
gagctcgcat catgatcatg catcatggac tcggcctact actgtggatt tgtatgccat     60
tatagacttg gtgctgtgaa agactgcttg atgatttgcg ggtttgttgc tgtgtaaaaa    120
aaggtccctt ggctcccaga agaccatgaa ggttcggatc tatcatgtaa ttccttgtta    180
tctgccaatt atgtatggac tatggacatg tgttgcgctg ttcaacttac tactacaaat    240
aagtaatcga tatgttccct tcccatgtct cggtgacaat tgtctggaga agcttagggg    300
tcgtttgttt gggattatgt ctggagaaac ttattttaaa ctaagtgtga gttcaagtta    360
```

agttagatta tataatctag gcagattata attccaagcg aacaggtcct tagtgttttt 420
ggaaaatcct aggtgttctt ttggctacat tgttgtgtgt gcagatccct tgttggtctg 480
taagcgtggg gaagtaagaa tcgtccgttt ctactgaaga cctgctcgag ttaggcaccg 540
aggatgccgg taaccaaaca gagcaatagt gtctctgtgg gcacagtgga gtgtgaatct 600
gtgtgatgca aatccgtcat ttgtttagca aaatttccag cgttgcatga tgcagtttct 660
ttaacacgga cttaagggaa gggaaaaaaa tgttgagcca ggagatcctt caatgtgtta 720
gactgacgtg atagccaact aaaccacgac gcaatgttgt cgttaatgac aaaaaaacta 780
tttgttccta aatccttggc gacattgcat ggctgtctca tgagataatg gtctcatctc 840
ttatttatct cttatttata gccggaagtg gtagtgaccc ctgcttgatt gctcgtatgc 900
catctcaagt tctcaaccgt gtcgagcagc cattttccca tctcaagcgc atcatcgttt 960
cgtttgacct catctgctat cctgctccta gtgcaaatca catgcgacag aaagtgtggc 1020
gcgccactag t 1031

<210> SEQ ID NO 15
<211> LENGTH: 1031
<212> TYPE: DNA
<213> ORGANISM: Zea mays

<400> SEQUENCE: 15
gagctcgcat catgatcatg catcatggac tcggcctact actgtggatt tgtatgccat 60
tatagacttg gtgctgtgaa agactgcttg atgatttgcg ggtttgttgc tgtgtaaaaa 120
aaggtccctt ggctcccaga agaccatgaa ggttcggatc tatcatgtaa ttccttgtta 180
tctgccaatt atgtatggac tatggacatg tgttgcgctg ttcaacttac tactacaaat 240
aagtaatcga tatgttccct tcccatgtct cggtgacaat tgtctggaga agcttagggg 300
tcgtttgttt gggattatgt ctggagaaac ttattttaaa ctaagtgtga gttcaagtta 360
agttagatta tataatctag gcagattata attccaagcg aacaggtcct tagtgttttt 420
ggaaaatcct aggtgttctt ttggctacat tgttgtgtgt gcagatccct tgttggtctg 480
taagcgtggg gaagtaagaa tcgtccgttt ctactgaaga cctgctcgag ttaggcaccg 540
aggatgccgg taaccaaaca gagcaatagt gtctctgtgg gcacagtgga gtgtgaatct 600
gtgtgatgca aatccgtcat ttgtttagca aaatttccag cgttgcatga tgcagtttct 660
ttaacacgga cttaagggaa gggaaaaaaa tgttgagcca ggagatcctt caatgtgtta 720
gactgacgtg atagccaact aaaccacgac gcaatgttgt cgttaatgac aaaaaaacta 780
tttgttccta aatccttggc gacattgcat ggctgtctca tgagataatg gtctcatctc 840
ttatttatct cttatttata gccggaagtg gtagtgaccc ctgcttgatt gctcgtatgc 900
catctcaagt tctcaaccgt gtcgagcagc cattttccca tctcaagcgc atcatcgttt 960
cgtttgacct catctgctat cctgctccta gtgcaaatca catgcgacag aaagtgtggc 1020
gcgccactag t 1031

<210> SEQ ID NO 16
<211> LENGTH: 1031
<212> TYPE: DNA
<213> ORGANISM: Zea mays

<400> SEQUENCE: 16
gagctcgcat catgatcatg catcatggac tcggcctact actgtggatt tgtatgccat 60
tatagacttg gtgctgtgaa agactgcttg atgatttgcg ggtttgttgc tgtgtaaaaa 120

```
aaggtccctt ggctcccaga agaccatgaa ggttcggatc tatcatgtaa ttccttgtta    180

tctgccaatt atgtatggac tatggacatg tgttgcgctg ttcaacttac tactacaaat    240

aagtaatcga tatgttccct tcccatgtct cggtgacaat tgtctggaga agcttagggg    300

tcgtttgttt gggattatgt ctggagaaac ttattttaaa ctaagtgtga gttcaagtta    360

agttagatta tataatctag gcagattata attccaagcg aacaggtcct tagtgttttt    420

ggaaaatcct aggtgttctt ttggctacat tgttgtgtgt gcagatccct tgttggtctg    480

taagcgtggg gaagtaagaa tcgtccgttt ctactgaaga cctgctcgag ttaggcaccg    540

aggatgccgg taaccaaaca gagcaatagt gtctctgtgg gcacagtgga gtgtgaatct    600

gtgtgatgca aatccgtcat ttgtttagca aaatttccag cgttgcatga tgcagtttct    660

ttaacacgga cttaagggaa gggaaaaaaa tgttgagcca ggagatcctt caatgtgtta    720

gactgacgtg atagccaact aaaccacgac gcaatgttgt cgttaatgac aaaaaaacta    780

tttgttccta aatccttggc gacattgcat ggctgtctca tgagataatg gtctcatctc    840

ttatttatct cttatttata gccggaagtg gtagtgaccc ctgcttgatt gctcgtatgc    900

catctcaagt tctcaaccgt gtcgagcagc cattttccca tctcaagcgc atcatcgttt    960

cgtttgacct catctgctat cctgctccta gtgcaaatca catgcgacag aaagtgtggc   1020

gcgccactag t                                                        1031
```

<210> SEQ ID NO 17
<211> LENGTH: 1031
<212> TYPE: DNA
<213> ORGANISM: Zea mays

<400> SEQUENCE: 17

```
gagctcgcat catgatcatg catcatggac tcggcctact actgtggatt tgtatgccat     60

tatagacttg gtgctgtgaa agactgcttg atgatttgcg ggtttgttgc tgtgtaaaaa    120

aaggtccctt ggctcccaga agaccatgaa ggttcggatc tatcatgtaa ttccttgtta    180

tctgccaatt atgtatggac tatggacatg tgttgcgctg ttcaacttac tactacaaat    240

aagtaatcga tatgttccct tcccatgtct cggtgacaat tgtctggaga agcttagggg    300

tcgtttgttt gggattatgt ctggagaaac ttattttaaa ctaagtgtga gttcaagtta    360

agttagatta tataatctag gcagattata attccaagcg aacaggtcct tagtgttttt    420

ggaaaatcct aggtgttctt ttggctacat tgttgtgtgt gcagatccct tgttggtctg    480

taagcgtggg gaagtaagaa tcgtccgttt ctactgaaga cctgctcgag ttaggcaccg    540

aggatgccgg taaccaaaca gagcaatagt gtctctgtgg gcacagtgga gtgtgaatct    600

gtgtgatgca aatccgtcat ttgtttagca aaatttccag cgttgcatga tgcagtttct    660

ttaacacgga cttaagggaa gggaaaaaaa tgttgagcca ggagatcctt caatgtgtta    720

gactgacgtg atagccaact aaaccacgac gcaatgttgt cgttaatgac aaaaaaacta    780

tttgttccta aatccttggc gacattgcat ggctgtctca tgagataatg gtctcatctc    840

ttatttatct cttatttata gccggaagtg gtagtgaccc ctgcttgatt gctcgtatgc    900

catctcaagt tctcaaccgt gtcgagcagc cattttccca tctcaagcgc atcatcgttt    960

cgtttgacct catctgctat cctgctccta gtgcaaatca catgcgacag aaagtgtggc   1020

gcgccactag t                                                        1031
```

<210> SEQ ID NO 18

-continued

<211> LENGTH: 8546
<212> TYPE: DNA
<213> ORGANISM: Artificial sequence
<220> FEATURE:
<223> OTHER INFORMATION: plasmid pNOV1321

<400> SEQUENCE: 18
cttgcatgcc tgcagtgcag cgtgacccgg tcgtgcccct ctctagagat aatgagcatt 60
gcatgtctaa gttataaaaa attaccacat attttttttg tcacacttgt ttgaagtgca 120
gtttatctat ctttatacat atatttaaac tttactctac gaataatata atctatagta 180
ctacaataat atcagtgttt tagagaatca tataaatgaa cagttagaca tggtctaaag 240
gacaattgag tattttgaca acaggactct acagttttat ctttttagtg tgcatgtgtt 300
ctcctttttt tttgcaaata gcttcaccta tataatactt catccatttt attagtacat 360
ccatttaggg tttagggtta atggttttta tagactaatt tttttagtac atctatttta 420
ttctatttta gcctctaaat taagaaaact aaaactctat tttagttttt ttatttaata 480
atttagatat aaaatagaat aaaataaagt gactaaaaat taaacaaata ccctttaaga 540
aattaaaaaa actaaggaaa catttttctt gtttcgagta gataatgcca gcctgttaaa 600
cgccgtcgac gagtctaacg gacaccaacc agcgaaccag cagcgtcgcg tcgggccaag 660
cgaagcagac ggcacggcat ctctgtcgct gcctctggac ccctctcgag agttccgctc 720
caccgttgga cttgctccgc tgtcggcatc cagaaattgc gtggcggagc ggcagacgtg 780
agccggcacg gcaggcggcc tcctcctcct ctcacggcac cggcagctac gggggattcc 840
tttcccaccg ctccttcgct ttcccttcct cgcccgccgt aataaataga caccccctcc 900
acaccctctt tccccaacct cgtgttgttc ggagcgcaca cacacacaac cagatctccc 960
ccaaatccac ccgtcggcac ctccgcttca aggtacgccg ctcgtcctcc cccccccccc 1020
ctctctacct tctctagatc ggcgttccgg tccatggtta gggcccggta gttctacttc 1080
tgttcatgtt tgtgttagat ccgtgtttgt gttagatccg tgctgctagc gttcgtacac 1140
ggatgcgacc tgtacgtcag acacgttctg attgctaact tgccagtgtt tctctttggg 1200
gaatcctggg atggctctag ccgttccgca gacgggatcg atttcatgat tttttttgtt 1260
tcgttgcata gggtttggtt tgcccttttc ctttatttca atatatgccg tgcacttgtt 1320
tgtcgggtca tcttttcatg cttttttttg tcttggttgt gatgatgtgg tctggttggg 1380
cggtcgttct agatcggagt agaattctgt ttcaaactac ctggtggatt tattaatttt 1440
ggatctgtat gtgtgtgcca tacatattca tagttacgaa ttgaagatga tggatggaaa 1500
tatcgatcta ggataggtat acatgttgat gcgggtttta ctgatgcata tacagagatg 1560
ctttttgttc gcttggttgt gatgatgtgg tgtggttggg cggtcgttca ttcgttctag 1620
atcggagtag aatactgttt caaactacct ggtgtattta ttaattttgg aactgtatgt 1680
gtgtgtcata catcttcata gttacgagtt taagatggat ggaaatatcg atctaggata 1740
ggtatacatg ttgatgtggg ttttactgat gcatatacat gatggcatat gcagcatcta 1800
ttcatatgct ctaaccttga gtacctatct attataataa acaagtatgt tttataatta 1860
ttttgatctt gatatacttg gatgatggca tatgcagcag ctatatgtgg atttttttag 1920
ccctgccttc atacgctatt tatttgcttg gtactgtttc ttttgtcgat gctcaccctg 1980
ttgtttggtg ttacttctgc agggatccaa caatggacaa caaccccaac atcaacgagt 2040
gcatccccta caactgcctg agcaaccccg aggtggaggt gctgggcggc gagcgcatcg 2100
agaccggcta caccccoatc gacatcagcc tgagcctgac ccagttcctg ctgagcgagt 2160

-continued tcgtgcccgg cgccggcttc gtgctgggcc tggtggacat catctggggc atcttcggcc 2220
ccagccagtg ggacgccttc ctggtgcaga tcgagcagtt gataaaccaa cgcatagagg 2280
aattcgcccg caaccaggcc atcagccgcc tggagggcct gagcaacctg taccaaatct 2340
acgccgagag cttccgcgag tgggaggccg accccaccaa ccccgccctg cgcgaggaga 2400
tgcgcatcca gttcaacgac atgaacagcg ccctgaccac cgccatcccc ctgttcgccg 2460
tgcagaacta ccaggtgccc ctgctgagcg tgtacgtgca ggccgccaac ctgcacctga 2520
gcgtgctgcg cgacgtcagc gtgttcggcc agcgctgggg cttcgacgcc gccaccatca 2580
acagccgcta caacgacctg acccgcctga tcggcaacta caccgaccac gccgtgcgct 2640
ggtacaacac cggcctggag cgcgtgtggg gtcccgacag ccgcgactgg atcaggtaca 2700
accagttccg ccgcgagctg accctgaccg tgctggacat cgtgagcctg ttccccaact 2760
acgacagccg cacctacccc atccgcaccg tgagccagct gacccgcgag atttacacca 2820
accccgtgct ggagaacttc gacggcagct tccgcggcag cgcccagggc atcgagggca 2880
gcatccgcag cccccacctg atggacatcc tgaacagcat caccatctac accgacgccc 2940
accgcggcga gtactactgg agcggccacc agatcatggc cagccccgtc ggcttcagcg 3000
gccccgagtt caccttcccc ctgtacggca ccatgggcaa cgctgcacct cagcagcgca 3060
tcgtggcaca gctgggccag ggagtgtacc gcaccctgag cagcaccctg taccgtcgac 3120
ctttcaacat cggcatcaac aaccagcagc tgagcgtgct ggacggcacc gagttcgcct 3180
acggcaccag cagcaacctg cccagcgccg tgtaccgcaa gagcggcacc gtggacagcc 3240
tggacgagat ccccccctcag aacaacaacg tgccacctcg acagggcttc agccaccgtc 3300
tgagccacgt gagcatgttc cgcagtggct tcagcaacag cagcgtgagc atcatccgtg 3360
cacctatgtt cagctggatt caccgcagtg ccgagttcaa caacatcatc cccagcagcc 3420
agatcaccca gatccccctg accaagagca ccaacctggg cagcggcacc agcgtggtga 3480
agggccccgg cttcaccggc ggcgacatcc tgcgccgcac cagccccggc cagatcagca 3540
ccctgcgcgt gaacatcacc gccccctga gccagcgcta ccgcgtccgc atccgctacg 3600
ccagcaccac caacctgcag ttccacacca gcatcgacgg ccgccccatc aaccagggca 3660
acttcagcgc caccatgagc agcggcagca acctgcagag cggcagcttc cgcaccgtgg 3720
gcttcaccac cccttcaac ttcagcaacg gcagcagcgt gttcaccctg agcgcccacg 3780
tgttcaacag cggcaacgag gtgtacatcg accgcatcga gttcgtgccc gccgaggtga 3840
ccttcgaggc cgagtacgac ctggagaggg ctcagaaggc cgtgaacgag ctgttcacca 3900
gcagcaacca gatcggcctg aagaccgacg tgaccgacta ccacatcgac caggtgagca 3960
acctggtgga gtgcttaagc gacgagttct gcctggacga gaagaaggag ctgagcgaga 4020
aggtgaagca cgccaagcgc ctgagcgacg agcgcaacct gctgcaggac cccaacttcc 4080
gcggcatcaa ccgccagctg gaccgcggct ggcgaggcag caccgatatc accatccagg 4140
gcggcgacga cgtgttcaag gagaactacg tgaccctgct gggcaccttc gacgagtgct 4200
accccaccta cctgtaccag aagatcgacg agagcaagct gaaggcctac acccgctacc 4260
agctgcgcgg ctacatcgag gacagccagg acctggaaat ctacctgatc cgctacaacg 4320
cgaagcacga gaccgtgaac gtgcccggca ccggcagcct gtggcccctg agcgcccccca 4380
gccccatcgg caagtgcggg gagccgaatc gatgcgctcc gcacctggag tggaacccgg 4440
acctagactg cagctgcagg gacggggaga agtgcgccca ccacagccac cacttcagcc 4500

-continued

```
tggacatcga cgtgggctgc accgacctga acgaggacct gggcgtgtgg gtgatcttca   4560
agatcaagac ccaggacggc cacgcccgcc tgggcaatct agagttcctg gaggagaagc   4620
ccctggtggg cgaggccctg gcccgcgtga agcgtgctga gaagaagtgg cgcgacaagc   4680
gcgagaagct ggagtgggag accaacatcg tgtacaagga ggccaaggag agcgtggacg   4740
ccctgttcgt gaacagccag tacgaccgcc tgcaggccga caccaacatc gccatgatcc   4800
acgccgccga caagcgcgtg cacagcattc gcgaggccta cctgcccgag ctgagcgtga   4860
tccccggtgt gaacgccgcc atcttcgagg aactcgaggg ccgcatcttc accgccttca   4920
gcctgtacga cgcccgcaac gtgatcaaga acggcgactt caacaacggc ctgagctgct   4980
ggaacgtgaa gggccacgtg gacgtggagg agcagaacaa ccaccgcagc gtgctggtgg   5040
tgcccgagtg ggaggccgag gtgagccagg aggtgcgcgt gtgccccggc cgcggctaca   5100
tcctgcgcgt gaccgcctac aaggagggct acggcgaggg ctgcgtgacc atccacgaga   5160
tcgagaacaa caccgacgaa ctcaagttca gcaactgcgt ggaggaggag gtttacccca   5220
acaacaccgt gacctgcaac gactacaccg cgacccagga ggagtacgaa ggcacctaca   5280
cctctcgcaa caggggttac gacggcgcct acgagtccaa cagctccgtg ccagctgact   5340
acgccagcgc ctacgaggag aaagcctaca ccgacggtag acgcgacaac ccatgtgaga   5400
gcaacagagg ctacggcgac tacacccccc tgcccgctgg atacgtgacc aaggagctgg   5460
agtacttccc cgagaccgac aaggtgtgga tcgagattgg cgagaccgag ggcaccttca   5520
tcgtggacag cgtggagctg ctgctgatgg aggagtagta gatccatctg cagatgagct   5580
ctagatcccc gaatttcccc gatcgttcaa acatttggca ataaagtttc ttaagattga   5640
atcctgttgc cggtcttgcg atgattatca tataatttct gttgaattac gttaagcatg   5700
taataattaa catgtaatgc atgacgttat ttatgagatg ggtttttatg attagagtcc   5760
cgcaattata catttaatac gcgatagaaa acaaaatata gcgcgcaaac taggataaat   5820
tatcgcgcgc ggtgtcatct atgttactag atcgggaatt gggtaccgaa ttcactggcc   5880
gtcgttttac aacgtcgtga ctgggaaaac cctggcgtta cccaacttaa tcgccttgca   5940
gcacatcccc ctttcgccag ctggcgtaat agcgaagagg cccgcaccga tcgcccttcc   6000
caacagttgc gcagcctgaa tggcgaatgg cgcctgatgc ggtattttct ccttacgcat   6060
ctgtgcggta tttcacaccg catatggtgc actctcagta caatctgctc tgatgccgca   6120
tagttaagcc agccccgaca cccgccaaca cccgctgacg cgccctgacg ggcttgtctg   6180
ctcccggcat ccgcttacag acaagctgtg accgtctccg ggagctgcat gtgtcagagg   6240
ttttcaccgt catcaccgaa acgcgcgaga cgaaagggcc tcgtgatacg cctattttta   6300
taggttaatg tcatgataat aatggtttct tagacgtcag gtggcacttt tcggggaaat   6360
gtgcgcggaa cccctatttg tttatttttc taaatacatt caaatatgta tccgctcatg   6420
agacaataac cctgataaat gcttcaatgg cgcgccgcgg ccgcttaaga atattgaaaa   6480
aggaagagta tgagtattca acatttccgt gtcgccctta ttcccttttt tgcggcattt   6540
tgccttcctg tttttgctca cccagaaacg ctggtgaaag taaaagatgc tgaagatcag   6600
ttgggtgcac gagtgggtta catcgaactg gatctcaaca gcggtaagat ccttgagagt   6660
tttcgccccg aagaacgttt tccaatgatg agcactttta aagttctgct atgtggcgcg   6720
gtattatccc gtattgacgc cgggcaagag caactcggtc gccgcataca ctattctcag   6780
aatgacttgg ttgagtactc accagtcaca gaaaagcatc ttacggatgg catgacagta   6840
agagaattat gcagtgctgc cataaccatg agtgataaca ctgcggccaa cttacttctg   6900
```

-continued acaacgatcg gaggaccgaa ggagctaacc gctttttgc acaacatggg ggatcatgta 6960
actcgccttg atcgttggga accggagctg aatgaagcca taccaaacga cgagcgtgac 7020
accacgatgc ctgtagcaat ggcaacaacg ttgcgcaaac tattaactgg cgaactactt 7080
actctagctt cccggcaaca attaatagac tggatggagg cggataaagt tgcaggacca 7140
cttctgcgct cggcccttcc ggctggctgg tttattgctg ataaatctgg agccggtgag 7200
cgtgggtctc gcggtatcat tgcagcactg gggccagatg gtaagccctc ccgtatcgta 7260
gttatctaca cgacggggag tcaggcaact atggatgaac gaaatagaca gatcgctgag 7320
ataggtgcct cactgattaa gcattggtaa ctgtcagacc aagtttactc atatatactt 7380
tagattgatt taaaacttca tttttaattt aaaaggatct aggtgaagat cctttttgat 7440
aatctcatga ccaaaatccc ttaacgtgag ttttcgttcc actgagcgtc agaccccgta 7500
gaaaagatca aaggatcttc ttgagatcct ttttttctgc gcgtaatctg ctgcttgcaa 7560
acaaaaaaac caccgctacc agcggtggtt tgtttgccgg atcaagagct accaactctt 7620
tttccgaagg taactggctt cagcagagcg cagataccaa atactgtcct tctagtgtag 7680
ccgtagttag gccaccactt caagaactct gtagcaccgc ctacatacct cgctctgcta 7740
atcctgttac cagtggctgc tgccagtggc gataagtcgt gtcttaccgg gttggactca 7800
agacgatagt taccggataa ggcgcagcgg tcgggctgaa cggggggttc gtgcacacag 7860
cccagcttgg agcgaacgac ctacaccgaa ctgagatacc tacagcgtga gctatgagaa 7920
agcgccacgc ttcccgaagg gagaaaggcg gacaggtatc cggtaagcgg cagggtcgga 7980
acaggagagc gcacgaggga gcttccaggg ggaaacgcct ggtatcttta tagtcctgtc 8040
gggtttcgcc acctctgact tgagcgtcga tttttgtgat gctcgtcagg ggggcggagc 8100
ctatggaaaa acgccagcaa cgcggccttt ttacggttcc tggccttttg ctggcctttt 8160
gctcacatgt tctttcctgc gttatcccct gattctgtgg ataaccgtat taccgccttt 8220
gagtgagctg ataccgctcg ccgcagccga acgaccgagc gcagcgagtc agtgagcgag 8280
gaagcggaag agcttaagcg gccgcggcgc gccgcccaat acgcaaaccg cctctccccg 8340
cgcgttggcc gattcattaa tgcagctggc acgacaggtt tcccgactgg aaagcgggca 8400
gtgagcgcaa cgcaattaat gtgagttagc tcactcatta ggcaccccag gctttacact 8460
ttatgcttcc ggctcgtatg ttgtgtggaa ttgtgagcgg ataacaattt cacacaggaa 8520
acagctatga ccatgattac gccaag 8546

<210> SEQ ID NO 19
<211> LENGTH: 23
<212> TYPE: DNA
<213> ORGANISM: Artificial sequence
<220> FEATURE:
<223> OTHER INFORMATION: forward primer ABT P1 forw

<400> SEQUENCE: 19
cgaccagcgc gacatgcatg gca 23

<210> SEQ ID NO 20
<211> LENGTH: 23
<212> TYPE: DNA
<213> ORGANISM: Artificial sequence
<220> FEATURE:
<223> OTHER INFORMATION: reverse primer ABT P2 rev

<400> SEQUENCE: 20
accccagggc gtacgacaag gcc 23

<210> SEQ ID NO 21
<211> LENGTH: 29
<212> TYPE: DNA
<213> ORGANISM: Artificial sequence
<220> FEATURE:
<223> OTHER INFORMATION: oligonucleotide pABT mut1

<400> SEQUENCE: 21
gatggccgga ttgggctccc ggggtggag 29

<210> SEQ ID NO 22
<211> LENGTH: 29
<212> TYPE: DNA
<213> ORGANISM: Artificial sequence
<220> FEATURE:
<223> OTHER INFORMATION: oligonucleotide pABT mut2

<400> SEQUENCE: 22
ctgggaggcg cgcaaggggc agttcctcg 29

<210> SEQ ID NO 23
<211> LENGTH: 30
<212> TYPE: DNA
<213> ORGANISM: Artificial sequence
<220> FEATURE:
<223> OTHER INFORMATION: oligonucleotide pABT mut3

<400> SEQUENCE: 23
cccaccgccg gagcaccgaa aggccccgcg 30

<210> SEQ ID NO 24
<211> LENGTH: 27
<212> TYPE: DNA
<213> ORGANISM: Artificial sequence
<220> FEATURE:
<223> OTHER INFORMATION: oligonucleotide pABT mut4

<400> SEQUENCE: 24
gtcacccggg agcacttccc ggcgccg 27

<210> SEQ ID NO 25
<211> LENGTH: 27
<212> TYPE: DNA
<213> ORGANISM: Artificial sequence
<220> FEATURE:
<223> OTHER INFORMATION: oligonucleotide pABT mut5

<400> SEQUENCE: 25
cattgggccg agcacggctt cttccgc 27

<210> SEQ ID NO 26
<211> LENGTH: 31
<212> TYPE: DNA
<213> ORGANISM: Artificial sequence
<220> FEATURE:
<223> OTHER INFORMATION: oligonucleotide pABT mut6

<400> SEQUENCE: 26
ggggtacggt gttcttgagt cgtgaagcga c 31

<210> SEQ ID NO 27
<211> LENGTH: 39
<212> TYPE: DNA
<213> ORGANISM: Artificial sequence
<220> FEATURE:
<223> OTHER INFORMATION: forward primer pABT amp1

<400> SEQUENCE: 27
gcgtctagag ggaccccgac cagcgcgaca tgcatggca 39

<210> SEQ ID NO 28
<211> LENGTH: 36
<212> TYPE: DNA
<213> ORGANISM: Artificial sequence
<220> FEATURE:
<223> OTHER INFORMATION: reverse primer pABT amp2

<400> SEQUENCE: 28
accccagggc gtacgacaag gccccaccat gggcgc 36

<210> SEQ ID NO 29
<211> LENGTH: 45
<212> TYPE: DNA
<213> ORGANISM: Artificial sequence
<220> FEATURE:
<223> OTHER INFORMATION: forward primer ABT P4

<400> SEQUENCE: 29
tatatagagc tcgaatcgaa gaagccacac tgtaaatctg ccggg 45

<210> SEQ ID NO 30
<211> LENGTH: 45
<212> TYPE: DNA
<213> ORGANISM: Artificial sequence
<220> FEATURE:
<223> OTHER INFORMATION: reverse primer ABT P5

<400> SEQUENCE: 30
agcaaggcat atgcagcagc tgctggtcgg accgggccct atata 45

<210> SEQ ID NO 31
<211> LENGTH: 29
<212> TYPE: DNA
<213> ORGANISM: Artificial sequence
<220> FEATURE:
<223> OTHER INFORMATION: oligonucleotide ABTt m1

<400> SEQUENCE: 31
gtcatgcatg ggcatgtgaa ggaggagcc 29

<210> SEQ ID NO 32
<211> LENGTH: 29
<212> TYPE: DNA
<213> ORGANISM: Artificial sequence
<220> FEATURE:
<223> OTHER INFORMATION: oligonucleotide ABTt m2

<400> SEQUENCE: 32
gttgcatgca tgctgcatgg cgtcgagat 29

<210> SEQ ID NO 33
<211> LENGTH: 873
<212> TYPE: DNA
<213> ORGANISM: Zea mays

<400> SEQUENCE: 33
tgggaggcgc gcatggggca gttcctcggc aagaaggcgt acgacaaggc cgcgatcaaa 60
tgcaacggta gagaggccgt gacgaacttc gagcccagca cgtacgacgg ggagctgctg 120

-continued

```
ctgactgctg aagctagcgc agaagttgct gacgacgttg atctgaactt gagcatctcg    180

caaccggcat cgtcccagag ccccaaaaga gacaagaact gccttggtcc gcagctccac    240

caccaccatg ggcggccgtt tgacggctcc gccgttctga agaaaaccaa gatcgatgct    300

ccgtctgagc tgtcgtcggc gggccgccct caccggtcgt tcctccctca tctcgtggct    360

gccgagcatc taccgcctcg gtctcacccc ttcttcatca cacaccatga gagtgatgca    420

tcaagaagag atcccagctg ggcagcagca gcagcatgga aggtgaccgc agctgcacct    480

cctcctccta ccaccaccct gttgccgttg ccgctgccgt cgacgtcgtc cgctgcagca    540

tcatcaggat tctccaatac cgccacgaca gctgccgccg ccccatcggc cgcctcctcc    600

cgccggttcg acccgccgcc accgtcgtcg tcctcctcct cgagccatca ccaccaccac    660

caccgccgct gagaatcgaa gaagccacac tgtaaatctg ccgggaagcg gctggtggca    720

tccggcccgc tcctccctcc gggcgccgca actttttttcg atcggttttg cgccgcccgg    780

gacgggttgt agttgatcga ttggattctt cataactgta tttgcgtact gcttacacta    840

cccaagtgaa atcgaaaatg gcgccttctc tcg                                 873
```

<210> SEQ ID NO 34
<211> LENGTH: 921
<212> TYPE: DNA
<213> ORGANISM: Zea mays

<400> SEQUENCE: 34

```
gaggcgcgca tggggcagtt cctcggcaag aagtacatat atcttgggct attcgacagc     60

gaagtagagg ctgcaagggc gtacgacaag gccgcgatca aatgcaacgg tagagaggcc    120

gtgacgaact tcgagcccag cacgtacgac ggggagctgc tgctgactgc tgaagctagc    180

gcagaagttg ctgacgacgt tgatctgaac ttgagcatct cgcaaccggc atcgtcccag    240

agccccaaaa gagacaagaa ctgccttggt ccgcagctcc accaccacca tgggcggccg    300

tttgacggct ccgccgttct gaagaaaacc aagatcgatg ctccgtctga gctgtcgtcg    360

gcgggccgcc ctcaccggtc gttcctccct catctcgtgg ctgccgagca tctaccgcct    420

cggtctcacc ccttcttcat cacacaccat gagagtgatg catcaagaag agatcccagc    480

tgggcagcag cagcagcatg gaaggtgacc gcagctgcac ctcctcctcc taccaccacc    540

ctgttgccgt tgccgctgcc gtcgacgtcg tccgctgcag catcatcagg attctccaat    600

accgccacga cagctgccgc cgccccatcg gccgcctcct cccgccggtt cgacccgccg    660

ccaccgtcgt cgtcctcctc ctcgagccat caccaccacc accaccgccg ctgagaatcg    720

aagaagccac actgtaaatc tgccgggaag cggctggtgg catccggccc gctcctccct    780

ccgggcgccg caactttttt cgatcggttt tgcgccgccc gggacgggtt gtagttgatc    840

gattggattc ttcataactg tatttgcgta ctgcttacac tacccaagtg aaatcgaaaa    900

tggcgccttc tctcgttgaa t                                              921
```

<210> SEQ ID NO 35
<211> LENGTH: 2644
<212> TYPE: DNA
<213> ORGANISM: Zea mays

<400> SEQUENCE: 35

```
gcgtctagag ggaccccgac cagcgcgaca tgcatggcat ggcaaactat atatcgtcat     60

catcattatt atcatctgac cctctttttt tttcactctc actcccatgt ttttattccc    120

gggcggggcc gtgtgggtgt gggttgggat ggccggattg ggctcccggg gtggagaaat    180
```

```
gacaaatcca ggcccgcagg cggccaccca ccaaatcgga cgacgcaggg tgcccaaatc    240

aggaaggatt ttaaggttaa ccggccaccg gcggtgaccg acgccccacc ccactctcct    300

tctcctattc tatctatata tcacccgcct ctttttttctc cctcactccg ccacaccttc    360

cctcttcttc ctcagctccg tcgcccaccg ccggagcacc gaaaggcccc gcgcccgccg    420

cctttcctgt aaaaaaccca acctttagct agctaaccgc tcctcttctc cccctactcc    480

ccttgcccaa atcagagaag atatttaacg gaggagggga aggagaggat atttagctga    540

ttgttgattg gtggtccggg gtacggtgtt cttgagtcgt gaagcgaccg tacagtggct    600

agggccgtct ccgggttgcg tgcaggatgg tcgtcagaga tcgggagtga ggaggcagct    660

cgtggtcgtg gaggctaaat gtaccgcaag aacgactcgg cactctcctg tttctacctc    720

ttcctcctct ggttcttctt cttgaaatag accagcgcca gccaccaggt agctacctac    780

tagctagcag cccagttgcg actggggacg ggctgctgct tgcaagttgg aatcttggag    840

caggagcaga ggagcgggag atggagctgg atctgaacgt ggccgaggtg gcgccggaga    900

agccatcggc ggcgctggag gcgagcgact cggggtcctc gggctcgtcg gtgctgaacg    960

cggaggcggc atcggcgggc ggcggggggc ccgcgccggg ggaggagggg tcaagctcga   1020

cgccggccgt gctcgagttc agcatcctca ggagcgacag cgacgcggcc ggcgcggacg   1080

ccgacgacgg cgacgccacg ccgtcgccac ctcgccacca ccagcagcag ctcgtcaccc   1140

gggagcactt cccggcgccg cagcattggg ccgagcacgg cttcttccgc gccggcccgc   1200

agcagcagcc ggacatcagg gtcctgccgc acccgcaccc gtaccgcccc cgccgccgc   1260

ccgcgcagcc gcagcaggcc aagaagagcc gccgcggccc gcgctcccgc agctcgcagt   1320

accgcggcgt caccttctac cgccgcaccg gccgctggga gtcccacatc tggtcagtag   1380

cactgcaagc tcaccatgcg ccctttcacc taccgaccaa taatcgcttg tgattctgac   1440

acccaaatgt ttcgtcttcc tgtgctgtcc tgttcctcgg aaatggcagg gattgcggga   1500

agcaggtgta cttaggtgag cagcaataag cagatcgatc tgcagcataa atttcccgtt   1560

attaactagt tcgtgatctc gatcgaatgg cctaattaac cgattcggtg atctggccga   1620

tggccaatct acgcaggtgg attcgacact gctcatgccg ctgcaaggta acgatcaatc   1680

catccatcca cccttgtcta gctaccccac cgaccggccg gattaatgga ccgctagctc   1740

tcgggacggg cttgctgcag ggcgtacgac cgagcggcga tcaagttccg cggcgtcgac   1800

gccgacataa acttcaacct cagcgactac gacgacgata tgaagcaggt acatacacga   1860

gtgttcttgc agctagcacc gactgaaaca tctgctgaac gtacacgcat ggccctgtgc   1920

accagatgaa gagcctgtcc aaggaggagt tcgttcacgc cctgcggcgg cagagcaccg   1980

gcttctcccg cggcagctcc aagtacaggg gcgtcaccct gcacaagtgc ggccgctggg   2040

aggcgcgcaa ggggcagttc ctcggcaaga agtaagaaac aacacttcgt ttgcaggcgc   2100

tgtactttgc tgcagattat ttcatttcat ccttgcatgt gcctttcctt tccatccact   2160

cacttgatgg ctgtagtctc gatagagttc gttcgttcgt acttcgcacc agatgaactc   2220

ccacgcacat gatttagtac tagttttacc atgcattgtt cagtaaaagt atatgcttgc   2280

ttgatcagtg gttgtttcaa tcagaagatt aaaaaaacgg aatattaata taaaaaaaag   2340

gggaagtggc tagggaattc ctcagtccta gctagctagc tcaccggtgg gaacgccatg   2400

cttggcttgg gtgcaggtac atatatcttg ggctattcga cagcgaagta gaggctgcaa   2460

ggttgttcac ctcggacgat tctgccattt gttcatatac accatgcctt ttgatttctc   2520
```

-continued tcttgcaatt tctcttcttt tatcatggct tttgattccc aaagggttga gtaccgactc 2580
gatattcgat tctccctgcc gtttcgtgac cccagggcgt acgacaaggc cccaccatgg 2640
gcgc 2644

<210> SEQ ID NO 36
<211> LENGTH: 1069
<212> TYPE: DNA
<213> ORGANISM: Zea mays

<400> SEQUENCE: 36
tatatagagc tcgaatcgaa gaagccacac tgtaaatctg ccgggaagcg gctggtggca 60
tccggcccgc tcctccctcc gggcgccgca acttttttcg atcggttttg cgccgcccgg 120
gacgggttgt agttgatcga ttggattctt cataactgta tttgcgtact gcttacacta 180
cccaagtgaa atcgaaaatg gcgccttctc tcgttgaata aattgcacgt acgctactcg 240
atccgctgcg gctcttgctg gagtggccgc cgccgctata gatagaagga tcaagccaag 300
gaatctgtca tgcatgggca tgtgaaggag gagcctcctg caatgtttag tcttttttgg 360
tcgacgccca ccagagatat acgcactaga tttcatatag ctgagctaga tcgattccgt 420
tgcatgcatg ctgcatggcg tcgagattcg agctagcacc gcctgttcat catcgaccga 480
tccattctga tcgattcccc tctcgagctt tcacgaactg aacctaccta gtgagggtga 540
cgcctaacgc ctagtgcgcg cgcgtgggtc tccgatgtca gtggccgcac gcgcgcgcgc 600
gttctcgaga tcgcatgtgg tcatagcgca gcaggtttgc cctcagaacc tacagcaact 660
cgaccaccgg tttggatttc ttcttttttc aaggatatga tcggagagag agagctacct 720
aggcgtcgtc cttgttttct tgtatcgcat gtggtgtggg tctctctcct cctttcgtac 780
gcacgcatga ttccattctt accccccctc gagatcgaga ggaaatatat tgctatttta 840
tacacacacg gcgcccccag ctatacgtca ctgcttacgt taattccccc accggatagt 900
agttgtttaa tggcccaaac aaaccttgtt gttgcatgca tcatggacca aacaaaatac 960
atagttagtt aaatattact gttatatata caactaataa taattatatt attagttaaa 1020
acaaagcaag gcatatgcag cagctgctgg tcggaccggg ccctatata 1069

<210> SEQ ID NO 37
<211> LENGTH: 8599
<212> TYPE: DNA
<213> ORGANISM: Artificial sequence
<220> FEATURE:
<223> OTHER INFORMATION: ZmABP3-Cry1AbG6 Assembly construct

<400> SEQUENCE: 37
cggcgcgccg aaagtagcaa acaacaggtt catgtgcact ataaaaagac aaaattctcg 60
agtttcatct tttattccac ataagcctta tattttccat tttcatatga tttttagttt 120
aagtttgtgt cttaactttt tcgttaatac gtaattctat gcattatgga tgcgtgaagt 180
atttttgttt aaaaaaatga aatgtcaaaa tacgttttgt gatctatttc catgttttca 240
cctaacaggt ggtttttact atatattctg ccataactct agccttagat gtaaatcgaa 300
aaaaaatgag agatgagctg gagatagcct tagatgaagc gtctgaaata taaaagaaag 360
agtaatgttg aacgcagtag gtgtagcagc tgtagttcca tctctaggaa agggaactgc 420
aatccgggct ccgggcctcg cgcaatctgg cctgtcgtgt agatgcagcc ctgtccatga 480
cggcccaagc aacgcccgcg gctctcgatc caccacggaa cccactccga cacacactga 540
cacacacatg ctggatgtgg atgtgctgtc caattattag tagcaattcg gtaggcacag 600

-continued

```
gcacgtactg gccggtgttt tagctgtaag taccgaacca atcacggtta agaaccgatt    660
aatccgtgcc cagccgccga gtgcgttcgt acgtgcatcg gatgcactgc atgaattgag    720
agcatcatca tatcatacgc aggagtagta cgacgccgct gctgtcttgt ccggctaatg    780
ctttgctcac agattagtcc atcgcccacg gtcggtgtgg tgtggatcgc tgatgccact    840
gctttttgtt tggtttttat tcccctgata atcctccgcg tccctgaatg tatctattta    900
ttttcattcc gaaatccctt tcacgaaaaa gaaaacgaat aaaaagagag ttacgaatac    960
gcttccggcg gcccacatca ccttccagcg aacatcgcgc cgcgctgacg tgtcgcccat   1020
cgcggccgtc catatcgcca tccgacgacc gtggaagctg gcagcggccg ctccgttccg   1080
tcgaaggggc aggtcagtca ggtcacccac acggccacac ccgcgcgggg gatacgcggt   1140
ggaaaacccg gcgaccacat caaaacacga ggcgtctccc gcaggactgg tcactcggca   1200
cgcaggcaga ggcagcacag cagcagccag ctccatccat cctctttccc ctcctcgctt   1260
cgcttcctcg gcggattcct cctccctcgg ccgtccccgt ccccttcttc gccgcgccag   1320
ctcgcccgag ttggtaaggc cccctccacc cctccgcttc ccctcccccg ggcgcgctct   1380
ggcttcctcc ccggatcggc gcggggcgtg ctggctccgc gcctgatttc gggccttttg   1440
tttccttctc gcggagcgct cgtgtaacgc ttcggatcta gctggattca ggcgggatcg   1500
cggccgctcg gcttcctcgt ggcctgattc gtggttttcc tcggggaggg aatcctgatc   1560
ggatcatcgg gattcctcgt gcggccggga cacgcttgcg agccagaaac atagtctgcg   1620
tggccgggat tccacgatct gtgatctaga cgtcgggcgc ttcgtctatg tgctcgctgc   1680
aggctgtggc gtactggcgt ggtgcgcggc cgctatggat ccgtgcttgt ttgttcgccc   1740
tgtagcgtgt gaaatcgagc tgtgtagatc tatggtctgc gaggtgcggt ggcggtggaa   1800
tctcggttga tctttacctc agcggcgcca gtgtagctcg tgtggctgca gttcatctgc   1860
gaatttggct ctcggcggct taggtcgcgg agcttggatt atggagcacc agctgcagcg   1920
tgaccctgtt ggttctcatg tggatctgtt ggctgaggtt gcagacttca agtgccactg   1980
ccattgaccg gagctgctgc acgattatac tggaatatct agcggtagta tactctgcta   2040
gtactcaata cgggtctcct gacaaatgtc tttcgtgttt agggacctag cactctagtg   2100
tcaagactat ttgctggaat atctaatatt agcagtttct gtagtggctc agttgcagcc   2160
tggtttagaa tgatggggac agttggctgt gccatgcaaa ataaagtgtg tgaaagcaac   2220
tgcctcttaa actatgggtg gtgcaagcag gttatttgaa gggactctcc acactgtatc   2280
tccagttaac tatgactgaa cttgtggtcg caggcaaacc caccatggac aacaacccca   2340
acatcaacga gtgcatcccc tacaactgcc tgagcaaccc cgaggtggag gtgctgggcg   2400
gcgagcgcat cgagaccggc tacaccccca tcgacatcag cctgagcctg acccagttcc   2460
tgctgagcga gttcgtgccc ggcgccggct tcgtgctggg cctggtggac atcatctggg   2520
gcatcttcgg ccccagccag tgggacgcct tcctggtgca gatcgagcag ttgataaacc   2580
aacgcataga ggaattcgcc cgcaaccagg ccatcagccg cctggagggc ctgagcaacc   2640
tgtaccaaat ctacgccgag agcttccgcg agtgggaggc cgaccccacc aaccccgccc   2700
tgcgcgagga gatgcgcatc cagttcaacg acatgaacag cgccctgacc accgccatcc   2760
ccctgttcgc cgtgcagaac taccaggtgc ccctgctgag cgtgtacgtg caggccgcca   2820
acctgcacct gagcgtgctg cgcgacgtca gcgtgttcgg ccagcgctgg ggcttcgacg   2880
ccgccaccat caacagccgc tacaacgacc tgacccgcct gatcggcaac tacaccgacc   2940
```

acgccgtgcg ctggtacaac accggcctgg agcgcgtgtg gggtcccgac agccgcgact 3000
ggatcaggta caaccagttc cgccgcgagc tgaccctgac cgtgctggac atcgtgagcc 3060
tgttccccaa ctacgacagc cgcacctacc ccatccgcac cgtgagccag ctgacccgcg 3120
agatttacac caaccccgtg ctggagaact tcgacggcag cttccgcggc agcgcccagg 3180
gcatcgaggg cagcatccgc agcccccacc tgatggacat cctgaacagc atcaccatct 3240
acaccgacgc ccaccgcggc gagtactact ggagcggcca ccagatcatg gccagccccg 3300
tcggcttcag cggccccgag ttcaccttcc ccctgtacgg cacgatgggc aacgctgcac 3360
ctcagcagcg catcgtggca cagctgggcc agggagtgta ccgcaccctg agcagcaccc 3420
tgtaccgtcg acctttcaac atcggcatca acaaccagca gctgagcgtg ctggacggca 3480
ccgagttcgc ctacggcacc agcagcaacc tgcccagcgc cgtgtaccgc aagagcggca 3540
ccgtggacag cctggacgag atccccccto agaacaacaa cgtgccacct cgacagggct 3600
tcagccaccg tctgagccac gtgagcatgt tccgcagtgg cttcagcaac agcagcgtga 3660
gcatcatccg tgcacctatg ttcagctgga ttcaccgcag tgccgagttc aacaacatca 3720
tccccagcag ccagatcacc cagatccccc tgaccaagag caccaacctg ggcagcggca 3780
ccagcgtggt gaagggcccc ggcttcaccg gcggcgacat cctgcgccgc accagccccg 3840
gccagatcag caccctgcgc gtgaacatca ccgcccccct gagccagcgc taccgcgtcc 3900
gcatccgcta cgccagcacc accaacctgc agttccacac cagcatcgac ggccgcccca 3960
tcaaccaggg caacttcagc gccaccatga gcagcggcag caacctgcag agcggcagct 4020
tccgcaccgt gggcttcacc accccottca acttcagcaa cggcagcagc gtgttcaccc 4080
tgagcgccca cgtgttcaac agcggcaacg aggtgtacat cgaccgcatc gagttcgtgc 4140
ccgccgaggt gaccttcgag gccgagtacg acctggagag ggctcagaag gccgtgaacg 4200
agctgttcac cagcagcaac cagatcggcc tgaagaccga cgtgaccgac taccacatcg 4260
accaggtgag caacctggtg gagtgcttaa gcgacgagtt ctgcctggac gagaagaagg 4320
agctgagcga gaaggtgaag cacgccaagc gcctgagcga cgagcgcaac ctgctgcagg 4380
accccaactt ccgcggcatc aaccgccagc tggaccgcgg ctggcgaggc agcaccgata 4440
tcaccatcca gggcggcgac gacgtgttca aggagaacta cgtgaccctg ctgggcacct 4500
tcgacgagtg ctaccccacc tacctgtacc agaagatcga cgagagcaag ctgaaggcct 4560
acacccgcta ccagctgcgc ggctacatcg aggacagcca ggacctggaa atctacctga 4620
tccgctacaa cgcgaagcac gagaccgtga acgtgcccgg caccggcagc ctgtggcccc 4680
tgagcgcccc cagccccatc ggcaagtgcc accacagcca ccacttcagc ctggacatcg 4740
acgtgggctg caccgacctg aacgaggacc tgggcgtgtg ggtgatcttc aagatcaaga 4800
cccaggacgg ccacgcccgc ctgggcaatc tagagttcct ggaggagaag cccctggtgg 4860
gcgaggccct ggcccgcgtg aagcgtgctg agaagaagtg gcgcgacaag cgcgagaagc 4920
tggagtggga gaccaacatc gtgtacaagg aggccaagga gagcgtggac gccctgttcg 4980
tgaacagcca gtacgaccgc ctgcaggccg acaccaacat cgccatgatc cacgccgccg 5040
acaagcgcgt gcacagcatt cgcgaggcct acctgcccga gctgagcgtg atccccggtg 5100
tgaacgccgc catcttcgag gaactcgagg gccgcatcta ggagctcgca tcatgatcat 5160
gcatcatgga ctcggcctac tactgtggat ttgtatgcca ttatagactt ggtgctgtga 5220
aagactgctt gatgatttgc gggtttgttg ctgtgtaaaa aaaggtccct tggctcccag 5280
aagaccatga aggttcggat ctatcatgta attccttgtt atctgccaat tatgtatgga 5340

-continued

```
ctatggacat gtgttgcgct gttcaactta ctactacaaa taagtaatcg atatgttccc   5400
ttcccatgtc tcggtgacaa ttgtctggag aagcttaggg gtcgtttgtt tgggattatg   5460
tctggagaaa cttattttaa actaagtgtg agttcaagtt aagttagatt atataatcta   5520
ggcagattat aattccaagc gaacaggtcc ttagtgtttt tggaaaatcc taggtgttct   5580
tttggctaca ttgttgtgtg tgcagatccc ttgttggtct gtaagcgtgg ggaagtaaga   5640
atcgtccgtt tctactgaag acctgctcga gttaggcacc gaggatgccg gtaaccaaac   5700
agagcaatag tgtctctgtg ggcacagtgg agtgtgaatc tgtgtgatgc aaatccgtca   5760
tttgtttagc aaaatttcca gcgttgcatg atgcagtttc tttaacacgg acttaaggga   5820
agggaaaaaa atgttgagcc aggagatcct tcaatgtgtt agactgacgt gatagccaac   5880
taaaccacga cgcaatgttg tcgttaatga caaaaaaact atttgttcct aaatccttgg   5940
cgacattgca tggctgtctc atgagataat ggtctcatct cttatttatc tcttatttat   6000
agccggaagt ggtagtgacc cctgcttgat tgctcgtatg ccatctcaag ttctcaaccg   6060
tgtcgagcag ccattttccc atctcaagcg catcatcgtt tcgtttgacc tcatctgcta   6120
tcctgctcct agtgcaaatc acatgcgaca gaaagtgtgg cgcgccacta gtcccgggcc   6180
catcgatgat atcagatctg gttctatagt gtcacctaaa tcgtatgtgt atgatacata   6240
aggttatgta ttaattgtag ccgcgttcta acgacaatat gtccatatgg tgcactctca   6300
gtacaatctg ctctgatgcc gcatagttaa gccagccccg acacccgcca acacccgctg   6360
acgcgccctg acgggcttgt ctgctcccgg catccgctta cagacaagct gtgaccgtct   6420
ccgggagctg catgtgtcag aggttttcac cgtcatcacc gaaacgcgcg agacgaaagg   6480
gcctcgtgat acgcctattt ttataggtta atgtcatgat aataatggtt tcttagacgt   6540
caggtggcac ttttcgggga aatgtgcgcg gaacccctat ttgtttattt ttctaaatac   6600
attcaaatat gtatccgctc atgagacaat aaccctgata aatgcttcaa taatattgaa   6660
aaaggaagag tatgagtatt caacatttcc gtgtcgccct tattcccttt tttgcggcat   6720
tttgccttcc tgtttttgct cacccagaaa cgctggtgaa agtaaaagat gctgaagatc   6780
agttgggtgc acgagtgggt tacatcgaac tggatctcaa cagcggtaag atccttgaga   6840
gttttcgccc cgaagaacgt tttccaatga tgagcacttt taaagttctg ctatgtggcg   6900
cggtattatc ccgtattgac gccgggcaag agcaactcgg tcgccgcata cactattctc   6960
agaatgactt ggttgagtac tcaccagtca cagaaaagca tcttacggat ggcatgacag   7020
taagagaatt atgcagtgct gccataacca tgagtgataa cactgcggcc aacttacttc   7080
tgacaacgat cggaggaccg aaggagctaa ccgctttttt gcacaacatg ggggatcatg   7140
taactcgcct tgatcgttgg gaaccggagc tgaatgaagc cataccaaac gacgagcgtg   7200
acaccacgat gcctgtagca atggcaacaa cgttgcgcaa actattaact ggcgaactac   7260
ttactctagc ttcccggcaa caattaatag actggatgga ggcggataaa gttgcaggac   7320
cacttctgcg ctcggccctt ccggctggct ggtttattgc tgataaatct ggagccggtg   7380
agcgtgggtc tcgcggtatc attgcagcac tggggccaga tggtaagccc tcccgtatcg   7440
tagttatcta cacgacgggg agtcaggcaa ctatggatga acgaaataga cagatcgctg   7500
agataggtgc ctcactgatt aagcattggt aactgtcaga ccaagtttac tcatatatac   7560
tttagattga tttaaaactt catttttaat ttaaaaggat ctaggtgaag atcctttttg   7620
ataatctcat gaccaaaatc ccttaacgtg agttttcgtt ccactgagcg tcagaccccg   7680
```

-continued

```
tagaaaagat caaaggatct tcttgagatc cttttttct gcgcgtaatc tgctgcttgc   7740

aaacaaaaaa accaccgcta ccagcggtgg tttgtttgcc ggatcaagag ctaccaactc   7800

tttttccgaa ggtaactggc ttcagcagag cgcagatacc aaatactgtt cttctagtgt   7860

agccgtagtt aggccaccac ttcaagaact ctgtagcacc gcctacatac ctcgctctgc   7920

taatcctgtt accagtggct gctgccagtg gcgataagtc gtgtcttacc gggttggact   7980

caagacgata gttaccggat aaggcgcagc ggtcgggctg aacggggggt tcgtgcacac   8040

agcccagctt ggagcgaacg acctacaccg aactgagata cctacagcgt gagctatgag   8100

aaagcgccac gcttcccgaa gggagaaagg cggacaggta tccggtaagc ggcagggtcg   8160

gaacaggaga gcgcacgagg gagcttccag ggggaaacgc ctggtatctt tatagtcctg   8220

tcgggtttcg ccacctctga cttgagcgtc gatttttgtg atgctcgtca ggggggcgga   8280

gcctatggaa aaacgccagc aacgcggcct ttttacggtt cctggccttt tgctggcctt   8340

ttgctcacat gttctttcct gcgttatccc ctgattctgt ggataaccgt attaccgcct   8400

ttgagtgagc tgataccgct cgccgcagcc gaacgaccga gcgcagcgag tcagtgagcg   8460

aggaagcgga agagcgccca atacgcaaac cgcctctccc cgcgcgttgg ccgattcatt   8520

aatgcaggtt aacctggctt atcgaaatta atacgactca ctatagggag accggcctcg   8580

agcagctgaa gcttgcatg                                                8599
```

<210> SEQ ID NO 38
<211> LENGTH: 15162
<212> TYPE: DNA
<213> ORGANISM: Artificial sequence
<220> FEATURE:
<223> OTHER INFORMATION: ZmABP3-Cry1AbG6 binary construct

<400> SEQUENCE: 38

```
taattcctgt ggttggcatg cacatacaaa tggacgaacg gataaacctt ttcacgccct     60

tttaaatatc cgattattct aataaacgct cttttctctt aggtttaccc gccaatatat    120

cctgtcaaac actgatagtt taaactgaag gcgggaaacg acaatctgat catgagcgga    180

gaattaaggg agtcacgtta tgacccccgc cgatgacgcg ggacaagccg ttttacgttt    240

ggaactgaca gaaccgcaac gctgcaggaa ttggccgcag cggccattta aatcaattgg    300

gcgcgccaca ctttctgtcg catgtgattt gcactaggag caggatagca gatgaggtca    360

aacgaaacga tgatgcgctt gagatgggaa aatggctgct cgacacggtt gagaacttga    420

gatggcatac gagcaatcaa gcaggggtca ctaccacttc cggctataaa taagagataa    480

ataagagatg agaccattat ctcatgagac agccatgcaa tgtcgccaag gatttaggaa    540

caaatagttt ttttgtcatt aacgacaaca ttgcgtcgtg gtttagttgg ctatcacgtc    600

agtctaacac attgaaggat ctcctggctc aacatttttt tcccttccct taagtccgtg    660

ttaaagaaac tgcatcatgc aacgctggaa attttgctaa acaaatgacg gatttgcatc    720

acacagattc acactccact gtgcccacag agacactatt gctctgtttg gttaccggca    780

tcctcggtgc ctaactcgag caggtcttca gtagaaacgg acgattctta cttccccacg    840

cttacagacc aacaagggat ctgcacacac aacaatgtag ccaaaagaac acctaggatt    900

ttccaaaaac actaaggacc tgttcgcttg gaattataat ctgcctagat tatataatct    960

aacttaactt gaactcacac ttagtttaaa ataagtttct ccagacataa tcccaaacaa   1020

acgaccccta agcttctcca gacaattgtc accgagacat gggaagggaa catatcgatt   1080

acttatttgt agtagtaagt tgaacagcgc aacacatgtc catagtccat acataattgg   1140
```

-continued

```
cagataacaa ggaattacat gatagatccg aaccttcatg gtcttctggg agccaaggga   1200
cctttttta cacagcaaca aacccgcaaa tcatcaagca gtctttcaca gcaccaagtc   1260
tataatggca tacaaatcca cagtagtagg ccgagtccat gatgcatgat catgatgcga   1320
gctcctagat gcggccctcg agttcctcga agatggcggc gttcacaccg gggatcacgc   1380
tcagctcggg caggtaggcc tcgcgaatgc tgtgcacgcg cttgtcggcg gcgtggatca   1440
tggcgatgtt ggtgtcggcc tgcaggcggt cgtactggct gttcacgaac agggcgtcca   1500
cgctctcctt ggcctccttg tacacgatgt tggtctccca ctccagcttc tcgcgcttgt   1560
cgcgccactt cttctcagca cgcttcacgc gggccagggc ctcgcccacc aggggcttct   1620
cctccaggaa ctctagattg cccaggcggg cgtggccgtc ctgggtcttg atcttgaaga   1680
tcacccacac gcccaggtcc tcgttcaggt cggtgcagcc cacgtcgatg tccaggctga   1740
agtggtggct gtggtggcac ttgccgatgg ggctgggggc gctcaggggc cacaggctgc   1800
cggtgccggg cacgttcacg gtctcgtgct tcgcgttgta gcggatcagg tagatttcca   1860
ggtcctggct gtcctcgatg tagccgcgca gctggtagcg ggtgtaggcc ttcagcttgc   1920
tctcgtcgat cttctggtac aggtaggtgg ggtagcactc gtcgaaggtg cccagcaggg   1980
tcacgtagtt ctccttgaac acgtcgtcgc cgccctggat ggtgatatcg gtgctgcctc   2040
gccagccgcg gtccagctgg cggttgatgc cgcggaagtt ggggtcctgc agcaggttgc   2100
gctcgtcgct caggcgcttg gcgtgcttca ccttctcgct cagctccttc ttctcgtcca   2160
ggcagaactc gtcgcttaag cactccacca ggttgctcac ctggtcgatg tggtagtcgg   2220
tcacgtcggt cttcaggccg atctggttgc tgctggtgaa cagctcgttc acggccttct   2280
gagccctctc caggtcgtac tcggcctcga aggtcacctc ggcgggcacg aactcgatgc   2340
ggtcgatgta cacctcgttg ccgctgttga acacgtgggc gctcagggtg aacacgctgc   2400
tgccgttgct gaagttgaag gggtggtgga agcccacggt gcggaagctg ccgctctgca   2460
ggttgctgcc gctgctcatg gtggcgctga agttgccctg gttgatgggg cggccgtcga   2520
tgctggtgtg gaactgcagg ttggtggtgc tggcgtagcg gatgcggacg cggtagcgct   2580
ggctcagggg ggcggtgatg ttcacgcgca gggtgctgat ctggccgggg ctggtgcggc   2640
gcaggatgtc gccgccggtg aagccggggc ccttcaccac gctggtgccg ctgcccaggt   2700
tggtgctctt ggtcaggggg atctgggtga tctggctgct ggggatgatg ttgttgaact   2760
cggcactgcg gtgaatccag ctgaacatag gtgcacggat gatgctcacg ctgctgttgc   2820
tgaagccact gcggaacatg ctcacgtggc tcagacggtg gctgaagccc tgtcgaggtg   2880
gcacgttgtt gttctgaggg gggatctcgt ccaggctgtc cacggtgccg ctcttgcggt   2940
acacggcgct gggcaggttg ctgctggtgc cgtaggcgaa ctcggtgccg tccagcacgc   3000
tcagctgctg gttgttgatg ccgatgttga aaggtcgacg gtacagggtg ctgctcaggg   3060
tgcggtacac tccctggccc agctgtgcca cgatgcgctg ctgaggtgca gcgttgccca   3120
tcgtgccgta caggggggaag gtgaactcgg ggccgctgaa gccgacgggg ctggccatga   3180
tctggtggcc gctccagtag tactcgccgc ggtgggcgtc ggtgtagatg gtgatgctgt   3240
tcaggatgtc catcaggtgg gggctgcgga tgctgccctc gatgccctgg gcgctgccgc   3300
ggaagctgcc gtcgaagttc tccagcacgg ggttggtgta aatctcgcgg gtcagctggc   3360
tcacggtgcg gatggggtag gtgcggctgt cgtagttggg gaacaggctc acgatgtcca   3420
gcacggtcag ggtcagctcg cggcggaact ggttgtacct gatccagtcg cggctgtcgg   3480
```

gaccccacac gcgctccagg ccggtgttgt accagcgcac ggcgtggtcg gtgtagttgc 3540
cgatcaggcg ggtcaggtcg ttgtagcggc tgttgatggt ggcggcgtcg aagccccagc 3600
gctggccgaa cacgctgacg tcgcgcagca cgctcaggtg caggttggcg gcctgcacgt 3660
acacgctcag caggggcacc tggtagttct gcacggcgaa cagggggatg gcggtggtca 3720
gggcgctgtt catgtcgttg aactggatgc gcatctcctc gcgcagggcg gggttggtgg 3780
ggtcggcctc ccactcgcgg aagctctcgg cgtagatttg gtacaggttg ctcaggccct 3840
ccaggcggct gatggcctgg ttgcgggcga attcctctat gcgttggttt atcaactgct 3900
cgatctgcac caggaaggcg tcccactggc tggggccgaa gatgccccag atgatgtcca 3960
ccaggcccag cacgaagccg gcgccgggca cgaactcgct cagcaggaac tgggtcaggc 4020
tcaggctgat gtcgatgggg gtgtagccgg tctcgatgcg ctcgccgccc agcacctcca 4080
cctcggggtt gctcaggcag ttgtagggga tgcactcgtt gatgttgggg ttgttgtcca 4140
tggtgggttt gcctgcgacc acaagttcag tcatagttaa ctggagatac agtgtggaga 4200
gtcccttcaa ataacctgct tgcaccaccc atagtttaag aggcagttgc tttcacacac 4260
tttattttgc atggcacagc caactgtccc catcattcta aaccaggctg caactgagcc 4320
actacagaaa ctgctaatat tagatattcc agcaaatagt cttgacacta gagtgctagg 4380
tccctaaaca cgaaagacat ttgtcaggag acccgtattg agtactagca gagtatacta 4440
ccgctagata ttccagtata atcgtgcagc agctccggtc aatggcagtg gcacttgaag 4500
tctgcaacct cagccaacag atccacatga gaaccaacag ggtcacgctg cagctggtgc 4560
tccataatcc aagctccgcg acctaagccg ccgagagcca aattcgcaga tgaactgcag 4620
ccacacgagc tacactggcg ccgctgaggt aaagatcaac cgagattcca ccgccaccgc 4680
acctcgcaga ccatagatct acacagctcg atttcacacg ctacagggcg aacaaacaag 4740
cacggatcca tagcggccgc gcaccacgcc agtacgccac agcctgcagc gagcacatag 4800
acgaagcgcc cgacgtctag atcacagatc gtggaatccc ggccacgcag actatgtttc 4860
tggctcgcaa gcgtgtcccg gccgcacgag gaatcccgat gatccgatca ggattccctc 4920
cccgaggaaa accacgaatc aggccacgag gaagccgagc ggccgcgatc ccgcctgaat 4980
ccagctagat ccgaagcgtt acacgagcgc tccgcgagaa ggaaacaaaa ggcccgaaat 5040
caggcgcgga gccagcacgc cccgcgccga tccggggagg aagccagagc gcgcccgggg 5100
gaggggaagc ggaggggtgg agggggcctt accaactcgg gcgagctggc gcggcgaaga 5160
aggggacggg gacggccgag ggaggaggaa tccgccgagg aagcgaagcg aggaggggaa 5220
agaggatgga tggagctggc tgctgctgtg ctgcctctgc ctgcgtgccg agtgaccagt 5280
cctgcgggag acgcctcgtg ttttgatgtg gtcgccgggt tttccaccgc gtatcccccg 5340
cgcgggtgtg gccgtgtggg tgacctgact gacctgcccc ttcgacggaa cggagcggcc 5400
gctgccagct tccacggtcg tcggatggcg atatggacgg ccgcgatggg cgacacgtca 5460
gcgcggcgcg atgttcgctg gaaggtgatg tgggccgccg gaagcgtatt cgtaactctc 5520
tttttattcg ttttcttttt cgtgaaaggg atttcggaat gaaaataaat agatacattc 5580
agggacgcgg aggattatca ggggaataaa aaccaaacaa aaagcagtgg catcagcgat 5640
ccacaccaca ccgaccgtgg gcgatggact aatctgtgag caaagcatta gccggacaag 5700
acagcagcgg cgtcgtacta ctcctgcgta tgatatgatg atgctctcaa ttcatgcagt 5760
gcatccgatg cacgtacgaa cgcactcggc ggctgggcac ggattaatcg gttcttaacc 5820
gtgattggtt cggtacttac agctaaaaca ccggccagta cgtgcctgtg cctaccgaat 5880

-continued

```
tgctactaat aattggacag cacatccaca tccagcatgt gtgtgtcagt gtgtgtcgga   5940
gtgggttccg tggtggatcg agagccgcgg gcgttgcttg ggccgtcatg gacagggctg   6000
catctacacg acaggccaga ttgcgcgagg cccggagccc ggattgcagt tccctttcct   6060
agagatggaa ctacagctgc tacacctact gcgttcaaca ttactctttc ttttatattt   6120
cagacgcttc atctaaggct atctccagct catctctcat ttttttcga tttacatcta   6180
aggctagagt tatggcagaa tatatagtaa aaaccacctg ttaggtgaaa acatggaaat   6240
agatcacaaa acgtattttg acatttcatt tttttaaaca aaaatacttc acgcatccat   6300
aatgcataga attacgtatt aacgaaaaag ttaagacaca aacttaaact aaaaatcata   6360
tgaaaatgga aaatataagg cttatgtgga ataaaagatg aaactcgaga attttgtctt   6420
tttatagtgc acatgaacct gttgtttgct actttcggcg cgccagctgc ttgtggggac   6480
cagacaaaaa aggaatggtg cagaattgtt aggcgcacct accaaaagca tctttgcctt   6540
tattgcaaag ataaagcaga ttcctctagt acaagtgggg aacaaaataa cgtggaaaag   6600
agctgtcctg acagcccact cactaatgcg tatgacgaac gcagtgacga ccacaaaact   6660
cgagactttt caacaaaggg taatatccgg aaacctcctc ggattccatt gcccagctat   6720
ctgtcacttt attgtgaaga tagtggaaaa ggaaggtggc tcctacaaat gccatcattg   6780
cgataaagga aaggctatcg ttgaagatgc ctctgccgac agtggtccca aagatggacc   6840
cccacccacg aggagcatcg tggaaaaaga agacgttcca accacgtctt caaagcaagt   6900
ggattgatgt gatatctcca ctgacgtaag ggatgacgaa caatcccact atccttcggt   6960
accggaccgc gatcgcttaa ttaagcttgc atgcctgcag tgcagcgtga cccggtcgtg   7020
cccctctcta gagataatga gcattgcatg tctaagttat aaaaaattac cacatatttt   7080
ttttgtcaca cttgtttgaa gtgcagttta tctatcttta tacatatatt taaactttac   7140
tctacgaata atataatcta tagtactaca ataatatcag tgttttagag aatcatataa   7200
atgaacagtt agacatggtc taaaggacaa ttgagtattt tgacaacagg actctacagt   7260
tttatctttt tagtgtgcat gtgttctcct ttttttttgc aaatagcttc acctatataa   7320
tacttcatcc attttattag tacatccatt tagggtttag ggttaatggt ttttatagac   7380
taattttttt agtacatcta ttttattcta ttttagcctc taaattaaga aaactaaaac   7440
tctattttag ttttttttatt taataattta gatataaaat agaataaaat aaagtgacta   7500
aaaattaaac aaataccctt taagaaatta aaaaaactaa ggaaacattt ttcttgtttc   7560
gagtagataa tgccagcctg ttaaacgccg ccgacgagtc taacggacac caaccagcga   7620
accagcagcg tcgcgtcggg ccaagcgaag cagacggcac ggcatctctg tcgctgcctc   7680
tggacccctc tcgagagttc cgctccaccg ttggacttgc tccgctgtcg gcatccagaa   7740
attgcgtggc ggagcggcag acgtgagccg gcacggcagg cggcctcctc ctcctctcac   7800
ggcaccggca gctacggggg attcctttcc caccgctcct tcgctttccc ttcctcgccc   7860
gccgtaataa atagacaccc cctccacacc ctctttcccc aacctcgtgt tgttcggagc   7920
gcacacacac acaaccagat ctcccccaaa tccacccgtc ggcacctccg cttcaaggta   7980
cgccgctcgt cctccccccc ccccctctc taccttctct agatcggcgt tccggtccat   8040
agttagggcc cggtagttct acttctgttc atgtttgtgt tagatccgtg tttgtgttag   8100
atccgtgctg ttagcgttcg tacacggatg cgacctgtac gtcagacacg ttctgattgc   8160
taacttgcca gtgtttctct ttggggaatc ctgggatggc tctagccgtt ccgcagacgg   8220
```

```
gatcgatttc atgatttttt ttgtttcgtt gcatagggtt tggtttgccc ttttccttta   8280
tttcaatata tgccgtgcac ttgtttgtcg ggtcatcttt tcatgctttt ttttgtcttg   8340
gttgtgatga tgtggtctgg ttgggcggtc gttctagatc ggagtagaat tctgtttcaa   8400
actacctggt ggatttatta attttggatc tgtatgtgtg tgccatacat attcatagtt   8460
acgaattgaa gatgatggat ggaaatatcg atctaggata ggtatacatg ttgatgcggg   8520
ttttactgat gcatatacag agatgctttt tgttcgcttg gttgtgatga tgtggtgtgg   8580
ttgggcggtc gttcattcgt tctagatcgg agtagaatac tgtttcaaac tacctggtgt   8640
atttattaat tttggaactg tatgtgtgtg tcatacatct tcatagttac gagtttaaga   8700
tggatggaaa tatcgatcta ggataggtat acatgttgat gtgggtttta ctgatgcata   8760
tacatgatgg catatgcagc atctattcat atgctctaac cttgagtacc tatctattat   8820
aataaacaag tatgttttat aattattttg atcttgatat acttggatga tggcatatgc   8880
agcagctata tgtggatttt tttagccctg ccttcatacg ctatttattt gcttggtact   8940
gtttcttttg tcgatgctca ccctgttgtt tggtgttact tctgcaggga tccactagtc   9000
caccatgtct ccggagagga gaccagttga gattaggcca gctacagcag ctgatatggc   9060
cgcggtttgt gatatcgtta accattacat tgagacgtct acagtgaact ttaggacaga   9120
gccacaaaca ccacaagagt ggattgatga tctagagagg ttgcaagata gatacccttg   9180
gttggttgct gaggttgagg gtgttgtggc tggtattgct tacgctgggc cctggaaggc   9240
taggaacgct tacgattgga cagttgagag tactgtttac gtgtcacata ggcatcaaag   9300
gttgggccta ggatccacat tgtacacaca tttgcttaag tctatggagg cgcaaggttt   9360
taagtctgtg gttgctgtta taggccttcc aaacgatcca tctgttaggt tgcatgaggc   9420
tttgggatac acagcccggg gtacattgcg cgcagctgga tacaagcatg gtggatggca   9480
tgatgttggt ttttggcaaa gggattttga gttgccagct cctccaaggc cagttaggcc   9540
agttacccag atctgaacta gtgatatcgg cgccatgggt cgacctgcag atcgttcaaa   9600
catttggcaa taaagtttct taagattgaa tcctgttgcc ggtcttgcga tgattatcat   9660
ataatttctg ttgaattacg ttaagcatgt aataattaac atgtaatgca tgacgttatt   9720
tatgagatgg gtttttatga ttagagtccc gcaattatac atttaatacg cgatagaaaa   9780
caaaatatag cgcgcaaact aggataaatt atcgcgcgcg gtgtcatcta tgttactaga   9840
tctgctagcc ctgcaggaaa tttaccggtg cccgggcggc cagcatggcc gtatccgcaa   9900
tgtgttatta agttgtctaa gcgtcaattt gtttacacca caatatatcc tgccaccagc   9960
cagccaacag ctccccgacc ggcagctcgg cacaaaatca ccactcgata caggcagccc  10020
atcagaatta attctcatgt ttgacagctt atcatcgact gcacggtgca ccaatgcttc  10080
tggcgtcagg cagccatcgg aagctgtggt atggctgtgc aggtcgtaaa tcactgcata  10140
attcgtgtcg ctcaaggcgc actcccgttc tggataatgt tttttgcgcc gacatcataa  10200
cggttctggc aaatattctg aaatgagctg ttgacaatta atcatccggc tcgtataatg  10260
tgtggaattg tgagcggata acaatttcac acaggaaaca gaccatgagg gaagcgttga  10320
tcgccgaagt atcgactcaa ctatcagagg tagttggcgt catcgagcgc catctcgaac  10380
cgacgttgct ggccgtacat ttgtacggct ccgcagtgga tggcggcctg aagccacaca  10440
gtgatattga tttgctggtt acggtgaccg taaggcttga tgaaacaacg cggcgagctt  10500
tgatcaacga ccttttggaa acttcggctt cccctggaga gagcgagatt ctccgcgctg  10560
tagaagtcac cattgttgtg cacgacgaca tcattccgtg gcgttatcca gctaagcgcg  10620
```

```
aactgcaatt tggagaatgg cagcgcaatg acattcttgc aggtatcttc gagccagcca  10680
cgatcgacat tgatctggct atcttgctga caaaagcaag agaacatagc gttgccttgg  10740
taggtccagc ggcggaggaa ctctttgatc cggttcctga acaggatcta tttgaggcgc  10800
taaatgaaac cttaacgcta tggaactcgc cgcccgactg ggctggcgat gagcgaaatg  10860
tagtgcttac gttgtcccgc atttggtaca gcgcagtaac cggcaaaatc gcgccgaagg  10920
atgtcgctgc cgactgggca atggagcgcc tgccggccca gtatcagccc gtcatacttg  10980
aagctaggca ggcttatctt ggacaagaag atcgcttggc ctcgcgcgca gatcagttgg  11040
aagaatttgt tcactacgtg aaaggcgaga tcaccaaagt agtcggcaaa taaagctcta  11100
gtggatctcc gtacccaggg atctggctcg cggcggacgc acgacgccgg ggcgagacca  11160
taggcgatct cctaaatcaa tagtagctgt aacctcgaag cgtttcactt gtaacaacga  11220
ttgagaattt ttgtcataaa attgaaatac ttggttcgca tttttgtcat ccgcggtcag  11280
ccgcaattct gacgaactgc ccatttagct ggagatgatt gtacatcctt cacgtgaaaa  11340
tttctcaagc gctgtgaaca agggttcaga ttttagattg aaaggtgagc cgttgaaaca  11400
cgttcttctt gtcgatgacg acgtcgctat gcggcatctt attattgaat accttacgat  11460
ccacgccttc aaagtgaccg cggtagccga cagcacccag ttcacaagag tactctcttc  11520
cgcgacggtc gatgtcgtgg ttgttgatct agatttaggt cgtgaagatg ggctcgagat  11580
cgttcgtaat ctggcggcaa agtctgatat tccaatcata attatcagtg gcgaccgcct  11640
tgaggagacg gataaagttg ttgcactcga gctaggagca agtgatttta tcgctaagcc  11700
gttcagtatc agagagtttc tagcacgcat tcgggttgcc ttgcgcgtgc gccccaacgt  11760
tgtccgctcc aaagaccgac ggtctttttg ttttactgac tggacactta atctcaggca  11820
acgtcgcttg atgtccgaag ctggcggtga ggtgaaactt acggcaggtg agttcaatct  11880
tctcctcgcg tttttagaga aaccccgcga cgttctatcg cgcgagcaac ttctcattgc  11940
cagtcgagta cgcgacgagg aggtttatga caggagtata gatgttctca ttttgaggct  12000
gcgccgcaaa cttgaggcag atccgtcaag ccctcaactg ataaaaacag caagaggtgc  12060
cggttatttc tttgacgcgg acgtgcaggt ttcgcacggg gggacgatgg cagcctgagc  12120
caattcccag atccccgagg aatcggcgtg agcggtcgca aaccatccgg cccggtacaa  12180
atcggcgcgg cgctgggtga tgacctggtg gagaagttga aggccgcgca ggccgcccag  12240
cggcaacgca tcgaggcaga agcacgcccc ggtgaatcgt ggcaagcggc cgctgatcga  12300
atccgcaaag aatcccggca accgccggca gccggtgcgc cgtcgattag gaagccgccc  12360
aagggcgacg agcaaccaga tttttttcgtt ccgatgctct atgacgtggg cacccgcgat  12420
agtcgcagca tcatggacgt ggccgttttc cgtctgtcga agcgtgaccg acgagctggc  12480
gaggtgatcc gctacgagct tccagacggg cacgtagagg tttccgcagg gccggccggc  12540
atggccagtg tgtgggatta cgacctggta ctgatggcgg tttcccatct aaccgaatcc  12600
atgaaccgat accgggaagg gaagggagac aagcccggcc gcgtgttccg tccacacgtt  12660
gcggacgtac tcaagttctg ccggcgagcc gatggcggaa agcagaaaga cgacctggta  12720
gaaacctgca ttcggttaaa caccacgcac gttgccatgc agcgtacgaa gaaggccaag  12780
aacggccgcc tggtgacggt atccgagggt gaagccttga ttagccgcta caagatcgta  12840
aagagcgaaa ccgggcggcc ggagtacatc gagatcgagc tggctgattg gatgtaccgc  12900
gagatcacag aaggcaagaa cccggacgtg ctgacggttc accccgatta ctttttgatc  12960
```

gatcccggca tcggccgttt tctctaccgc ctggcacgcc gcgccgcagg caaggcagaa 13020
gccagatggt tgttcaagac gatctacgaa cgcagtggca gcgccggaga gttcaagaag 13080
ttctgtttca ccgtgcgcaa gctgatcggg tcaaatgacc tgccggagta cgatttgaag 13140
gaggaggcgg ggcaggctgg cccgatccta gtcatgcgct accgcaacct gatcgagggc 13200
gaagcatccg ccggttccta atgtacggag cagatgctag ggcaaattgc cctagcaggg 13260
gaaaaaggtc gaaaaggtct ctttcctgtg gatagcacgt acattgggaa cccaaagccg 13320
tacattggga accggaaccc gtacattggg aacccaaagc cgtacattgg gaaccggtca 13380
cacatgtaag tgactgatat aaaagagaaa aaaggcgatt tttccgccta aaactcttta 13440
aaacttatta aaactcttaa aacccgcctg gcctgtgcat aactgtctgg ccagcgcaca 13500
gccgaagagc tgcaaaaagc gcctaccctt cggtcgctgc gctccctacg ccccgccgct 13560
tcgcgtcggc ctatcgcggc cgctggccgc tcaaaaatgg ctggcctacg gccaggcaat 13620
ctaccagggc gcggacaagc cgcgccgtcg ccactcgacc gccggcgctg aggtctgcct 13680
cgtgaagaag gtgttgctga ctcataccag gcctgaatcg ccccatcatc cagccagaaa 13740
gtgagggagc cacggttgat gagagctttg ttgtaggtgg accagttggt gattttgaac 13800
ttttgctttg ccacggaacg gtctgcgttg tcgggaagat gcgtgatctg atccttcaac 13860
tcagcaaaag ttcgatttat tcaacaaagc cgccgtcccg tcaagtcagc gtaatgctct 13920
gccagtgtta caaccaatta accaattctg attagaaaaa ctcatcgagc atcaaatgaa 13980
actgcaattt attcatatca ggattatcaa taccatattt ttgaaaaagc cgtttctgta 14040
atgaaggaga aaactcaccg aggcagttcc ataggatggc aagatcctgg tatcggtctg 14100
cgattccgac tcgtccaaca tcaatacaac ctattaattt cccctcgtca aaaataaggt 14160
tatcaagtga gaaatcacca tgagtgacga ctgaatccgg tgagaatggc aaaagctctg 14220
cattaatgaa tcggccaacg cgcggggaga ggcggtttgc gtattgggcg ctcttccgct 14280
tcctcgctca ctgactcgct gcgctcggtc gttcggctgc ggcgagcggt atcagctcac 14340
tcaaaggcgg taatacggtt atccacagaa tcaggggata acgcaggaaa gaacatgtga 14400
gcaaaaggcc agcaaaaggc caggaaccgt aaaaaggccg cgttgctggc gtttttccat 14460
aggctccgcc cccctgacga gcatcacaaa aatcgacgct caagtcagag gtggcgaaac 14520
ccgacaggac tataaagata ccaggcgttt ccccctggaa gctccctcgt gcgctctcct 14580
gttccgaccc tgccgcttac cggatacctg tccgcctttc tcccttcggg aagcgtggcg 14640
ctttctcata gctcacgctg taggtatctc agttcggtgt aggtcgttcg ctccaagctg 14700
ggctgtgtgc acgaaccccc cgttcagccc gaccgctgcg ccttatccgg taactatcgt 14760
cttgagtcca acccggtaag acacgactta tcgccactgg cagcagccac tggtaacagg 14820
attagcagag cgaggtatgt aggcggtgct acagagttct tgaagtggtg gcctaactac 14880
ggctacacta gaagaacagt atttggtatc tgcgctctgc tgaagccagt taccttcgga 14940
aaaagagttg gtagctcttg atccggcaaa caaaccaccg ctggtagcgg tggttttttt 15000
gtttgcaagc agcagattac gcgcagaaaa aaaggatctc aagaagatcc tttgatcttt 15060
tctacggggt ctgacgctca gtggaacgaa aactcacgtt aagggatttt ggtcatgaga 15120
ttatcaaaaa ggatcttcac ctagatcctt ttgatccgga at 15162

<210> SEQ ID NO 39
<211> LENGTH: 15162
<212> TYPE: DNA
<213> ORGANISM: Artificial sequence
<220> FEATURE:
<223> OTHER INFORMATION: enhanced ZmABP3-Cry1AbG6 binary construct

<400> SEQUENCE: 39

```
taattcctgt ggttggcatg cacatacaaa tggacgaacg gataaacctt ttcacgccct     60
tttaaatatc cgattattct aataaacgct cttttctctt aggtttaccc gccaatatat    120
cctgtcaaac actgatagtt taaactgaag gcgggaaacg acaatctgat catgagcgga    180
gaattaaggg agtcacgtta tgacccccgc cgatgacgcg ggacaagccg ttttacgttt    240
ggaactgaca gaaccgcaac gctgcaggaa ttggccgcag cggccattta aatcaattgg    300
gcgcgccaca ctttctgtcg catgtgattt gcactaggag caggatagca gatgaggtca    360
aacgaaacga tgatgcgctt gagatgggaa aatggctgct cgacacggtt gagaacttga    420
gatggcatac gagcaatcaa gcaggggtca ctaccacttc cggctataaa taagagataa    480
ataagagatg agaccattat ctcatgagac agccatgcaa tgtcgccaag gatttaggaa    540
caaatagttt ttttgtcatt aacgacaaca ttgcgtcgtg gtttagttgg ctatcacgtc    600
agtctaacac attgaaggat ctcctggctc aacatttttt tcccttccct taagtccgtg    660
ttaaagaaac tgcatcatgc aacgctggaa attttgctaa acaaatgacg gatttgcatc    720
acacagattc acactccact gtgcccacag agacactatt gctctgtttg gttaccggca    780
tcctcggtgc ctaactcgag caggtcttca gtagaaacgg acgattctta cttccccacg    840
cttacagacc aacaagggat ctgcacacac aacaatgtag ccaaaagaac acctaggatt    900
ttccaaaaac actaaggacc tgttcgcttg gaattataat ctgcctagat tatataatct    960
aacttaactt gaactcacac ttagtttaaa ataagtttct ccagacataa tcccaaacaa   1020
acgaccccta agcttctcca gacaattgtc accgagacat gggaagggaa catatcgatt   1080
acttatttgt agtagtaagt tgaacagcgc aacacatgtc catagtccat acataattgg   1140
cagataacaa ggaattacat gatagatccg aaccttcatg gtcttctggg agccaaggga   1200
ccttttttta cacagcaaca aacccgcaaa tcatcaagca gtctttcaca gcaccaagtc   1260
tataatggca tacaaatcca cagtagtagg ccgagtccat gatgcatgat catgatgcga   1320
gctcctagat gcggccctcg agttcctcga agatggcggc gttcacaccg gggatcacgc   1380
tcagctcggg caggtaggcc tcgcgaatgc tgtgcacgcg cttgtcggcg gcgtggatca   1440
tggcgatgtt ggtgtcggcc tgcaggcggt cgtactggct gttcacgaac agggcgtcca   1500
cgctctcctt ggcctccttg tacacgatgt tggtctccca ctccagcttc tcgcgcttgt   1560
cgcgccactt cttctcagca cgcttcacgc gggccagggc ctcgcccacc aggggcttct   1620
cctccaggaa ctctagattg cccaggcggg cgtggccgtc ctgggtcttg atcttgaaga   1680
tcacccacac gcccaggtcc tcgttcaggt cggtgcagcc cacgtcgatg tccaggctga   1740
agtggtggct gtggtggcac ttgccgatgg ggctgggggc gctcaggggc cacaggctgc   1800
cggtgccggg cacgttcacg gtctcgtgct tcgcgttgta gcggatcagg tagatttcca   1860
ggtcctggct gtcctcgatg tagccgcgca gctggtagcg ggtgtaggcc ttcagcttgc   1920
tctcgtcgat cttctggtac aggtaggtgg ggtagcactc gtcgaaggtg cccagcaggg   1980
tcacgtagtt ctccttgaac acgtcgtcgc cgccctggat ggtgatatcg gtgctgcctc   2040
gccagccgcg gtccagctgg cggttgatgc cgcggaagtt ggggtcctgc agcaggttgc   2100
gctcgtcgct caggcgcttg gcgtgcttca ccttctcgct cagctccttc ttctcgtcca   2160
ggcagaactc gtcgcttaag cactccacca ggttgctcac ctggtcgatg tggtagtcgg   2220
```

-continued

```
tcacgtcggt cttcaggccg atctggttgc tgctggtgaa cagctcgttc acggccttct   2280
gagccctctc caggtcgtac tcggcctcga aggtcacctc ggcgggcacg aactcgatgc   2340
ggtcgatgta cacctcgttg ccgctgttga acacgtgggc gctcagggtg aacacgctgc   2400
tgccgttgct gaagttgaag gggtggtga agcccacggt gcggaagctg ccgctctgca    2460
ggttgctgcc gctgctcatg gtggcgctga agttgccctg gttgatgggg cggccgtcga   2520
tgctggtgtg gaactgcagg ttggtggtgc tggcgtagcg gatgcggacg cggtagcgct   2580
ggctcagggg ggcggtgatg ttcacgcgca gggtgctgat ctggccgggg ctggtgcggc   2640
gcaggatgtc gccgccggtg aagccggggc ccttcaccac gctggtgccg ctgcccaggt   2700
tggtgctctt ggtcaggggg atctgggtga tctggctgct ggggatgatg ttgttgaact   2760
cggcactgcg gtgaatccag ctgaacatag gtgcacggat gatgctcacg ctgctgttgc   2820
tgaagccact gcggaacatg ctcacgtggc tcagacggtg gctgaagccc tgtcgaggtg   2880
gcacgttgtt gttctgaggg gggatctcgt ccaggctgtc cacggtgccg ctcttgcggt   2940
acacggcgct gggcaggttg ctgctggtgc cgtaggcgaa ctcggtgccg tccagcacgc   3000
tcagctgctg gttgttgatg ccgatgttga aaggtcgacg gtacagggtg ctgctcaggg   3060
tgcggtacac tccctggccc agctgtgcca cgatgcgctg ctgaggtgca gcgttgccca   3120
tcgtgccgta caggggggaag gtgaactcgg ggccgctgaa gccgacgggg ctggccatga  3180
tctggtggcc gctccagtag tactcgccgc ggtgggcgtc ggtgtagatg gtgatgctgt   3240
tcaggatgtc catcaggtgg gggctgcgga tgctgccctc gatgccctgg gcgctgccgc   3300
ggaagctgcc gtcgaagttc tccagcacgg ggttggtgta aatctcgcgg gtcagctggc   3360
tcacggtgcg gatggggtag gtgcggctgt cgtagttggg gaacaggctc acgatgtcca   3420
gcacggtcag ggtcagctcg cggcggaact ggttgtacct gatccagtcg cggctgtcgg   3480
gaccccacac gcgctccagg ccggtgttgt accagcgcac ggcgtggtcg gtgtagttgc   3540
cgatcaggcg ggtcaggtcg ttgtagcggc tgttgatggt ggcggcgtcg aagccccagc   3600
gctggccgaa cacgctgacg tcgcgcagca cgctcaggtg caggttggcg gcctgcacgt   3660
acacgctcag caggggcacc tggtagttct gcacggcgaa cagggggatg gcggtggtca   3720
gggcgctgtt catgtcgttg aactggatgc gcatctcctc gcgcagggcg gggttggtgg   3780
ggtcggcctc ccactcgcgg aagctctcgg cgtagatttg gtacaggttg ctcaggccct   3840
ccaggcggct gatggcctgg ttgcgggcga attcctctat gcgttggttt atcaactgct   3900
cgatctgcac caggaaggcg tcccactggc tggggccgaa gatgccccag atgatgtcca   3960
ccaggcccag cacgaagccg gcgccgggca cgaactcgct cagcaggaac tgggtcaggc   4020
tcaggctgat gtcgatgggg gtgtagccgg tctcgatgcg ctcgccgccc agcacctcca   4080
cctcggggtt gctcaggcag ttgtagggga tgcactcgtt gatgttgggg ttgttgtcca   4140
tggtgggttt gcctgcgacc acaagttcag tcatagttaa ctggagatac agtgtggaga   4200
gtcccttcaa ataacctgct tgcaccaccc atagtttaag aggcagttgc tttcacacac   4260
tttattttgc atggcacagc caactgtccc catcattcta aaccaggctg caactgagcc   4320
actacagaaa ctgctaatat tagatattcc agcaaatagt cttgacacta gagtgctagg   4380
tccctaaaca cgaaagacat ttgtcaggag acccgtattg agtactagca gagtatacta   4440
ccgctagata ttccagtata atcgtgcagc agctccggtc aatggcagtg gcacttgaag   4500
tctgcaacct cagccaacag atccacatga gaaccaacag ggtcacgctg cagctggtgc   4560
tccataatcc aagctccgcg acctaagccg ccgagagcca aattcgcaga tgaactgcag   4620
```

-continued

```
ccacacgagc tacactggcg ccgctgaggt aaagatcaac cgagattcca ccgccaccgc   4680
acctcgcaga ccatagatct acacagctcg atttcacacg ctacagggcg aacaaacaag   4740
cacggatcca tagcggccgc gcaccacgcc agtacgccac agcctgcagc gagcacatag   4800
acgaagcgcc cgacgtctag atcacagatc gtggaatccc ggccacgcag actatgtttc   4860
tggctcgcaa gcgtgtcccg gccgcacgag gaatcccgat gatccgatca ggattccctc   4920
cccgaggaaa accacgaatc aggccacgag gaagccgagc ggccgcgatc ccgcctgaat   4980
ccagctagat ccgaagcgtt acacgagcgc tccgcgagaa ggaaacaaaa ggcccgaaat   5040
caggcgcgga gccagcacgc cccgcgccga tccggggagg aagccagagc gcgcccgggg   5100
gaggggaagc ggaggggtgg agggggcctt accaactcgg gcgagctggc gcggcgaaga   5160
aggggacggg gacggccgag ggaggaggaa tccgccgagg aagcgaagcg aggaggggaa   5220
agaggatgga tggagctggc tgctgctgtg ctgcctctgc ctgcgtgccg agtgaccagt   5280
cctgcgggag acgcctcgtg ttttgatgtg gtcgccgggt tttccaccgc gtatcccccg   5340
cgcgggtgtg gccgtgtggg tgacctgact gacctgcccc ttcgacggaa cggagcggcc   5400
gctgccagct tccacggtcg tcggatggcg atatggacgg ccgcgatggg cgacacgtca   5460
gcgcggcgcg atgttcgctg gaaggtgatg tgggccgccg gaagcgtatt cgtaactctc   5520
tttttattcg ttttcttttt cgtgaaaggg atttcggaat gaaaataaat agatacattc   5580
agggacgcgg aggattatca ggggaataaa aaccaaacaa aaagcagtgg catcagcgat   5640
ccacaccaca ccgaccgtgg gcgatggact aatctgtgag caaagcatta gccggacaag   5700
acagcagcgg cgtcgtacta ctcctgcgta tgatatgatg atgctctcaa ttcatgcagt   5760
gcatccgatg cacgtacgaa cgcactcggc ggctgggcac ggattaatcg gttcttaacc   5820
gtgattggtt cggtacttac agctaaaaca ccggccagta cgtgcctgtg cctaccgaat   5880
tgctactaat aattggacag cacatccaca tccagcatgt gtgtgtcagt gtgtgtcgga   5940
gtgggttccg tggtggatcg agagccgcgg gcgttgcttg ggccgtcatg gacagggctg   6000
catctacacg acaggccaga ttgcgcgagg cccggagccc ggattgcagt tccctttcct   6060
agagatggaa ctacagctgc tacacctact gcgttcaaca ttactctttc ttttatattt   6120
cagacgcttc atctaaggct atctccagct catctctcat tttttttcga tttacatcta   6180
aggctagagt tatggcagaa tatatagtaa aaaccacctg ttaggtgaaa acatggaaat   6240
agatcacaaa acgtattttg acatttcatt tttttaaaca aaaatacttc acgcatccat   6300
aatgcataga attacgtatt aacgaaaaag ttaagacaca aacttaaact aaaaatcata   6360
tgaaaatgga aaatataagg cttatgtgga ataaaagatg aaactcgaga attttgtctt   6420
tttatagtgc acatgaacct gttgtttgct actttcggcg cgccagctgc ttgtggggac   6480
cagacaaaaa aggaatggtg cagaattgtt aggcgcacct accaaaagca tctttgcctt   6540
tattgcaaag ataaagcaga ttcctctagt acaagtgggg aacaaaataa cgtggaaaag   6600
agctgtcctg acagcccact cactaatgcg tatgacgaac gcagtgacga ccacaaaact   6660
cgagactttt caacaaaggg taatatccgg aaacctcctc ggattccatt gcccagctat   6720
ctgtcacttt attgtgaaga tagtggaaaa ggaaggtggc tcctacaaat gccatcattg   6780
cgataaagga aaggctatcg ttgaagatgc ctctgccgac agtggtccca aagatggacc   6840
cccacccacg aggagcatcg tggaaaaaga agacgttcca accacgtctt caaagcaagt   6900
ggattgatgt gatatctcca ctgacgtaag ggatgacgaa caatcccact atccttcggt   6960
```

-continued

```
accggaccgc gatcgcttaa ttaagcttgc atgcctgcag tgcagcgtga cccggtcgtg   7020
cccctctcta gagataatga gcattgcatg tctaagttat aaaaaattac cacatatttt   7080
ttttgtcaca cttgtttgaa gtgcagttta tctatcttta tacatatatt taaactttac   7140
tctacgaata atataatcta tagtactaca ataatatcag tgttttagag aatcatataa   7200
atgaacagtt agacatggtc taaaggacaa ttgagtattt tgacaacagg actctacagt   7260
tttatctttt tagtgtgcat gtgttctcct ttttttttgc aaatagcttc acctatataa   7320
tacttcatcc attttattag tacatccatt tagggtttag ggttaatggt ttttatagac   7380
taattttttt agtacatcta ttttattcta ttttagcctc taaattaaga aaactaaaac   7440
tctattttag ttttttttatt taataattta gatataaaat agaataaaat aaagtgacta   7500
aaaattaaac aaataccctt taagaaatta aaaaaactaa ggaaacattt ttcttgtttc   7560
gagtagataa tgccagcctg ttaaacgccg ccgacgagtc taacggacac caaccagcga   7620
accagcagcg tcgcgtcggg ccaagcgaag cagacggcac ggcatctctg tcgctgcctc   7680
tggacccctc tcgagagttc cgctccaccg ttggacttgc tccgctgtcg gcatccagaa   7740
attgcgtggc ggagcggcag acgtgagccg gcacggcagg cggcctcctc ctcctctcac   7800
ggcaccggca gctacggggg attcctttcc caccgctcct tcgctttccc ttcctcgccc   7860
gccgtaataa atagacaccc cctccacacc ctctttcccc aacctcgtgt tgttcggagc   7920
gcacacacac acaaccagat ctcccccaaa tccacccgtc ggcacctccg cttcaaggta   7980
cgccgctcgt cctccccccc ccccctctc taccttctct agatcggcgt tccggtccat   8040
agttagggcc cggtagttct acttctgttc atgtttgtgt tagatccgtg tttgtgttag   8100
atccgtgctg ttagcgttcg tacacggatg cgacctgtac gtcagacacg ttctgattgc   8160
taacttgcca gtgtttctct ttggggaatc ctgggatggc tctagccgtt ccgcagacgg   8220
gatcgatttc atgatttttt ttgtttcgtt gcatagggtt tggtttgccc ttttccttta   8280
tttcaatata tgccgtgcac ttgtttgtcg ggtcatcttt tcatgctttt ttttgtcttg   8340
gttgtgatga tgtggtctgg ttgggcggtc gttctagatc ggagtagaat tctgtttcaa   8400
actacctggt ggatttatta attttggatc tgtatgtgtg tgccatacat attcatagtt   8460
acgaattgaa gatgatggat ggaaatatcg atctaggata ggtatacatg ttgatgcggg   8520
ttttactgat gcatatacag agatgctttt tgttcgcttg gttgtgatga tgtggtgtgg   8580
ttgggcggtc gttcattcgt tctagatcgg agtagaatac tgtttcaaac tacctggtgt   8640
atttattaat tttggaactg tatgtgtgtg tcatacatct tcatagttac gagtttaaga   8700
tggatggaaa tatcgatcta ggataggtat acatgttgat gtgggtttta ctgatgcata   8760
tacatgatgg catatgcagc atctattcat atgctctaac cttgagtacc tatctattat   8820
aataaacaag tatgttttat aattattttg atcttgatat acttggatga tggcatatgc   8880
agcagctata tgtggatttt tttagccctg ccttcatacg ctatttattt gcttggtact   8940
gtttcttttg tcgatgctca ccctgttgtt tggtgttact tctgcaggga tccactagtc   9000
caccatgtct ccggagagga gaccagttga gattaggcca gctacagcag ctgatatggc   9060
cgcggtttgt gatatcgtta accattacat tgagacgtct acagtgaact ttaggacaga   9120
gccacaaaca ccacaagagt ggattgatga tctagagagg ttgcaagata gatacccttg   9180
gttggttgct gaggttgagg gtgttgtggc tggtattgct tacgctgggc cctggaaggc   9240
taggaacgct tacgattgga cagttgagag tactgtttac gtgtcacata ggcatcaaag   9300
gttgggccta ggatccacat tgtacacaca tttgcttaag tctatggagg cgcaaggttt   9360
```

```
taagtctgtg gttgctgtta taggccttcc aaacgatcca tctgttaggt tgcatgaggc   9420
tttgggatac acagcccggg gtacattgcg cgcagctgga tacaagcatg gtggatggca   9480
tgatgttggt ttttggcaaa gggattttga gttgccagct cctccaaggc cagttaggcc   9540
agttacccag atctgaacta gtgatatcgg cgccatgggt cgacctgcag atcgttcaaa   9600
catttggcaa taaagtttct taagattgaa tcctgttgcc ggtcttgcga tgattatcat   9660
ataatttctg ttgaattacg ttaagcatgt aataattaac atgtaatgca tgacgttatt   9720
tatgagatgg gtttttatga ttagagtccc gcaattatac atttaatacg cgatagaaaa   9780
caaaatatag cgcgcaaact aggataaatt atcgcgcgcg gtgtcatcta tgttactaga   9840
tctgctagcc ctgcaggaaa tttaccggtg cccgggcggc cagcatggcc gtatccgcaa   9900
tgtgttatta agttgtctaa gcgtcaattt gtttacacca caatatatcc tgccaccagc   9960
cagccaacag ctccccgacc ggcagctcgg cacaaaatca ccactcgata caggcagccc  10020
atcagaatta attctcatgt ttgacagctt atcatcgact gcacggtgca ccaatgcttc  10080
tggcgtcagg cagccatcgg aagctgtggt atggctgtgc aggtcgtaaa tcactgcata  10140
attcgtgtcg ctcaaggcgc actcccgttc tggataatgt tttttgcgcc gacatcataa  10200
cggttctggc aaatattctg aaatgagctg ttgacaatta atcatccggc tcgtataatg  10260
tgtggaattg tgagcggata acaatttcac acaggaaaca gaccatgagg gaagcgttga  10320
tcgccgaagt atcgactcaa ctatcagagg tagttggcgt catcgagcgc catctcgaac  10380
cgacgttgct ggccgtacat ttgtacggct ccgcagtgga tggcggcctg aagccacaca  10440
gtgatattga tttgctggtt acggtgaccg taaggcttga tgaaacaacg cggcgagctt  10500
tgatcaacga ccttttggaa acttcggctt cccctggaga gagcgagatt ctccgcgctg  10560
tagaagtcac cattgttgtg cacgacgaca tcattccgtg gcgttatcca gctaagcgcg  10620
aactgcaatt tggagaatgg cagcgcaatg acattcttgc aggtatcttc gagccagcca  10680
cgatcgacat tgatctggct atcttgctga caaaagcaag agaacatagc gttgccttgg  10740
taggtccagc ggcggaggaa ctctttgatc cggttcctga acaggatcta tttgaggcgc  10800
taaatgaaac cttaacgcta tggaactcgc cgcccgactg ggctggcgat gagcgaaatg  10860
tagtgcttac gttgtcccgc atttggtaca gcgcagtaac cggcaaaatc gcgccgaagg  10920
atgtcgctgc cgactgggca atggagcgcc tgccggccca gtatcagccc gtcatacttg  10980
aagctaggca ggcttatctt ggacaagaag atcgcttggc ctcgcgcgca gatcagttgg  11040
aagaatttgt tcactacgtg aaaggcgaga tcaccaaagt agtcggcaaa taaagctcta  11100
gtggatctcc gtacccaggg atctggctcg cggcggacgc acgacgccgg ggcgagacca  11160
taggcgatct cctaaatcaa tagtagctgt aacctcgaag cgtttcactt gtaacaacga  11220
ttgagaattt ttgtcataaa attgaaatac ttggttcgca tttttgtcat ccgcggtcag  11280
ccgcaattct gacgaactgc ccatttagct ggagatgatt gtacatcctt cacgtgaaaa  11340
tttctcaagc gctgtgaaca agggttcaga ttttagattg aaaggtgagc cgttgaaaca  11400
cgttcttctt gtcgatgacg acgtcgctat gcggcatctt attattgaat accttacgat  11460
ccacgccttc aaagtgaccg cggtagccga cagcacccag ttcacaagag tactctcttc  11520
cgcgacggtc gatgtcgtgg ttgttgatct agatttaggt cgtgaagatg ggctcgagat  11580
cgttcgtaat ctggcggcaa agtctgatat tccaatcata attatcagtg gcgaccgcct  11640
tgaggagacg gataaagttg ttgcactcga gctaggagca agtgatttta tcgctaagcc  11700
```

gttcagtatc agagagtttc tagcacgcat tcgggttgcc ttgcgcgtgc gccccaacgt 11760
tgtccgctcc aaagaccgac ggtctttttg ttttactgac tggacactta atctcaggca 11820
acgtcgcttg atgtccgaag ctggcggtga ggtgaaactt acggcaggtg agttcaatct 11880
tctcctcgcg tttttagaga aaccccgcga cgttctatcg cgcgagcaac ttctcattgc 11940
cagtcgagta cgcgacgagg aggtttatga caggagtata gatgttctca ttttgaggct 12000
gcgccgcaaa cttgaggcag atccgtcaag ccctcaactg ataaaaacag caagaggtgc 12060
cggttatttc tttgacgcgg acgtgcaggt ttcgcacggg gggacgatgg cagcctgagc 12120
caattcccag atccccgagg aatcggcgtg agcggtcgca aaccatccgg cccggtacaa 12180
atcggcgcgg cgctgggtga tgacctggtg gagaagttga aggccgcgca ggccgcccag 12240
cggcaacgca tcgaggcaga agcacgcccc ggtgaatcgt ggcaagcggc cgctgatcga 12300
atccgcaaag aatcccggca accgccggca gccggtgcgc cgtcgattag gaagccgccc 12360
aagggcgacg agcaaccaga tttttcgtt ccgatgctct atgacgtggg cacccgcgat 12420
agtcgcagca tcatggacgt ggccgttttc cgtctgtcga agcgtgaccg acgagctggc 12480
gaggtgatcc gctacgagct tccagacggg cacgtagagg tttccgcagg gccggccggc 12540
atggccagtg tgtgggatta cgacctggta ctgatggcgg tttcccatct aaccgaatcc 12600
atgaaccgat accgggaagg gaagggagac aagcccggcc gcgtgttccg tccacacgtt 12660
gcggacgtac tcaagttctg ccggcgagcc gatggcggaa agcagaaaga cgacctggta 12720
gaaacctgca ttcggttaaa caccacgcac gttgccatgc agcgtacgaa gaaggccaag 12780
aacggccgcc tggtgacggt atccgagggt gaagccttga ttagccgcta caagatcgta 12840
aagagcgaaa ccgggcggcc ggagtacatc gagatcgagc tggctgattg gatgtaccgc 12900
gagatcacag aaggcaagaa cccggacgtg ctgacggttc accccgatta ctttttgatc 12960
gatcccggca tcggccgttt tctctaccgc ctggcacgcc gcgccgcagg caaggcagaa 13020
gccagatggt tgttcaagac gatctacgaa cgcagtggca gcgccggaga gttcaagaag 13080
ttctgtttca ccgtgcgcaa gctgatcggg tcaaatgacc tgccggagta cgatttgaag 13140
gaggaggcgg ggcaggctgg cccgatccta gtcatgcgct accgcaacct gatcgagggc 13200
gaagcatccg ccggttccta atgtacggag cagatgctag ggcaaattgc cctagcaggg 13260
gaaaaaggtc gaaaaggtct ctttcctgtg gatagcacgt acattgggaa cccaaagccg 13320
tacattggga accggaaccc gtacattggg aacccaaagc cgtacattgg gaaccggtca 13380
cacatgtaag tgactgatat aaaagagaaa aaaggcgatt tttccgccta aaactcttta 13440
aaacttatta aaactcttaa aacccgcctg gcctgtgcat aactgtctgg ccagcgcaca 13500
gccgaagagc tgcaaaaagc gcctaccctt cggtcgctgc gctccctacg ccccgccgct 13560
tcgcgtcggc ctatcgcggc cgctggccgc tcaaaaatgg ctggcctacg gccaggcaat 13620
ctaccagggc gcggacaagc cgcgccgtcg ccactcgacc gccggcgctg aggtctgcct 13680
cgtgaagaag gtgttgctga ctcataccag gcctgaatcg ccccatcatc cagccagaaa 13740
gtgagggagc cacggttgat gagagctttg ttgtaggtgg accagttggt gattttgaac 13800
ttttgctttg ccacggaacg gtctgcgttg tcgggaagat gcgtgatctg atccttcaac 13860
tcagcaaaag ttcgatttat tcaacaaagc cgccgtcccg tcaagtcagc gtaatgctct 13920
gccagtgtta caaccaatta accaattctg attagaaaaa ctcatcgagc atcaaatgaa 13980
actgcaattt attcatatca ggattatcaa taccatattt ttgaaaaagc cgtttctgta 14040
atgaaggaga aaactcaccg aggcagttcc ataggatggc aagatcctgg tatcggtctg 14100

```
cgattccgac tcgtccaaca tcaatacaac ctattaattt cccctcgtca aaaataaggt  14160

tatcaagtga gaaatcacca tgagtgacga ctgaatccgg tgagaatggc aaaagctctg  14220

cattaatgaa tcggccaacg cgcggggaga ggcggtttgc gtattgggcg ctcttccgct  14280

tcctcgctca ctgactcgct gcgctcggtc gttcggctgc ggcgagcggt atcagctcac  14340

tcaaaggcgg taatacggtt atccacagaa tcaggggata acgcaggaaa gaacatgtga  14400

gcaaaaggcc agcaaaaggc caggaaccgt aaaaaggccg cgttgctggc gtttttccat  14460

aggctccgcc cccctgacga gcatcacaaa aatcgacgct caagtcagag gtggcgaaac  14520

ccgacaggac tataaagata ccaggcgttt ccccctggaa gctccctcgt gcgctctcct  14580

gttccgaccc tgccgcttac cggatacctg tccgcctttc tcccttcggg aagcgtggcg  14640

ctttctcata gctcacgctg taggtatctc agttcggtgt aggtcgttcg ctccaagctg  14700

ggctgtgtgc acgaaccccc cgttcagccc gaccgctgcg ccttatccgg taactatcgt  14760

cttgagtcca acccggtaag acacgactta tcgccactgg cagcagccac tggtaacagg  14820

attagcagag cgaggtatgt aggcggtgct acagagttct tgaagtggtg gcctaactac  14880

ggctacacta gaagaacagt atttggtatc tgcgctctgc tgaagccagt taccttcgga  14940

aaaagagttg gtagctcttg atccggcaaa caaaccaccg ctggtagcgg tggttttttt  15000

gtttgcaagc agcagattac gcgcagaaaa aaaggatctc aagaagatcc tttgatcttt  15060

tctacggggt ctgacgctca gtggaacgaa aactcacgtt aagggatttt ggtcatgaga  15120

ttatcaaaaa ggatcttcac ctagatcctt ttgatccgga at                     15162


<210> SEQ ID NO 40
<211> LENGTH: 6472
<212> TYPE: DNA
<213> ORGANISM: Artificial sequence
<220> FEATURE:
<223> OTHER INFORMATION: ZmABP3-AmCyan assembly construct

<400> SEQUENCE: 40

taatacgact cactataggg agaccggcct cgagcagctg aagcttgcat gcggcgcgcc     60

gaaagtagca aacaacaggt tcatgtgcac tataaaaaga caaaattctc gagtttcatc    120

ttttattcca cataagcctt atattttcca ttttcatatg atttttagtt taagtttgtg    180

tcttaacttt ttcgttaata cgtaattcta tgcattatgg atgcgtgaag tatttttgtt    240

taaaaaaatg aaatgtcaaa atacgttttg tgatctattt ccatgtttc acctaacagg    300

tggtttttac tatatattct gccataactc tagccttaga tgtaaatcga aaaaaaatga    360

gagatgagct ggagatagcc ttagatgaag cgtctgaaat ataaaagaaa gagtaatgtt    420

gaacgcagta ggtgtagcag ctgtagttcc atctctagga aagggaactg caatccgggc    480

tccgggcctc gcgcaatctg gcctgtcgtg tagatgcagc cctgtccatg acggcccaag    540

caacgcccgc ggctctcgat ccaccacgga acccactccg acacacactg acacacacat    600

gctggatgtg gatgtgctgt ccaattatta gtagcaattc ggtaggcaca ggcacgtact    660

ggccggtgtt ttagctgtaa gtaccgaacc aatcacggtt aagaaccgat taatccgtgc    720

ccagccgccg agtgcgttcg tacgtgcatc ggatgcactg catgaattga gagcatcatc    780

atatcatacg caggagtagt acgacgccgc tgctgtcttg tccggctaat gctttgctca    840

cagattagtc catcgcccac ggtcggtgtg gtgtggatcg ctgatgccac tgctttttgt    900

ttggttttta ttcccctgat aatcctccgc gtccctgaat gtatctattt attttcattc    960
```

-continued

```
cgaaatccct ttcacgaaaa agaaaacgaa taaaaagaga gttacgaata cgcttccggc   1020
ggcccacatc accttccagc gaacatcgcg ccgcgctgac gtgtcgccca tcgcggccgt   1080
ccatatcgcc atccgacgac cgtggaagct ggcagcggcc gctccgttcc gtcgaagggg   1140
caggtcagtc aggtcaccca cacggccaca cccgcgcggg ggatacgcgg tggaaaaccc   1200
ggcgaccaca tcaaaacacg aggcgtctcc cgcaggactg gtcactcggc acgcaggcag   1260
aggcagcaca gcagcagcca gctccatcca tcctctttcc cctcctcgct tcgcttcctc   1320
ggcggattcc tcctccctcg gccgtccccg tccccttctt cgccgcgcca gctcgcccga   1380
gttggtaagg ccccctccac ccctccgctt cccctccccc gggcgcgctc tggcttcctc   1440
cccggatcgg cgcggggcgt gctggctccg cgcctgattt cgggcctttt gtttccttct   1500
cgcggagcgc tcgtgtaacg cttcggatct agctggattc aggcgggatc gcggccgctc   1560
ggcttcctcg tggcctgatt cgtggttttc ctcggggagg gaatcctgat cggatcatcg   1620
ggattcctcg tgcggccggg acacgcttgc gagccagaaa catagtctgc gtggccggga   1680
ttccacgatc tgtgatctag acgtcgggcg cttcgtctat gtgctcgctg caggctgtgg   1740
cgtactggcg tggtgcgcgg ccgctatgga tccgtgcttg tttgttcgcc ctgtagcgtg   1800
tgaaatcgag ctgtgtagat ctatggtctg cgaggtgcgg tggcggtgga atctcggttg   1860
atctttacct cagcggcgcc agtgtagctc gtgtggctgc agttcatctg cgaatttggc   1920
tctcggcggc ttaggtcgcg gagcttggat tatggagcac cagctgcagc gtgaccctgt   1980
tggttctcat gtggatctgt tggctgaggt tgcagacttc aagtgccact gccattgacc   2040
ggagctgctg cacgattata ctggaatatc tagcggtagt atactctgct agtactcaat   2100
acgggtctcc tgacaaatgt ctttcgtgtt tagggaccta gcactctagt gtcaagacta   2160
tttgctggaa tatctaatat tagcagtttc tgtagtggct cagttgcagc ctggtttaga   2220
atgatgggga cagttggctg tgccatgcaa aataaagtgt gtgaaagcaa ctgcctctta   2280
aactatgggt ggtgcaagca ggttatttga agggactctc cacactgtat ctccagttaa   2340
ctatgactga acttgtggtc gcaggcaaac ccaccatggc cctgtccaac aagttcatcg   2400
gcgacgacat gaagatgacc taccacatgg acggctgcgt gaacggccac tacttcaccg   2460
tgaagggcga gggcagcggc aagccctacg agggcaccca gacctccacc ttcaaggtga   2520
cgatggccaa cggcggcccc ctggccttct ccttcgacat cctgtccacc gtgttcatgt   2580
acggcaaccg ctgcttcacc gcctacccca ccagcatgcc cgactacttc aagcaggcct   2640
tccccgacgg catgtcctac gagagaacct tcacctacga ggacggcggc gtggccaccg   2700
ccagctggga gatcagcctg aagggcaact gcttcgagca caagtccacc ttccacggcg   2760
tgaacttccc cgccgacggc cccgtgatgg ccaagaagac caccggctgg gacccctcct   2820
tcgagaagat gaccgtgtgc gacggcatct tgaagggcga cgtgaccgcc ttcctgatgc   2880
tgcagggcgg cggcaactac agatgccagt tccacacctc ctacaagacc aagaagcccg   2940
tgaccatgcc ccccaaccac gtggtggagc accgcatcgc cagaaccgac ctggacaagg   3000
gcggcaacag cgtgcagctg accgagcacg ccgtggccca catcacctcc gtggtgccct   3060
tctgagagct cgcatcatga tcatgcatca tggactcggc ctactactgt ggatttgtat   3120
gccattatag acttggtgct gtgaaagact gcttgatgat ttgcgggttt gttgctgtgt   3180
aaaaaaaggt ccccttggctc ccagaagacc atgaaggttc ggatctatca tgtaattcct   3240
tgttatctgc caattatgta tggactatgg acatgtgttg cgctgttcaa cttactacta   3300
caaataagta atcgatatgt tcccttccca tgtctcggtg acaattgtct ggagaagctt   3360
```

-continued

```
aggggtcgtt tgtttgggat tatgtctgga gaaacttatt ttaaactaag tgtgagttca   3420
agttaagtta gattatataa tctaggcaga ttataattcc aagcgaacag gtccttagtg   3480
tttttggaaa atcctaggtg ttcttttggc tacattgttg tgtgtgcaga tcccttgttg   3540
gtctgtaagc gtggggaagt aagaatcgtc cgtttctact gaagacctgc tcgagttagg   3600
caccgaggat gccggtaacc aaacagagca atagtgtctc tgtgggcaca gtggagtgtg   3660
aatctgtgtg atgcaaatcc gtcatttgtt tagcaaaatt tccagcgttg catgatgcag   3720
tttctttaac acggacttaa gggaagggaa aaaaatgttg agccaggaga tccttcaatg   3780
tgttagactg acgtgatagc caactaaacc acgacgcaat gttgtcgtta atgacaaaaa   3840
aactatttgt tcctaaatcc ttggcgacat tgcatggctg tctcatgaga taatggtctc   3900
atctcttatt tatctcttat ttatagccgg aagtggtagt gacccctgct tgattgctcg   3960
tatgccatct caagttctca accgtgtcga gcagccattt tcccatctca agcgcatcat   4020
cgtttcgttt gacctcatct gctatcctgc tcctagtgca aatcacatgc gacagaaagt   4080
gtggcgcgcc actagtcccg ggcccatcga tgatatcaga tctggttcta tagtgtcacc   4140
taaatcgtat gtgtatgata cataaggtta tgtattaatt gtagccgcgt tctaacgaca   4200
atatgtccat atggtgcact ctcagtacaa tctgctctga tgccgcatag ttaagccagc   4260
cccgacaccc gccaacaccc gctgacgcgc cctgacgggc ttgtctgctc ccggcatccg   4320
cttacagaca agctgtgacc gtctccggga gctgcatgtg tcagaggttt tcaccgtcat   4380
caccgaaacg cgcgagacga aagggcctcg tgatacgcct atttttatag gttaatgtca   4440
tgataataat ggtttcttag acgtcaggtg gcacttttcg gggaaatgtg cgcggaaccc   4500
ctatttgttt atttttctaa atacattcaa atatgtatcc gctcatgaga caataaccct   4560
gataaatgct tcaataatat tgaaaaagga agagtatgag tattcaacat ttccgtgtcg   4620
cccttattcc cttttttgcg gcattttgcc ttcctgtttt tgctcaccca gaaacgctgg   4680
tgaaagtaaa agatgctgaa gatcagttgg gtgcacgagt gggttacatc gaactggatc   4740
tcaacagcgg taagatcctt gagagttttc gccccgaaga acgttttcca atgatgagca   4800
cttttaaagt tctgctatgt ggcgcggtat tatcccgtat tgacgccggg caagagcaac   4860
tcggtcgccg catacactat tctcagaatg acttggttga gtactcacca gtcacagaaa   4920
agcatcttac ggatggcatg acagtaagag aattatgcag tgctgccata accatgagtg   4980
ataacactgc ggccaactta cttctgacaa cgatcggagg accgaaggag ctaaccgctt   5040
ttttgcacaa catgggggat catgtaactc gccttgatcg ttgggaaccg gagctgaatg   5100
aagccatacc aaacgacgag cgtgacacca cgatgcctgt agcaatggca acaacgttgc   5160
gcaaactatt aactggcgaa ctacttactc tagcttcccg gcaacaatta atagactgga   5220
tggaggcgga taaagttgca ggaccacttc tgcgctcggc ccttccggct ggctggttta   5280
ttgctgataa atctggagcc ggtgagcgtg ggtctcgcgg tatcattgca gcactggggc   5340
cagatggtaa gccctcccgt atcgtagtta tctacacgac ggggagtcag gcaactatgg   5400
atgaacgaaa tagacagatc gctgagatag gtgcctcact gattaagcat tggtaactgt   5460
cagaccaagt ttactcatat atactttaga ttgatttaaa acttcatttt taatttaaaa   5520
ggatctaggt gaagatcctt tttgataatc tcatgaccaa aatcccttaa cgtgagtttt   5580
cgttccactg agcgtcagac cccgtagaaa agatcaaagg atcttcttga gatccttttt   5640
ttctgcgcgt aatctgctgc ttgcaaacaa aaaaaccacc gctaccagcg gtggtttgtt   5700
```

tgccggatca agagctacca actctttttc cgaaggtaac tggcttcagc agagcgcaga 5760
taccaaatac tgttcttcta gtgtagccgt agttaggcca ccacttcaag aactctgtag 5820
caccgcctac atacctcgct ctgctaatcc tgttaccagt ggctgctgcc agtggcgata 5880
agtcgtgtct taccgggttg gactcaagac gatagttacc ggataaggcg cagcggtcgg 5940
gctgaacggg gggttcgtgc acacagccca gcttggagcg aacgacctac accgaactga 6000
gatacctaca gcgtgagcta tgagaaagcg ccacgcttcc cgaagggaga aaggcggaca 6060
ggtatccggt aagcggcagg gtcggaacag gagagcgcac gagggagctt ccagggggaa 6120
acgcctggta tctttatagt cctgtcgggt ttcgccacct ctgacttgag cgtcgatttt 6180
tgtgatgctc gtcagggggg cggagcctat ggaaaaacgc cagcaacgcg gcctttttac 6240
ggttcctggc cttttgctgg ccttttgctc acatgttctt tcctgcgtta tcccctgatt 6300
ctgtggataa ccgtattacc gcctttgagt gagctgatac cgctcgccgc agccgaacga 6360
ccgagcgcag cgagtcagtg agcgaggaag cggaagagcg cccaatacgc aaaccgcctc 6420
tccccgcgcg ttggccgatt cattaatgca ggttaacctg gcttatcgaa at 6472

<210> SEQ ID NO 41
<211> LENGTH: 13200
<212> TYPE: DNA
<213> ORGANISM: Artificial sequence
<220> FEATURE:
<223> OTHER INFORMATION: ZmABP3-AmCyan binary construct

<400> SEQUENCE: 41
aattaattcc tgtggttggc atgcacatac aaatggacga acggataaac cttttcacgc 60
ccttttaaat atccgattat tctaataaac gctcttttct cttaggttta cccgccaata 120
tatcctgtca aacactgata gtttaaactg aaggcgggaa acgacaatct gatcatgagc 180
ggagaattaa gggagtcacg ttatgacccc cgccgatgac gcgggacaag ccgttttacg 240
tttggaactg acagaaccgc aacgctgcag gaattggccg cagcggccat ttaaatcaat 300
tgggcgcgcc gaaagtagca aacaacaggt tcatgtgcac tataaaaaga caaaattctc 360
gagtttcatc ttttattcca cataagcctt atattttcca ttttcatatg atttttagtt 420
taagtttgtg tcttaacttt ttcgttaata cgtaattcta tgcattatgg atgcgtgaag 480
tatttttgtt taaaaaaatg aaatgtcaaa atacgttttg tgatctattt ccatgttttc 540
acctaacagg tggtttttac tatatattct gccataactc tagccttaga tgtaaatcga 600
aaaaaaatga gagatgagct ggagatagcc ttagatgaag cgtctgaaat ataaaagaaa 660
gagtaatgtt gaacgcagta ggtgtagcag ctgtagttcc atctctagga aagggaactg 720
caatccgggc tccgggcctc gcgcaatctg gcctgtcgtg tagatgcagc cctgtccatg 780
acggcccaag caacgcccgc ggctctcgat ccaccacgga acccactccg acacacactg 840
acacacacat gctggatgtg gatgtgctgt ccaattatta gtagcaattc ggtaggcaca 900
ggcacgtact ggccggtgtt ttagctgtaa gtaccgaacc aatcacggtt aagaaccgat 960
taatccgtgc ccagccgccg agtgcgttcg tacgtgcatc ggatgcactg catgaattga 1020
gagcatcatc atatcatacg caggagtagt acgacgccgc tgctgtcttg tccggctaat 1080
gctttgctca cagattagtc catcgcccac ggtcggtgtg gtgtggatcg ctgatgccac 1140
tgctttttgt ttggttttta ttcccctgat aatcctccgc gtccctgaat gtatctattt 1200
attttcattc cgaaatccct ttcacgaaaa agaaaacgaa taaaaagaga gttacgaata 1260
cgcttccggc ggcccacatc accttccagc gaacatcgcg ccgcgctgac gtgtcgccca 1320

-continued

```
tcgcggccgt ccatatcgcc atccgacgac cgtggaagct ggcagcggcc gctccgttcc   1380
gtcgaagggg caggtcagtc aggtcaccca cacggccaca cccgcgcggg ggatacgcgg   1440
tggaaaaccc ggcgaccaca tcaaaacacg aggcgtctcc cgcaggactg gtcactcggc   1500
acgcaggcag aggcagcaca gcagcagcca gctccatcca tcctctttcc cctcctcgct   1560
tcgcttcctc ggcggattcc tcctccctcg gccgtccccg tccccttctt cgccgcgcca   1620
gctcgcccga gttggtaagg ccccctccac ccctccgctt cccctccccc gggcgcgctc   1680
tggcttcctc cccggatcgg cgcggggcgt gctggctccg cgcctgattt cgggcctttt   1740
gtttccttct cgcggagcgc tcgtgtaacg cttcggatct agctggattc aggcgggatc   1800
gcggccgctc ggcttcctcg tggcctgatt cgtggttttc ctcggggagg gaatcctgat   1860
cggatcatcg ggattcctcg tgcggccggg acacgcttgc gagccagaaa catagtctgc   1920
gtggccggga ttccacgatc tgtgatctag acgtcgggcg cttcgtctat gtgctcgctg   1980
caggctgtgg cgtactggcg tggtgcgcgg ccgctatgga tccgtgcttg tttgttcgcc   2040
ctgtagcgtg tgaaatcgag ctgtgtagat ctatggtctg cgaggtgcgg tggcggtgga   2100
atctcggttg atctttacct cagcggcgcc agtgtagctc gtgtggctgc agttcatctg   2160
cgaatttggc tctcggcggc ttaggtcgcg gagcttggat tatggagcac cagctgcagc   2220
gtgaccctgt tggttctcat gtggatctgt tggctgaggt tgcagacttc aagtgccact   2280
gccattgacc ggagctgctg cacgattata ctggaatatc tagcggtagt atactctgct   2340
agtactcaat acgggtctcc tgacaaatgt ctttcgtgtt tagggaccta gcactctagt   2400
gtcaagacta tttgctggaa tatctaatat tagcagtttc tgtagtggct cagttgcagc   2460
ctggtttaga atgatgggga cagttggctg tgccatgcaa aataaagtgt gtgaaagcaa   2520
ctgcctctta aactatgggt ggtgcaagca ggttatttga agggactctc cacactgtat   2580
ctccagttaa ctatgactga acttgtggtc gcaggcaaac ccaccatggc cctgtccaac   2640
aagttcatcg gcgacgacat gaagatgacc taccacatgg acggctgcgt gaacggccac   2700
tacttcaccg tgaagggcga gggcagcggc aagccctacg agggcaccca gacctccacc   2760
ttcaaggtga cgatggccaa cggcggcccc ctggccttct ccttcgacat cctgtccacc   2820
gtgttcatgt acggcaaccg ctgcttcacc gcctacccca ccagcatgcc cgactacttc   2880
aagcaggcct tccccgacgg catgtcctac gagagaacct tcacctacga ggacggcggc   2940
gtggccaccg ccagctggga gatcagcctg aagggcaact gcttcgagca caagtccacc   3000
ttccacggcg tgaacttccc cgccgacggc cccgtgatgg ccaagaagac caccggctgg   3060
gacccctcct tcgagaagat gaccgtgtgc gacggcatct tgaagggcga cgtgaccgcc   3120
ttcctgatgc tgcagggcgg cggcaactac agatgccagt tccacacctc ctacaagacc   3180
aagaagcccg tgaccatgcc ccccaaccac gtggtggagc accgcatcgc cagaaccgac   3240
ctggacaagg gcggcaacag cgtgcagctg accgagcacg ccgtggccca catcacctcc   3300
gtggtgccct tctgagagct cgcatcatga tcatgcatca tggactcggc ctactactgt   3360
ggatttgtat gccattatag acttggtgct gtgaaagact gcttgatgat ttgcgggttt   3420
gttgctgtgt aaaaaaaggt cccttggctc ccagaagacc atgaaggttc ggatctatca   3480
tgtaattcct tgttatctgc caattatgta tggactatgg acatgtgttg cgctgttcaa   3540
cttactacta caaataagta atcgatatgt tcccttccca tgtctcggtg acaattgtct   3600
ggagaagctt aggggtcgtt tgtttgggat tatgtctgga gaaacttatt ttaaactaag   3660
```

-continued

```
tgtgagttca agttaagtta gattatataa tctaggcaga ttataattcc aagcgaacag   3720
gtccttagtg tttttggaaa atcctaggtg ttcttttggc tacattgttg tgtgtgcaga   3780
tcccttgttg gtctgtaagc gtggggaagt aagaatcgtc cgtttctact gaagacctgc   3840
tcgagttagg caccgaggat gccggtaacc aaacagagca atagtgtctc tgtgggcaca   3900
gtggagtgtg aatctgtgtg atgcaaatcc gtcatttgtt tagcaaaatt tccagcgttg   3960
catgatgcag tttctttaac acggacttaa gggaagggaa aaaaatgttg agccaggaga   4020
tccttcaatg tgttagactg acgtgatagc caactaaacc acgacgcaat gttgtcgtta   4080
atgacaaaaa aactatttgt tcctaaatcc ttggcgacat tgcatggctg tctcatgaga   4140
taatggtctc atctcttatt tatctcttat ttatagccgg aagtggtagt gacccctgct   4200
tgattgctcg tatgccatct caagttctca accgtgtcga gcagccattt tcccatctca   4260
agcgcatcat cgtttcgttt gacctcatct gctatcctgc tcctagtgca aatcacatgc   4320
gacagaaagt gtggcgcgcc gaattcgagc tcggtaccgg accgcgatcg cttaattaag   4380
cttgcatgcc tgcagtgcag cgtgacccgg tcgtgcccct ctctagagat aatgagcatt   4440
gcatgtctaa gttataaaaa attaccacat atttttttg tcacacttgt ttgaagtgca   4500
gtttatctat ctttatacat atatttaaac tttactctac gaataatata atctatagta   4560
ctacaataat atcagtgttt tagagaatca tataaatgaa cagttagaca tggtctaaag   4620
gacaattgag tattttgaca acaggactct acagttttat ctttttagtg tgcatgtgtt   4680
ctcctttttt tttgcaaata gcttcaccta tataatactt catccatttt attagtacat   4740
ccatttaggg tttagggtta atggttttta tagactaatt tttttagtac atctatttta   4800
ttctatttta gcctctaaat taagaaaact aaaactctat tttagttttt ttatttaata   4860
atttagatat aaaatagaat aaaataaagt gactaaaaat taaacaaata ccctttaaga   4920
aattaaaaaa actaaggaaa catttttctt gtttcgagta gataatgcca gcctgttaaa   4980
cgccgtcgac gagtctaacg gacaccaacc agcgaaccag cagcgtcgcg tcgggccaag   5040
cgaagcagac ggcacggcat ctctgtcgct gcctctggac ccctctcgag agttccgctc   5100
caccgttgga cttgctccgc tgtcggcatc cagaaattgc gtggcggagc ggcagacgtg   5160
agccggcacg gcaggcggcc tcctcctcct ctcacggcac cggcagctac gggggattcc   5220
tttcccaccg ctccttcgct ttcccttcct cgcccgccgt aataaataga caccccctcc   5280
acaccctctt tccccaacct cgtgttgttc ggagcgcaca cacacacaac cagatctccc   5340
ccaaatccac ccgtcggcac ctccgcttca aggtacgccg ctcgtcctcc cccccccccc   5400
ctctctacct tctctagatc ggcgttccgg tccatggtta gggcccggta gttctacttc   5460
tgttcatgtt tgtgttagat ccgtgtttgt gttagatccg tgctgctagc gttcgtacac   5520
ggatgcgacc tgtacgtcag acacgttctg attgctaact tgccagtgtt tctctttggg   5580
gaatcctggg atggctctag ccgttccgca gacgggatcg atttcatgat ttttttttgtt   5640
tcgttgcata gggtttggtt tgcccttttc ctttatttca atatatgccg tgcacttgtt   5700
tgtcgggtca tcttttcatg cttttttttg tcttggttgt gatgatgtgg tctggttggg   5760
cggtcgttct agatcggagt agaattctgt ttcaaactac ctggtggatt tattaatttt   5820
ggatctgtat gtgtgtgcca tacatattca tagttacgaa ttgaagatga tggatggaaa   5880
tatcgatcta ggataggtat acatgttgat gcgggtttta ctgatgcata tacagagatg   5940
ctttttgttc gcttggttgt gatgatgtgg tgtggttggg cggtcgttca ttcgttctag   6000
atcggagtag aatactgttt caaactacct ggtgtattta ttaattttgg aactgtatgt   6060
```

-continued gtgtgtcata catcttcata gttacgagtt taagatggat ggaaatatcg atctaggata 6120
ggtatacatg ttgatgtggg ttttactgat gcatatacat gatggcatat gcagcatcta 6180
ttcatatgct ctaaccttga gtacctatct attataataa acaagtatgt tttataatta 6240
ttttgatctt gatatacttg gatgatggca tatgcagcag ctatatgtgg attttttag 6300
ccctgccttc atacgctatt tatttgcttg gtactgtttc ttttgtcgat gctcaccctg 6360
ttgtttggtg ttacttctgc agggatcccc gatcatgcaa aaactcatta actcagtgca 6420
aaactatgcc tggggcagca aaacggcgtt gactgaactt tatggtatgg aaaatccgtc 6480
cagccagccg atggccgagc tgtggatggg cgcacatccg aaaagcagtt cacgagtgca 6540
gaatgccgcc ggagatatcg tttcactgcg tgatgtgatt gagagtgata aatcgactct 6600
gctcggagag gccgttgcca aacgctttgg cgaactgcct ttcctgttca aagtattatg 6660
cgcagcacag ccactctcca ttcaggttca tccaaacaaa cacaattctg aaatcggttt 6720
tgccaaagaa aatgccgcag gtatcccgat ggatgccgcc gagcgtaact ataaagatcc 6780
taaccacaag ccggagctgg tttttgcgct gacgcctttc cttgcgatga acgcgtttcg 6840
tgaattttcc gagattgtct ccctactcca gccggtcgca ggtgcacatc cggcgattgc 6900
tcacttttta caacagcctg atgccgaacg tttaagcgaa ctgttcgcca gcctgttgaa 6960
tatgcagggt gaagaaaaat cccgcgcgct ggcgatttta aaatcggccc tcgatagcca 7020
gcagggtgaa ccgtggcaaa cgattcgttt aatttctgaa ttttacccgg aagacagcgg 7080
tctgttctcc ccgctattgc tgaatgtggt gaaattgaac cctggcgaag cgatgttcct 7140
gttcgctgaa acaccgcacg cttacctgca aggcgtggcg ctggaagtga tggcaaactc 7200
cgataacgtg ctgcgtgcgg gtctgacgcc taaatacatt gatattccgg aactggttgc 7260
caatgtgaaa ttcgaagcca aaccggctaa ccagttgttg acccagccgg tgaaacaagg 7320
tgcagaactg gacttcccga ttccagtgga tgattttgcc ttctcgctgc atgaccttag 7380
tgataaagaa accaccatta gccagcagag tgccgccatt ttgttctgcg tcgaaggcga 7440
tgcaacgttg tggaaaggtt ctcagcagtt acagcttaaa ccgggtgaat cagcgtttat 7500
tgccgccaac gaatcaccgg tgactgtcaa aggccacggc cgtttagcgc gtgtttacaa 7560
caagctgtaa gagcttactg aaaaaattaa catctcttgc taagctggga gctcgatccg 7620
tcgacctgca gatcgttcaa acatttggca ataaagtttc ttaagattga atcctgttgc 7680
cggtcttgcg atgattatca tataatttct gttgaattac gttaagcatg taataattaa 7740
catgtaatgc atgacgttat ttatgagatg ggtttttatg attagagtcc cgcaattata 7800
catttaatac gcgatagaaa acaaaatata gcgcgcaaac taggataaat tatcgcgcgc 7860
ggtgtcatct atgttactag atctgctagc cctgcaggaa atttaccggt gcccgggcgg 7920
ccagcatggc cgtatccgca atgtgttatt aagttgtcta agcgtcaatt tgtttacacc 7980
acaatatatc ctgccaccag ccagccaaca gctccccgac cggcagctcg gcacaaaatc 8040
accactcgat acaggcagcc catcagaatt aattctcatg tttgacagct tatcatcgac 8100
tgcacggtgc accaatgctt ctggcgtcag gcagccatcg gaagctgtgg tatggctgtg 8160
caggtcgtaa atcactgcat aattcgtgtc gctcaaggcg cactcccgtt ctggataatg 8220
ttttttgcgc cgacatcata acggttctgg caaatattct gaaatgagct gttgacaatt 8280
aatcatccgg ctcgtataat gtgtggaatt gtgagcggat aacaatttca cacaggaaac 8340
agaccatgag ggaagcgttg atcgccgaag tatcgactca actatcagag gtagttggcg 8400

-continued

```
tcatcgagcg ccatctcgaa ccgacgttgc tggccgtaca tttgtacggc tccgcagtgg   8460
atggcggcct gaagccacac agtgatattg atttgctggt tacggtgacc gtaaggcttg   8520
atgaaacaac gcggcgagct ttgatcaacg accttttgga aacttcggct tcccctggag   8580
agagcgagat tctccgcgct gtagaagtca ccattgttgt gcacgacgac atcattccgt   8640
ggcgttatcc agctaagcgc gaactgcaat ttggagaatg gcagcgcaat gacattcttg   8700
caggtatctt cgagccagcc acgatcgaca ttgatctggc tatcttgctg acaaaagcaa   8760
gagaacatag cgttgccttg gtaggtccag cggcggagga actctttgat ccggttcctg   8820
aacaggatct atttgaggcg ctaaatgaaa ccttaacgct atggaactcg ccgcccgact   8880
gggctggcga tgagcgaaat gtagtgctta cgttgtcccg catttggtac agcgcagtaa   8940
ccggcaaaat cgcgccgaag gatgtcgctg ccgactgggc aatggagcgc ctgccggccc   9000
agtatcagcc cgtcatactt gaagctaggc aggcttatct tggacaagaa gatcgcttgg   9060
cctcgcgcgc agatcagttg gaagaatttg ttcactacgt gaaaggcgag atcaccaaag   9120
tagtcggcaa ataaagctct agtggatctc cgtacccggg gatctggctc gcggcggacg   9180
cacgacgccg gggcgagacc ataggcgatc tcctaaatca atagtagctg taacctcgaa   9240
gcgtttcact tgtaacaacg attgagaatt tttgtcataa aattgaaata cttggttcgc   9300
atttttgtca tccgcggtca gccgcaattc tgacgaactg cccatttagc tggagatgat   9360
tgtacatcct tcacgtgaaa atttctcaag cgctgtgaac aagggttcag attttagatt   9420
gaaaggtgag ccgttgaaac acgttcttct tgtcgatgac gacgtcgcta tgcggcatct   9480
tattattgaa taccttacga tccacgcctt caaagtgacc gcggtagccg acagcaccca   9540
gttcacaaga gtactctctt ccgcgacggt cgatgtcgtg gttgttgatc tagatttagg   9600
tcgtgaagat gggctcgaga tcgttcgtaa tctggcggca aagtctgata ttccaatcat   9660
aattatcagt ggcgaccgcc ttgaggagac ggataaagtt gttgcactcg agctaggagc   9720
aagtgatttt atcgctaagc cgttcagtat cagagagttt ctagcacgca ttcgggttgc   9780
cttgcgcgtg cgccccaacg ttgtccgctc caaagaccga cggtcttttt gttttactga   9840
ctggacactt aatctcaggc aacgtcgctt gatgtccgaa gctggcggtg aggtgaaact   9900
tacggcaggt gagttcaatc ttctcctcgc gtttttagag aaaccccgcg acgttctatc   9960
gcgcgagcaa cttctcattg ccagtcgagt acgcgacgag gaggtttatg acaggagtat  10020
agatgttctc attttgaggc tgcgccgcaa acttgaggca gatccgtcaa gccctcaact  10080
gataaaaaca gcaagaggtg ccggttattt ctttgacgcg gacgtgcagg tttcgcacgg  10140
ggggacgatg gcagcctgag ccaattccca gatccccgag gaatcggcgt gagcggtcgc  10200
aaaccatccg gcccggtaca aatcggcgcg gcgctgggtg atgacctggt ggagaagttg  10260
aaggccgcgc aggccgccca gcggcaacgc atcgaggcag aagcacgccc cggtgaatcg  10320
tggcaagcgg ccgctgatcg aatccgcaaa gaatcccggc aaccgccggc agccggtgcg  10380
ccgtcgatta ggaagccgcc caagggcgac gagcaaccag atttttcgt tccgatgctc  10440
tatgacgtgg gcacccgcga tagtcgcagc atcatggacg tggccgtttt ccgtctgtcg  10500
aagcgtgacc gacgagctgg cgaggtgatc cgctacgagc ttccagacgg gcacgtagag  10560
gtttccgcag ggccggccgg catggccagt gtgtgggatt acgacctggt actgatggcg  10620
gtttcccatc taaccgaatc catgaaccga taccgggaag ggaagggaga caagcccggc  10680
cgcgtgttcc gtccacacgt tgcggacgta ctcaagttct gccggcgagc cgatggcgga  10740
aagcagaaag acgacctggt agaaacctgc attcggttaa acaccacgca cgttgccatg  10800
```

```
cagcgtacga agaaggccaa gaacggccgc ctggtgacgg tatccgaggg tgaagccttg  10860
attagccgct acaagatcgt aaagagcgaa accgggcggc cggagtacat cgagatcgag  10920
ctagctgatt ggatgtaccg cgagatcaca gaaggcaaga acccggacgt gctgacggtt  10980
caccccgatt actttttgat cgatcccggc atcggccgtt ttctctaccg cctggcacgc  11040
cgcgccgcag gcaaggcaga agccagatgg ttgttcaaga cgatctacga acgcagtggc  11100
agcgccggag agttcaagaa gttctgtttc accgtgcgca agctgatcgg gtcaaatgac  11160
ctgccggagt acgatttgaa ggaggaggcg gggcaggctg gcccgatcct agtcatgcgc  11220
taccgcaacc tgatcgaggg cgaagcatcc gccggttcct aatgtacgga gcagatgcta  11280
gggcaaattg ccctagcagg ggaaaaaggt cgaaaaggtc tctttcctgt ggatagcacg  11340
tacattggga acccaaagcc gtacattggg aaccggaacc cgtacattgg gaacccaaag  11400
ccgtacattg ggaaccggtc acacatgtaa gtgactgata taaaagagaa aaaaggcgat  11460
ttttccgcct aaaactcttt aaaacttatt aaaactctta aaacccgcct ggcctgtgca  11520
taactgtctg gccagcgcac agccgaagag ctgcaaaaag cgcctaccct tcggtcgctg  11580
cgctccctac gccccgccgc ttcgcgtcgg cctatcgcgg ccgctggccg ctcaaaaatg  11640
gctggcctac ggccaggcaa tctaccaggg cgcggacaag ccgcgccgtc gccactcgac  11700
cgccggcgct gaggtctgcc tcgtgaagaa ggtgttgctg actcatacca ggcctgaatc  11760
gccccatcat ccagccagaa agtgagggag ccacggttga tgagagcttt gttgtaggtg  11820
gaccagttgg tgattttgaa cttttgcttt gccacggaac ggtctgcgtt gtcgggaaga  11880
tgcgtgatct gatccttcaa ctcagcaaaa gttcgattta ttcaacaaag ccgccgtccc  11940
gtcaagtcag cgtaatgctc tgccagtgtt acaaccaatt aaccaattct gattagaaaa  12000
actcatcgag catcaaatga aactgcaatt tattcatatc aggattatca ataccatatt  12060
tttgaaaaag ccgtttctgt aatgaaggag aaaactcacc gaggcagttc cataggatgg  12120
caagatcctg gtatcggtct gcgattccga ctcgtccaac atcaatacaa cctattaatt  12180
tcccctcgtc aaaaataagg ttatcaagtg agaaatcacc atgagtgacg actgaatccg  12240
gtgagaatgg caaaagctct gcattaatga atcggccaac gcgcggggag aggcggtttg  12300
cgtattgggc gctcttccgc ttcctcgctc actgactcgc tgcgctcggt cgttcggctg  12360
cggcgagcgg tatcagctca ctcaaaggcg gtaatacggt tatccacaga atcaggggat  12420
aacgcaggaa agaacatgtg agcaaaaggc cagcaaaagg ccaggaaccg taaaaaggcc  12480
gcgttgctgg cgtttttcca taggctccgc cccccctgacg agcatcacaa aaatcgacgc  12540
tcaagtcaga ggtggcgaaa cccgacagga ctataaagat accaggcgtt tccccctgga  12600
agctccctcg tgcgctctcc tgttccgacc ctgccgctta ccggatacct gtccgccttt  12660
ctcccttcgg gaagcgtggc gctttctcat agctcacgct gtaggtatct cagttcggtg  12720
taggtcgttc gctccaagct gggctgtgtg cacgaacccc ccgttcagcc cgaccgctgc  12780
gccttatccg gtaactatcg tcttgagtcc aacccggtaa gacacgactt atcgccactg  12840
gcagcagcca ctggtaacag gattagcaga gcgaggtatg taggcggtgc tacagagttc  12900
ttgaagtggt ggcctaacta cggctacact agaagaacag tatttggtat ctgcgctctg  12960
ctgaagccag ttaccttcgg aaaaagagtt ggtagctctt gatccggcaa acaaaccacc  13020
gctggtagcg gtggtttttt tgtttgcaag cagcagatta cgcgcagaaa aaaaggatct  13080
caagaagatc tttgatcttt ttctacgggg tctgacgctc agtggaacga aaactcacgt  13140
```

taagggattt tggtcatgag attatcaaaa aggatcttca cctagatcct tttgatccgg 13200

<210> SEQ ID NO 42
<211> LENGTH: 8961
<212> TYPE: DNA
<213> ORGANISM: Artificial sequence
<220> FEATURE:
<223> OTHER INFORMATION: ZmABP3-AtAVP1D assembly construct

<400> SEQUENCE: 42
gggacccaaa gtagcaaaca acaggttcat gtgcactata aaaagacaaa attctcgagt 60
ttcatctttt attccacata agccttatat tttccatttt catatgattt ttagtttaag 120
tttgtgtctt aactttttcg ttaatacgta attctatgca ttatggatgc gtgaagtatt 180
tttgtttaaa aaaatgaaat gtcaaaatac gttttgtgat ctatttccat gttttcacct 240
aacaggtggt ttttactata tattctgcca taactctagc cttagatgta aatcgaaaaa 300
aaatgagaga tgagctggag atagccttag atgaagcgtc tgaaatataa aagaaagagt 360
aatgttgaac gcagtaggtg tagcagctgt agttccatct ctaggaaagg gaactgcaat 420
ccgggctccg ggcctcgcgc aatctggcct gtcgtgtaga tgcagccctg tccatgacgg 480
cccaagcaac gcccgcggct ctcgatccac cacggaaccc actccgacac acactgacac 540
acacatgctg gatgtggatg tgctgtccaa ttattagtag caattcggta ggcacaggca 600
cgtactggcc ggtgttttag ctgtaagtac cgaaccaatc acggttaaga accgattaat 660
ccgtgcccag ccgccgagtg cgttcgtacg tgcatcggat gcactgcatg aattgagagc 720
atcatcatat catacgcagg agtagtacga cgccgctgct gtcttgtccg gctaatgctt 780
tgctcacaga ttagtccatc gcccacggtc ggtgtggtgt ggatcgctga tgccactgct 840
ttttgtttgg tttttattcc cctgataatc ctccgcgtcc ctgaatgtat ctatttattt 900
tcattccgaa atccctttca cgaaaaagaa aacgaataaa aagagagtta cgaatacgct 960
tccggcggcc cacatcacct tccagcgaac atcgcgccgc gctgacgtgt cgcccatcgc 1020
ggccgtccat atcgccatcc gacgaccgtg gaagctggca gcggccgctc cgttccgtcg 1080
aaggggcagg tcagtcaggt cacccacacg gccacacccg cgcgggggat acgcggtgga 1140
aaacccggcg accacatcaa aacacgaggc gtctcccgca ggactggtca ctcggcacgc 1200
aggcagaggc agcacagcag cagccagctc catccatcct ctttcccctc ctcgcttcgc 1260
ttcctcggcg gattcctcct ccctcggccg tccccgtccc cttcttcgcc gcgccagctc 1320
gcccgagttg gtaaggcccc ctccacccct ccgcttcccc tcccccgggc gcgctctggc 1380
ttcctccccg gatcggcgcg gggcgtgctg gctccgcgcc tgatttcggg ccttttgttt 1440
ccttctcgcg gagcgctcgt gtaacgcttc ggatctagct ggattcaggc gggatcgcgg 1500
ccgctcggct tcctcgtggc ctgattcgtg gttttcctcg gggagggaat cctgatcgga 1560
tcatcgggat tcctcgtgcg gccgggacac gcttgcgagc cagaaacata gtctgcgtgg 1620
ccgggattcc acgatctgtg atctagacgt cgggcgcttc gtctatgtgc tcgctgcagg 1680
ctgtggcgta ctggcgtggt gcgcggccgc tatggatccg tgcttgtttg ttcgccctgt 1740
agcgtgtgaa atcgagctgt gtagatctat ggtctgcgag gtgcggtggc ggtggaatct 1800
cggttgatct ttacctcagc ggcgccagtg tagctcgtgt ggctgcagtt catctgcgaa 1860
tttggctctc ggcggcttag gtcgcggagc ttggattatg gagcaccagc tgcagcgtga 1920
ccctgttggt tctcatgtgg atctgttggc tgaggttgca gacttcaagt gccactgcca 1980
ttgaccggag ctgctgcacg attatactgg aatatctagc ggtagtatac tctgctagta 2040

-continued

```
ctcaatacgg gtctcctgac aaatgtcttt cgtgtttagg gacctagcac tctagtgtca   2100
agactatttg ctggaatatc taatattagc agtttctgta gtggctcagt tgcagcctgg   2160
tttagaatga tggggacagt tggctgtgcc atgcaaaata aagtgtgtga aagcaactgc   2220
ctcttaaact atgggtggtg caagcaggtt atttgaaggg actctccaca ctgtatctcc   2280
agttaacttt gactgaactt gtggtcgcag gcaaacccac catggttgca ccagcattgc   2340
ttccggaact gtggacggag atactggtcc caatctgcgc tgtgatcggc atagccttca   2400
gcctgttcca gtggtacgtc gtgtcaaggg tgaagctcac gagcgacttg ggagccagta   2460
gtagcggagg ggcgaacaac gggaagaacg gctatggcga ctatctgatc gaggaggaag   2520
agggtgtgaa cgaccaatca gtggtggcga agtgtgcgga gattcagacc gccattagcg   2580
agggagctac gagcttcctg tttacggagt acaagtacgt gggcgtcttc atgatcttct   2640
tcgctgccgt catcttcgtg ttcctgggtt ctgtcgaagg cttctccacc gacaacaagc   2700
cgtgcactta cgacaccacc agaacctgca aacctgcact ggccactgct gcgttctcca   2760
ccatagcgtt cgtgcttggt gctgtgacaa gcgtcctgag tggcttcttg gggatgaaga   2820
tcgctaccta cgccaatgcc agaaccacac tggaggcaag gaaaggtgtc gggaaagcct   2880
tcatcgtggc ctttcggagt ggtgctgtca tgggcttcct gcttgctgcc agtggattgc   2940
tcgtgctcta catcaccatc aacgtgttca agatctacta cggcgacgat tgggaagggc   3000
tcttcgacgc aatcactggc tatgggttgg gtggctcttc aatggcgctc ttcggaagag   3060
tgggaggtgg catctacacg aaagcggctg atgtgggagc tgacctggtc gggaagatcg   3120
agcgcaacat cccggaagat gacccaagga acccagcagt gatcgccgac aatgtcggcg   3180
acaatgtcgg tgacatagcg ggtatgggaa gcgacctctt tggctcatac gccgaagcca   3240
gctgcgcagc gcttgttgtc gcctccatct ccagcttcgg gatcaaccac gacttcacag   3300
ccatgtgcta tcccctcctg atcagcagca tgggcatact ggtgtgcctc atcaccacgc   3360
tgtttgcgac cgacttcttc gagatcaagc tggtgaagga gatcgaacct gcgctgaaga   3420
accagctgat catctcgacc gtgatcatga ccgttgggat cgccatcgtc tcatgggtgg   3480
gtcttcctac ctcgttcacc atcttcaact ttggcactca gaaggtggtg aagaactggc   3540
agctcttcct ctgcgtttgc gtcggacttt gggctgggct gatcatcggc tttgtcacgg   3600
agtactacac ctccaacgcc tacagtcctg tgcaggatgt ggccgattct tgccgtactg   3660
gtgctgcaac gaacgtcatc ttcggtcttg cactgggcta caagtcggtc atcatcccca   3720
tcttcgccat tgccatctcc atcttcgtga gcttctcgtt cgcagccatg tacggtgttg   3780
ccgttgctgc attgggcatg ctctccacca tcgctactgg cctcgctatt gacgcgtatg   3840
gtccgatttc ggacaatgct ggagggattg ccgagatggc tgggatgtcg cacaggatca   3900
gagagcgtac ggatgcactg gatgctgcag ggaacactac cgctgccatt ggcaagggct   3960
ttgccatagg gtctgctgca ctcgttagcc tggccttgtt tggcgctttc gtgtcgagag   4020
ctggcatcca cacagtggac gttctgactc ccaaggtgat catcggactt ctggtgggag   4080
ctatgctccc gtactggttc tctgcgatga cgatgaagtc ggtcggatca gcagcgctga   4140
agatggtcga ggaggttagg aggcagttca acacgatccc cggattgatg gagggcacag   4200
ctaagccgga ctatgctacc tgcgtgaaga tctccacaga cgcctccatc aaggagatga   4260
tccctccagg gtgcctggtg atgcttactc cgctgattgt gggcttcttc ttcggcgtgg   4320
agacactttc cggcgtgttg gcaggaagcc tcgtgagtgg agtgcagatc gcgatcagtg   4380
```

```
ccagcaatac tggaggggca tgggacaacg cgaagaagta catcgaagcc ggcgtctcag   4440
aacacgcgaa gtctctgggt ccgaaagggt cagaacccca taaggccgct gtgatcggcg   4500
atacgattgg cgatcccttg aaggacactt ctggcccatc cctcaacatc ctgatcaagc   4560
tcatggcagt ggagagcctc gttttcgcgc ctttcttcgc gactcatggt ggcatcctgt   4620
tcaagtactt ctagagctcg catcatgatc atgcatcatg gactcggcct actactgtgg   4680
atttgtatgc cattatagac ttggtgctgt gaaagactgc ttgatgattt gcgggtttgt   4740
tgctgtgtaa aaaaaggtcc cttggctccc agaagaccat gaaggttcgg atctatcatg   4800
taattccttg ttatctgcca attatgtatg gactatggac atgtgttgcg ctgttcaact   4860
tactactaca aataagtaat cgatatgttc ccttcccatg tctcggtgac aattgtctgg   4920
agaagcttag ggtcgtttg tttgggatta tgtctggaga aacttatttt aaactaagtg   4980
tgagttcaag ttaagttaga ttatataatc taggcagatt ataattccaa gcgaacaggt   5040
ccttagtgtt tttggaaaat cctaggtgtt cttttggcta cattgttgtg tgtgcagatc   5100
ccttgttggt ctgtaagcgt ggggaagtaa gaatcgtccg tttctactga agacctgctc   5160
gagttaggca ccgaggatgc cggtaaccaa acagagcaat agtgtctctg tgggcacagt   5220
ggagtgtgaa tctgtgtgat gcaaatccgt catttgttta gcaaaatttc cagcgttgca   5280
tgatgcagtt tctttaacac ggacttaagg gaagggaaaa aaatgttgag ccaggagatc   5340
cttcaatgtg ttagactgac gtgatagcca actaaaccac gacgcaatgt tgtcgttaat   5400
gacaaaaaaa ctatttgttc ctaaatcctt ggcgacattg catggctgtc tcatgagata   5460
atggtctcat ctcttattta tctcttattt atagccggaa gtggtagtga cccctgcttg   5520
attgctcgta tgccatctca agttctcaac cgtgtcgagc agccattttc ccatctcaag   5580
cgcatcatcg tttcgtttga cctcatctgc tatcctgctc ctagtgcaaa tcacatgcga   5640
cagaaagtgt cggaccgcag ctccagcttt tgttcccttt agtgagggtt aattgcgcgc   5700
ttggcgtaat catggtcata gctgtttcct gtgtgaaatt gttatccgct cacaattcca   5760
cacaacatac gagccggaag cataaagtgt aaagcctggg gtgcctaatg agtgagctaa   5820
ctcacattaa ttgcgttgcg ctcactgccc gctttccagt cgggaaacct gtcgtgccag   5880
ctgcattaat gaatcggcca acgcgcgggg agaggcggtt tgcgtattgg gcgctcttcc   5940
gcttcctcgc tcactgactc gctgcgctcg gtcgttcggc tgcggcgagc ggtatcagct   6000
cactcaaagg cggtaatacg gttatccaca gaatcagggg ataacgcagg aaagaacatg   6060
tgagcaaaag gccagcaaaa ggccaggaac cgtaaaaagg ccgcgttgct ggcgtttttc   6120
cataggctcc gcccccctga cgagcatcac aaaaatcgac gctcaagtca gaggtggcga   6180
aacccgacag gactataaag ataccaggcg tttccccctg gaagctccct cgtgcgctct   6240
cctgttccga ccctgccgct taccggatac ctgtccgcct ttctcccttc gggaagcgtg   6300
gcgctttctc atagctcacg ctgtaggtat ctcagttcgg tgtaggtcgt tcgctccaag   6360
ctgggctgtg tgcacgaacc ccccgttcag cccgaccgct gcgccttatc cggtaactat   6420
cgtcttgagt ccaacccggt aagacacgac ttatcgccac tggcagcagc cactggtaac   6480
aggattagca gagcgaggta tgtaggcggt gctacagagt tcttgaagtg gtggcctaac   6540
tacggctaca ctagaaggac agtatttggt atctgcgctc tgctgaagcc agttaccttc   6600
ggaaaaagag ttggtagctc ttgatccggc aaacaaacca ccgctggtag cggtggtttt   6660
tttgtttgca agcagcagat tacgcgcaga aaaaaaggat ctcaagaaga tcctttgatc   6720
ttttctacgg ggtctgacgc tcagtggaac gaaaactcac gttaagggat tttggtcatg   6780
```

```
agattatcaa aaaggatctt cacctagatc cttttcgacc gaataaatac ctgtgacgga   6840
agatcacttc gcagaataaa taaatcctgg tgtccctgtt gataccggga agccctgggc   6900
caacttttgg cgaaaatgag acgttgatcg gcacgtaaga ggttccaact ttcaccataa   6960
tgaaataaga tcactaccgg gcgtattttt tgagttgtcg agattttcag gagctaagga   7020
agctaaaatg gagaaaaaaa tcactggata taccaccgtt gatatatccc aatggcatcg   7080
taaagaacat tttgaggcat ttcagtcagt tgctcaatgt acctataacc agaccgttca   7140
gctggatatt acggcctttt taaagaccgt aaagaaaaat aagcacaagt tttatccggc   7200
ctttattcac attcttgccc gcctgatgaa tgctcatccg gaattacgta tggcaatgaa   7260
agacggtgag ctggtgatat gggatagtgt tcacccttgt tacaccgttt tccatgagca   7320
aactgaaacg ttttcatcgc tctggagtga ataccacgac gatttccggc agtttctaca   7380
catatattcg caagatgtgg cgtgttacgg tgaaaacctg gcctatttcc ctaaagggtt   7440
tattgagaat atgtttttcg tctcagccaa tccctgggtg agtttcacca gttttgattt   7500
aaacgtggcc aatatggaca acttcttcgc ccccgttttc actatgggca aatattatac   7560
gcaaggcgac aaggtgctga tgccgctggc gattcaggtt catcatgccg tttgtgatgg   7620
cttccatgtc ggcagaatgc ttaatgaatt acaacagtac tgcgatgagt ggcagggcgg   7680
ggcgtaattt ttttaaggca gttattggtg cccttaaacg cctggttgct acgcctgaat   7740
aagtgataat aagcggatga atggcagaaa ttcgaaagca aattcgaccc ggtcgtcggt   7800
tcagggcagg gtcgttaaat agccgcttat gtctattgct ggtttaccgg tttattgact   7860
accggaagca gtgtgaccgt gtgcttctca aatgcctgag gccagtttgc tcaggctctc   7920
cccgtggagg taataattga cgatatgatc cttttttttct gatcaaaagt gctcatcatt   7980
ggaaaacgtt cttcggggcg aaaactctca aggatcttac cgctgttgag atccagttcg   8040
atgtaaccca ctcgtgcacc caactgatct tcagcatctt ttactttcac cagcgtttct   8100
gggtgagcaa aaacaggaag gcaaaatgcc gcaaaaaagg gaataagggc gacacggaaa   8160
tgttgaatac tcatactctt cctttttcaa tattattgaa gcatttatca agggttattg   8220
tctcatgagc ggatacatat ttgaatgtat ttagaaaaat aaacaaatag gggttccgcg   8280
cacatttccc cgaaaagtgc cacctaaatt gtaagcgtta atattttgtt aaaattcgcg   8340
ttaaattttt gttaaatcag ctcatttttt aaccaatagg ccgaaatcgg caaaatccct   8400
tataaatcaa aagaatagac cgagataggg ttgagtgttg ttccagtttg gaacaagagt   8460
ccactattaa agaacgtgga ctccaacgtc aaagggcgaa aaaccgtcta tcagggcgat   8520
ggcccactac gtgaaccatc accctaatca agttttttgg ggtcgaggtg ccgtaaagca   8580
ctaaatcgga accctaaagg gagcccccga tttagagctt gacggggaaa gccggcgaac   8640
gtggcgagaa aggaagggaa gaaagcgaaa ggagcgggcg ctagggcgct ggcaagtgta   8700
gcggtcacgc tgcgcgtaac caccacaccc gccgcgctta atgcgccgct acagggcgcg   8760
tcccattcgc cattcaggct gcgcaactgt tgggaagggc gatcggtgcg ggcctcttcg   8820
ctattacgcc agctggcgaa agggggatgt gctgcaaggc gattaagttg ggtaacgcca   8880
gggttttccc agtcacgacg ttgtaaaacg acggccagtg agcgcgcgta atacgactca   8940
ctatagggcg aattgggtac g                                               8961
```

<210> SEQ ID NO 43
<211> LENGTH: 15301
<212> TYPE: DNA

<213> ORGANISM: Artificial sequence
<220> FEATURE:
<223> OTHER INFORMATION: ZmABP3-AtAVP1D binary construct

<400> SEQUENCE: 43

```
aattcctgtg gttggcatgc acatacaaat ggacgaacgg ataaaccttt tcacgccctt      60
ttaaatatcc gattattcta ataaacgctc ttttctctta ggtttacccg ccaatatatc     120
ctgtcaaaca ctgatagttt aaactgaagg cgggaaacga caatctgatc atgagcggag     180
aattaaggga gtcacgttat gacccccgcc gatgacgcgg gacaagccgt tttacgtttg     240
gaactgacag aaccgcaacg ctgcaggaat tggccgcagc ggccatttaa atcaattggg     300
cgcgccagct gcttgtgggg accagacaaa aaaggaatgg tgcagaattg ttaggcgcac     360
ctaccaaaag catctttgcc tttattgcaa agataaagca gattcctcta gtacaagtgg     420
ggaacaaaat aacgtggaaa agagctgtcc tgacagccca ctcactaatg cgtatgacga     480
acgcagtgac gaccacaaaa ctcgagactt ttcaacaaag ggtaatatcc ggaaacctcc     540
tcggattcca ttgcccagct atctgtcact ttattgtgaa gatagtggaa aaggaaggtg     600
gctcctacaa atgccatcat tgcgataaag gaaaggctat cgttgaagat gcctctgccg     660
acagtggtcc caaagatgga cccccaccca cgaggagcat cgtggaaaaa gaagacgttc     720
caaccacgtc ttcaaagcaa gtggattgat gtgatatctc cactgacgta agggatgacg     780
aacaatccca ctatccttcg gtaccggacc caaagtagca aacaacaggt tcatgtgcac     840
tataaaaaga caaaattctc gagtttcatc ttttattcca cataagcctt atattttcca     900
ttttcatatg atttttagtt taagtttgtg tcttaacttt ttcgttaata cgtaattcta     960
tgcattatgg atgcgtgaag tatttttgtt taaaaaaatg aaatgtcaaa atacgttttg    1020
tgatctattt ccatgttttc acctaacagg tggtttttac tatatattct gccataactc    1080
tagccttaga tgtaaatcga aaaaaaatga gagatgagct ggagatagcc ttagatgaag    1140
cgtctgaaat ataaaagaaa gagtaatgtt gaacgcagta ggtgtagcag ctgtagttcc    1200
atctctagga aagggaactg caatccgggc tccgggcctc gcgcaatctg gcctgtcgtg    1260
tagatgcagc cctgtccatg acggcccaag caacgcccgc ggctctcgat ccaccacgga    1320
acccactccg acacacactg acacacacat gctggatgtg gatgtgctgt ccaattatta    1380
gtagcaattc ggtaggcaca ggcacgtact ggccggtgtt ttagctgtaa gtaccgaacc    1440
aatcacggtt aagaaccgat taatccgtgc ccagccgccg agtgcgttcg tacgtgcatc    1500
ggatgcactg catgaattga gagcatcatc atatcatacg caggagtagt acgacgccgc    1560
tgctgtcttg tccggctaat gctttgctca cagattagtc catcgcccac ggtcggtgtg    1620
gtgtggatcg ctgatgccac tgctttttgt ttggttttta ttcccctgat aatcctccgc    1680
gtccctgaat gtatctattt attttcattc cgaaatccct ttcacgaaaa agaaaacgaa    1740
taaaaagaga gttacgaata cgcttccggc ggcccacatc accttccagc gaacatcgcg    1800
ccgcgctgac gtgtcgccca tcgcggccgt ccatatcgcc atccgacgac cgtggaagct    1860
ggcagcggcc gctccgttcc gtcgaagggg caggtcagtc aggtcaccca cacggccaca    1920
cccgcgcggg ggatacgcgg tggaaaaccc ggcgaccaca tcaaaacacg aggcgtctcc    1980
cgcaggactg gtcactcggc acgcaggcag aggcagcaca gcagcagcca gctccatcca    2040
tcctctttcc cctcctcgct tcgcttcctc ggcggattcc tcctccctcg gccgtccccg    2100
tcccctctt cgccgcgcca gctcgcccga gttggtaagg ccccctccac ccctccgctt    2160
cccctccccc gggcgcgctc tggcttcctc cccggatcgg cgcggggcgt gctggctccg    2220
```

cgcctgattt cgggcctttt gtttccttct cgcggagcgc tcgtgtaacg cttcggatct 2280
agctggattc aggcgggatc gcggccgctc ggcttcctcg tggcctgatt cgtggttttc 2340
ctcggggagg gaatcctgat cggatcatcg ggattcctcg tgcggccggg acacgcttgc 2400
gagccagaaa catagtctgc gtggccggga ttccacgatc tgtgatctag acgtcgggcg 2460
cttcgtctat gtgctcgctg caggctgtgg cgtactggcg tggtgcgcgg ccgctatgga 2520
tccgtgcttg tttgttcgcc ctgtagcgtg tgaaatcgag ctgtgtagat ctatggtctg 2580
cgaggtgcgg tggcggtgga atctcggttg atctttacct cagcggcgcc agtgtagctc 2640
gtgtggctgc agttcatctg cgaatttggc tctcggcggc ttaggtcgcg gagcttggat 2700
tatggagcac cagctgcagc gtgaccctgt tggttctcat gtggatctgt tggctgaggt 2760
tgcagacttc aagtgccact gccattgacc ggagctgctg cacgattata ctggaatatc 2820
tagcggtagt atactctgct agtactcaat acgggtctcc tgacaaatgt ctttcgtgtt 2880
tagggaccta gcactctagt gtcaagacta tttgctggaa tatctaatat tagcagtttc 2940
tgtagtggct cagttgcagc ctggtttaga atgatgggga cagttggctg tgccatgcaa 3000
aataaagtgt gtgaaagcaa ctgcctctta aactatgggt ggtgcaagca ggttatttga 3060
agggactctc cacactgtat ctccagttaa ctttgactga acttgtggtc gcaggcaaac 3120
ccaccatggt tgcaccagca ttgcttccgg aactgtggac ggagatactg gtcccaatct 3180
gcgctgtgat cggcatagcc ttcagcctgt tccagtggta cgtcgtgtca agggtgaagc 3240
tcacgagcga cttgggagcc agtagtagcg gaggggcgaa caacgggaag aacggctatg 3300
gcgactatct gatcgaggag gaagagggtg tgaacgacca atcagtggtg gcgaagtgtg 3360
cggagattca gaccgccatt agcgagggag ctacgagctt cctgtttacg gagtacaagt 3420
acgtgggcgt cttcatgatc ttcttcgctg ccgtcatctt cgtgttcctg ggttctgtcg 3480
aaggcttctc caccgacaac aagccgtgca cttacgacac caccagaacc tgcaaacctg 3540
cactggccac tgctgcgttc tccaccatag cgttcgtgct tggtgctgtg acaagcgtcc 3600
tgagtggctt cttggggatg aagatcgcta cctacgccaa tgccagaacc acactggagg 3660
caaggaaagg tgtcgggaaa gccttcatcg tggcctttcg gagtggtgct gtcatgggct 3720
tcctgcttgc tgccagtgga ttgctcgtgc tctacatcac catcaacgtg ttcaagatct 3780
actacggcga cgattgggaa gggctcttcg acgcaatcac tggctatggg ttgggtggct 3840
cttcaatggc gctcttcgga agagtgggag gtggcatcta cacgaaagcg gctgatgtgg 3900
gagctgacct ggtcgggaag atcgagcgca acatcccgga agatgaccca aggaacccag 3960
cagtgatcgc cgacaatgtc ggcgacaatg tcggtgacat agcgggtatg ggaagcgacc 4020
tctttggctc atacgccgaa gccagctgcg cagcgcttgt tgtcgcctcc atctccagct 4080
tcgggatcaa ccacgacttc acagccatgt gctatcccct cctgatcagc agcatgggca 4140
tactggtgtg cctcatcacc acgctgtttg cgaccgactt cttcgagatc aagctggtga 4200
aggagatcga acctgcgctg aagaaccagc tgatcatctc gaccgtgatc atgaccgttg 4260
ggatcgccat cgtctcatgg gtgggtcttc ctacctcgtt caccatcttc aactttggca 4320
ctcagaaggt ggtgaagaac tggcagctct tcctctgcgt ttgcgtcgga ctttgggctg 4380
ggctgatcat cggctttgtc acggagtact acacctccaa cgcctacagt cctgtgcagg 4440
atgtggccga ttcttgccgt actggtgctg caacgaacgt catcttcggt cttgcactgg 4500
gctacaagtc ggtcatcatc cccatcttcg ccattgccat ctccatcttc gtgagcttct 4560

```
cgttcgcagc catgtacggt gttgccgttg ctgcattggg catgctctcc accatcgcta   4620
ctggcctcgc tattgacgcg tatggtccga tttcggacaa tgctggaggg attgccgaga   4680
tggctgggat gtcgcacagg atcagagagc gtacggatgc actggatgct gcagggaaca   4740
ctaccgctgc cattggcaag ggctttgcca tagggtctgc tgcactcgtt agcctggcct   4800
tgtttggcgc tttcgtgtcg agagctggca tccacacagt ggacgttctg actcccaagg   4860
tgatcatcgg acttctggtg ggagctatgc tcccgtactg gttctctgcg atgacgatga   4920
agtcggtcgg atcagcagcg ctgaagatgg tcgaggaggt taggaggcag ttcaacacga   4980
tccccggatt gatggagggc acagctaagc cggactatgc tacctgcgtg aagatctcca   5040
cagacgcctc catcaaggag atgatccctc cagggtgcct ggtgatgctt actccgctga   5100
ttgtgggctt cttcttcggc gtggagacac tttccggcgt gttggcagga agcctcgtga   5160
gtggagtgca gatcgcgatc agtgccagca atactggagg ggcatgggac aacgcgaaga   5220
agtacatcga agccggcgtc tcagaacacg cgaagtctct gggtccgaaa gggtcagaac   5280
cccataaggc cgctgtgatc ggcgatacga ttggcgatcc cttgaaggac acttctggcc   5340
catccctcaa catcctgatc aagctcatgg cagtggagag cctcgttttc gcgcctttct   5400
tcgcgactca tggtggcatc ctgttcaagt acttctagag ctcgcatcat gatcatgcat   5460
catggactcg gcctactact gtggatttgt atgccattat agacttggtg ctgtgaaaga   5520
ctgcttgatg atttgcgggt ttgttgctgt gtaaaaaaag gtcccttggc tcccagaaga   5580
ccatgaaggt tcggatctat catgtaattc cttgttatct gccaattatg tatggactat   5640
ggacatgtgt tgcgctgttc aacttactac tacaaataag taatcgatat gttcccttcc   5700
catgtctcgg tgacaattgt ctggagaagc ttaggggtcg tttgtttggg attatgtctg   5760
gagaaactta ttttaaacta agtgtgagtt caagttaagt tagattatat aatctaggca   5820
gattataatt ccaagcgaac aggtccttag tgtttttgga aaatcctagg tgttcttttg   5880
gctacattgt tgtgtgtgca gatcccttgt tggtctgtaa gcgtggggaa gtaagaatcg   5940
tccgtttcta ctgaagacct gctcgagtta ggcaccgagg atgccggtaa ccaaacagag   6000
caatagtgtc tatgtgggca cagtggagtg tgaatctgtg tgatgcaaat ccgtcatttg   6060
tttagcaaaa tttccagcgt tgcatgatgc agtttcttta acacggactt aagggaaggg   6120
aaaaaaatgt tgagccagga gatccttcaa tgtgttagac tgacgtgata gccaactaaa   6180
ccacgacgca atgttgtcgt taatgacaaa aaaactattt gttcctaaat ccttggcgac   6240
attgcatggc tgtctcatga gataatggtc tcatctctta tttatctctt atttatagcc   6300
ggaagtggta gtgacccctg cttgattgct cgtatgccat ctcaagttct caaccgtgtc   6360
gagcagccat tttcccatct caagcgcatc atcgtttcgt ttgacctcat ctgctatcct   6420
gctcctagtg caaatcacat gcgacagaaa gtgtcggacc gcgatcgctt aattaagctt   6480
gcatgcctgc agtgcagcgt gacccggtcg tgcccctctc tagagataat gagcattgca   6540
tgtctaagtt ataaaaaatt accacatatt ttttttgtca cacttgtttg aagtgcagtt   6600
tatctatctt tatacatata tttaaacttt actctacgaa taatataatc tatagtacta   6660
caataatatc agtgttttag agaatcatat aaatgaacag ttagacatgg tctaaaggac   6720
aattgagtat tttgacaaca ggactctaca gttttatctt tttagtgtgc atgtgttctc   6780
cttttttttt gcaaatagct tcacctatat aatacttcat ccattttatt agtacatcca   6840
tttagggttt agggttaatg gtttttatag actaattttt ttagtacatc tattttattc   6900
tattttagcc tctaaattaa gaaaactaaa actctatttt agttttttta tttaataatt   6960
```

tagatataaa atagaataaa ataaagtgac taaaaattaa acaaataccc tttaagaaat 7020
taaaaaaact aaggaaacat ttttcttgtt tcgagtagat aatgccagcc tgttaaacgc 7080
cgtcgacgag tctaacggac accaaccagc gaaccagcag cgtcgcgtcg ggccaagcga 7140
agcagacggc acggcatctc tgtcgctgcc tctggacccc tctcgagagt tccgctccac 7200
cgttggactt gctccgctgt cggcatccag aaattgcgtg gcggagcggc agacgtgagc 7260
cggcacggca ggcggcctcc tcctcctctc acggcaccgg cagctacggg ggattccttt 7320
cccaccgctc cttcgctttc ccttcctcgc ccgccgtaat aaatagacac cccctccaca 7380
ccctctttcc ccaacctcgt gttgttcgga gcgcacacac acacaaccag atctccccca 7440
aatccacccg tcggcacctc cgcttcaagg tacgccgctc gtcctccccc ccccccccctc 7500
tctaccttct ctagatcggc gttccggtcc atggttaggg cccggtagtt ctacttctgt 7560
tcatgtttgt gttagatccg tgtttgtgtt agatccgtgc tgctagcgtt cgtacacgga 7620
tgcgacctgt acgtcagaca cgttctgatt gctaacttgc cagtgtttct ctttggggaa 7680
tcctgggatg gctctagccg ttccgcagac gggatcgatt tcatgatttt ttttgtttcg 7740
ttgcataggg tttggtttgc ccttttcctt tatttcaata tatgccgtgc acttgtttgt 7800
cgggtcatct tttcatgctt ttttttgtct tggttgtgat gatgtggtct ggttgggcgg 7860
tcgttctaga tcggagtaga attctgtttc aaactacctg gtggatttat taattttgga 7920
tctgtatgtg tgtgccatac atattcatag ttacgaattg aagatgatgg atggaaatat 7980
cgatctagga taggtataca tgttgatgcg ggttttactg atgcatatac agagatgctt 8040
tttgttcgct tggttgtgat gatgtggtgt ggttgggcgg tcgttcattc gttctagatc 8100
ggagtagaat actgtttcaa actacctggt gtatttatta attttggaac tgtatgtgtg 8160
tgtcatacat cttcatagtt acgagtttaa gatggatgga aatatcgatc taggataggt 8220
atacatgttg atgtgggttt tactgatgca tatacatgat ggcatatgca gcatctattc 8280
atatgctcta accttgagta cctatctatt ataataaaca agtatgtttt ataattattt 8340
tgatcttgat atacttggat gatggcatat gcagcagcta tatgtggatt tttttagccc 8400
tgccttcata cgctatttat ttgcttggta ctgtttcttt tgtcgatgct caccctgttg 8460
tttggtgtta cttctgcagg gatccccgat catgcaaaaa ctcattaact cagtgcaaaa 8520
ctatgcctgg ggcagcaaaa cggcgttgac tgaactttat ggtatggaaa atccgtccag 8580
ccagccgatg gccgagctgt ggatgggcgc acatccgaaa agcagttcac gagtgcagaa 8640
tgccgccgga gatatcgttt cactgcgtga tgtgattgag agtgataaat cgactctgct 8700
cggagaggcc gttgccaaac gctttggcga actgcctttc ctgttcaaag tattatgcgc 8760
agcacagcca ctctccattc aggttcatcc aaacaaacac aattctgaaa tcggttttgc 8820
caaagaaaat gccgcaggta tcccgatgga tgccgccgag cgtaactata aagatcctaa 8880
ccacaagccg gagctggttt ttgcgctgac gcctttcctt gcgatgaacg cgtttcgtga 8940
attttccgag attgtctccc tactccagcc ggtcgcaggt gcacatccgg cgattgctca 9000
ctttttacaa cagcctgatg ccgaacgttt aagcgaactg ttcgccagcc tgttgaatat 9060
gcagggtgaa gaaaaatccc gcgcgctggc gattttaaaa tcggccctcg atagccagca 9120
gggtgaaccg tggcaaacga ttcgtttaat ttctgaattt tacccggaag acagcggtct 9180
gttctccccg ctattgctga atgtggtgaa attgaaccct ggcgaagcga tgttcctgtt 9240
cgctgaaaca ccgcacgctt acctgcaagg cgtggcgctg gaagtgatgg caaactccga 9300

-continued

```
taacgtgctg cgtgcgggtc tgacgcctaa atacattgat attccggaac tggttgccaa   9360
tgtgaaattc gaagccaaac cggctaacca gttgttgacc cagccggtga aacaaggtgc   9420
agaactggac ttcccgattc cagtggatga ttttgccttc tcgctgcatg accttagtga   9480
taaagaaacc accattagcc agcagagtgc cgccattttg ttctgcgtcg aaggcgatgc   9540
aacgttgtgg aaaggttctc agcagttaca gcttaaaccg ggtgaatcag cgtttattgc   9600
cgccaacgaa tcaccggtga ctgtcaaagg ccacggccgt ttagcgcgtg tttacaacaa   9660
gctgtaagag cttactgaaa aaattaacat ctcttgctaa gctgggagct cgatccgtcg   9720
acctgcagat cgttcaaaca tttggcaata aagtttctta agattgaatc ctgttgccgg   9780
tcttgcgatg attatcatat aatttctgtt gaattacgtt aagcatgtaa taattaacat   9840
gtaatgcatg acgttattta tgagatgggt ttttatgatt agagtcccgc aattatacat   9900
ttaatacgcg atagaaaaca aaatatagcg cgcaaactag gataaattat cgcgcgcggt   9960
gtcatctatg ttactagatc tgctagccct gcaggaaatt taccggtgcc cgggcggcca  10020
gcatggccgt atccgcaatg tgttattaag ttgtctaagc gtcaatttgt ttacaccaca  10080
atatatcctg ccaccagcca gccaacagct ccccgaccgg cagctcggca caaaatcacc  10140
actcgataca ggcagcccat cagaattaat tctcatgttt gacagcttat catcgactgc  10200
acggtgcacc aatgcttctg gcgtcaggca gccatcggaa gctgtggtat ggctgtgcag  10260
gtcgtaaatc actgcataat tcgtgtcgct caaggcgcac tcccgttctg gataatgttt  10320
tttgcgccga catcataacg gttctggcaa atattctgaa atgagctgtt gacaattaat  10380
catccggctc gtataatgtg tggaattgtg agcggataac aatttcacac aggaaacaga  10440
ccatgaggga agcgttgatc gccgaagtat cgactcaact atcagaggta gttggcgtca  10500
tcgagcgcca tctcgaaccg acgttgctgg ccgtacattt gtacggctcc gcagtggatg  10560
gcggcctgaa gccacacagt gatattgatt tgctggttac ggtgaccgta aggcttgatg  10620
aaacaacgcg gcgagctttg atcaacgacc ttttggaaac ttcggcttcc cctggagaga  10680
gcgagattct ccgcgctgta gaagtcacca ttgttgtgca cgacgacatc attccgtggc  10740
gttatccagc taagcgcgaa ctgcaatttg gagaatggca gcgcaatgac attcttgcag  10800
gtatcttcga gccagccacg atcgacattg atctggctat cttgctgaca aaagcaagag  10860
aacatagcgt tgccttggta ggtccagcgg cggaggaact ctttgatccg gttcctgaac  10920
aggatctatt tgaggcgcta aatgaaacct taacgctatg gaactcgccg cccgactggg  10980
ctggcgatga gcgaaatgta gtgcttacgt tgtcccgcat ttggtacagc gcagtaaccg  11040
gcaaaatcgc gccgaaggat gtcgctgccg actgggcaat ggagcgcctg ccggcccagt  11100
atcagcccgt catacttgaa gctaggcagg cttatcttgg acaagaagat cgcttggcct  11160
cgcgcgcaga tcagttggaa gaatttgttc actacgtgaa aggcgagatc accaaagtag  11220
tcggcaaata aagctctagt ggatctccgt acccggggat ctggctcgcg gcggacgcac  11280
gacgccgggg cgagaccata ggcgatctcc taaatcaata gtagctgtaa cctcgaagcg  11340
tttcacttgt aacaacgatt gagaattttt gtcataaaat tgaaatactt ggttcgcatt  11400
tttgtcatcc gcggtcagcc gcaattctga cgaactgccc atttagctgg agatgattgt  11460
acatccttca cgtgaaaatt tctcaagcgc tgtgaacaag ggttcagatt ttagattgaa  11520
aggtgagccg ttgaaacacg ttcttcttgt cgatgacgac gtcgctatgc ggcatcttat  11580
tattgaatac cttacgatcc acgccttcaa agtgaccgcg gtagccgaca gcacccagtt  11640
cacaagagta ctctcttccg cgacggtcga tgtcgtggtt gttgatctag atttaggtcg  11700
```

```
tgaagatggg ctcgagatcg ttcgtaatct ggcggcaaag tctgatattc caatcataat  11760
tatcagtggc gaccgccttg aggagacgga taaagttgtt gcactcgagc taggagcaag  11820
tgattttatc gctaagccgt tcagtatcag agagtttcta gcacgcattc gggttgcctt  11880
gcgcgtgcgc cccaacgttg tccgctccaa agaccgacgg tctttttgtt ttactgactg  11940
gacacttaat ctcaggcaac gtcgcttgat gtccgaagct ggcggtgagg tgaaacttac  12000
ggcaggtgag ttcaatcttc tcctcgcgtt tttagagaaa ccccgcgacg ttctatcgcg  12060
cgagcaactt ctcattgcca gtcgagtacg cgacgaggag gtttatgaca ggagtataga  12120
tgttctcatt ttgaggctgc gccgcaaact tgaggcagat ccgtcaagcc ctcaactgat  12180
aaaaacagca agaggtgccg gttatttctt tgacgcggac gtgcaggttt cgcacggggg  12240
gacgatggca gcctgagcca attcccagat ccccgaggaa tcggcgtgag cggtcgcaaa  12300
ccatccggcc cggtacaaat cggcgcggcg ctgggtgatg acctggtgga gaagttgaag  12360
gccgcgcagg ccgcccagcg gcaacgcatc gaggcagaag cacgccccgg tgaatcgtgg  12420
caagcggccg ctgatcgaat ccgcaaagaa tcccggcaac cgccggcagc cggtgcgccg  12480
tcgattagga agccgcccaa gggcgacgag caaccagatt ttttcgttcc gatgctctat  12540
gacgtgggca cccgcgatag tcgcagcatc atggacgtgg ccgttttccg tctgtcgaag  12600
cgtgaccgac gagctggcga ggtgatccgc tacgagcttc cagacgggca cgtagaggtt  12660
tccgcagggc cggccggcat ggccagtgtg tgggattacg acctggtact gatggcggtt  12720
tcccatctaa ccgaatccat gaaccgatac cgggaaggga agggagacaa gcccggccgc  12780
gtgttccgtc cacacgttgc ggacgtactc aagttctgcc ggcgagccga tggcggaaag  12840
cagaaagacg acctggtaga aacctgcatt cggttaaaca ccacgcacgt tgccatgcag  12900
cgtacgaaga aggccaagaa cggccgcctg gtgacggtat ccgagggtga agccttgatt  12960
agccgctaca agatcgtaaa gagcgaaacc gggcggccgg agtacatcga gatcgagcta  13020
gctgattgga tgtaccgcga gatcacagaa ggcaagaacc cggacgtgct gacggttcac  13080
cccgattact tttgatcgga tcccggcatc ggccgttttc tctaccgcct ggcacgccgc  13140
gccgcaggca aggcagaagc cagatggttg ttcaagacga tctacgaacg cagtggcagc  13200
gccggagagt tcaagaagtt ctgtttcacc gtgcgcaagc tgatcgggtc aaatgacctg  13260
ccggagtacg atttgaagga ggaggcgggg caggctggcc cgatcctagt catgcgctac  13320
cgcaacctga tcgagggcga agcatccgcc ggttcctaat gtacggagca gatgctaggg  13380
caaattgccc tagcagggga aaaaggtcga aaaggtctct ttcctgtgga tagcacgtac  13440
attgggaacc caaagccgta cattgggaac cggaacccgt acattgggaa cccaaagccg  13500
tacattggga accggtcaca catgtaagtg actgatataa aagagaaaaa aggcgatttt  13560
tccgcctaaa actctttaaa acttattaaa actcttaaaa cccgcctggc ctgtgcataa  13620
ctgtctggcc agcgcacagc cgaagagctg caaaaagcgc ctacccttcg gtcgctgcgc  13680
tccctacgcc ccgccgcttc gcgtcggcct atcgcggccg ctggccgctc aaaaatggct  13740
ggcctacggc caggcaatct accagggcgc ggacaagccg cgccgtcgcc actcgaccgc  13800
cggcgctgag gtctgcctcg tgaagaaggt gttgctgact cataccaggc ctgaatcgcc  13860
ccatcatcca gccagaaagt gagggagcca cggttgatga gagctttgtt gtaggtggac  13920
cagttggtga ttttgaactt ttgctttgcc acggaacggt ctgcgttgtc gggaagatgc  13980
gtgatctgat ccttcaactc agcaaaagtt cgatttattc aacaaagccg ccgtcccgtc  14040
```

aagtcagcgt aatgctctgc cagtgttaca accaattaac caattctgat tagaaaaact 14100
catcgagcat caaatgaaac tgcaatttat tcatatcagg attatcaata ccatattttt 14160
gaaaaagccg tttctgtaat gaaggagaaa actcaccgag gcagttccat aggatggcaa 14220
gatcctggta tcggtctgcg attccgactc gtccaacatc aatacaacct attaatttcc 14280
cctcgtcaaa aataaggtta tcaagtgaga aatcaccatg agtgacgact gaatccggtg 14340
agaatggcaa aagctctgca ttaatgaatc ggccaacgcg cggggagagg cggtttgcgt 14400
attgggcgct cttccgcttc ctcgctcact gactcgctgc gctcggtcgt tcggctgcgg 14460
cgagcggtat cagctcactc aaaggcggta atacggttat ccacagaatc aggggataac 14520
gcaggaaaga acatgtgagc aaaaggccag caaaaggcca ggaaccgtaa aaaggccgcg 14580
ttgctggcgt ttttccatag gctccgcccc cctgacgagc atcacaaaaa tcgacgctca 14640
agtcagaggt ggcgaaaccc gacaggacta taaagatacc aggcgtttcc ccctggaagc 14700
tccctcgtgc gctctcctgt tccgaccctg ccgcttaccg gatacctgtc cgcctttctc 14760
ccttcgggaa gcgtggcgct ttctcatagc tcacgctgta ggtatctcag ttcggtgtag 14820
gtcgttcgct ccaagctggg ctgtgtgcac gaaccccccg ttcagcccga ccgctgcgcc 14880
ttatccggta actatcgtct tgagtccaac ccggtaagac acgacttatc gccactggca 14940
gcagccactg gtaacaggat tagcagagcg aggtatgtag gcggtgctac agagttcttg 15000
aagtggtggc ctaactacgg ctacactaga agaacagtat ttggtatctg cgctctgctg 15060
aagccagtta ccttcggaaa aagagttggt agctcttgat ccggcaaaca aaccaccgct 15120
ggtagcggtg gtttttttgt ttgcaagcag cagattacgc gcagaaaaaa aggatctcaa 15180
gaagatcctt tgatcttttc tacggggtct gacgctcagt ggaacgaaaa ctcacgttaa 15240
gggattttgg tcatgagatt atcaaaaagg atcttcacct agatcctttt gatccggaat 15300
t 15301

<210> SEQ ID NO 44
<211> LENGTH: 8342
<212> TYPE: DNA
<213> ORGANISM: Artificial sequence
<220> FEATURE:
<223> OTHER INFORMATION: plasmid 15772 ZmABT Assembly

<400> SEQUENCE: 44
ccccgaccag cgcgacatgc atggcatggc aaactatata tcgtcatcat cattattatc 60
atctgaccct cttttttttt cactctcact cccatgtttt tattcccggg cggggccgtg 120
tgggtgtggg ttgggatggc cggattgggc tcccggggtg gagaaatgac aaatccaggc 180
ccgcaggcgg ccacccacca aatcggacga cgcagggtgc ccaaatcagg aaggatttta 240
aggttaaccg gccaccggcg gtgaccgacg ccccacccca ctctccttct cctattctat 300
ctatatatca cccgcctctt ttttctccct cactccgcca caccttccct cttcttcctc 360
agctccgtcg cccaccgccg gagcaccgaa aggccccgcg cccgccgcct ttcctgtaaa 420
aaacccaacc tttagctagc taaccgctcc tcttctcccc ctactcccct tgcccaaatc 480
agagaagata tttaacggag gaggggaagg agaggatatt tagctgattg ttgattggtg 540
gtccggggta cggtgttctt gagtcgtgaa gcgaccgtac agtggctagg gccgtctccg 600
ggttgcgtgc aggatggtcg tcagagatcg ggagtgagga ggcagctcgt ggtcgtggag 660
gctaaatgta ccgcaagaac gactcggcac tctcctgttt ctacctcttc ctcctctggt 720
tcttcttctt gaaatagacc agcgccagcc accaggtagc tacctactag ctagcagccc 780

```
agttgcgact ggggacgggc tgctgcttgc aagttggaat cttggagcag gagcagagga    840
gcgggagatg gagctggatc tgaacgtggc cgaggtggcg ccggagaagc catcggcggc    900
gctggaggcg agcgactcgg ggtcctcggg ctcgtcggtg ctgaacgcgg aggcggcatc    960
ggcgggcggc ggggggcccg cgccggggga ggaggggtca agctcgacgc cggccgtgct   1020
cgagttcagc atcctcagga gcgacagcga cgcggccggc gcggacgccg acgacggcga   1080
cgccacgccg tcgccacctc gccaccacca gcagcagctc gtcacccggg agcacttccc   1140
ggcgccgcag cattgggccg agcacggctt cttccgcgcc ggcccgcagc agcagccgga   1200
catcagggtc ctgccgcacc cgcacccgta cccgcccccg ccgccgcccg cgcagccgca   1260
gcaggccaag aagagccgcc gcggcccgcg ctcccgcagc tcgcagtacc gcggcgtcac   1320
cttctaccgc cgcaccggcc gctgggagtc ccacatctgg tcagtagcac tgcaagctca   1380
ccatgcgccc tttcacctac cgaccaataa tcgcttgtga ttctgacacc caaatgtttc   1440
gtcttcctgt gctgtcctgt tcctcggaaa tggcagggat tgcgggaagc aggtgtactt   1500
aggtgagcag caataagcag atcgatctgc agcataaatt tcccgttatt aactagttcg   1560
tgatctcgat cgaatggcct aattaaccga ttcggtgatc tggccgatgg ccaatctacg   1620
caggtggatt cgacactgct catgccgctg caaggtaacg atcaatccat ccatccaccc   1680
ttgtctagct accccaccga ccggccggat taatggaccg ctagctctcg ggacgggctt   1740
gctgcagggc gtacgaccga gcggcgatca agttccgcgg cgtcgacgcc gacataaact   1800
tcaacctcag cgactacgac gacgatatga agcaggtaca tacacgagtg ttcttgcagc   1860
tagcaccgac tgaaacatct gctgaacgta cacgcatggc cctgtgcacc agatgaagag   1920
cctgtccaag gaggagttcg ttcacgccct gcggcggcag agcaccggct tctcccgcgg   1980
cagctccaag tacaggggcg tcaccctgca caagtgcggc cgctgggagg cgcgcaaggg   2040
gcagttcctc ggcaagaagt aagaaacaac acttcgtttg caggcgctgt actttgctgc   2100
agattatttc atttcatcct tgcatgtgcc tttcctttcc atccactcac ttgatggctg   2160
tagtctcgat agagttcgtt cgttcgtact tcgcaccaga tgaactccca cgcacatgat   2220
ttagtactag ttttaccatg cattgttcag taaaagtata tgcttgcttg atcagtggtt   2280
gtttcaatca gaagattaaa aaaacggaat attaatataa aaaaaagggg aagtggctag   2340
ggaattcctc agtcctagct agctagctca ccggtgggaa cgccatgctt ggcttgggtg   2400
caggtacata tatcttgggc tattcgacag cgaagtagag gctgcaaggt tgttcacctc   2460
ggacgattct gccatttgtt catatacacc atgccttttg atttctctct tgcaatttct   2520
cttcttttat catggctttt gattcccaaa gggttgagta ccgactcgat attcgattct   2580
ccctgccgtt tcgtgacccc agggcgtacg acaaggcccc accatggtac gtcctgtaga   2640
aaccccaacc cgtgaaatca aaaaactcga cggcctgtgg gcattcagtc tggatcgcga   2700
aaactgtgga attgatcagc gttggtggga aagcgcgtta caagaaagcc gggcaattgc   2760
tgtgccaggc agttttaacg atcagttcgc cgatgcagat attcgtaatt atgcgggcaa   2820
cgtctggtat cagcgcgaag tctttatacc gaaaggttgg gcaggccagc gtatcgtgct   2880
gcgtttcgat gcggtcactc attacggcaa agtgtgggtc aataatcagg aagtgatgga   2940
gcatcagggc ggctatacgc catttgaagc cgatgtcacg ccgtatgtta ttgccgggaa   3000
aagtgtacgt atcaccgttt gtgtgaacaa cgaactgaac tggcagacta tcccgccggg   3060
aatggtgatt accgacgaaa acggcaagaa aaagcagtct tacttccatg atttctttaa   3120
```

```
ctatgccgga atccatcgca gcgtaatgct ctacaccacg ccgaacacct gggtggacga      3180

tatcaccgtg gtgacgcatg tcgcgcaaga ctgtaaccac gcgtctgttg actggcaggt      3240

accaagctgc gaatcttcgt ttttttaagg aattctcgat ctttatggtg tataggctct      3300

gggttttctg ttttttgtat ctcttaggat tttgtaaatt ccagatcttt ctatggccac      3360

ttagtagtat atttcaaaaa ttctccaatc gagttcttca ttcgcatttt cagtcatttt      3420

ctcttcgacg ttgtttttaa gcctgggtat tactcctatt tagttgaact ctgcagcaat      3480

cttagaaaat tagggttttg aggtttcgat ttctctaggt aaccgatcta ttgcattcat      3540

ctgaatttct gcatatatgt cttagatttc tgataagctt acgatacgtt aggtgtaatt      3600

gaagtttatt tttcaagagt gttattttt gtttctgaat ttttcaggtg gtggccaatg      3660

gtgatgtcag cgttgaactg cgtgatgcgg atcaacaggt ggttgcaact ggacaaggca      3720

ctagcgggac tttgcaagtg gtgaatccgc acctctggca accgggtgaa ggttatctct      3780

atgaactgtg cgtcacagcc aaaagccaga cagagtgtga tatctacccg cttcgcgtcg      3840

gcatccggtc agtggcagtg aagggcgaac agttcctgat taaccacaaa ccgttctact      3900

ttactggctt tggtcgtcat gaagatgcgg acttgcgtgg caaaggattc gataacgtgc      3960

tgatggtgca cgaccacgca ttaatggact ggattggggc caactcctac cgtacctcgc      4020

attaccctta cgctgaagag atgctcgact gggcagatga acatggcatc gtggtgattg      4080

atgaaactgc tgctgtcggc tttaacctct ctttaggcat tggtttcgaa gcgggcaaca      4140

agccgaaaga actgtacagc gaagaggcag tcaacgggga aactcagcaa gcgcacttac      4200

aggcgattaa agagctgata gcgcgtgaca aaaaccaccc aagcgtggtg atgtggagta      4260

ttgccaacga accggatacc cgtccgcaag gtgcacggga atatttcgcg ccactggcgg      4320

aagcaacgcg taaactcgac ccgacgcgtc cgatcacctg cgtcaatgta atgttctgcg      4380

acgctcacac cgataccatc agcgatctct ttgatgtgct gtgcctgaac cgttattacg      4440

gatggtatgt ccaaagcggc gatttggaaa cggcagagaa ggtactggaa aaagaacttc      4500

tggcctggca ggagaaactg catcagccga ttatcatcac cgaatacggc gtggatacgt      4560

tagccgggct gcactcaatg tacaccgaca tgtggagtga agagtatcag tgtgcatggc      4620

tggatatgta tcaccgcgtc tttgatcgcg tcagcgccgt cgtcggtgaa caggtatgga      4680

atttcgccga ttttgcgacc tcgcaaggca tattgcgcgt tggcggtaac aagaaaggga      4740

tcttcactcg cgaccgcaaa ccgaagtcgg cggcttttct gctgcaaaaa cgctggactg      4800

gcatgaactt cggtgaaaaa ccgcagcagg gaggcaaaca atgagagctc gaatcgaaga      4860

agccacactg taaatctgcc gggaagcggc tggtggcatc cggcccgctc ctccctccgg      4920

gcgccgcaac ttttttcgat cggttttgcg ccgcccggga cgggttgtag ttgatcgatt      4980

ggattcttca taactgtatt tgcgtactgc ttacactacc caagtgaaat cgaaaatggc      5040

gccttctctc gttgaataaa ttgcacgtac gctactcgat ccgctgcggc tcttgctgga      5100

gtggccgccg ccgctataga tagaaggatc aagccaagga atctgtcatg catgggcatg      5160

tgaaggagga gcctcctgca atgtttagtc tttttggtc gacgcccacc agagatatac      5220

gcactagatt tcatatagct gagctagatc gattccgttg catgcatgct gcatggcgtc      5280

gagattcgag ctagcaccgc ctgttcatca tcgaccgatc cattctgatc gattcccctc      5340

tcgagctttc acgaactgaa cctacctagt gagggtgacg cctaacgcct agtgcgcgcg      5400

cgtgggtctc cgatgtcagt ggccgcacgc gcgcgcgcgt tctcgagatc gcatgtggtc      5460

atagcgcagc aggtttgccc tcagaaccta cagcaactcg accaccggtt tggatttctt      5520
```

-continued

```
cttttttcaa ggatatgatc ggagagagag agctacctag gcgtcgtcct tgttttcttg   5580

tatcgcatgt ggtgtgggtc tctctcctcc tttcgtacgc acgcatgatt ccattcttac   5640

ccccccctcga gatcgagagg aaatatattg ctattttata cacacacggc gcccccagct   5700

atacgtcact gcttacgtta attcccccac cggatagtag ttgtttaatg gcccaaacaa   5760

accttgttgt tgcatgcatc atggaccaaa caaaatacat agttagttaa atattactgt   5820

tatatataca actaataata attatattat tagttaaaac aaagcaaggc atatgcagca   5880

gctgctggtc ggaccgggcc catcgatgat atcagatctg gttctatagt gtcacctaaa   5940

tcgtatgtgt atgatacata aggttatgta ttaattgtag ccgcgttcta acgacaatat   6000

gtccatatgg tgcactctca gtacaatctg ctctgatgcc gcatagttaa gccagccccg   6060

acacccgcca acacccgctg acgcgccctg acgggcttgt ctgctcccgg catccgctta   6120

cagacaagct gtgaccgtct ccgggagctg catgtgtcag aggttttcac cgtcatcacc   6180

gaaacgcgcg agacgaaagg gcctcgtgat acgcctattt ttataggtta atgtcatgat   6240

aataatggtt tcttagacgt caggtggcac ttttcgggga aatgtgcgcg gaacccctat   6300

ttgtttattt ttctaaatac attcaaatat gtatccgctc atgagacaat aaccctgata   6360

aatgcttcaa taatattgaa aaaggaagag tatgagtatt caacatttcc gtgtcgccct   6420

tattcccttt tttgcggcat tttgccttcc tgtttttgct cacccagaaa cgctggtgaa   6480

agtaaaagat gctgaagatc agttgggtgc acgagtgggt tacatcgaac tggatctcaa   6540

cagcggtaag atccttgaga gttttcgccc cgaagaacgt tttccaatga tgagcacttt   6600

taaagttctg ctatgtggcg cggtattatc ccgtattgac gccgggcaag agcaactcgg   6660

tcgccgcata cactattctc agaatgactt ggttgagtac tcaccagtca cagaaaagca   6720

tcttacggat ggcatgacag taagagaatt atgcagtgct gccataacca tgagtgataa   6780

cactgcggcc aacttacttc tgacaacgat cggaggaccg aaggagctaa ccgctttttt   6840

gcacaacatg ggggatcatg taactcgcct tgatcgttgg gaaccggagc tgaatgaagc   6900

cataccaaac gacgagcgtg acaccacgat gcctgtagca atggcaacaa cgttgcgcaa   6960

actattaact ggcgaactac ttactctagc ttcccggcaa caattaatag actggatgga   7020

ggcggataaa gttgcaggac cacttctgcg ctcggccctt ccggctggct ggtttattgc   7080

tgataaatct ggagccggtg agcgtgggtc tcgcggtatc attgcagcac tggggccaga   7140

tggtaagccc tcccgtatcg tagttatcta cacgacgggg agtcaggcaa ctatggatga   7200

acgaaataga cagatcgctg agataggtgc ctcactgatt aagcattggt aactgtcaga   7260

ccaagtttac tcatatatac tttagattga tttaaaactt catttttaat ttaaaaggat   7320

ctaggtgaag atcctttttg ataatctcat gaccaaaatc ccttaacgtg agttttcgtt   7380

ccactgagcg tcagaccccg tagaaaagat caaaggatct tcttgagatc cttttttttct   7440

gcgcgtaatc tgctgcttgc aaacaaaaaa accaccgcta ccagcggtgg tttgtttgcc   7500

ggatcaagag ctaccaactc tttttccgaa ggtaactggc ttcagcagag cgcagatacc   7560

aaatactgtt cttctagtgt agccgtagtt aggccaccac ttcaagaact ctgtagcacc   7620

gcctacatac ctcgctctgc taatcctgtt accagtggct gctgccagtg gcgataagtc   7680

gtgtcttacc gggttggact caagacgata gttaccggat aaggcgcagc ggtcgggctg   7740

aacggggggt tcgtgcacac agcccagctt ggagcgaacg acctacaccg aactgagata   7800

cctacagcgt gagctatgag aaagcgccac gcttcccgaa gggagaaagg cggacaggta   7860
```

tccggtaagc ggcagggtcg gaacaggaga gcgcacgagg gagcttccag ggggaaacgc 7920
ctggtatctt tatagtcctg tcgggtttcg ccacctctga cttgagcgtc gatttttgtg 7980
atgctcgtca ggggggcgga gcctatggaa aaacgccagc aacgcggcct ttttacggtt 8040
cctggccttt tgctggcctt ttgctcacat gttctttcct gcgttatccc ctgattctgt 8100
ggataaccgt attaccgcct ttgagtgagc tgataccgct cgccgcagcc gaacgaccga 8160
gcgcagcgag tcagtgagcg aggaagcgga agagcgccca atacgcaaac cgcctctccc 8220
cgcgcgttgg ccgattcatt aatgcaggtt aacctggctt atcgaaatta atacgactca 8280
ctatagggag accggcctcg agcagctgaa gcttgcatgc ctgcaggtcg actctagagg 8340
ga 8342

<210> SEQ ID NO 45
<211> LENGTH: 15544
<212> TYPE: DNA
<213> ORGANISM: Artificial sequence
<220> FEATURE:
<223> OTHER INFORMATION: plasmid 15773

<400> SEQUENCE: 45
attcctgtgg ttggcatgca catacaaatg gacgaacgga taaacctttt cacgcccttt 60
taaatatccg attattctaa taaacgctct tttctcttag gtttacccgc caatatatcc 120
tgtcaaacac tgatagttta aactgaaggc gggaaacgac aatctgatca tgagcggaga 180
attaagggag tcacgttatg acccccgccg atgacgcggg acaagccgtt ttacgtttgg 240
aactgacaga accgcaacgc tgcaggaatt ggccgcagcg gccatttaaa tcaattgggc 300
gcgccagctg cttgtgggga ccagacaaaa aaggaatggt gcagaattgt taggcgcacc 360
taccaaaagc atctttgcct ttattgcaaa gataaagcag attcctctag tacaagtggg 420
gaacaaaata acgtggaaaa gagctgtcct gacagcccac tcactaatgc gtatgacgaa 480
cgcagtgacg accacaaaac tcgagacttt tcaacaaagg gtaatatccg gaaacctcct 540
cggattccat tgcccagcta tctgtcactt tattgtgaag atagtggaaa aggaaggtgg 600
ctcctacaaa tgccatcatt gcgataaagg aaaggctatc gttgaagatg cctctgccga 660
cagtggtccc aaagatggac ccccacccac gaggagcatc gtggaaaaag aagacgttcc 720
aaccacgtct tcaaagcaag tggattgatg tgatatctcc actgacgtaa gggatgacga 780
acaatcccac tatccttcgg taccggaccc cgaccagcgc gacatgcatg gcatggcaaa 840
ctatatatcg tcatcatcat tattatcatc tgaccctctt ttttttttcac tctcactccc 900 atgtttttat tcccgggcgg ggccgtgtgg gtgtgggttg ggatggccgg attgggctcc 960
cggggtggag aaatgacaaa tccaggcccg caggcggcca ccccaccaaat cggacgacgc 1020 agggtgccca aatcaggaag gattttaagg ttaaccggcc accggcggtg accgacgccc 1080
caccccactc tccttctcct attctatcta tatatcaccc gcctcttttt tctccctcac 1140
tccgccacac cttccctctt cttcctcagc tccgtcgccc accgccggag caccgaaagg 1200
ccccgcgccc gccgcctttc ctgtaaaaaa cccaaccttt agctagctaa ccgctcctct 1260
tctcccccta ctccccttgc ccaaatcaga gaagatattt aacggaggag gggaaggaga 1320
ggatatttag ctgattgttg attggtggtc cggggtacgg tgttcttgag tcgtgaagcg 1380
accgtacagt ggctagggcc gtctccgggt tgcgtgcagg atggtcgtca gagatcggga 1440
gtgaggaggc agctcgtggt cgtggaggct aaatgtaccg caagaacgac tcggcactct 1500
cctgtttcta cctcttcctc ctctggttct tcttcttgaa atagaccagc gccagccacc 1560

-continued

```
aggtagctac ctactagcta gcagcccagt tgcgactggg gacgggctgc tgcttgcaag   1620
ttggaatctt ggagcaggag cagaggagcg ggagatggag ctggatctga acgtggccga   1680
ggtggcgccg gagaagccat cggcggcgct ggaggcgagc gactcggggt cctcgggctc   1740
gtcggtgctg aacgcggagg cggcatcggc gggcggcggg gggcccgcgc cgggggagga   1800
ggggtcaagc tcgacgccgg ccgtgctcga gttcagcatc ctcaggagcg acagcgacgc   1860
ggccggcgcg gacgccgacg acggcgacgc cacgccgtcg ccacctcgcc accaccagca   1920
gcagctcgtc acccgggagc acttcccggc gccgcagcat tgggccgagc acggcttctt   1980
ccgcgccggc ccgcagcagc agccggacat cagggtcctg ccgcacccgc acccgtaccc   2040
gccccgccg ccgcccgcgc agccgcagca ggccaagaag agccgccgcg gcccgcgctc   2100
ccgcagctcg cagtaccgcg gcgtcacctt ctaccgccgc accggccgct gggagtccca   2160
catctggtca gtagcactgc aagctcacca tgcgcccttt cacctaccga ccaataatcg   2220
cttgtgattc tgacacccaa atgtttcgtc ttcctgtgct gtcctgttcc tcggaaatgg   2280
cagggattgc gggaagcagg tgtacttagg tgagcagcaa taagcagatc gatctgcagc   2340
ataaatttcc cgttattaac tagttcgtga tctcgatcga atggcctaat taaccgattc   2400
ggtgatctgg ccgatggcca atctacgcag gtggattcga cactgctcat gccgctgcaa   2460
ggtaacgatc aatccatcca tccacccttg tctagctacc ccaccgaccg gccggattaa   2520
tggaccgcta gctctcggga cggcttgct gcagggcgta cgaccgagcg gcgatcaagt   2580
tccgcggcgt cgacgccgac ataaacttca acctcagcga ctacgacgac gatatgaagc   2640
aggtacatac acgagtgttc ttgcagctag caccgactga aacatctgct gaacgtacac   2700
gcatggccct gtgcaccaga tgaagagcct gtccaaggag gagttcgttc acgccctgcg   2760
gcggcagagc accggcttct cccgcggcag ctccaagtac aggggcgtca ccctgcacaa   2820
gtgcggccgc tgggaggcgc gcaaggggca gttcctcggc aagaagtaag aaacaacact   2880
tcgtttgcag gcgctgtact ttgctgcaga ttatttcatt tcatccttgc atgtgccttt   2940
cctttccatc cactcacttg atggctgtag tctcgataga gttcgttcgt tcgtacttcg   3000
caccagatga actcccacgc acatgattta gtactagttt taccatgcat tgttcagtaa   3060
aagtatatgc ttgcttgatc agtggttgtt tcaatcagaa gattaaaaaa acggaatatt   3120
aatataaaaa aaaggggaag tggctaggga attcctcagt cctagctagc tagctcaccg   3180
gtgggaacgc catgcttggc ttgggtgcag gtacatatat cttgggctat tcgacagcga   3240
agtagaggct gcaaggttgt tcacctcgga cgattctgcc atttgttcat atacaccatg   3300
ccttttgatt tctctcttgc aatttctctt cttttatcat ggcttttgat tcccaaaggg   3360
ttgagtaccg actcgatatt cgattctccc tgccgtttcg tgaccccagg gcgtacgaca   3420
aggccccacc atggtacgtc ctgtagaaac cccaacccgt gaaatcaaaa aactcgacgg   3480
cctgtgggca ttcagtctgg atcgcgaaaa ctgtggaatt gatcagcgtt ggtgggaaag   3540
cgcgttacaa gaaagccggg caattgctgt gccaggcagt tttaacgatc agttcgccga   3600
tgcagatatt cgtaattatg cgggcaacgt ctggtatcag cgcgaagtct ttataccgaa   3660
aggttgggca ggccagcgta tcgtgctgcg tttcgatgcg gtcactcatt acggcaaagt   3720
gtgggtcaat aatcaggaag tgatggagca tcagggcggc tatacgccat ttgaagccga   3780
tgtcacgccg tatgttattg ccgggaaaag tgtacgtatc accgtttgtg tgaacaacga   3840
actgaactgg cagactatcc cgccgggaat ggtgattacc gacgaaaacg gcaagaaaaa   3900
```

-continued

```
gcagtcttac ttccatgatt tctttaacta tgccggaatc catcgcagcg taatgctcta   3960
caccacgccg aacacctggg tggacgatat caccgtggtg acgcatgtcg cgcaagactg   4020
taaccacgcg tctgttgact ggcaggtacc aagctgcgaa tcttcgtttt tttaaggaat   4080
tctcgatctt tatggtgtat aggctctggg ttttctgttt tttgtatctc ttaggatttt   4140
gtaaattcca gatctttcta tggccactta gtagtatatt tcaaaaattc tccaatcgag   4200
ttcttcattc gcattttcag tcattttctc ttcgacgttg tttttaagcc tgggtattac   4260
tcctatttag ttgaactctg cagcaatctt agaaaattag ggttttgagg tttcgatttc   4320
tctaggtaac cgatctattg cattcatctg aatttctgca tatatgtctt agatttctga   4380
taagcttacg atacgttagg tgtaattgaa gtttattttt caagagtgtt atttttttgtt   4440
tctgaatttt tcaggtggtg gccaatggtg atgtcagcgt tgaactgcgt gatgcggatc   4500
aacaggtggt tgcaactgga caaggcacta gcgggacttt gcaagtggtg aatccgcacc   4560
tctggcaacc gggtgaaggt tatctctatg aactgtgcgt cacagccaaa agccagacag   4620
agtgtgatat ctacccgctt cgcgtcggca tccggtcagt ggcagtgaag ggcgaacagt   4680
tcctgattaa ccacaaaccg ttctacttta ctggctttgg tcgtcatgaa gatgcggact   4740
tgcgtggcaa aggattcgat aacgtgctga tggtgcacga ccacgcatta atggactgga   4800
ttggggccaa ctcctaccgt acctcgcatt acccttacgc tgaagagatg ctcgactggg   4860
cagatgaaca tggcatcgtg gtgattgatg aaactgctgc tgtcggcttt aacctctctt   4920
taggcattgg tttcgaagcg ggcaacaagc cgaaagaact gtacagcgaa gaggcagtca   4980
acggggaaac tcagcaagcg cacttacagg cgattaaaga gctgatagcg cgtgacaaaa   5040
accacccaag cgtggtgatg tggagtattg ccaacgaacc ggatacccgt ccgcaaggtg   5100
cacgggaata tttcgcgcca ctggcggaag caacgcgtaa actcgacccg acgcgtccga   5160
tcacctgcgt caatgtaatg ttctgcgacg ctcacaccga taccatcagc gatctctttg   5220
atgtgctgtg cctgaaccgt tattacggat ggtatgtcca aagcggcgat ttggaaacgg   5280
cagagaaggt actggaaaaa gaacttctgg cctggcagga gaaactgcat cagccgatta   5340
tcatcaccga atacggcgtg gatacgttag ccgggctgca ctcaatgtac accgacatgt   5400
ggagtgaaga gtatcagtgt gcatggctgg atatgtatca ccgcgtcttt gatcgcgtca   5460
gcgccgtcgt cggtgaacag gtatggaatt tcgccgattt tgcgacctcg caaggcatat   5520
tgcgcgttgg cggtaacaag aaagggatct tcactcgcga ccgcaaaccg aagtcggcgg   5580
cttttctgct gcaaaaacgc tggactggca tgaacttcgg tgaaaaaccg cagcagggag   5640
gcaaacaatg agagctcgaa tcgaagaagc cacactgtaa atctgccggg aagcggctgg   5700
tggcatccgg cccgctcctc cctccgggcg ccgcaacttt tttcgatcgg ttttgcgccg   5760
cccgggacgg gttgtagttg atcgattgga ttcttcataa ctgtatttgc gtactgctta   5820
cactacccaa gtgaaatcga aaatggcgcc ttctctcgtt gaataaattg cacgtacgct   5880
actcgatccg ctgcggctct tgctggagtg gccgccgccg ctatagatag aaggatcaag   5940
ccaaggaatc tgtcatgcat gggcatgtga aggaggagcc tcctgcaatg tttagtcttt   6000
tttggtcgac gcccaccaga gatatacgca ctagatttca tatagctgag ctagatcgat   6060
tccgttgcat gcatgctgca tggcgtcgag attcgagcta gcaccgcctg ttcatcatcg   6120
accgatccat tctgatcgat tcccctctcg agctttcacg aactgaacct acctagtgag   6180
ggtgacgcct aacgcctagt gcgcgcgcgt gggtctccga tgtcagtggc cgcacgcgcg   6240
cgcgcgttct cgagatcgca tgtggtcata gcgcagcagg tttgccctca gaacctacag   6300
```

```
caactcgacc accggtttgg atttcttctt ttttcaagga tatgatcgga gagagagagc   6360
tacctaggcg tcgtccttgt tttcttgtat cgcatgtggt gtgggtctct ctcctccttt   6420
cgtacgcacg catgattcca ttcttacccc ccctcgagat cgagaggaaa tatattgcta   6480
ttttatacac acacggcgcc cccagctata cgtcactgct tacgttaatt cccccaccgg   6540
atagtagttg tttaatggcc caaacaaacc ttgttgttgc atgcatcatg gaccaaacaa   6600
aatacatagt tagttaaata ttactgttat atatacaact aataataatt atattattag   6660
ttaaaacaaa gcaaggcata tgcagcagct gctggtcgga ccgcgatcgc ttaattaagc   6720
ttgcatgcct gcagtgcagc gtgacccggt cgtgcccctc tctagagata atgagcattg   6780
catgtctaag ttataaaaaa ttaccacata ttttttttgt cacacttgtt tgaagtgcag   6840
tttatctatc tttatacata tatttaaact ttactctacg aataatataa tctatagtac   6900
tacaataata tcagtgtttt agagaatcat ataaatgaac agttagacat ggtctaaagg   6960
acaattgagt attttgacaa caggactcta cagttttatc tttttagtgt gcatgtgttc   7020
tccttttttt ttgcaaatag cttcacctat ataatacttc atccatttta ttagtacatc   7080
catttagggt ttagggttaa tggtttttat agactaattt ttttagtaca tctattttat   7140
tctattttag cctctaaatt aagaaaacta aaactctatt ttagtttttt tatttaataa   7200
tttagatata aaatagaata aaataaagtg actaaaaatt aaacaaatac cctttaagaa   7260
attaaaaaaa ctaaggaaac atttttcttg tttcgagtag ataatgccag cctgttaaac   7320
gccgtcgacg agtctaacgg acaccaacca gcgaaccagc agcgtcgcgt cgggccaagc   7380
gaagcagacg gcacggcatc tctgtcgctg cctctggacc cctctcgaga gttccgctcc   7440
accgttggac ttgctccgct gtcggcatcc agaaattgcg tggcggagcg gcagacgtga   7500
gccggcacgg caggcggcct cctcctcctc tcacggcacc ggcagctacg gggattcct    7560
ttcccaccgc tccttcgctt tcccttcctc gcccgccgta ataaatagac accccctcca   7620
caccctcttt ccccaacctc gtgttgttcg gagcgcacac acacacaacc agatctcccc   7680
caaatccacc cgtcggcacc tccgcttcaa ggtacgccgc tcgtcctccc cccccccccc   7740
tctctacctt ctctagatcg gcgttccggt ccatggttag ggcccggtag ttctacttct   7800
gttcatgttt gtgttagatc cgtgtttgtg ttagatccgt gctgctagcg ttcgtacacg   7860
gatgcgacct gtacgtcaga cacgttctga ttgctaactt gccagtgttt ctctttgggg   7920
aatcctggga tggctctagc cgttccgcag acgggatcga tttcatgatt ttttttgttt   7980
cgttgcatag ggtttggttt gcccttttcc tttatttcaa tatatgccgt gcacttgttt   8040
gtcgggtcat cttttcatgc ttttttttgt cttggttgtg atgatgtggt ctggttgggc   8100
ggtcgttcta gatcggagta gaattctgtt tcaaactacc tggtggattt attaattttg   8160
gatctgtatg tgtgtgccat acatattcat agttacgaat tgaagatgat ggatggaaat   8220
atcgatctag gataggtata catgttgatg cgggttttac tgatgcatat acagagatgc   8280
tttttgttcg cttggttgtg atgatgtggt gtggttgggc ggtcgttcat tcgttctaga   8340
tcggagtaga atactgtttc aaactacctg gtgtatttat taattttgga actgtatgtg   8400
tgtgtcatac atcttcatag ttacgagttt aagatggatg gaaatatcga tctaggatag   8460
gtatacatgt tgatgtgggt tttactgatg catatacatg atggcatatg cagcatctat   8520
tcatatgctc taaccttgag tacctatcta ttataataaa caagtatgtt ttataattat   8580
tttgatcttg atatacttgg atgatggcat atgcagcagc tatatgtgga tttttttagc   8640
```

-continued

```
cctgccttca tacgctattt atttgcttgg tactgtttct tttgtcgatg ctcaccctgt   8700
tgtttggtgt tacttctgca gggatccccg atcatgcaaa aactcattaa ctcagtgcaa   8760
aactatgcct ggggcagcaa aacggcgttg actgaacttt atggtatgga aaatccgtcc   8820
agccagccga tggccgagct gtggatgggc gcacatccga aaagcagttc acgagtgcag   8880
aatgccgccg gagatatcgt ttcactgcgt gatgtgattg agagtgataa atcgactctg   8940
ctcggagagg ccgttgccaa acgctttggc gaactgcctt tcctgttcaa agtattatgc   9000
gcagcacagc cactctccat tcaggttcat ccaaacaaac acaattctga aatcggtttt   9060
gccaaagaaa atgccgcagg tatcccgatg gatgccgccg agcgtaacta taaagatcct   9120
aaccacaagc cggagctggt ttttgcgctg acgcctttcc ttgcgatgaa cgcgtttcgt   9180
gaattttccg agattgtctc cctactccag ccggtcgcag gtgcacatcc ggcgattgct   9240
cactttttac aacagcctga tgccgaacgt ttaagcgaac tgttcgccag cctgttgaat   9300
atgcagggtg aagaaaaatc ccgcgcgctg gcgattttaa aatcggccct cgatagccag   9360
cagggtgaac cgtggcaaac gattcgttta atttctgaat tttacccgga agacagcggt   9420
ctgttctccc cgctattgct gaatgtggtg aaattgaacc ctggcgaagc gatgttcctg   9480
ttcgctgaaa caccgcacgc ttacctgcaa ggcgtggcgc tggaagtgat ggcaaactcc   9540
gataacgtgc tgcgtgcggg tctgacgcct aaatacattg atattccgga actggttgcc   9600
aatgtgaaat tcgaagccaa accggctaac cagttgttga cccagccggt gaaacaaggt   9660
gcagaactgg acttcccgat tccagtggat gattttgcct tctcgctgca tgaccttagt   9720
gataaagaaa ccaccattag ccagcagagt gccgccattt tgttctgcgt cgaaggcgat   9780
gcaacgttgt ggaaaggttc tcagcagtta cagcttaaac cgggtgaatc agcgtttatt   9840
gccgccaacg aatcaccggt gactgtcaaa ggccacggcc gtttagcgcg tgtttacaac   9900
aagctgtaag agcttactga aaaaattaac atctcttgct aagctgggag ctcgatccgt   9960
cgacctgcag atcgttcaaa catttggcaa taaagtttct taagattgaa tcctgttgcc  10020
ggtcttgcga tgattatcat ataatttctg ttgaattacg ttaagcatgt aataattaac  10080
atgtaatgca tgacgttatt tatgagatgg gtttttatga ttagagtccc gcaattatac  10140
atttaatacg cgatagaaaa caaaatatag cgcgcaaact aggataaatt atcgcgcgcg  10200
gtgtcatcta tgttactaga tctgctagcc ctgcaggaaa tttaccggtg cccgggcggc  10260
cagcatggcc gtatccgcaa tgtgttatta agttgtctaa gcgtcaattt gtttacacca  10320
caatatatcc tgccaccagc cagccaacag ctccccgacc ggcagctcgg cacaaaatca  10380
ccactcgata caggcagccc atcagaatta attctcatgt ttgacagctt atcatcgact  10440
gcacggtgca ccaatgcttc tggcgtcagg cagccatcgg aagctgtggt atggctgtgc  10500
aggtcgtaaa tcactgcata attcgtgtcg ctcaaggcgc actcccgttc tggataatgt  10560
tttttgcgcc gacatcataa cggttctggc aaatattctg aaatgagctg ttgacaatta  10620
atcatccggc tcgtataatg tgtggaattg tgagcggata acaatttcac acaggaaaca  10680
gaccatgagg gaagcgttga tcgccgaagt atcgactcaa ctatcagagg tagttggcgt  10740
catcgagcgc catctcgaac cgacgttgct ggccgtacat ttgtacggct ccgcagtgga  10800
tggcggcctg aagccacaca gtgatattga tttgctggtt acggtgaccg taaggcttga  10860
tgaaacaacg cggcgagctt tgatcaacga ccttttggaa acttcggctt cccctggaga  10920
gagcgagatt ctccgcgctg tagaagtcac cattgttgtg cacgacgaca tcattccgtg  10980
gcgttatcca gctaagcgcg aactgcaatt tggagaatgg cagcgcaatg acattcttgc  11040
```

aggtatcttc gagccagcca cgatcgacat tgatctggct atcttgctga caaaagcaag 11100
agaacatagc gttgccttgg taggtccagc ggcggaggaa ctctttgatc cggttcctga 11160
acaggatcta tttgaggcgc taaatgaaac cttaacgcta tggaactcgc cgcccgactg 11220
ggctggcgat gagcgaaatg tagtgcttac gttgtcccgc atttggtaca gcgcagtaac 11280
cggcaaaatc gcgccgaagg atgtcgctgc cgactgggca atggagcgcc tgccggccca 11340
gtatcagccc gtcatacttg aagctaggca ggcttatctt ggacaagaag atcgcttggc 11400
ctcgcgcgca gatcagttgg aagaatttgt tcactacgtg aaaggcgaga tcaccaaagt 11460
agtcggcaaa taaagctcta gtggatctcc gtacccgggg atctggctcg cggcggacgc 11520
acgacgccgg ggcgagacca taggcgatct cctaaatcaa tagtagctgt aacctcgaag 11580
cgtttcactt gtaacaacga ttgagaattt ttgtcataaa attgaaatac ttggttcgca 11640
tttttgtcat ccgcggtcag ccgcaattct gacgaactgc ccatttagct ggagatgatt 11700
gtacatcctt cacgtgaaaa tttctcaagc gctgtgaaca agggttcaga ttttagattg 11760
aaaggtgagc cgttgaaaca cgttcttctt gtcgatgacg acgtcgctat gcggcatctt 11820
attattgaat accttacgat ccacgccttc aaagtgaccg cggtagccga cagcacccag 11880
ttcacaagag tactctcttc cgcgacggtc gatgtcgtgg ttgttgatct agatttaggt 11940
cgtgaagatg ggctcgagat cgttcgtaat ctggcggcaa agtctgatat tccaatcata 12000
attatcagtg gcgaccgcct tgaggagacg gataaagttg ttgcactcga gctaggagca 12060
agtgatttta tcgctaagcc gttcagtatc agagagtttc tagcacgcat tcgggttgcc 12120
ttgcgcgtgc gccccaacgt tgtccgctcc aaagaccgac ggtctttttg ttttactgac 12180
tggacactta atctcaggca acgtcgcttg atgtccgaag ctggcggtga ggtgaaactt 12240
acggcaggtg agttcaatct tctcctcgcg tttttagaga aaccccgcga cgttctatcg 12300
cgcgagcaac ttctcattgc cagtcgagta cgcgacgagg aggtttatga caggagtata 12360
gatgttctca ttttgaggct gcgccgcaaa cttgaggcag atccgtcaag ccctcaactg 12420
ataaaaacag caagaggtgc cggttatttc tttgacgcgg acgtgcaggt ttcgcacggg 12480
gggacgatgg cagcctgagc caattcccag atccccgagg aatcggcgtg agcggtcgca 12540
aaccatccgg cccggtacaa atcggcgcgg cgctgggtga tgacctggtg gagaagttga 12600
aggccgcgca ggccgcccag cggcaacgca tcgaggcaga agcacgcccc ggtgaatcgt 12660
ggcaagcggc cgctgatcga atccgcaaag aatcccggca accgccggca gccggtgcgc 12720
cgtcgattag gaagccgccc aagggcgacg agcaaccaga tttttcgtt ccgatgctct 12780
atgacgtggg cacccgcgat agtcgcagca tcatggacgt ggccgttttc cgtctgtcga 12840
agcgtgaccg acgagctggc gaggtgatcc gctacgagct tccagacggg cacgtagagg 12900
tttccgcagg gccggccggc atggccagtg tgtgggatta cgacctggta ctgatggcgg 12960
tttcccatct aaccgaatcc atgaaccgat accgggaagg gaagggagac aagcccggcc 13020
gcgtgttccg tccacacgtt gcggacgtac tcaagttctg ccggcgagcc gatggcggaa 13080
agcagaaaga cgacctggta gaaacctgca ttcggttaaa caccacgcac gttgccatgc 13140
agcgtacgaa gaaggccaag aacggccgcc tggtgacggt atccgagggt gaagccttga 13200
ttagccgcta caagatcgta aagagcgaaa ccgggcggcc ggagtacatc gagatcgagc 13260
tagctgattg gatgtaccgc gagatcacag aaggcaagaa cccggacgtg ctgacggttc 13320
accccgatta ctttttgatc gatcccggca tcggccgttt tctctaccgc ctggcacgcc 13380

-continued

```
gcgccgcagg caaggcagaa gccagatggt tgttcaagac gatctacgaa cgcagtggca  13440
gcgccggaga gttcaagaag ttctgtttca ccgtgcgcaa gctgatcggg tcaaatgacc  13500
tgccggagta cgatttgaag gaggaggcgg ggcaggctgg cccgatccta gtcatgcgct  13560
accgcaacct gatcgagggc gaagcatccg ccggttccta atgtacggag cagatgctag  13620
ggcaaattgc cctagcaggg gaaaaaggtc gaaaaggtct ctttcctgtg gatagcacgt  13680
acattgggaa cccaaagccg tacattggga accggaaccc gtacattggg aacccaaagc  13740
cgtacattgg gaaccggtca cacatgtaag tgactgatat aaaagagaaa aaaggcgatt  13800
tttccgccta aaactcttta aaacttatta aaactcttaa aacccgcctg gcctgtgcat  13860
aactgtctgg ccagcgcaca gccgaagagc tgcaaaaagc gcctaccctt cggtcgctgc  13920
gctccctacg ccccgccgct tcgcgtcggc ctatcgcggc cgctggccgc tcaaaaatgg  13980
ctggcctacg gccaggcaat ctaccagggc gcggacaagc cgcgccgtcg ccactcgacc  14040
gccggcgctg aggtctgcct cgtgaagaag gtgttgctga ctcataccag gcctgaatcg  14100
ccccatcatc cagccagaaa gtgagggagc cacggttgat gagagctttg ttgtaggtgg  14160
accagttggt gattttgaac ttttgctttg ccacggaacg gtctgcgttg tcgggaagat  14220
gcgtgatctg atccttcaac tcagcaaaag ttcgatttat tcaacaaagc cgccgtcccg  14280
tcaagtcagc gtaatgctct gccagtgtta caaccaatta accaattctg attagaaaaa  14340
ctcatcgagc atcaaatgaa actgcaattt attcatatca ggattatcaa taccatattt  14400
ttgaaaaagc cgtttctgta atgaaggaga aaactcaccg aggcagttcc ataggatggc  14460
aagatcctgg tatcggtctg cgattccgac tcgtccaaca tcaatacaac ctattaattt  14520
cccctcgtca aaaataaggt tatcaagtga gaaatcacca tgagtgacga ctgaatccgg  14580
tgagaatggc aaaagctctg cattaatgaa tcggccaacg cgcgggggaga ggcggtttgc  14640
gtattgggcg ctcttccgct tcctcgctca ctgactcgct gcgctcggtc gttcggctgc  14700
ggcgagcggt atcagctcac tcaaaggcgg taatacggtt atccacagaa tcaggggata  14760
acgcaggaaa gaacatgtga gcaaaaggcc agcaaaaggc caggaaccgt aaaaaggccg  14820
cgttgctggc gtttttccat aggctccgcc cccctgacga gcatcacaaa aatcgacgct  14880
caagtcagag gtggcgaaac ccgacaggac tataaagata ccaggcgttt ccccctggaa  14940
gctccctcgt gcgctctcct gttccgaccc tgccgcttac cggatacctg tccgcctttc  15000
tcccttcggg aagcgtggcg ctttctcata gctcacgctg taggtatctc agttcggtgt  15060
aggtcgttcg ctccaagctg ggctgtgtgc acgaaccccc cgttcagccc gaccgctgcg  15120
ccttatccgg taactatcgt cttgagtcca acccggtaag acacgactta tcgccactgg  15180
cagcagccac tggtaacagg attagcagag cgaggtatgt aggcggtgct acagagttct  15240
tgaagtggtg gcctaactac ggctacacta gaagaacagt atttggtatc tgcgctctgc  15300
tgaagccagt taccttcgga aaaagagttg gtagctcttg atccggcaaa caaaccaccg  15360
ctggtagcgg tggttttttt gtttgcaagc agcagattac gcgcagaaaa aaaggatctc  15420
aagaagatcc tttgatcttt tctacggggt ctgacgctca gtggaacgaa aactcacgtt  15480
aagggatttt ggtcatgaga ttatcaaaaa ggatcttcac ctagatcctt ttgatccgga  15540
atta                                                               15544
```

<210> SEQ ID NO 46
<211> LENGTH: 7127
<212> TYPE: DNA
<213> ORGANISM: Zea mays

<400> SEQUENCE: 46

```
agagaggaga tattttcgac cagcgcgaca tgcatggcat ggcaaactat atatcgtcat     60
catcattatt atcatctgac cctctttttt tttcactctc actcccatgt ttttattccc    120
gggcggggcc gtgtgggtgt gggttgggat ggccggattg gggtcccggg gtggagaaat    180
gacaaatcca ggcccgcagg cggccaccca ccaaatcgga cgacgcaggg tgcccaaatc    240
aggaaggatt ttaaggttaa ccggccaccg gcggtgaccg acgccccacc ccactctcct    300
tctcctattc tatctatata tcacccgcct ctttttctc cctcactccg ccacaccttc     360
cctcttcttc ctcagctccg tcgcccaccg ccggagctcc gaaaggcccc gcgcccgccg    420
cctttcctgt aaaaaaccca acctttagct agctaaccgc tcctcttctc cccctactcc    480
ccttgcccaa atcagagaag atatttaacg gaggagggga aggagaggat atttagctga    540
ttgttgattg gtggtccggg gtacggtgtt cttgagtcgt gaagcgaccg tacagtggct    600
agggccgtct ccgggttgcg tgcaggatgg tcgtcagaga tcgggagtga ggaggcagct    660
cgtggtcgtg gaggctaaat gtaccgcaag aacgactcgg cactctcctg tttctacctc    720
ttcctcctct ggttcttctt cttgaaatag accagcgcca gccaccaggt agctacctac    780
tagctagcag cccagttgcg actggggacg ggctgctgct tgcaagttgg aatcttggag    840
caggagcaga ggagcgggag atggagctgg atctgaacgt ggccgaggtg gcgccggaga    900
agccatcggc ggcgctggag gcgagcgact cggggtcctc gggctcgtcg gtgctgaacg    960
cggaggcggc atcggcgggc ggcggggggc ccgcgccggg ggaggagggg tcaagctcga   1020
cgccggccgt gctcgagttc agcatcctca ggagcgacag cgacgcggcc ggcgcggacg   1080
ccgacgacgg cgacgccacg ccgtcgccac ctcgccacca ccagcagcag ctcgtcaccc   1140
gggagctctt cccggcgccg cagcattggg ccgagctcgg cttcttccgc gccggcccgc   1200
agcagcagcc ggacatcagg gtcctgccgc acccgcaccc gtacccgccc ccgccgccgc   1260
ccgcgcagcc gcagcaggcc aagaagagcc gccgcggccc gcgctcccgc agctcgcagt   1320
accgcggcgt caccttctac cgccgcaccg gccgctggga gtcccacatc tggtcagtag   1380
cactgcaagc tcaccatgcg ccctttcacc taccgaccaa taatcgcttg tgattctgac   1440
acccaaatgt ttcgtcttcc tgtgctgtcc tgttcctcgg aaatggcagg gattgcggga   1500
agcaggtgta cttaggtgag cagcaataag cagatcgatc tgcagcataa atttcccgtt   1560
attaactagt tcgtgatctc gatcgaatgg cctaattaac cgattcggtg atctggccga   1620
tggccaatct acgcaggtgg attcgacact gctcatgccg ctgcaaggta acgatcaatc   1680
catccatcca cccttgtcta gctaccccac cgaccggccg gattaatgga ccgctagctc   1740
tcgggacggg cttgctgcag ggcgtacgac cgagcggcga tcaagttccg cggcgtcgac   1800
gccgacataa acttcaacct cagcgactac gacgacgata tgaagcaggt acatacacga   1860
gtgttcttgc agctagcacc gactgaaaca tctgctgaac gtacacgcat ggccctgtgc   1920
accagatgaa gagcctgtcc aaggaggagt tcgttcacgc cctgcggcgg cagagcaccg   1980
gcttctcccg cggcagctcc aagtacaggg gcgtcaccct gcacaagtgc ggccgctggg   2040
aggcgcgcat ggggcagttc ctcggcaaga agtaagaaac aacacttcgt ttgcaggcgc   2100
tgtactttgc tgcagattat ttcatttcat ccttgcatgt gcctttcctt tccatccact   2160
cacttgatgg ctgtagtctc gatagagttc gttcgttcgt acttcgcacc agatgaactc   2220
ccacgcacat gatttagtac tagttttacc atgcattgtt cagtaaaagt atatgcttgc   2280
```

-continued

```
ttgatcagtg gttgtttcaa tcagaagatt aaaaaaacgg aatattaata taaaaaaaag   2340
gggaagtggc tagggaattc ctcagtccta gctagctagc tcaccggtgg gaacgccatg   2400
cttggcttgg gtgcaggtac atatatcttg ggctattcga cagcgaagta gaggctgcaa   2460
ggttgttcac ctcggacgat tctgccattt gttcatatac accatgcctt ttgatttctc   2520
tcttgcaatt tctcttcttt tatcatggct tttgattccc aaagggttga gtaccgactc   2580
gatattcgat tctccctgcc gtttcgtgac cccagggcgt acgacaaggc cgcgatcaaa   2640
tgcaacggta gagaggccgt gacgaacttc gagcccagca cgtacgacgg ggagctgctg   2700
ctgactgctg aagctagcgc agaaggtaat taagtagctg ctcgctgcca tgtaatcttc   2760
agatgacgcc gctgttaatt attagctcat cagctttcgg acgatgccct tgtttttcgg   2820
ttgaaccggg gtgaactttc tgaatttgag atttgatttt ttttgtttct gcttctgcag   2880
ttgctgacga cgttgatctg aacttgagca tctcgcaacc ggcatcgtcc cagagcccca   2940
aaagagacaa gaactgcctt ggtccgcagc tccaccacca ccatgggcgg ccgtttgacg   3000
gctccgccgt tctgaagaaa accaaggcaa gcgctaagta ataacgctac gtaccttgac   3060
aagtatcaaa atcagtaaaa ctttcctctt cgtcaaaccc tatctctacc gacggctgtt   3120
agttgcccgg ttttgatcat ttgacaatta aacacatacc ctctcgcaag tcgggatcat   3180
ttttagctag gcggactagt ttatcgccaa gcagcgagtt tctctttcgg ggtgggtgat   3240
cgcgacagct gagcagaata cttcttcttc gtctactttt tctccttcct cctaccaaaa   3300
ttgaattgtt taaggaaaat ttatacagag agcggcgtgg acagctttgg atggagctgc   3360
cgataattca actgaaaatc tctcgcttct tcttcttctc atgcagatcg atgctccgtc   3420
tgagctgtcg tcggcgggcc gccctcaccg gtcgttcctc cctcatctcg tggctgccga   3480
gcatctaccg cctcggtctc accccttctt catcacacac catgaggtta gacgacacta   3540
tacagtactg aatcatttgc aaaggtttgt caagctagct agattggcat cataatacac   3600
ggatcaggtg tcagattgtt catgcagtgc agtatgcagc ctgaaggtgt atgcagtttc   3660
agatagcaga tttttagcag ctggttaatt tctctcttgc gtgcggctgt cagtcagtgt   3720
agctctcgtc gtcgcccgct ttatttcctt ggattctagc tagagtccgc ctgtcacccg   3780
tcgatttcag tgaagttaat gggatgcgcg aattttttttt ctcccccgta taggccggct   3840
gttgaatata tgtgtctatc ttgaattggc ctaatatggg aataatagta ctagcagctt   3900
tatggctaga tcagaatatg tacatgtgtt tgattttttt tctctctctc ccttagcttc   3960
cttgaaaagg aaaggtccta gacctagcta ccggccagca gcgacacttc aactctaagg   4020
gcatgtacag tggagagacg ccaaaacggt tctccaagca taggagacaa ctaagagact   4080
ctattgtaca atggagtgtc tctaaacgta gtctattaat aaatacagaa ttaaatgtat   4140
ttgtatagca tcagatcgat agaacagacg acaaattcgt acagtgggaa gtgaggcgtc   4200
tgttgttact tggtttacga gccagaggcg tctcttcacg gagagacggc tctaagattt   4260
ttttgcaaat aacccccctaa aacaccttaa gagcccccac attaaacacc actgtacatg   4320
ccctaagccc tgcctggcct gcctaatcaa accctctcgg tcaactatgc tatgcctgcc   4380
tgcctgcttt caacacgtac tgttcctttt tcaaaccttc cctggaaacg aaaacagaag   4440
atgcatggta tttatgcttg gggatttgcc ttcttttcag tgtactaata agcttggggt   4500
ttgtttagtc gttcagcaat caacttggac gagtgttgat aaataaaact cgatctccaa   4560
cctttcgttc ataaatgggt cagctaactt tgaggtcggt ctcactctca caccagtgtc   4620
gctttctgat tgtattgtat tggacgggaa gagctgaggt cgacgctttt ctgcccccag   4680
```

ctgaactgat gggaaacgct aagctaatta tattggtgga acgagtctcc tgccgtttgc 4740
tctctttttt gttttgtttc tcttaaaaaa aacatgcttc catgcatcag aaagcgttat 4800
tacttaggat gattaatttg aactgttcat cagttcgttg aattggtcct agggtgaatg 4860
aactttcagt ttatttgttg accatgcatg cagagtgatg catcaagaag agatcccagc 4920
tgggcagcag cagcagcatg gaaggtgacc gcagctgcac ctcctcctcc taccaccacc 4980
ctgttgccgt tgccgctgcc gtcgacgtcg tccgctgcag catcatcagg attctccaat 5040
accgccacga cagctgccgc cgccccatcg gccgcctcct cccgccggtt cgacccgccg 5100
ccaccgtcgt cgtcctcctc ctcgagccat caccaccacc accaccgccg ctgagaatcg 5160
aagaagccac actgtaaatc tgccgggaag cggctggtgg catccggccc gctcctccct 5220
ccgggcgccg caactttttt cgatcggttt tgcgccgccc gggacgggtt gtagttgatc 5280
gattggattc ttcataactg tatttgcgta ctgcttacac tacccaagtg aaatcgaaaa 5340
tggcgccttc tctcgttgaa taaattgcac gtacgctact cgatccgctg cggctcttgc 5400
tggagtggcc gccgccgcta tagatagaag gatcaagcca aggaatctgt catgcatggg 5460
catgtgaagg aggagcctcc tgcaatgttt agtctttttt ggtcgacgcc caccagagat 5520
atacgcacta gatttcatat agctgagcta gatcgattcc gttgcatgca tgctccatgg 5580
cgtcgagatt cgagctagca ccgcctgttc atcatcgacc gatccattct gatcgattcc 5640
cctctcgagc tttcacgaac tgaacctacc tagtgagggt gacgcctaac gcctagtgcg 5700
cgcgcgtggg tctccgatgt cagtggccgc acgcgcgcgc gcgttctcga gatcgcatgt 5760
ggtcatagcg cagcaggttt gccctcagaa cctacagcaa ctcgaccacc ggtttggatt 5820
tcttcttttt tcaaggatat gatcggagag agagagctac ctaggcgtcg tccttgtttt 5880
cttgtatcgc atgtggtgtg ggtctctctc ctcctttcgt acgcacgcat gattccattc 5940
ttaccccccc tcgagatcga gaggaaatat attgctattt tatacacaca cggcgccccc 6000
agctatacgt cactgcttac gttaattccc ccaccggata gtagttgttt aatggcccaa 6060
acaaaccttg ttgttgcatg catcatggac caaacaaaat acatagttag ttaaatatta 6120
ctgttatata tacaactaat aataattata ttattagtta aaacaaagca aggcatatgc 6180
agcagctgct ggtactaccc agtacatggc acatgcgttt gtttaatccc ctgttgctgt 6240
gtgtgtgatt gattccttgt attagctaat aattagttag gtcggtcgtc gtctcccctc 6300
taatccctct tcgatttaga attagtagtc ttgtacgttg tttaatatgc ttggacgacg 6360
acgctctttg ttgggtgtgc acttcatctt tccatctaca ctagctagct agacacacat 6420
gtactatagc tagctacttg ttttagtatg ctgctcttct aattaactaa ccaacatgat 6480
tgcactgcta agcaaggcta cctttggtac ggtcttaaac tttgtgtggc ccatatgctg 6540
ctatactata tcatgcatgt agattcttcc tgccaaggtg catggttttt ttatgttaat 6600
aggtacggtt agttgtcgta gtacatacta aggcatcgat cgtccactta tatatatcaa 6660
accctgcagc tcaaacaagc tgcaaataaa aaaaaaactg aagctggtat atgagtgtat 6720
attgtatatg aaataataat gcatatgcgg ctgcatgcat cagggagctg agtcagatga 6780
caggtgtagg tttgaagcag cttgctgtac gtgtgcaatt tttttctctc cataatgatg 6840
tctcagattg gtgatctgat gacgctgtga ttattctatt ctattcatct ttggttgtag 6900
acactccttt tcatttgtta atagttttct ggtccagttg atagatagag gttaaataaa 6960
agccagttgt agtctacctt aactagtacg atagtacaac aggattggcc ggcggcgtta 7020

-continued gtaaatttat aatttcgtat acaagctgtt attgttatta catacactag ccggttactc 7080
gtgcttttct atagttgtta tatattatat actcgaggcg tctagag 7127

<210> SEQ ID NO 47
<211> LENGTH: 439
<212> TYPE: DNA
<213> ORGANISM: Zea mays

<400> SEQUENCE: 47
tattaaggct gcttctgagg gcccactcaa gggtattatg ggctacgtgg aggaggatct 60
ggtttccacc gacttcaccg gtgacagcag gtcgagcatc ttcgacgcca aggccgggat 120
tgccctgaac gaccacttca tcaagctcgt ctcttggtac gacaacgagt ggggctacag 180
caaccgcgtc gtcgacctga tccgccacat gttcaagacc cagtagagag agatatttct 240
gcctccctat cgagggtcgt ccccgatggc ctttggtcgc agaccatctt tgctgcttgt 300
ctatgctgag aataaatgtg aacggtgccc ctggacgctg gatccatgct ggttttggac 360
acggttgtct ttttgtgttt aacttatctg ctgccgtccg tcctgtaacg aattcgctaa 420
gttttagttc ttttgtgct 439

<210> SEQ ID NO 48
<211> LENGTH: 391
<212> TYPE: DNA
<213> ORGANISM: Zea mays

<400> SEQUENCE: 48
catgtccttg attattggtg tctacgacga gccaatgact ccagggcaat gcaacatggt 60
ggtggagagg ctcggcgatt acctgatcga gcagggcttc taaaagttcg tcatgttctg 120
ttttggtcat ttgggcacca aagtttgcgc ctcatttggt tctgtaatcc gtgagctcgt 180
gcatgtactt ggcgtattgc atgcagtgaa taatttagct tgggtttgtt tgttgggggc 240
agtgttgggg acggatttgg attggggttt atgcttggca tcgcgtcgta tcgaaactca 300
gctgctgttt cgctgagtaa tgtacatttc cctggtaatg gtacttgtgg actctgatgc 360
ttttatggga acgagtgcat tttactgcaa a 391

<210> SEQ ID NO 49
<211> LENGTH: 136
<212> TYPE: DNA
<213> ORGANISM: Zea mays

<400> SEQUENCE: 49
attgggttac aagaattatg gcgtttgtca atatggtcgt aatgtcgtag gatggtggaa 60
tgtggtcaca aactttgcgt atgttgggtc tactggtggt gtctgaatct atgtatggat 120
gtcatgagtt tgtcta 136

<210> SEQ ID NO 50
<211> LENGTH: 63
<212> TYPE: DNA
<213> ORGANISM: Zea mays

<400> SEQUENCE: 50
ggtgtatccg cgttagaacc ttttgttggt gaacaatatt atcgtggcac gcgttttaag 60
taa 63

<210> SEQ ID NO 51
<211> LENGTH: 632

<212> TYPE: DNA
<213> ORGANISM: Zea mays

<400> SEQUENCE: 51
cgctgtgaat gacgagtgca tgctcaagtt cggcgagctg cagtcgaaga ggctgcaccg 60
cttcctaact ttcaagatgg acgacaagtt caaggagatc gttgtggacc aggtcgggga 120
tcgcgctacc agctacgagg acttcacaaa cagcctcccc gagaatgact gccgatacgc 180
gatctatgat ttcgactttg tcactgcaga agatgtccag aagagcagga tcttctatat 240
cctatggtcc ccatcctccg ccaaggtgaa gagcaagatg ctttatgcaa gctcaaacca 300
aaaattcaag agtgggctca atggcattca ggtggaactg caggctactg atgcaagtga 360
aatcagcctt gatgagatca aggatcgggc tcgctaggca tcatgatcat gcatcatgga 420
ctcggcctac tactgtggat ttgtatgcca ttatagactt ggtgctgtga aagactgctt 480
gatgatttgc gggtttgttg ctgtgtaaaa aaaggtccca tggctcccag aagaccatga 540
aggttcggat ctatcatgta attccttgtt atctgccaat tatgtatgga ctatggacat 600
gtgttgcgct gttcaactta ctactacaaa ta 632

<210> SEQ ID NO 52
<211> LENGTH: 598
<212> TYPE: DNA
<213> ORGANISM: Zea mays

<400> SEQUENCE: 52
gggttgaact atgagcgccg tggcggtttc gtcgtcgctg aacccggacg cgccgctctt 60
catcccggcg gcgctgctgc aggtggagga cttctcgccg cagtggtggg acctcatcac 120
caccactgcc tggttccgcg accactggtc ccgcgagcgc gcccacctgg acgagatggc 180
cgagcagatc gacgcggccg gcctcctccc cgacgacgag gacctcttct acgacgacca 240
gctcgagcag ggccccgtcg ccgccgccct taagacagat tcggtgctca aggcgctgaa 300
catgacctcc ccgaagggcg gcggcgacgc cccgcggggg ttccgggaga aacccaggaa 360
cgccgagaag ccgaccaagt acgccggcag ccccaagagc agcgcccccc gcgtgatcca 420
ccagcctcgc taggttcgct gggggaactc atcaggaagg ctgctgcccc tcttgcagcc 480
ttgctcctgg ctgccgcccg ctgtcgtggt ctgctctttc aagtcgaagt aacggtggtt 540
cgagctagtg gatagtgtgg ctcaactgta gaagttcctt ttgtatagca agcaagta 598

<210> SEQ ID NO 53
<211> LENGTH: 516
<212> TYPE: DNA
<213> ORGANISM: Zea mays

<400> SEQUENCE: 53
atggctgtcc gcatcatcaa gcataccctg gagatcatcc acctgctcac cgatgccaac 60
cccatccagg tcgtcgtcga cgcgatcatc aacagtggcc cccgtgagga tgccacccgt 120
attggttccg ctggtgttgt gaggaggcag gccgtggata tctcacccct gaggagggtg 180
aaccaggcca tctacctcct caccactggt gccagggaga gtgctttccg gaacatcaaa 240
accattgccg agtgccttgc agatgagctg atcaacgctg ccaagggctc atccaacagt 300
tacgccatca agaagaagga cgagattgag cgtgttgcca aggccaaccg ttgaactgag 360
cttgtatcct ggtgcactct gcgctggaaa cttttatgtc gctggcagtc gtatcggttc 420
ttgttttacc aatgtttaga gttttttgag acctatatgc ggttttggtt ttcagtgcac 480
aattaaaatt actgagtaat gtagttgatt gggaac 516

<210> SEQ ID NO 54
<211> LENGTH: 64
<212> TYPE: DNA
<213> ORGANISM: Zea mays

<400> SEQUENCE: 54
gtgttcggtg aaatcagagt cgtcagtcat ctacatagct tttcttggtt gatagactgt 60
tatt 64

<210> SEQ ID NO 55
<211> LENGTH: 195
<212> TYPE: DNA
<213> ORGANISM: Zea mays

<400> SEQUENCE: 55
ataaaatagc atgccgtctc tgtcactggc aatggacggt ggtgcctagc gcaactcagc 60
gcacaactgt gtgtcttgat ttttcttctg tttatcacgg cattagtgcc atgccgtttt 120
atgttacagt gttgtgtgct cgcaagcatc cgaaaatatg cgtctgagtt tagggttggg 180
tcaaacttgt cgaat 195

<210> SEQ ID NO 56
<211> LENGTH: 52
<212> TYPE: DNA
<213> ORGANISM: Zea mays

<400> SEQUENCE: 56
gagaaccatc gcctgcattt cgatctgttt caccgcaatt cgcattgtta gt 52

<210> SEQ ID NO 57
<211> LENGTH: 90
<212> TYPE: DNA
<213> ORGANISM: Zea mays

<400> SEQUENCE: 57
ctatgttgta taaggctagt gcagctgtgc aggttactct atattcttac tctatatcac 60
tatttgtagt ctactcatca attaataaat 90

<210> SEQ ID NO 58
<211> LENGTH: 549
<212> TYPE: DNA
<213> ORGANISM: Zea mays

<400> SEQUENCE: 58
tggtcaacgt gcacgcggtc cacagggacc ccgcggtgtg ggacgacccg gacaggttcg 60
tgccggagcg gttcgagggc gccggcggca aggccgaggg gcgcctgctg aagccgttcg 120
ggatggggcg gcgcaagtgc cccggggaga cgctcgcgct gcggaccgtc gggctggtgc 180
tcgccacgct gctccagtgc ttcgactggg acacggttga tggagctcag gttgacatga 240
aggctagcgg cgggctgacc atgccccggg ccgtcccgtt ggaggccatg tgcaggccgc 300
gtacagctat gcgtggtgtt cttaagaggc tctgaaaacc tcatggatcg aattgctggc 360
atcgtctgaa gggtgtatga cgtagcttcc gagttccgag catatatatt cacttgcctt 420
gtactagttg attttcgccg agtgtatgga atggattttc tttttttttc ttgcaatgga 480
tgtgaatttt gtttttctcg acgttacaag aagtgaatca acctagcttc tctttgagcg 540
acagcaacg 549

<210> SEQ ID NO 59
<211> LENGTH: 538
<212> TYPE: DNA
<213> ORGANISM: Zea mays

<400> SEQUENCE: 59
cgacttgttt cattgattct tcaagagatc gagcttcttt tgcaccacaa ggtcgaggat 60
gtcttgcagc tgcggatcaa gctgcggctg cggctcaagc tgcaagtgcg gcaagaagta 120
ccctgacctg gaggagacga gcaccgccgc gcagcccacc gtcgtcctcg gggtggcccc 180
ggagaagaag gccgcgcccg agttcgtcga ggccgcggcg gagtccggcg aggcggccca 240
cggctgcagc tgcggtagcg gctgcaagtg cgacccctgc aactgctgat cacatcgatc 300
gacgaccatg gatgattatt atctatctag cttgtggtgg tggttgaaca ataataagcg 360
aggccgagct ggctgccata cataggtatt gtgtggtgtg tgtgtgagag agagagaaac 420
agagttcttc agtttgctat ctctctctgc atgtttggcg tcagtctttg tgctcatgta 480
cgtgtgtcta catgcatgtt ggttgatccg attgcgtctg ctgtaaccat atattaat 538

<210> SEQ ID NO 60
<211> LENGTH: 228
<212> TYPE: DNA
<213> ORGANISM: Zea mays

<400> SEQUENCE: 60
tctacccgcc cgagaaggtc tacgacttcg tctgcgggat gaagaagagg ctgggcatcg 60
agtagagcat ccatcggtcg gccggtggct ggccgggagt aataatgacg aaccaataat 120
ctagttttgg ttttagtgtg ctcagcagag cagttcgtgt tcatgagttc gtcgtcgttg 180
tattttctat tgtcagcggt ggcagcgccg tacgtgttgc ctcgtaca 228

<210> SEQ ID NO 61
<211> LENGTH: 737
<212> TYPE: DNA
<213> ORGANISM: Zea mays

<400> SEQUENCE: 61
ccgccgagct cgaccgcgtg attggggcac ggccgctggg tcacagagcg cgacctcccg 60
gacctcccct acatcgacgc cgtcgtgaag gagacgatgc ggctgcaccc ggtcggcccg 120
ctcctcgtcc cgcaccacgc ccgcgagcac acggtggtgg ccggctacga cgtccccgcc 180
ggtgcgcgcg tgctggtgaa cgtgtgggcc atcgctcgcg accccgcgtc atggcctgac 240
gcgcctgacg cgttccggcc ggagcggttc ttgaacggca gctccggcgc cagcgtcgac 300
gtgcgcggcg cgcactttga gctgctgccg ttcggggccg ggcggcggat gtgccccgcg 360
cacggcctcg cgatgaagct ggtgaccgct ggcgtggcga acctggtgca cgggttcgcg 420
tggcggctgc cggacggtat ggcgccggag gatgtgagca tggaggagct atttgggctt 480
tccacgcgcc ggaaggttcc gctcgtcgcc gtcgcggagc ccaggctgcc ggcgcacctc 540
tacactaatg tcacgccgcc acagcaggtc gcgggctcca cgattgcgaa cttgtccacc 600
aggccggagt acaagctcgt gttctgaatc attcaccgcc actaaaaata aagcaggaaa 660
aactacactt cctgcgtgct agacgtccgg gcggaacaca acagtgcttg ctcacgttct 720
tctattggtt gtactaa 737

<210> SEQ ID NO 62

<211> LENGTH: 141
<212> TYPE: DNA
<213> ORGANISM: Zea mays

<400> SEQUENCE: 62
gcgcaatcgt atcgtacgtg catgatacgc atacatctgg aaactactat accaatgcaa 60
acagagatct atacgtacga gtatgtataa cgacgagtga tgtttgtatg gatctacgta 120
tgtaacaagg acctctcgta g 141

<210> SEQ ID NO 63
<211> LENGTH: 672
<212> TYPE: DNA
<213> ORGANISM: Zea mays

<400> SEQUENCE: 63
ctccaagcac ttgttagccg gcgtacagca agaagaacct cggacgcgac cgacatggtc 60
gctctctcag gcgctcacac aatcgggcag gcccagtgct cgagcttcaa cggccacatc 120
tacaacgaca cgaacatcaa cgcggccttc gcgacgtcgc tcaaggccaa ctgccccatg 180
tccggcggca gcagcctggc gccgctggac accatgaccc cgaccgtgtt cgacaacgac 240
tactacaaga acctgctgtc gcagaagggg ctgctgcact cggaccagga gctgttcaac 300
aacggcagca ccgacagcac ggtcagcaac tttgcgtcca gctcggccgc cttcaccagc 360
gccttcacgg cggccatggt gaagatgggg aacctcggcc cgctcaccgg gaccagtggg 420
cagatcaggc tcacctgctg gaagctcaac tcgtcctaat aattaaggac ggacgtccga 480
tagacgatcc tgcgcaatcg tatcgtacgt gcatgatacg catacatctg gaaactacta 540
taccaatgca aacagagatc tatacgtacg agtatgtata acgacgagtg atgtttgtat 600
ggatctacgt atgtaacaag gacctctcgt agcgcaaagg cgcgcgttgg gagattaatt 660
aggtacacaa gc 672

<210> SEQ ID NO 64
<211> LENGTH: 83
<212> TYPE: DNA
<213> ORGANISM: Zea mays

<400> SEQUENCE: 64
tacgtatact aaagacctta ctaggtacct cgcgtgattg ttgttcaagt gtactagcta 60
ccaagctagt gacaagaatg ttg 83

<210> SEQ ID NO 65
<211> LENGTH: 640
<212> TYPE: DNA
<213> ORGANISM: Zea mays

<400> SEQUENCE: 65
tgaggttgcg acagcgtggc taaacaacaa tagcgtcaga tccgctatcc atgccgaacc 60
agtcagttca atcggaccct gggaattatg cacggataaa ctggattttg atcatgatgc 120
cggcagcatg atcatctatc acaagaacct cacgagtcag ggctaccgtg ctttcatcta 180
cagcggcgac catgacatgt gtgtacctta caccgggact gaagcatgga ctgcgtcttt 240
aggctacgcc gtcgttgatc cgtggcgaca gtggattgtc gacgaacaag ttgccgggta 300
cacccaagga tatgaaaagg gccttacttt tgccactatt aagggtgctg ggcacacagt 360
tcctgagtac aaaccacagg aagcactagc tttctacagc cgttggcttg ccggtgctaa 420
actgtgagga ggcctatttt gtgtgcaaag gtcatgcagt actgaatcaa acagaagttg 480

```
gataaagcat gcagcaataa ggcagtcgaa ggatcaaagt atccaacgcg ccaactacaa    540

tgttgcattc attttcacat gttataccaa tgcagttgct aattacctgc attgttcatg    600

agttcacagt ccatctaatt ggttgaccac accgtcctat                          640

<210> SEQ ID NO 66
<211> LENGTH: 125
<212> TYPE: DNA
<213> ORGANISM: Zea mays

<400> SEQUENCE: 66

tatcactctc attgtggcta catatctata tctctgaggc caaatgcttg ggtgtccagt    60

actaattaat aataattcag tgcgtatgca agatttgtgg gcaaatattg gtttacgatt    120

tcgga                                                                125

<210> SEQ ID NO 67
<211> LENGTH: 136
<212> TYPE: DNA
<213> ORGANISM: Zea mays

<400> SEQUENCE: 67

gcaccacctt ggtttgagca aacgcgcggc gccgtgtttt ggcatctgtc accgtaggtg    60

ggcggggata cagtgaagtg ataatgcgct tgtgttaggc gcatgtatat atataataat    120

tagatggata cccgtg                                                    136

<210> SEQ ID NO 68
<211> LENGTH: 142
<212> TYPE: DNA
<213> ORGANISM: Zea mays

<400> SEQUENCE: 68

gcaccacctt ggtttgagca aacgcgcggc gccgtgtttt ggcatctgtc accgtaggtg    60

ggcggggata cagtgaagtg ataatgcgct tgtgttaggc gcatgtatat atataataat    120

tagatggata cccgtgcgtt ac                                             142

<210> SEQ ID NO 69
<211> LENGTH: 154
<212> TYPE: DNA
<213> ORGANISM: Zea mays

<400> SEQUENCE: 69

gagcggccgc ggatctgttc aagaaccacg acctcgcttt cgcctcccgc ccacgcagcg    60

tgggagggga taagctgatg tatgagtgca gcaacgtgtc gttcgcgcct tacggcgaga    120

actggcgccg gggcaagaag atcgctgtgg tcca                                154

<210> SEQ ID NO 70
<211> LENGTH: 289
<212> TYPE: DNA
<213> ORGANISM: Zea mays

<400> SEQUENCE: 70

gagcggccgc ggatctgttc aagaaccacg acctcgcttt cgcctcccgc ccacgcagcg    60

tgggagggga taagctgatg tatgagtgca gcaacgtgtc gttcgcgcct tacggcgaga    120

actggcgccg gggcaagaag atcgctgtgg tccacctcct ctctccacgg cgcgtggaat    180

cgttcgcgcc cgtaagggcc gccgaggtag ccgcgctcgt cgcacggaca cgccgcaccg    240
```

-continued cggaggctgg ggaggccgtg gagttgaggg agctcctgaa cggctacgc 289

<210> SEQ ID NO 71
<211> LENGTH: 686
<212> TYPE: DNA
<213> ORGANISM: Zea mays

<400> SEQUENCE: 71
gtagccaggc tctttttgca agatcagact cgaggcatca caaaccacat cgttgggaca 60
ttcggctaca tgtctcccga gtatgtgatg cgtggacaat actccataaa atctagatgt 120
atttagtttc ggcatccttg ttatagagat tgtaacagga caaaagaaca atgggcatta 180
cttcgacgag caaaacgagg atgttgtgag cattgtatgg aagcactgga gcgagggaac 240
acttgcagag attatagatg attctttagg gagaaactac tcagagactg aggtgctaaa 300
atgtgttaac attggcttgt ggtgccttca acagaatcca atggaccgac ctacaatgtc 360
agatgtcatg gtgatgctca atgatgatga tactagttct ctacctgctg ctgcaaaacc 420 aactttttc ttggatgcaa gctcaggcta ctcttacacc tcgggcacca tttcacatcc 480
ttctgcaagg tagtgtaggc taaggcctaa tgcacacctt tatatgaata tcgacatatt 540
gttgcttgtt tgtttcttat tgtgtattgg ttgaaagaaa catggaattc accctgaatt 600
gtaatagctt gtgctcatta ttagtttctt ccaaatcctc aaatataaat tttctcttac 660
tagatgtcct acaagctttc agaaag 686

<210> SEQ ID NO 72
<211> LENGTH: 337
<212> TYPE: DNA
<213> ORGANISM: Zea mays

<400> SEQUENCE: 72
tcaccaccat cctgcgcaag aagatgggcg acgcgcagct cgtcgaggtc gccgaggaca 60
agaagaagga ggagaagaag cccgaccccg tcgccgaagc tgcggcggcg tactacaacc 120
agtactacta ccactaccca ccgccggccg ccgtcgttta cgacccctac ccacggccgg 180
gcaacacctg ctccataatg tagactcagc ctgtggacat atgcaagtta agttttgtgt 240
gtagcggtgc gtgtgtgggg gaggcgcgca agtgtagttt ctatacggaa ttcttctctt 300
atctcccttt tgaggttaag ggcatgtgca gtcccag 337

<210> SEQ ID NO 73
<211> LENGTH: 186
<212> TYPE: DNA
<213> ORGANISM: Zea mays

<400> SEQUENCE: 73
ggttccgcgg ccagtagctg ctgcttgggg ctggtgcacg acctgacgcg ctgcttggcc 60
acgctgggca ccgccctcca ctaccgtggt tactacaatg gttgacgttg taacgcggga 120
agcttggaaa ttatgcgtgc atagccatag catcggcact ctggagatgg atctcccagc 180
tctgaa 186

<210> SEQ ID NO 74
<211> LENGTH: 187
<212> TYPE: DNA
<213> ORGANISM: Zea mays

<400> SEQUENCE: 74
accaccgccg ctgagaatcg aagaagccac actgtaaatc tgccgggaag cggctggtgg 60
catccggccc gctcctccct ccgggcgccg caacttttt cgatcggttt tgcgccgccc 120
gggacgggtt gtagttgatc gattggattc ttcataactg tatttgcgta ctgcttacac 180
tacccaa 187

<210> SEQ ID NO 75
<211> LENGTH: 238
<212> TYPE: DNA
<213> ORGANISM: Zea mays
<220> FEATURE:
<221> NAME/KEY: variation
<222> LOCATION: 184
<223> OTHER INFORMATION: nucleotide a at this position can be
substituted with any nucleotide c, g, or t

<400> SEQUENCE: 75
tggtcgttgg gtccgggtgc cacggcgggg accagaccgt gtacgtgctc cgcgaggagg 60
gcgggagacc tgcgtcctgg tcgcgcgcgc cgccgccgcc gccggagttc gccgggcacg 120
tgcaggcctc ctacttcctt gaactctgaa ctctgaagtg gagggtgtgt acctacacgt 180
accagtggtg gctgtgcata catgacggaa ctacgctacc gtacttgttg tgccactg 238

<210> SEQ ID NO 76
<211> LENGTH: 169
<212> TYPE: DNA
<213> ORGANISM: Zea mays

<400> SEQUENCE: 76
cttgtttcat tgattcttga agagatcgag cttcttttgc accacaaggt cgagatgtct 60
tgcaactgcg gtggcaactg caagtgcgac ccctgcaact gctgatcaca tcgatcgacg 120
accatggata tgattattat ctatctagct tgtggtggtg gttgaacaa 169

<210> SEQ ID NO 77
<211> LENGTH: 114
<212> TYPE: DNA
<213> ORGANISM: Zea mays

<400> SEQUENCE: 77
cgagaacgat ttcgcaggtg tatcagtgta gtatgtatag ccgtatagca agtgcgcatc 60
tcatctcgtg tacgtgaaat tagttggtta ggacgaacag cagcgtgtga tgtt 114

<210> SEQ ID NO 78
<211> LENGTH: 916
<212> TYPE: DNA
<213> ORGANISM: Zea mays

<400> SEQUENCE: 78
gccattcggc gccacgattg cagagccaga gcgagacgcg actgcttttc tgcttcatcc 60
acattggtag ctagctagct tacacgttca cgcatcgctt tccgggccgt ctccggtggt 120
ttagctcagc agagcgggga aggaagaaga tgacctccgt gagcgcgagg cccgttggcg 180
tggggtactg cttcggcggg gcgaggtgcc agccacggtc gcgggtgcgg gtttcggccg 240
cggcctcggc agtggccgcg cccgcgcccg cgatggcggc gacgatgtac gagctgctcg 300
ccgtcgagga gacggcgggg cccgacgaga tcaaggcggc gtaccggcgc gccgcgcggc 360
ggtggcaccc ggacgcgtgc cccggcggcg ccgaccgctt catggcggcg cgggaggcct 420
acgaggtgct gtccgacccc gagcgcaggc gcggctacga catccagctc cgctgcggcg 480
cccacttcgg cgacgccggg taccgcgcgg cacgccgcgc cgggttcgcc gactgggagg 540

```
cgcagctgac cgggctgcag tggcgcgcgg cggggcggcg cgggcgcgcc ggcggggaga    600

cttggggcag caggatgcgc caggcggccg cgcagccgtc cttgtagcgg cgtcgccggt    660

ggctggcctt tgatagttca tacttcgtag tactagtgta ctaccctacc ttcccctttc    720

ctcttcgaca atcgaatggc ccgagaagct gtaattgcgc tgttctgcag cgttttctct    780

tgccaacacg tcatcctcgt cgcactgttc ggagtgcaga cgagcttgaa gtctagaagc    840

agtagacatt ttcccccct ttgaagtgta gtactgtcaa cttttagttc ccactcggtt    900

acatacggtt cgaatc                                                    916


<210> SEQ ID NO 79
<211> LENGTH: 446
<212> TYPE: DNA
<213> ORGANISM: Zea mays

<400> SEQUENCE: 79

tgctccatga agaagtcggt ccacccaatc tcgctgcggc gggcgtctgt agagcctgcg     60

ttacgtgtac ggcgcgtgta cgtatacggc cgtagcgtac atgctcgcct ttgcactcag    120

atgcacaata taacacacag tcacacacac acacacacac acacgacaca cgctgtatac    180

actggatcct aggtgttttt ttagcttagc taggaatgca aatttcttga ttcgttggag    240

ggtttttttt ctagcacgcg gcgcggccgg tgcccatctg tctcgcaccg tcgcacgcct    300

cttcatacac tctctcctgt actcggctac tagtgctact gcatgtagac atgtagtgaa    360

tgtgaagtac aaagaataca atacacggag tatagtagtg tagtcttgta tgcatatgta    420

aactactata ctctgtttta cgaaat                                         446


<210> SEQ ID NO 80
<211> LENGTH: 9651
<212> TYPE: DNA
<213> ORGANISM: Artificial sequence
<220> FEATURE:
<223> OTHER INFORMATION: Vector 15289

<400> SEQUENCE: 80

aattaattcc tgtggttggc atgcacatac aaatggacga acggataaac cttttcacgc     60

ccttttaaat atccgattat tctaataaac gctcttttct cttaggttta cccgccaata    120

tatcctgtca aacactgata gtttaaactg aaggcgggaa acgacaatct gatcatgagc    180

ggagaattaa gggagtcacg ttatgacccc cgccgatgac gcgggacaag ccgttttacg    240

tttggaactg acagaaccgc aacgctgcag gaattggccg cagcggccat ttaaatcaat    300

tgggcgcgcc agctgcttgt ggggaccaga caaaaaagga atggtgcaga attgttaggc    360

gcacctacca aaagcatctt tgcctttatt gcaaagataa agcagattcc tctagtacaa    420

gtggggaaca aaataacgtg gaaaagagct gtcctgacag cccactcact aatgcgtatg    480

acgaacgcag tgacgaccac aaaactcgag acttttcaac aaagggtaat atccggaaac    540

ctcctcggat tccattgccc agctatctgt cactttattg tgaagatagt ggaaaaggaa    600

ggtggctcct acaaatgcca tcattgcgat aaaggaaagg ctatcgttga agatgcctct    660

gccgacagtg gtcccaaaga tggaccccca cccacgagga gcatcgtgga aaaagaagac    720

gttccaacca cgtcttcaaa gcaagtggat tgatgtgata tctccactga cgtaagggat    780

gacgaacaat cccactatcc ttcggtaccg gaccgcgatc gcttaattaa gcttgcatgc    840

ctgcagtgca gcgtgacccg gtcgtgcccc tctctagaga taatgagcat tgcatgtcta    900
```

-continued

```
agttataaaa aattaccaca tattttttt gtcacacttg tttgaagtgc agtttatcta    960
tctttataca tatatttaaa ctttactcta cgaataatat aatctatagt actacaataa   1020
tatcagtgtt ttagagaatc atataaatga acagttagac atggtctaaa ggacaattga   1080
gtattttgac aacaggactc tacagtttta tctttttagt gtgcatgtgt tctccttttt   1140
ttttgcaaat agcttcacct atataatact tcatccattt tattagtaca tccatttagg   1200
gtttagggtt aatggttttt atagactaat ttttttagta catctatttt attctatttt   1260
agcctctaaa ttaagaaaac taaaactcta ttttagtttt tttatttaat aatttagata   1320
taaaatagaa taaaataaag tgactaaaaa ttaaacaaat accctttaag aaattaaaaa   1380
aactaaggaa acatttttct tgtttcgagt agataatgcc agcctgttaa acgccgtcga   1440
cgagtctaac ggacaccaac cagcgaacca gcagcgtcgc gtcgggccaa gcgaagcaga   1500
cggcacggca tctctgtcgc tgcctctgga cccctctcga gagttccgct ccaccgttgg   1560
acttgctccg ctgtcggcat ccagaaattg cgtggcggag cggcagacgt gagccggcac   1620
ggcaggcggc ctcctcctcc tctcacggca ccggcagcta cgggggattc ctttcccacc   1680
gctccttcgc tttcccttcc tcgcccgccg taataaatag acaccccctc cacaccctct   1740
ttccccaacc tcgtgttgtt cggagcgcac acacacacaa ccagatctcc cccaaatcca   1800
cccgtcggca cctccgcttc aaggtacgcc gctcgtcctc cccccccccc cctctctacc   1860
ttctctagat cggcgttccg gtccatggtt agggcccggt agttctactt ctgttcatgt   1920
ttgtgttaga tccgtgtttg tgttagatcc gtgctgctag cgttcgtaca cggatgcgac   1980
ctgtacgtca gacacgttct gattgctaac ttgccagtgt ttctctttgg ggaatcctgg   2040
gatggctcta gccgttccgc agacgggatc gatttcatga ttttttttgt ttcgttgcat   2100
agggtttggt ttgccctttt cctttatttc aatatatgcc gtgcacttgt ttgtcgggtc   2160
atcttttcat gcttttttt gtcttggttg tgatgatgtg gtctggttgg gcggtcgttc   2220
tagatcggag tagaattctg tttcaaacta cctggtggat ttattaattt tggatctgta   2280
tgtgtgtgcc atacatattc atagttacga attgaagatg atggatggaa atatcgatct   2340
aggataggta tacatgttga tgcgggtttt actgatgcat atacagagat gctttttgtt   2400
cgcttggttg tgatgatgtg gtgtggttgg gcggtcgttc attcgttcta gatcggagta   2460
gaatactgtt tcaaactacc tggtgtattt attaattttg gaactgtatg tgtgtgtcat   2520
acatcttcat agttacgagt ttaagatgga tggaaatatc gatctaggat aggtatacat   2580
gttgatgtgg gttttactga tgcatataca tgatggcata tgcagcatct attcatatgc   2640
tctaaccttg agtacctatc tattataata aacaagtatg ttttataatt attttgatct   2700
tgatatactt ggatgatggc atatgcagca gctatatgtg gattttttta gccctgcctt   2760
catacgctat ttatttgctt ggtactgttt cttttgtcga tgctcaccct gttgtttggt   2820
gttacttctg cagggatccc cgatcatgca aaaactcatt aactcagtgc aaaactatgc   2880
ctggggcagc aaaacggcgt tgactgaact ttatggtatg gaaaatccgt ccagccagcc   2940
gatggccgag ctgtggatgg gcgcacatcc gaaaagcagt tcacgagtgc agaatgccgc   3000
cggagatatc gtttcactgc gtgatgtgat tgagagtgat aaatcgactc tgctcggaga   3060
ggccgttgcc aaacgctttg gcgaactgcc tttcctgttc aaagtattat gcgcagcaca   3120
gccactctcc attcaggttc atccaaacaa acacaattct gaaatcggtt ttgccaaaga   3180
aaatgccgca ggtatcccga tggatgccgc cgagcgtaac tataaagatc ctaaccacaa   3240
gccggagctg gtttttgcgc tgacgccttt ccttgcgatg aacgcgtttc gtgaattttc   3300
```

```
cgagattgtc tccctactcc agccggtcgc aggtgcacat ccggcgattg ctcacttttt   3360
acaacagcct gatgccgaac gtttaagcga actgttcgcc agcctgttga atatgcaggg   3420
tgaagaaaaa tcccgcgcgc tggcgatttt aaaatcggcc ctcgatagcc agcagggtga   3480
accgtggcaa acgattcgtt taatttctga attttacccg gaagacagcg gtctgttctc   3540
cccgctattg ctgaatgtgg tgaaattgaa ccctggcgaa gcgatgttcc tgttcgctga   3600
aacaccgcac gcttacctgc aaggcgtggc gctggaagtg atggcaaact ccgataacgt   3660
gctgcgtgcg ggtctgacgc ctaaatacat tgatattccg gaactggttg ccaatgtgaa   3720
attcgaagcc aaaccggcta accagttgtt gacccagccg gtgaaacaag gtgcagaact   3780
ggacttcccg attccagtgg atgattttgc cttctcgctg catgacctta gtgataaaga   3840
aaccaccatt agccagcaga gtgccgccat tttgttctgc gtcgaaggcg atgcaacgtt   3900
gtggaaaggt tctcagcagt tacagcttaa accgggtgaa tcagcgttta ttgccgccaa   3960
cgaatcaccg gtgactgtca aaggccacgg ccgtttagcg cgtgtttaca acaagctgta   4020
agagcttact gaaaaaatta acatctcttg ctaagctggg agctcgatcc gtcgacctgc   4080
agatcgttca aacatttggc aataaagttt cttaagattg aatcctgttg ccggtcttgc   4140
gatgattatc atataatttc tgttgaatta cgttaagcat gtaataatta acatgtaatg   4200
catgacgtta tttatgagat gggtttttat gattagagtc ccgcaattat acatttaata   4260
cgcgatagaa aacaaaatat agcgcgcaaa ctaggataaa ttatcgcgcg cggtgtcatc   4320
tatgttacta gatctgctag ccctgcagga aatttaccgg tgcccgggcg gccagcatgg   4380
ccgtatccgc aatgtgttat taagttgtct aagcgtcaat ttgtttacac cacaatatat   4440
cctgccacca gccagccaac agctccccga ccggcagctc ggcacaaaat caccactcga   4500
tacaggcagc ccatcagaat taattctcat gtttgacagc ttatcatcga ctgcacggtg   4560
caccaatgct tctggcgtca ggcagccatc ggaagctgtg gtatggctgt gcaggtcgta   4620
aatcactgca taattcgtgt cgctcaaggc gcactcccgt tctggataat gttttttgcg   4680
ccgacatcat aacggttctg gcaaatattc tgaaatgagc tgttgacaat taatcatccg   4740
gctcgtataa tgtgtggaat tgtgagcgga taacaatttc acacaggaaa cagaccatga   4800
gggaagcgtt gatcgccgaa gtatcgactc aactatcaga ggtagttggc gtcatcgagc   4860
gccatctcga accgacgttg ctggccgtac atttgtacgg ctccgcagtg gatggcggcc   4920
tgaagccaca cagtgatatt gatttgctgg ttacggtgac cgtaaggctt gatgaaacaa   4980
cgcggcgagc tttgatcaac gaccttttgg aaacttcggc ttcccctgga gagagcgaga   5040
ttctccgcgc tgtagaagtc accattgttg tgcacgacga catcattccg tggcgttatc   5100
cagctaagcg cgaactgcaa tttggagaat ggcagcgcaa tgacattctt gcaggtatct   5160
tcgagccagc cacgatcgac attgatctgg ctatcttgct gacaaaagca agagaacata   5220
gcgttgcctt ggtaggtcca gcggcggagg aactctttga tccggttcct gaacaggatc   5280
tatttgaggc gctaaatgaa accttaacgc tatggaactc gccgcccgac tgggctggcg   5340
atgagcgaaa tgtagtgctt acgttgtccc gcatttggta cagcgcagta accggcaaaa   5400
tcgcgccgaa ggatgtcgct gccgactggg caatggagcg cctgccggcc cagtatcagc   5460
ccgtcatact tgaagctagg caggcttatc ttggacaaga agatcgcttg gcctcgcgcg   5520
cagatcagtt ggaagaattt gttcactacg tgaaaggcga gatcaccaaa gtagtcggca   5580
aataaagctc tagtggatct ccgtacccgg ggatctggct cgcggcggac gcacgacgcc   5640
```

-continued

```
ggggcgagac cataggcgat ctcctaaatc aatagtagct gtaacctcga agcgtttcac   5700
ttgtaacaac gattgagaat ttttgtcata aaattgaaat acttggttcg catttttgtc   5760
atccgcggtc agccgcaatt ctgacgaact gcccatttag ctggagatga ttgtacatcc   5820
ttcacgtgaa aatttctcaa gcgctgtgaa caagggttca gattttagat tgaaaggtga   5880
gccgttgaaa cacgttcttc ttgtcgatga cgacgtcgct atgcggcatc ttattattga   5940
ataccttacg atccacgcct tcaaagtgac cgcggtagcc gacagcaccc agttcacaag   6000
agtactctct tccgcgacgg tcgatgtcgt ggttgttgat ctagatttag gtcgtgaaga   6060
tgggctcgag atcgttcgta atctggcggc aaagtctgat attccaatca taattatcag   6120
tggcgaccgc cttgaggaga cggataaagt tgttgcactc gagctaggag caagtgattt   6180
tatcgctaag ccgttcagta tcagagagtt tctagcacgc attcgggttg ccttgcgcgt   6240
gcgccccaac gttgtccgct ccaaagaccg acggtctttt tgttttactg actggacact   6300
taatctcagg caacgtcgct tgatgtccga agctggcggt gaggtgaaac ttacggcagg   6360
tgagttcaat cttctcctcg cgtttttaga gaaaccccgc gacgttctat cgcgcgagca   6420
acttctcatt gccagtcgag tacgcgacga ggaggtttat gacaggagta tagatgttct   6480
cattttgagg ctgcgccgca aacttgaggc agatccgtca agccctcaac tgataaaaac   6540
agcaagaggt gccggttatt tctttgacgc ggacgtgcag gtttcgcacg gggggacgat   6600
ggcagcctga gccaattccc agatccccga ggaatcggcg tgagcggtcg caaaccatcc   6660
ggcccggtac aaatcggcgc ggcgctgggt gatgacctgg tggagaagtt gaaggccgcg   6720
caggccgccc agcggcaacg catcgaggca gaagcacgcc ccggtgaatc gtggcaagcg   6780
gccgctgatc gaatccgcaa agaatcccgg caaccgccgg cagccggtgc gccgtcgatt   6840
aggaagccgc ccaagggcga cgagcaacca gatttttcg ttccgatgct ctatgacgtg   6900
ggcacccgcg atagtcgcag catcatggac gtggccgttt tccgtctgtc gaagcgtgac   6960
cgacgagctg gcgaggtgat ccgctacgag cttccagacg ggcacgtaga ggtttccgca   7020
gggccggccg gcatggccag tgtgtgggat tacgacctgg tactgatggc ggtttcccat   7080
ctaaccgaat ccatgaaccg ataccgggaa gggaagggag acaagcccgg ccgcgtgttc   7140
cgtccacacg ttgcggacgt actcaagttc tgccggcgag ccgatggcgg aaagcagaaa   7200
gacgacctgg tagaaacctg cattcggtta aacaccacgc acgttgccat gcagcgtacg   7260
aagaaggcca agaacggccg cctggtgacg gtatccgagg gtgaagcctt gattagccgc   7320
tacaagatcg taaagagcga aaccgggcgg ccggagtaca tcgagatcga gctagctgat   7380
tggatgtacc gcgagatcac agaaggcaag aacccggacg tgctgacggt tcaccccgat   7440
tactttttga tcgatcccgg catcggccgt tttctctacc gcctggcacg ccgcgccgca   7500
ggcaaggcag aagccagatg gttgttcaag acgatctacg aacgcagtgg cagcgccgga   7560
gagttcaaga agttctgttt caccgtgcgc aagctgatcg ggtcaaatga cctgccggag   7620
tacgatttga aggaggaggc ggggcaggct ggcccgatcc tagtcatgcg ctaccgcaac   7680
ctgatcgagg gcgaagcatc cgccggttcc taatgtacgg agcagatgct agggcaaatt   7740
gccctagcag gggaaaaagg tcgaaaaggt ctctttcctg tggatagcac gtacattggg   7800
aacccaaagc cgtacattgg gaaccggaac ccgtacattg ggaacccaaa gccgtacatt   7860
gggaaccggt cacacatgta agtgactgat ataaaagaga aaaaaggcga tttttccgcc   7920
taaaactctt taaaacttat taaaactctt aaaacccgcc tggcctgtgc ataactgtct   7980
ggccagcgca cagccgaaga gctgcaaaaa gcgcctaccc ttcggtcgct gcgctcccta   8040
```

```
cgccccgccg cttcgcgtcg gcctatcgcg gccgctggcc gctcaaaaat ggctggccta   8100

cggccaggca atctaccagg gcgcggacaa gccgcgccgt cgccactcga ccgccggcgc   8160

tgaggtctgc ctcgtgaaga aggtgttgct gactcatacc aggcctgaat cgccccatca   8220

tccagccaga aagtgaggga gccacggttg atgagagctt tgttgtaggt ggaccagttg   8280

gtgattttga acttttgctt tgccacggaa cggtctgcgt tgtcgggaag atgcgtgatc   8340

tgatccttca actcagcaaa agttcgattt attcaacaaa gccgccgtcc cgtcaagtca   8400

gcgtaatgct ctgccagtgt tacaaccaat taaccaattc tgattagaaa aactcatcga   8460

gcatcaaatg aaactgcaat ttattcatat caggattatc aataccatat ttttgaaaaa   8520

gccgtttctg taatgaagga gaaaactcac cgaggcagtt ccataggatg gcaagatcct   8580

ggtatcggtc tgcgattccg actcgtccaa catcaataca acctattaat ttcccctcgt   8640

caaaaataag gttatcaagt gagaaatcac catgagtgac gactgaatcc ggtgagaatg   8700

gcaaaagctc tgcattaatg aatcggccaa cgcgcgggga gaggcggttt gcgtattggg   8760

cgctcttccg cttcctcgct cactgactcg ctgcgctcgg tcgttcggct gcggcgagcg   8820

gtatcagctc actcaaaggc ggtaatacgg ttatccacag aatcagggga taacgcagga   8880

aagaacatgt gagcaaaagg ccagcaaaag gccaggaacc gtaaaaaggc cgcgttgctg   8940

gcgtttttcc ataggctccg cccccctgac gagcatcaca aaaatcgacg ctcaagtcag   9000

aggtggcgaa acccgacagg actataaaga taccaggcgt ttccccctgg aagctccctc   9060

gtgcgctctc ctgttccgac cctgccgctt accggatacc tgtccgcctt tctcccttcg   9120

ggaagcgtgg cgctttctca tagctcacgc tgtaggtatc tcagttcggt gtaggtcgtt   9180

cgctccaagc tgggctgtgt gcacgaaccc cccgttcagc ccgaccgctg cgccttatcc   9240

ggtaactatc gtcttgagtc caacccggta agacacgact tatcgccact ggcagcagcc   9300

actggtaaca ggattagcag agcgaggtat gtaggcggtg ctacagagtt cttgaagtgg   9360

tggcctaact acggctacac tagaagaaca gtatttggta tctgcgctct gctgaagcca   9420

gttaccttcg gaaaaagagt tggtagctct tgatccggca aacaaaccac cgctggtagc   9480

ggtggttttt ttgtttgcaa gcagcagatt acgcgcagaa aaaaaggatc tcaagaagat   9540

cctttgatct tttctacggg gtctgacgct cagtggaacg aaaactcacg ttaagggatt   9600

ttggtcatga gattatcaaa aaggatcttc acctagatcc ttttgatccg g            9651
```

```
<210> SEQ ID NO 81
<211> LENGTH: 21593
<212> TYPE: DNA
<213> ORGANISM: Artificial sequence
<220> FEATURE:
<223> OTHER INFORMATION: ZmABP-948-binary

<400> SEQUENCE: 81
```

```
ttcctgtggt tggcatgcac atacaaatgg acgaacggat aaaccttttc acgccctttt     60

aaatatccga ttattctaat aaacgctctt ttctcttagg tttacccgcc aatatatcct    120

gtcaaacact gatagtttaa actgaaggcg ggaaacgaca atctgatcat gagcggagaa    180

ttaagggagt cacgttatga cccccgccga tgacgcggga caagccgttt tacgtttgga    240

actgacagaa ccgcaacgct gcaggaattg gccgcagcgg ccatttaaat caattgggcg    300

cgccagctgc ttgtggggac cagacaaaaa aggaatggtg cagaattgtt aggcgcacct    360

accaaaagca tctttgcctt tattgcaaag ataaagcaga ttcctctagt acaagtgggg    420
```

-continued

```
aacaaaataa cgtggaaaag agctgtcctg acagcccact cactaatgcg tatgacgaac    480
gcagtgacga ccacaaaact cgagactttt caacaaaggg taatatccgg aaacctcctc    540
ggattccatt gcccagctat ctgtcacttt attgtgaaga tagtggaaaa ggaaggtggc    600
tcctacaaat gccatcattg cgataaagga aaggctatcg ttgaagatgc ctctgccgac    660
agtggtccca aagatggacc cccacccacg aggagcatcg tggaaaaaga agacgttcca    720
accacgtctt caaagcaagt ggattgatgt gatatctcca ctgacgtaag ggatgacgaa    780
caatcccact atccttcggt accggaccct atagaatagc tcactatcct atttattata    840
gtttaagtat atagccaata ttttaaattt actatttatt aaattctagg gaagatagtc    900
tcaattcata actttattat aatacgtttg aaattttaaa tctttaggaa attttcttaa    960
ttcacctaga tacgattctg gagtgttaca agctgcgaat atactggtgc cattgagtat   1020
acataaatgg atttaggtgg tgctcaatag gtgaaaatga gatactaatc acttaaattt   1080
caaaatttct atggtgccac tgtactcgga taggtctatc tagggctgga caaaatgctc   1140
gtggctcgct ggctcgctcg tttcgtggtc agctcggctc ggctcggatc ggctcatttg   1200
aattttgtca cgagctgagc tgacattcta gctcggttcg ttaacgagcc agctcgcgag   1260
ctaaacgagc taccatattc tagtaaaacg aaattatatt catatcattt atagaataat   1320
tgatgaacat gttatatata tgtgagatgt ctatggccta tgaattaaac taatgattaa   1380
tgaactatgc ctatgtgtta atttggtcta tgcaaatata attatgggtt aaactgatga   1440
acatgcatgt gaattgtgaa ttaatgagtg atgaattgtg ctaatttggt gttatattga   1500
catggtttgt gaaactatga gtataattac tattttctat tgttaaatta gtttgaaatt   1560
aactaaaaaa taattattat atacatttta tttttttct gctctggctc gcgagctaaa    1620
cgagccagct cgacctcgta aacgagccga gccgagctga ctctgtggct cgttacctta   1680
acgagccgag ccgagctggc tcgttagctt aacgagccag ctcgaactcg gacgagccga   1740
gccgagctgg ctcgttatcc acccctaggt ctatctagct tctgatgttt gcaaacctta   1800
gagttggagt gttcagccag ctactccttt gctttgctga ataaccatac caaacacgcc   1860
catattaata cccgctcggc ggtggttctg caatcaaacg caggccgcag tcgcgtgcgg   1920
aactagaggt ccttcagaga agtgccgtgc cagtgccacc gccggccgca tcatcgttcc   1980
gccccccctgg tacgagcact tcgcagagct gcaacctaca tccctttac ataaatctat   2040
tgtctcgtat tgccgttgac gccggaatag tcttcgcatc ccttttacat aaatccgatg   2100
ttttctttct ccgattcctt tgaggaatca tcacgggtca gggcaggtgt tctgccgttt   2160
gccctttct ttatattctc cttagaagaa atatttagtt ggaggctgga catagccgga    2220
ggagctaact aatcgagcgg tgtactggca aaacaaaagg agcggagcaa gaaaggggag   2280
aaaaaactag ccactgccgg agcgctattg gccgtgttgg gcctggaagc ttgcatcaat   2340
acttccctcg ccccgatttg gttccaaaat catacaagtc ccaaagttgt caagatattg   2400
gaggtatgca agcgacttgg atctcaaaat agaagaaatt tcggatctga gcacaaatct   2460
gagttgaaaa aactgcaact caaaatcatc aaaaaaagaa gaagaaagaa acgaatatat   2520
tcgctcctct tctcagccga acccaaagga attgaatcca aaccctgggt aggcagacag   2580
tgagatatgg aggagagcag gaggcgaaca agagaggctg cggccacgaa tatctcacga   2640
acaagcacat catgggtcca cggagcgggc agggtgacgg gctcccgacg gcgagctaca   2700
tctcggaaga gcaccagggc agcatgtcgt gttgggcagg ttggccgtct ggcggacggc   2760
ggacggtgac tcgtggtcag ggtgcacctg ctcgattaag gcgcctgact actcatgtct   2820
```

```
tcgtctcttt gcttgtgttt gctatatgct gctcgtacct catgagcata ctaagttgac   2880
tgctcagtct gctgagtctg tttttctagg gtatagtgct gagcacaagg gatatcattg   2940
ttgggatatg attgctcgtt ggatgagggt ctcttgggat gttgtctttg atgaggctca   3000
ttctttttat tcttgtcctt ctttcgatgc tttgtcaaca tccttggttg atcccatctc   3060
ttttctatat tttctagatg cccgtgttac tattggacct gcctcacgct tggtgcgccc   3120
acgatagtag ccttagctcc ttctgacatg ttcatctctc tttcggtgcc ttcctttgtg   3180
gtgccttcta tagtgttttc tttggagcct gctgctttag cccctgacta cgctatgaac   3240
acttgtctac acccgccggg tcatcaattc ttttggtaca ccatcatcct ctcatgcgtt   3300
gccctcttat gatgtgcgct cttctgcaac tcattcattt tcttgcgatt tacctttgac   3360
tgatgctccc tattcatctc tggatccagc ttcctcagtt gactctttgc tggagccacc   3420
tcttagacgg agtcatcgtt ttcgtcagcc acctaatggg tactctcctt caggtttagt   3480
cgctaccgtt ctttctgagc tgacttctta tcatgatgct attcttcatc tgtaacgaca   3540
acatgcgatt tctgaggaga ttgctactct tgagcgcact agcacgttgg aacttgttcc   3600
ttgtccatca cgtgtttgtc ctatcaccag tatgtgggtc tataaggtca agacccgttc   3660
tgatggttct cttgatcgct ataaatctcg tctagttgcc caaggcttcc agtaggaaca   3720
tggttgtggc tatgatgaga tttttgcacc tgttgctcat atgaccactg ttcgcactct   3780
tcttgctatg gcctctgttc gtgcgtggtc catctctcat cttgatgtca agaatacctt   3840
tcttgatggt aagctacttg agttctatat gtagccatcg cctaggtatt ctatttctgc   3900
ttgtatggtt tgttgtcttc gccgttcccc ttatggcctc aagcaggctc cacattcttg   3960
gtttcagctc tttgcttcta tgataactgt tgttggtttt tctaccagta atcatggtcc   4020
tgcactcttt gtgtactacc tcctctcggg gtcggactct tctttatgtt gatgatataa   4080
ttatcactgg agataacctt gagtatgttg actttgttaa ggcacgtctt agttatcatt   4140
ttctcatgtc tgatcttggt cctctgtgtt actttcttgg gacaaaggtt tcttctttgt   4200
ctcagggcct ttatctatct caagaggagt acattcaaga ttttcttcat cgggcttctc   4260
ttaccgatca ctagattgtt gagactccca agcagctcaa tcttcacctt agtgccgatg   4320
atggcgagtc ttttcccgac catactcgtt atcgtcaaca tactgtagga agttttgttt   4380
atctctgtgt cactcgtctt gacatttcat atgttgtgtg tatcctgagt tagtttgctt   4440
cagatcccat ccaggtacac tatagtcact tgctttgtgt cctacaatat ctttgtggaa   4500
ccatatctag atgtatgttc tttccacatt ctagctcgtt gcaactgcaa tcttgttctg   4560
atgctacttg ggctagtgat tttttcgata gttggtctct ttctcaatat tgtgtttttc   4620
ttggtggttc tctcattgct cggaagacta agtagcaggt agcagtttct cgtttgagta   4680
ccgaggctga gttgcgtgct atggcccttg tgactgcaga ggttacttgg ttacgatagt   4740
tgcttgagga ttttcatgtt tctgtttcca tgacgactcc ttttgtctga cagtacaggt   4800
gttatcagta ttgctcgtga tgcggtgaag catgaggtca ccaagcatat tggagttgat   4860
gtttcgtata cacgagctga agtctaggat gatgttatct tgatttggta tgtgccttta   4920
gagcttcagt tggctaattt cttcacgagg gcacaggctc gcgctgagca taaatttttc   4980
ctctcaaaac tcagtgttat agatccacct tgagtttgag ggagtattag atagatatgg   5040
gtttatttgt atttttccat tttataaggg tattagatag ataggcaacg actgctatgc   5100
aagtagtcat tctgtgcaag cgtgcaagca aaccatctga tccattatat cgtgatccaa   5160
```

-continued

```
ccgtgggtca catttaacac ttaaaccctt ccaccaccaa ctcaataatc tttataaaaa   5220
aacccctaac aaacaatggt tatatctgtg gttggatcgt aatctaatag atcagatggt   5280
ttgcttgtac gcttgcacag aatgactgct tgcatagcag ttgttgccta gatagatatg   5340
ggtttatttg tatttttctc ttaagggttt ttgtgtatat ttgtactcat gtacctatat   5400
atttgtgcta gttgacccca taatgaatag acctgctatt cataatattt gcaaaccatg   5460
aaaatttgat tattacgaac tatccaaata ctcgaacaca tgggcattat agctcacaaa   5520
aatggaaggt tgagctgctg cttgaagaac ctcaacatct ttgaacaaca acctcaacga   5580
aacttgtata tgaaccaact tccaaacaat cccttgtgga aggatagtaa tgacttcagg   5640
gcattgatca cacatatccg acggtggaac tactgtaaca accctctttt ctgtggaata   5700
tagttgaaac tctacaactt gaccaaaacc aagatgacga catatggtgg aactaacaaa   5760
acaagaggac tacactacct cattagctta ttaagcacaa tctcttggca ccacaacaac   5820
gaacaacaaa accatcattt ggatgctctg tgggcgacta aatgcaaatt ctttgcatgg   5880
ttgatcatcc caaattggtg gcacttagct ataggctagc agtgagagga tggccgaaca   5940
acatgcattg tccactatgt tggtgtagcc atgagaccaa ccaccacata aatgccaaac   6000
gttcattcac caaaaaaatc taggcaacaa tggcttggat ttcttacctg cagctccacc   6060
aagctaactg gagttcaatt aggtcaacgt atgggtggtg gtcgagtata gcagtcacaa   6120
atgatgttct aaagatgggg ttgtgttaac acatcttgct tgtagcacga gaacactgga   6180
aggagtgaaa ccaaagaatc tttcaacaca aggacctatc aacgctatcc atgattggga   6240
aattcaagga cgaaactaga atttgggtga acacatgcac aaggcaccta ggagagcctt   6300
tcttttgtac tgttaatccc tttttaaact ctctctgtcc ttaggagttc gtttcttccg   6360
ctctattcaa tgaagttagg cacaatcttg tgtgatttca ttagaaaaac acaagtaaat   6420
tgcatggtca gtacttgaag tattacagga atctcgtctg cccccaaact attaaacctt   6480
atatttggct ccctaatgta cttaactgat ctcattctgg tcaaactaaa catggtgatg   6540
gcaaggagcc gatatggtcg cccatgtgga tgtgatttaa gcaaaaaatc tcatggtcca   6600
tagctgtgtc aacaagccaa catgccatcg cttccttatg ccgagactgc ccatgtcgct   6660
cgcttttact gtcatcatca tcaaactgcc tgtcatgtct acggatgcca tgaccgctgt   6720
cacacatgat gtggagatga acctgtccat caacttccac gtgctgccac tatcgctagc   6780
tgacaccgtc ttggtcattg ctgtgtaggg ctaggctaag agtcgctgaa tgatcctttc   6840
gctctccttt acaggaacat gctgtttact ttgtgtcgcc aaggcgtgct agagtacctc   6900
ttctacacct ccagcaccag tagccttatt gttagcttgc acatcccaca taagcaggcc   6960
gatgtgaatg ataacttcag ggacgtcgac ggcatgtcac tgccaagagt catttggtgg   7020
gaagcgttgt catgccatct gtcgtgccat tttgtcctca gttcgaccgc cattaccgtg   7080
agcacaacct ttgcgcatgg ttggccgctt ccatcaccct tattccgttt cctcgtgttg   7140
gtcttgcccc aaggctatgg ttagcagacc gtgcatatgg ccggcaaaag actattttgc   7200
actgtagatt gcactcttta tatagtgaag tttaaaatag gagatgagat gaataaggct   7260
gctggagata gcctaaaccc ttgcagctcg tgcttgcatc gggggagcca aaaggcgtcc   7320
acctccacca tcgccgaagc actgagcact actctggctt gtgtttcagc accacaccgc   7380
agagtgctta gggccaccaa cctcctcttg cctctgtgcc cagagcacca tcagctctgc   7440
tgcctccctc tgttccttgt gcttgctagg caggcaattc cgagctgggg cccaacttgt   7500
aacgctgatt tcaccatctt gccactgccg ggcaccaagt ggacacattt gacttggcct   7560
```

-continued

```
agtgggtttt ctgcataaat cacatacatg tggatgccat atcaggctct ttggtgttgt   7620
cgtgtctact ttcgacaagg atgagatcac ttaaacatat tagggagcca agtatgtaat   7680
ttcatagttt agggacctac acaaaaatcg tataatactt tagaacagcc gtgcagttta   7740
ctcaatcaac acatacaaag tcagatctta agctctgata cttcaaagga atggttgagc   7800
ccagttgaca aacaatcttg cttcattcat tgaattgttt ataggagtgg ctatgtaact   7860
actgggtggt tttgtttgac ctgtcatcca aattgtgtag tcaaccataa acatacacgt   7920
cacacaatac attttggatg tgacagatag gatttaggcg agagaatgta caatgtcact   7980
gaaaaattac cactgtatgg aaaggacaat ctaagtgaaa agagaaccag ggcctaatgg   8040
tttcaggact tcaaactccg gccaaatgaa tttacagtgc ttaaattaac tcatgttaat   8100
catgatagcc aaagcatggg caaaagagaa actatgaata aatcgacaat gtattctata   8160
tagcagtaat ataccatgtc acgagctttt acactaatgg gctgtatttt tctgcagtta   8220
ttttaactgg caatattcta tgtcacagta atatttgtta aattttttcc agaatagcaa   8280
ctgaactaga agtctagtat ttcttaattg gataacaaaa ggaattagtg tgcatttggc   8340
ttacgaacaa tcagtcaccc aacattgaat ttgaagttct gtttcctctt tgttcagacg   8400
acactctcca aatgaatgcc ttatattttg tgttgctcct cttttctgca gagtgttcag   8460
taacttcttc cgatgtaaac catggtacgt cctgtagaaa ccccaacccg tgaaatcaaa   8520
aaactcgacg gcctgtgggc attcagtctg gatcgcgaaa actgtggaat tgatcagcgt   8580
tggtgggaaa gcgcgttaca agaaagccgg gcaattgctg tgccaggcag ttttaacgat   8640
cagttcgccg atgcagatat tcgtaattat gcgggcaacg tctggtatca gcgcgaagtc   8700
tttataccga aaggttgggc aggccagcgt atcgtgctgc gtttcgatgc ggtcactcat   8760
tacggcaaag tgtgggtcaa taatcaggaa gtgatggagc atcagggcgg ctatacgcca   8820
tttgaagccg atgtcacgcc gtatgttatt gccgggaaaa gtgtacgtat caccgtttgt   8880
gtgaacaacg aactgaactg gcagactatc ccgccgggaa tggtgattac cgacgaaaac   8940
ggcaagaaaa agcagtctta cttccatgat ttctttaact atgccggaat ccatcgcagc   9000
gtaatgctct acaccacgcc gaacacctgg gtggacgata tcaccgtggt gacgcatgtc   9060
gcgcaagact gtaaccacgc gtctgttgac tggcaggtac caagctgcga atcttcgttt   9120
ttttaaggaa ttctcgatct ttatggtgta taggctctgg gttttctgtt ttttgtatct   9180
cttaggattt tgtaaattcc agatctttct atggccactt agtagtatat ttcaaaaatt   9240
ctccaatcga gttcttcatt cgcattttca gtcattttct cttcgacgtt gtttttaagc   9300
ctgggtatta ctcctattta gttgaactct gcagcaatct tagaaaatta gggttttgag   9360
gtttcgattt ctctaggtaa ccgatctatt gcattcatct gaatttctgc atatatgtct   9420
tagatttctg ataagcttac gatacgttag gtgtaattga agtttatttt tcaagagtgt   9480
tattttttgt ttctgaattt ttcaggtggt ggccaatggt gatgtcagcg ttgaactgcg   9540
tgatgcggat caacaggtgg ttgcaactgg acaaggcact agcgggactt tgcaagtggt   9600
gaatccgcac ctctggcaac cgggtgaagg ttatctctat gaactgtgcg tcacagccaa   9660
aagccagaca gagtgtgata tctacccgct tcgcgtcggc atccggtcag tggcagtgaa   9720
gggcgaacag ttcctgatta accacaaacc gttctacttt actggctttg gtcgtcatga   9780
agatgcggac ttgcgtggca aaggattcga taacgtgctg atggtgcacg accacgcatt   9840
aatggactgg attggggcca actcctaccg tacctcgcat tacccttacg ctgaagagat   9900
```

-continued

```
gctcgactgg gcagatgaac atggcatcgt ggtgattgat gaaactgctg ctgtcggctt   9960
taacctctct ttaggcattg gtttcgaagc gggcaacaag ccgaaagaac tgtacagcga  10020
agaggcagtc aacggggaaa ctcagcaagc gcacttacag gcgattaaag agctgatagc  10080
gcgtgacaaa aaccacccaa gcgtggtgat gtggagtatt gccaacgaac cggatacccg  10140
tccgcaaggt gcacgggaat atttcgcgcc actggcggaa gcaacgcgta aactcgaccc  10200
gacgcgtccg atcacctgcg tcaatgtaat gttctgcgac gctcacaccg ataccatcag  10260
cgatctcttt gatgtgctgt gcctgaaccg ttattacgga tggtatgtcc aaagcggcga  10320
tttggaaacg gcagagaagg tactggaaaa agaacttctg gcctggcagg agaaactgca  10380
tcagccgatt atcatcaccg aatacggcgt ggatacgtta gccgggctgc actcaatgta  10440
caccgacatg tggagtgaag agtatcagtg tgcatggctg gatatgtatc accgcgtctt  10500
tgatcgcgtc agcgccgtcg tcggtgaaca ggtatggaat ttcgccgatt ttgcgacctc  10560
gcaaggcata ttgcgcgttg gcggtaacaa gaaagggatc ttcactcgcg accgcaaacc  10620
gaagtcggcg gcttttctgc tgcaaaaacg ctggactggc atgaacttcg gtgaaaaacc  10680
gcagcaggga ggcaaacaat gagagctcga ggtacaaatc tcatctgtgc cttgctctag  10740
tttcccaaat ggaattaact atgcatgatt tgtttggaaa ctcttattgc atccatccag  10800
ataatgcatc caccataagg taatatcttg atgacatctg tgcctgatgg tgtaccaaat  10860
gtctctatct ctgcattgag ccacgagtag gaggatagcc taggggtgcc ttgactccaa  10920
agttgtattg aaaaagatgg atgaagcagg caaatgctgc ctgaatccat gactcagggc  10980
acagattttc cactcaaagg aagataagat tgcattactt catgatcttt tgaactgcct  11040
ctgcaagacg ggactcggat agtggatgca aagatctaat actggcctca ggcaacgagt  11100
tgtttcactc gaaagtctag aaatgaccgg gctcaaattt tgcaccccaa ggaaagtgag  11160
tttgcattac ttcatgacct tttgaactgc ctctgcaaga ctggactcag attacgcttg  11220
attggttgcc ggcctcacct tcgcctggct tgcgcgagcc tgcgtctata gaaatgcgcc  11280
ggactcacgt ctccgtcgat gcaggcattc gactgaaaaa acatttaaac tgcacccatg  11340
cgtgcgggct gagcttatgt catacaagta accaatcaca ggcttaagtt cagtcaacgc  11400
atgcgctaag cttggatgtg gctgaccggg caaccaatca cacagatagt ggatgcacgg  11460
atctaatatt ggctaatttg gttaaacttg tctaacctta gacgtggcaa gtgagtcagc  11520
ggatcaaatc tgctctaaaa ttgtctgcct cctagatgtc cttggtgttc caagatttaa  11580
tcatcactgc actatttctt tgcgttgctt cgctgcagct tcgcgttact tgcattcgct  11640
taatcaggat tactttgatc aactaggttt ctaacttcta ctaccttcac ttgcacaggg  11700
tgcccgtcct gctagccggt gtgcttgctg tgcgatcgtt tggcatgtgc ttgttgaggg  11760
gttgctaggg gattggagag gattgaaggg attaaatctc ctcctattca attttgaata  11820
ggaggggatt taatcccctt caatccccct caaaccacta gtaaccgaac gtggcctgag  11880
ggggcgggcg agtctttata ttgaatgaaa ctacataaaa tagcatgccg tctctgtcac  11940
tggcaatgga cggtggtgcc tagcgcaact cagcgcacaa ctgtgtgtct tgatttttct  12000
tctgtttatc acggcattag tgccatgccg ttttatgtta cagtgttgtg tgctcgcaag  12060
catccgaaaa tatgcgtctg agtttagggt tgggtcaaac ttgtcgaatt tggggttctg  12120
ttataatatg ttgagcatga ataaagatgg atgctggtga ctctgtcgcc atcgccgtcc  12180
atcatgagtg tcctgtaatt caacttatat ctatcatgta tgtatgtatg tatgtatgta  12240
tgtatgtata tgctgtctac tatgcttctt tgttttaact gaaatgtgtg ttacagtgtt  12300
```

-continued

```
acttctctgg ggtccattta aaacggcatt tcgtttacga taggaaccag ccattataat  12360
ctttaaccaa taatttcgct aaccaatttc aactattgca atgcgaactt aatattatca  12420
gatttataac cgaatgcgct atcaaataat cataaggttg taatcataat aatataatat  12480
aaaataaatg agtgctcgaa gtgaaatttt agagagcgtt ataagaaaaa ttgatgtgat  12540
ctccaagaat aatagcccct cccggctccc ggtacaaaca tagggcttct ttagaatgca  12600
ggattgtgag aacataggaa taggaaaaat ataggaattc tataggaatg tatatggaaa  12660
acagaggatt gaaaaacaca gaaaaaatgt gaaagcaagt ctttggatga agcgtaggaa  12720
acttatagga ataggaattc ataacggacc gcgatcgctt aattaagctt gcatgcctgc  12780
agtgcagcgt gacccggtcg tgcccctctc tagagataat gagcattgca tgtctaagtt  12840
ataaaaaatt accacatatt ttttttgtca cacttgtttg aagtgcagtt tatctatctt  12900
tatacatata tttaaacttt actctacgaa taatataatc tatagtacta caataatatc  12960
agtgttttag agaatcatat aaatgaacag ttagacatgg tctaaaggac aattgagtat  13020
tttgacaaca ggactctaca gttttatctt tttagtgtgc atgtgttctc cttttttttt  13080
gcaaatagct tcacctatat aatacttcat ccattttatt agtacatcca tttagggttt  13140
agggttaatg gtttttatag actaattttt ttagtacatc tattttattc tattttagcc  13200
tctaaattaa gaaaactaaa actctatttt agttttttta tttaataatt tagatataaa  13260
atagaataaa ataaagtgac taaaaattaa acaaataccc tttaagaaat taaaaaaact  13320
aaggaaacat ttttcttgtt tcgagtagat aatgccagcc tgttaaacgc cgtcgacgag  13380
tctaacggac accaaccagc gaaccagcag cgtcgcgtcg ggccaagcga agcagacggc  13440
acggcatctc tgtcgctgcc tctggacccc tctcgagagt tccgctccac cgttggactt  13500
gctccgctgt cggcatccag aaattgcgtg gcggagcggc agacgtgagc cggcacggca  13560
ggcggcctcc tcctcctctc acggcaccgg cagctacggg ggattccttt cccaccgctc  13620
cttcgctttc ccttcctcgc ccgccgtaat aaatagacac cccctccaca ccctctttcc  13680
ccaacctcgt gttgttcgga gcgcacacac acacaaccag atctccccca aatccacccg  13740
tcggcacctc cgcttcaagg tacgccgctc gtcctccccc ccccccccctc tctaccttct  13800
ctagatcggc gttccggtcc atggttaggg cccggtagtt ctacttctgt tcatgtttgt  13860
gttagatccg tgtttgtgtt agatccgtgc tgctagcgtt cgtacacgga tgcgacctgt  13920
acgtcagaca cgttctgatt gctaacttgc cagtgtttct ctttggggaa tcctgggatg  13980
gctctagccg ttccgcagac gggatcgatt tcatgatttt ttttgtttcg ttgcataggg  14040
tttggtttgc ccttttcctt tatttcaata tatgccgtgc acttgtttgt cgggtcatct  14100
tttcatgctt ttttttgtct tggttgtgat gatgtggtct ggttgggcgg tcgttctaga  14160
tcggagtaga attctgtttc aaactacctg gtggatttat taattttgga tctgtatgtg  14220
tgtgccatac atattcatag ttacgaattg aagatgatgg atggaaatat cgatctagga  14280
taggtataca tgttgatgcg ggttttactg atgcatatac agagatgctt tttgttcgct  14340
tggttgtgat gatgtggtgt ggttgggcgg tcgttcattc gttctagatc ggagtagaat  14400
actgtttcaa actacctggt gtatttatta attttggaac tgtatgtgtg tgtcatacat  14460
cttcatagtt acgagtttaa gatggatgga aatatcgatc taggataggt atacatgttg  14520
atgtgggttt tactgatgca tatacatgat ggcatatgca gcatctattc atatgctcta  14580
accttgagta cctatctatt ataataaaca agtatgtttt ataattattt tgatcttgat  14640
```

-continued

```
atacttggat gatggcatat gcagcagcta tatgtggatt tttttagccc tgccttcata  14700
cgctatttat ttgcttggta ctgtttcttt tgtcgatgct caccctgttg tttggtgtta  14760
cttctgcagg gatccccgat catgcaaaaa ctcattaact cagtgcaaaa ctatgcctgg  14820
ggcagcaaaa cggcgttgac tgaactttat ggtatggaaa atccgtccag ccagccgatg  14880
gccgagctgt ggatgggcgc acatccgaaa agcagttcac gagtgcagaa tgccgccgga  14940
gatatcgttt cactgcgtga tgtgattgag agtgataaat cgactctgct cggagaggcc  15000
gttgccaaac gctttggcga actgcctttc ctgttcaaag tattatgcgc agcacagcca  15060
ctctccattc aggttcatcc aaacaaacac aattctgaaa tcggttttgc caaagaaaat  15120
gccgcaggta tcccgatgga tgccgccgag cgtaactata aagatcctaa ccacaagccg  15180
gagctggttt ttgcgctgac gcctttcctt gcgatgaacg cgtttcgtga attttccgag  15240
attgtctccc tactccagcc ggtcgcaggt gcacatccgg cgattgctca ctttttacaa  15300
cagcctgatg ccgaacgttt aagcgaactg ttcgccagcc tgttgaatat gcagggtgaa  15360
gaaaaatccc gcgcgctggc gattttaaaa tcggccctcg atagccagca gggtgaaccg  15420
tggcaaacga ttcgtttaat ttctgaattt tacccggaag acagcggtct gttctccccg  15480
ctattgctga atgtggtgaa attgaaccct ggcgaagcga tgttcctgtt cgctgaaaca  15540
ccgcacgctt acctgcaagg cgtggcgctg gaagtgatgg caaactccga taacgtgctg  15600
cgtgcgggtc tgacgcctaa atacattgat attccggaac tggttgccaa tgtgaaattc  15660
gaagccaaac cggctaacca gttgttgacc cagccggtga aacaaggtgc agaactggac  15720
ttcccgattc cagtggatga ttttgccttc tcgctgcatg accttagtga taaagaaacc  15780
accattagcc agcagagtgc cgccattttg ttctgcgtcg aaggcgatgc aacgttgtgg  15840
aaaggttctc agcagttaca gcttaaaccg ggtgaatcag cgtttattgc cgccaacgaa  15900
tcaccggtga ctgtcaaagg ccacggccgt ttagcgcgtg tttacaacaa gctgtaagag  15960
cttactgaaa aaattaacat ctcttgctaa gctgggagct cgatccgtcg acctgcagat  16020
cgttcaaaca tttggcaata aagtttctta agattgaatc ctgttgccgg tcttgcgatg  16080
attatcatat aatttctgtt gaattacgtt aagcatgtaa taattaacat gtaatgcatg  16140
acgttattta tgagatgggt ttttatgatt agagtcccgc aattatacat ttaatacgcg  16200
atagaaaaca aaatatagcg cgcaaactag gataaattat cgcgcgcggt gtcatctatg  16260
ttactagatc tgctagccct gcaggaaatt taccggtgcc cgggcggcca gcatggccgt  16320
atccgcaatg tgttattaag ttgtctaagc gtcaatttgt ttacaccaca atatatcctg  16380
ccaccagcca gccaacagct ccccgaccgg cagctcggca caaaatcacc actcgataca  16440
ggcagcccat cagaattaat tctcatgttt gacagcttat catcgactgc acggtgcacc  16500
aatgcttctg gcgtcaggca gccatcggaa gctgtggtat ggctgtgcag gtcgtaaatc  16560
actgcataat tcgtgtcgct caaggcgcac tcccgttctg gataatgttt tttgcgccga  16620
catcataacg gttctggcaa atattctgaa atgagctgtt gacaattaat catccggctc  16680
gtataatgtg tggaattgtg agcggataac aatttcacac aggaaacaga ccatgaggga  16740
agcgttgatc gccgaagtat cgactcaact atcagaggta gttggcgtca tcgagcgcca  16800
tctcgaaccg acgttgctgg ccgtacattt gtacggctcc gcagtggatg gcggcctgaa  16860
gccacacagt gatattgatt tgctggttac ggtgaccgta aggcttgatg aaacaacgcg  16920
gcgagctttg atcaacgacc ttttggaaac ttcggcttcc cctggagaga gcgagattct  16980
ccgcgctgta gaagtcacca ttgttgtgca cgacgacatc attccgtggc gttatccagc  17040
```

```
taagcgcgaa ctgcaatttg gagaatggca gcgcaatgac attcttgcag gtatcttcga  17100
gccagccacg atcgacattg atctggctat cttgctgaca aaagcaagag aacatagcgt  17160
tgccttggta ggtccagcgg cggaggaact ctttgatccg gttcctgaac aggatctatt  17220
tgaggcgcta aatgaaacct taacgctatg gaactcgccg cccgactggg ctggcgatga  17280
gcgaaatgta gtgcttacgt tgtcccgcat ttggtacagc gcagtaaccg gcaaaatcgc  17340
gccgaaggat gtcgctgccg actgggcaat ggagcgcctg ccggcccagt atcagcccgt  17400
catacttgaa gctaggcagg cttatcttgg acaagaagat cgcttggcct cgcgcgcaga  17460
tcagttggaa gaatttgttc actacgtgaa aggcgagatc accaaagtag tcggcaaata  17520
aagctctagt ggatctccgt acccggggat ctggctcgcg gcggacgcac gacgccgggg  17580
cgagaccata ggcgatctcc taaatcaata gtagctgtaa cctcgaagcg tttcacttgt  17640
aacaacgatt gagaattttt gtcataaaat tgaaatactt ggttcgcatt tttgtcatcc  17700
gcggtcagcc gcaattctga cgaactgccc atttagctgg agatgattgt acatccttca  17760
cgtgaaaatt tctcaagcgc tgtgaacaag ggttcagatt ttagattgaa aggtgagccg  17820
ttgaaacacg ttcttcttgt cgatgacgac gtcgctatgc ggcatcttat tattgaatac  17880
cttacgatcc acgccttcaa agtgaccgcg gtagccgaca gcacccagtt cacaagagta  17940
ctctcttccg cgacggtcga tgtcgtggtt gttgatctag atttaggtcg tgaagatggg  18000
ctcgagatcg ttcgtaatct ggcggcaaag tctgatattc caatcataat tatcagtggc  18060
gaccgccttg aggagacgga taaagttgtt gcactcgagc taggagcaag tgattttatc  18120
gctaagccgt tcagtatcag agagtttcta gcacgcattc gggttgcctt gcgcgtgcgc  18180
cccaacgttg tccgctccaa agaccgacgg tctttttgtt ttactgactg gacacttaat  18240
ctcaggcaac gtcgcttgat gtccgaagct ggcggtgagg tgaaacttac ggcaggtgag  18300
ttcaatcttc tcctcgcgtt tttagagaaa ccccgcgacg ttctatcgcg cgagcaactt  18360
ctcattgcca gtcgagtacg cgacgaggag gtttatgaca ggagtataga tgttctcatt  18420
ttgaggctgc gccgcaaact tgaggcagat ccgtcaagcc ctcaactgat aaaaacagca  18480
agaggtgccg gttatttctt tgacgcggac gtgcaggttt cgcacggggg gacgatggca  18540
gcctgagcca attcccagat ccccgaggaa tcggcgtgag cggtcgcaaa ccatccggcc  18600
cggtacaaat cggcgcggcg ctgggtgatg acctggtgga gaagttgaag gccgcgcagg  18660
ccgcccagcg gcaacgcatc gaggcagaag cacgccccgg tgaatcgtgg caagcggccg  18720
ctgatcgaat ccgcaaagaa tcccggcaac cgccggcagc cggtgcgccg tcgattagga  18780
agccgcccaa gggcgacgag caaccagatt ttttcgttcc gatgctctat gacgtgggca  18840
cccgcgatag tcgcagcatc atggacgtgg ccgttttccg tctgtcgaag cgtgaccgac  18900
gagctggcga ggtgatccgc tacgagcttc cagacgggca cgtagaggtt tccgcagggc  18960
cggccggcat ggccagtgtg tgggattacg acctggtact gatggcggtt tcccatctaa  19020
ccgaatccat gaaccgatac cgggaaggga agggagacaa gcccggccgc gtgttccgtc  19080
cacacgttgc ggacgtactc aagttctgcc ggcgagccga tggcggaaag cagaaagacg  19140
acctggtaga aacctgcatt cggttaaaca ccacgcacgt tgccatgcag cgtacgaaga  19200
aggccaagaa cggccgcctg gtgacggtat ccgagggtga agccttgatt agccgctaca  19260
agatcgtaaa gagcgaaacc gggcggccgg agtacatcga gatcgagcta gctgattgga  19320
tgtaccgcga gatcacagaa ggcaagaacc cggacgtgct gacggttcac cccgattact  19380
```

-continued

```
ttttgatcga tcccggcatc ggccgttttc tctaccgcct ggcacgccgc gccgcaggca  19440
aggcagaagc cagatggttg ttcaagacga tctacgaacg cagtggcagc gccggagagt  19500
tcaagaagtt ctgtttcacc gtgcgcaagc tgatcgggtc aaatgacctg ccggagtacg  19560
atttgaagga ggaggcgggg caggctggcc cgatcctagt catgcgctac cgcaacctga  19620
tcgagggcga agcatccgcc ggttcctaat gtacggagca gatgctaggg caaattgccc  19680
tagcagggga aaaaggtcga aaaggtctct ttcctgtgga tagcacgtac attgggaacc  19740
caaagccgta cattgggaac cggaacccgt acattgggaa cccaaagccg tacattggga  19800
accggtcaca catgtaagtg actgatataa aagagaaaaa aggcgatttt tccgcctaaa  19860
actctttaaa acttattaaa actcttaaaa cccgcctggc ctgtgcataa ctgtctggcc  19920
agcgcacagc cgaagagctg caaaaagcgc ctacccttcg gtcgctgcgc tccctacgcc  19980
ccgccgcttc gcgtcggcct atcgcggccg ctggccgctc aaaaatggct ggcctacggc  20040
caggcaatct accagggcgc ggacaagccg cgccgtcgcc actcgaccgc cggcgctgag  20100
gtctgcctcg tgaagaaggt gttgctgact cataccaggc ctgaatcgcc ccatcatcca  20160
gccagaaagt gagggagcca cggttgatga gagctttgtt gtaggtggac cagttggtga  20220
ttttgaactt ttgctttgcc acggaacggt ctgcgttgtc gggaagatgc gtgatctgat  20280
ccttcaactc agcaaaagtt cgatttattc aacaaagccg ccgtcccgtc aagtcagcgt  20340
aatgctctgc cagtgttaca accaattaac caattctgat tagaaaaact catcgagcat  20400
caaatgaaac tgcaatttat tcatatcagg attatcaata ccatattttt gaaaaagccg  20460
tttctgtaat gaaggagaaa actcaccgag gcagttccat aggatggcaa gatcctggta  20520
tcggtctgcg attccgactc gtccaacatc aatacaacct attaatttcc cctcgtcaaa  20580
aataaggtta tcaagtgaga aatcaccatg agtgacgact gaatccggtg agaatggcaa  20640
aagctctgca ttaatgaatc ggccaacgcg cggggagagg cggtttgcgt attgggcgct  20700
cttccgcttc ctcgctcact gactcgctgc gctcggtcgt tcggctgcgg cgagcggtat  20760
cagctcactc aaaggcggta atacggttat ccacagaatc aggggataac gcaggaaaga  20820
acatgtgagc aaaaggccag caaaaggcca ggaaccgtaa aaaggccgcg ttgctggcgt  20880
ttttccatag gctccgcccc cctgacgagc atcacaaaaa tcgacgctca agtcagaggt  20940
ggcgaaaccc gacaggacta taaagatacc aggcgtttcc ccctggaagc tccctcgtgc  21000
gctctcctgt tccgaccctg ccgcttaccg gatacctgtc cgcctttctc ccttcgggaa  21060
gcgtggcgct ttctcatagc tcacgctgta ggtatctcag ttcggtgtag gtcgttcgct  21120
ccaagctggg ctgtgtgcac gaaccccccg ttcagcccga ccgctgcgcc ttatccggta  21180
actatcgtct tgagtccaac ccggtaagac acgacttatc gccactggca gcagccactg  21240
gtaacaggat tagcagagcg aggtatgtag gcggtgctac agagttcttg aagtggtggc  21300
ctaactacgg ctacactaga agaacagtat ttggtatctg cgctctgctg aagccagtta  21360
ccttcggaaa aagagttggt agctcttgat ccggcaaaca aaccaccgct ggtagcggtg  21420
gtttttttgt ttgcaagcag cagattacgc gcagaaaaaa aggatctcaa gaagatcctt  21480
tgatcttttc tacggggtct gacgctcagt ggaacgaaaa ctcacgttaa gggattttgg  21540
tcatgagatt atcaaaaagg atcttcacct agatcctttt gatccggaat taa         21593
```

<210> SEQ ID NO 82
<211> LENGTH: 15097
<212> TYPE: DNA
<213> ORGANISM: Artificial sequence
<220> FEATURE:
<223> OTHER INFORMATION: ZmABT-990-binary

<400> SEQUENCE: 82
attcctgtgg ttggcatgca catacaaatg gacgaacgga taaacctttt cacgcccttt 60
taaatatccg attattctaa taaacgctct tttctcttag gtttacccgc caatatatcc 120
tgtcaaacac tgatagttta aactgaaggc gggaaacgac aatctgatca tgagcggaga 180
attaagggag tcacgttatg acccccgccg atgacgcggg acaagccgtt ttacgtttgg 240
aactgacaga accgcaacgc tgcaggaatt ggccgcagcg gccatttaaa tcaattgggc 300
gcgccagctg cttgtgggga ccagacaaaa aaggaatggt gcagaattgt taggcgcacc 360
taccaaaagc atctttgcct ttattgcaaa gataaagcag attcctctag tacaagtggg 420
gaacaaaata acgtggaaaa gagctgtcct gacagcccac tcactaatgc gtatgacgaa 480
cgcagtgacg accacaaaac tcgagacttt tcaacaaagg gtaatatccg gaaacctcct 540
cggattccat tgcccagcta tctgtcactt tattgtgaag atagtggaaa aggaaggtgg 600
ctcctacaaa tgccatcatt gcgataaagg aaaggctatc gttgaagatg cctctgccga 660
cagtggtccc aaagatggac ccccacccac gaggagcatc gtggaaaaag aagacgttcc 720
aaccacgtct tcaaagcaag tggattgatg tgatatctcc actgacgtaa gggatgacga 780
acaatcccac tatccttcgg taccggaccc ggtctgagtt gttaggtgaa ttttactact 840
atccagcgac aactaaaaaa gaaacagagt gagtactaag gaagactata tattttgtat 900
attaacgaga agagatagtt agttacagca catccattgg agcgccggcc aaagcagata 960
tatagtgtcg ttacgtttgt aatcatagtt ctggtttttc tactatgtat aattaaacat 1020
aatgcaacct tcttaagacg gatgtatcaa ttcgatgggc tcattccctt cttttttta 1080
tttatcgcaa tttagtttaa aaaagatcta gcggacgata aatatttaag aatgaagata 1140
gtaattatct tcagtcaata caatagtttc tcaacaatat ataatatata tttgcgcgcc 1200
tgtggggtgt gtgtttttac aacacaaaca accgacaggg aattctaacg caaatgcttc 1260
cgtttgtact tgattatcaa gacataaaga cgaagatggt tacgttacga tgcttctagt 1320
tggcatctgc acataacatg catgcatgcg ccgggtttaa tgcataatgc tgtgtacata 1380
cattatttgc agcacacacg cgtattgctc atgtgacgtg ccgcctgtct gtctatcctt 1440
gaccggcact tggtaccaac cattatgttc gttgtattgc gagctagcta gctgcctgta 1500
ctatataact gcagaaaggt acactacaga atgcagatgc tgcgccactg gttcgcatac 1560
actattctat tccactggcc acctataaac atatgcatga caattgacaa acaagctagc 1620
gtctctagaa agttggtgcc ggccatagca attattcccg actggagtga agaaaagaaa 1680
ctaccatttc catgtgggtt tcctttgcat atcatagaat caagatgtaa atatctatga 1740
gataccatta tagaattttg ctgacgtggc tgcattgtat gatatagtgt tgcggacagc 1800
ctcagcagcc agctggagct gacaggggag ttcaaaagaa acacacgtac accaaccagc 1860
tagtatctcc tcaacgacat cggctaaatt atcttgtcgg tatgcatact tttcttcgcg 1920
cgcgggggc ctttcattag atgcttgcac ataaaactgc gctagctgat gctgaatctc 1980
agcctaacat atatactcct atatatatat attctcttgt attttatgcc aattaatgta 2040
acgcaattca gatgtgctgg ctggtcaaca cactgtgtgc atatgctggc tttcggagac 2100
taaacctgga ccaagtttgg cgcccgattt ggatggtttc tggtccccta gcggcatgca 2160
ggcatcagtg ggccctataa atatgcatgg agtagagcaa cctctatgca caccacacaa 2220

-continued

```
cacaacacaa taatacagca aaggaggcta gcagaagtgc aggattaata agctaagcta   2280
gtagaaatta agcaaagcat aggcacagcc ttggctacct cctctggttc ttgccttatt   2340
attagcctgt tggtggtggt ggtggcggcg gcgctgtcgg cctcaacggc gtcggcacag   2400
ctgtcgtcga cgttctacga cacgtcgtgc cccagcgcgt tgtccaccat cagcagcggc   2460
gtgaactccg ccgtggcgca gcaggctcgt gtgggggcgt cgctgctccg gctccacttc   2520
cacgactgct tcgtccaagc aagtctagct gtctcagatg catctatcta tctacttata   2580
tataagcatg atttcctttc tagctagcta gcatcgtcgt gcattttaat ttgaagataa   2640
aagattagca cgtcgtatat gcatgcgatt aattaaccag gaggcatcaa ggtgaaattt   2700
ctggtggtcc accagggctg cgacgcgtcc attctgctga acgacacgtc cggggagcag   2760
acccagccgc cgaacctaac tctgaacccg agggccttcg acgtcgtcaa cagcatcaag   2820
gcgcaggtgg aggcggcgtg cgcgggcgtc gtctcctgcg ccgacatcct cgccgtcgcc   2880
gcccgcgacg gagttgacgc ggtacgtagc tacatcaccg tgcctattaa tttgctggct   2940
agtagcttgt tggtttgcaa actaactaac taattccgat cgtatgcgtg gtgcatatgc   3000
agctcggcgg gccttcgtaa accatggtac gtcctgtaga aaccccaacc cgtgaaatca   3060
aaaaactcga cggcctgtgg gcattcagtc tggatcgcga aaactgtgga attgatcagc   3120
gttggtggga aagcgcgtta caagaaagcc gggcaattgc tgtgccaggc agttttaacg   3180
atcagttcgc cgatgcagat attcgtaatt atgcgggcaa cgtctggtat cagcgcgaag   3240
tctttatacc gaaaggttgg gcaggccagc gtatcgtgct gcgtttcgat gcggtcactc   3300
attacggcaa agtgtgggtc aataatcagg aagtgatgga gcatcagggc ggctatacgc   3360
catttgaagc cgatgtcacg ccgtatgtta ttgccgggaa aagtgtacgt atcaccgttt   3420
gtgtgaacaa cgaactgaac tggcagacta tcccgccggg aatggtgatt accgacgaaa   3480
acggcaagaa aaagcagtct tacttccatg atttctttaa ctatgccgga atccatcgca   3540
gcgtaatgct ctacaccacg ccgaacacct gggtggacga tatcaccgtg gtgacgcatg   3600
tcgcgcaaga ctgtaaccac gcgtctgttg actggcaggt accaagctgc gaatcttcgt   3660
tttttaagg aattctcgat ctttatggtg tataggctct gggttttctg ttttttgtat   3720
ctcttaggat tttgtaaatt ccagatcttt ctatggccac ttagtagtat atttcaaaaa   3780
ttctccaatc gagttcttca ttcgcatttt cagtcatttt ctcttcgacg ttgtttttaa   3840
gcctgggtat tactcctatt tagttgaact ctgcagcaat cttagaaaat tagggttttg   3900
aggtttcgat ttctctaggt aaccgatcta ttgcattcat ctgaatttct gcatatatgt   3960
cttagatttc tgataagctt acgatacgtt aggtgtaatt gaagtttatt tttcaagagt   4020
gttatttttt gtttctgaat ttttcaggtg gtggccaatg gtgatgtcag cgttgaactg   4080
cgtgatgcgg atcaacaggt ggttgcaact ggacaaggca ctagcgggac tttgcaagtg   4140
gtgaatccgc acctctggca accgggtgaa ggttatctct atgaactgtg cgtcacagcc   4200
aaaagccaga cagagtgtga tatctacccg cttcgcgtcg gcatccggtc agtggcagtg   4260
aagggcgaac agttcctgat taaccacaaa ccgttctact ttactggctt tggtcgtcat   4320
gaagatgcgg acttgcgtgg caaaggattc gataacgtgc tgatggtgca cgaccacgca   4380
ttaatggact ggattggggc caactcctac cgtacctcgc attaccctta cgctgaagag   4440
atgctcgact gggcagatga acatggcatc gtggtgattg atgaaactgc tgctgtcggc   4500
tttaacctct ctttaggcat tggtttcgaa gcgggcaaca agccgaaaga actgtacagc   4560
gaagaggcag tcaacgggga aactcagcaa gcgcacttac aggcgattaa agagctgata   4620
```

```
gcgcgtgaca aaaaccaccc aagcgtggtg atgtggagta ttgccaacga accggatacc   4680
cgtccgcaag gtgcacggga atatttcgcg ccactggcgg aagcaacgcg taaactcgac   4740
ccgacgcgtc cgatcacctg cgtcaatgta atgttctgcg acgctcacac cgataccatc   4800
agcgatctct ttgatgtgct gtgcctgaac cgttattacg gatggtatgt ccaaagcggc   4860
gatttggaaa cggcagagaa ggtactggaa aaagaacttc tggcctggca ggagaaactg   4920
catcagccga ttatcatcac cgaatacggc gtggatacgt tagccgggct gcactcaatg   4980
tacaccgaca tgtggagtga agagtatcag tgtgcatggc tggatatgta tcaccgcgtc   5040
tttgatcgcg tcagcgccgt cgtcggtgaa caggtatgga atttcgccga ttttgcgacc   5100
tcgcaaggca tattgcgcgt tggcggtaac aagaaaggga tcttcactcg cgaccgcaaa   5160
ccgaagtcgg cggcttttct gctgcaaaaa cgctggactg gcatgaactt cggtgaaaaa   5220
ccgcagcagg gaggcaaaca atgagagctc ccgcgtacag caagaagaac ctcgacgcga   5280
ccgacatggt cgctctctca ggcgctcaca caatcgggca ggcccagtgc tccagcttca   5340
acggccacat ctacaacgac acgaacatca acgcggcctt cgcgacgtcg ctcaaggcca   5400
actgccccat gtccggcggc agcagcctgg cgccgctgga caccatgacc ccgaccgtgt   5460
tcgacaacga ctactacaag aacctgctgt cgcagaaggg gctgctgcac tcggaccagg   5520
agctgttcaa caacggcagc accgacagca cggtcagcaa ctttgcgtcc agctcggccg   5580
ccttcaccag cgccttcacg gcggccttgg tgaagatggg gaacctcggc ccgctcaccg   5640
ggaccagtgg gcagatcagg ctcacctgct ggaagctcaa ctcgtcctaa taattaagga   5700
cggacgtccg atagacgatc ctgcgcaatc gtatcgtacg tgcatgatac gcatacatct   5760
ggaaactact ataccaatgc aaacagagat ctatacgtac gagtatgtat aacgacgagt   5820
gatgtttgta tggatctacg tatgtaacaa ggacctctcg tagcgcaaag gcgcgcgttg   5880
ggagattaat taggtacaca agctattacc acattatata tcactctcat tgtggctaca   5940
tatctatatc tctgaggcca aatgcttggg tgtccagtac taattaataa taattcagtg   6000
cgtatgcaag atttgtgggc aaatattggt ttacgatttc ggaaaaaaca aatttcggcc   6060
cccggcgaaa aacaagaaat ttccgaattt tcggaaattc taggtcaaaa tcaaatagat   6120
tcaatacttt ttaaaacaaa gaatgatata atttatatta aaaataccaa ttttggaagc   6180
atatattttt tcggacccca ccaaaatcaa ggcaatttcg gaaattttcg tccgaaattg   6240
taaaccctgc ggaccgcgat cgcttaatta agcttgcatg cctgcagtgc agcgtgaccc   6300
ggtcgtgccc ctctctagag ataatgagca ttgcatgtct aagttataaa aaattaccac   6360
atattttttt tgtcacactt gtttgaagtg cagtttatct atctttatac atatatttaa   6420
actttactct acgaataata taatctatag tactacaata atatcagtgt tttagagaat   6480
catataaatg aacagttaga catggtctaa aggacaattg agtattttga caacaggact   6540
ctacagtttt atctttttag tgtgcatgtg ttctcctttt tttttgcaaa tagcttcacc   6600
tatataatac ttcatccatt ttattagtac atccatttag ggtttagggt taatggtttt   6660
tatagactaa ttttttagt acatctattt tattctattt tagcctctaa attaagaaaa   6720
ctaaaactct attttagttt ttttatttaa taatttagat ataaaataga ataaaataaa   6780
gtgactaaaa attaaacaaa taccctttaa gaaattaaaa aaactaagga aacatttttc   6840
ttgtttcgag tagataatgc cagcctgtta aacgccgtcg acgagtctaa cggacaccaa   6900
ccagcgaacc agcagcgtcg cgtcgggcca agcgaagcag acggcacggc atctctgtcg   6960
```

-continued

```
ctgcctctgg accccctctcg agagttccgc tccaccgttg gacttgctcc gctgtcggca   7020
tccagaaatt gcgtggcgga gcggcagacg tgagccggca cggcaggcgg cctcctcctc   7080
ctctcacggc accggcagct acgggggatt cctttcccac cgctccttcg ctttcccttc   7140
ctcgcccgcc gtaataaata gacacccccct ccacaccctc tttccccaac ctcgtgttgt   7200
tcggagcgca cacacacaca accagatctc ccccaaatcc acccgtcggc acctccgctt   7260
caaggtacgc cgctcgtcct cccccccccc ccctctctac cttctctaga tcggcgttcc   7320
ggtccatggt tagggcccgg tagttctact tctgttcatg tttgtgttag atccgtgttt   7380
gtgttagatc cgtgctgcta gcgttcgtac acggatgcga cctgtacgtc agacacgttc   7440
tgattgctaa cttgccagtg tttctctttg gggaatcctg ggatggctct agccgttccg   7500
cagacgggat cgatttcatg atttttttttg tttcgttgca tagggtttgg tttgcccttt   7560
tcctttattt caatatatgc cgtgcacttg tttgtcgggt catcttttca tgcttttttt   7620
tgtcttggtt gtgatgatgt ggtctggttg ggcggtcgtt ctagatcgga gtagaattct   7680
gtttcaaact acctggtgga tttattaatt ttggatctgt atgtgtgtgc catacatatt   7740
catagttacg aattgaagat gatggatgga aatatcgatc taggataggt atacatgttg   7800
atgcgggttt tactgatgca tatacagaga tgctttttgt tcgcttggtt gtgatgatgt   7860
ggtgtggttg ggcggtcgtt cattcgttct agatcggagt agaatactgt ttcaaactac   7920
ctggtgtatt tattaatttt ggaactgtat gtgtgtgtca tacatcttca tagttacgag   7980
tttaagatgg atggaaatat cgatctagga taggtataca tgttgatgtg ggttttactg   8040
atgcatatac atgatggcat atgcagcatc tattcatatg ctctaacctt gagtacctat   8100
ctattataat aaacaagtat gttttataat tattttgatc ttgatatact tggatgatgg   8160
catatgcagc agctatatgt ggattttttt agccctgcct tcatacgcta tttatttgct   8220
tggtactgtt tcttttgtcg atgctcaccc tgttgtttgg tgttacttct gcagggatcc   8280
ccgatcatgc aaaaactcat taactcagtg caaaactatg cctggggcag caaaacggcg   8340
ttgactgaac tttatggtat ggaaaatccg tccagccagc cgatggccga gctgtggatg   8400
ggcgcacatc cgaaaagcag ttcacgagtg cagaatgccg ccggagatat cgtttcactg   8460
cgtgatgtga ttgagagtga taaatcgact ctgctcggag aggccgttgc caaacgcttt   8520
ggcgaactgc ctttcctgtt caaagtatta tgcgcagcac agccactctc cattcaggtt   8580
catccaaaca aacacaattc tgaaatcggt tttgccaaag aaaatgccgc aggtatcccg   8640
atggatgccg ccgagcgtaa ctataaagat cctaaccaca agccggagct ggtttttgcg   8700
ctgacgcctt tccttgcgat gaacgcgttt cgtgaatttt ccgagattgt ctccctactc   8760
cagccggtcg caggtgcaca tccggcgatt gctcactttt tacaacagcc tgatgccgaa   8820
cgtttaagcg aactgttcgc cagcctgttg aatatgcagg gtgaagaaaa atcccgcgcg   8880
ctggcgattt taaaatcggc cctcgatagc cagcagggtg aaccgtggca aacgattcgt   8940
ttaatttctg aattttaccc ggaagacagc ggtctgttct ccccgctatt gctgaatgtg   9000
gtgaaattga accctggcga agcgatgttc ctgttcgctg aaacaccgca cgcttacctg   9060
caaggcgtgg cgctggaagt gatggcaaac tccgataacg tgctgcgtgc gggtctgacg   9120
cctaaataca ttgatattcc ggaactggtt gccaatgtga aattcgaagc caaaccggct   9180
aaccagttgt tgacccagcc ggtgaaacaa ggtgcagaac tggacttccc gattccagtg   9240
gatgattttg ccttctcgct gcatgacctt agtgataaag aaaccaccat tagccagcag   9300
agtgccgcca ttttgttctg cgtcgaaggc gatgcaacgt tgtggaaagg ttctcagcag   9360
```

```
ttacagctta aaccgggtga atcagcgttt attgccgcca acgaatcacc ggtgactgtc   9420
aaaggccacg gccgtttagc gcgtgtttac aacaagctgt aagagcttac tgaaaaaatt   9480
aacatctctt gctaagctgg gagctcgatc cgtcgacctg cagatcgttc aaacatttgg   9540
caataaagtt tcttaagatt gaatcctgtt gccggtcttg cgatgattat catataattt   9600
ctgttgaatt acgttaagca tgtaataatt aacatgtaat gcatgacgtt atttatgaga   9660
tgggttttta tgattagagt cccgcaatta tacatttaat acgcgataga aaacaaaata   9720
tagcgcgcaa actaggataa attatcgcgc gcggtgtcat ctatgttact agatctgcta   9780
gccctgcagg aaatttaccg gtgcccgggc ggccagcatg gccgtatccg caatgtgtta   9840
ttaagttgtc taagcgtcaa tttgtttaca ccacaatata tcctgccacc agccagccaa   9900
cagctccccg accggcagct cggcacaaaa tcaccactcg atacaggcag cccatcagaa   9960
ttaattctca tgtttgacag cttatcatcg actgcacggt gcaccaatgc ttctggcgtc  10020
aggcagccat cggaagctgt ggtatggctg tgcaggtcgt aaatcactgc ataattcgtg  10080
tcgctcaagg cgcactcccg ttctggataa tgttttttgc gccgacatca taacggttct  10140
ggcaaatatt ctgaaatgag ctgttgacaa ttaatcatcc ggctcgtata atgtgtggaa  10200
ttgtgagcgg ataacaattt cacacaggaa acagaccatg agggaagcgt tgatcgccga  10260
agtatcgact caactatcag aggtagttgg cgtcatcgag cgccatctcg aaccgacgtt  10320
gctggccgta catttgtacg gctccgcagt ggatggcggc ctgaagccac acagtgatat  10380
tgatttgctg gttacggtga ccgtaaggct tgatgaaaca acgcggcgag ctttgatcaa  10440
cgaccttttg gaaacttcgg cttcccctgg agagagcgag attctccgcg ctgtagaagt  10500
caccattgtt gtgcacgacg acatcattcc gtggcgttat ccagctaagc gcgaactgca  10560
atttggagaa tggcagcgca atgacattct tgcaggtatc ttcgagccag ccacgatcga  10620
cattgatctg gctatcttgc tgacaaaagc aagagaacat agcgttgcct tggtaggtcc  10680
agcggcggag gaactctttg atccggttcc tgaacaggat ctatttgagg cgctaaatga  10740
aaccttaacg ctatggaact cgccgcccga ctgggctggc gatgagcgaa atgtagtgct  10800
tacgttgtcc cgcatttggt acagcgcagt aaccggcaaa atcgcgccga aggatgtcgc  10860
tgccgactgg gcaatggagc gcctgccggc ccagtatcag cccgtcatac ttgaagctag  10920
gcaggcttat cttggacaag aagatcgctt ggcctcgcgc gcagatcagt tggaagaatt  10980
tgttcactac gtgaaaggcg agatcaccaa agtagtcggc aaataaagct ctagtggatc  11040
tccgtacccg gggatctggc tcgcggcgga cgcacgacgc cggggcgaga ccataggcga  11100
tctcctaaat caatagtagc tgtaacctcg aagcgtttca cttgtaacaa cgattgagaa  11160
tttttgtcat aaaattgaaa tacttggttc gcatttttgt catccgcggt cagccgcaat  11220
tctgacgaac tgcccattta gctggagatg attgtacatc cttcacgtga aaatttctca  11280
agcgctgtga acaagggttc agattttaga ttgaaaggtg agccgttgaa acacgttctt  11340
cttgtcgatg acgacgtcgc tatgcggcat cttattattg aataccttac gatccacgcc  11400
ttcaaagtga ccgcggtagc cgacagcacc cagttcacaa gagtactctc ttccgcgacg  11460
gtcgatgtcg tggttgttga tctagattta ggtcgtgaag atgggctcga gatcgttcgt  11520
aatctggcgg caaagtctga tattccaatc ataattatca gtggcgaccg ccttgaggag  11580
acggataaag ttgttgcact cgagctagga gcaagtgatt ttatcgctaa gccgttcagt  11640
atcagagagt ttctagcacg cattcgggtt gccttgcgcg tgcgccccaa cgttgtccgc  11700
```

-continued

```
tccaaagacc gacggtcttt ttgttttact gactggacac ttaatctcag gcaacgtcgc  11760
ttgatgtccg aagctggcgg tgaggtgaaa cttacggcag gtgagttcaa tcttctcctc  11820
gcgtttttag agaaaccccg cgacgttcta tcgcgcgagc aacttctcat tgccagtcga  11880
gtacgcgacg aggaggttta tgacaggagt atagatgttc tcattttgag gctgcgccgc  11940
aaacttgagg cagatccgtc aagccctcaa ctgataaaaa cagcaagagg tgccggttat  12000
ttctttgacg cggacgtgca ggtttcgcac gggggacga tggcagcctg agccaattcc  12060
cagatccccg aggaatcggc gtgagcggtc gcaaaccatc cggcccggta caaatcggcg  12120
cggcgctggg tgatgacctg gtggagaagt tgaaggccgc gcaggccgcc cagcggcaac  12180
gcatcgaggc agaagcacgc cccggtgaat cgtggcaagc ggccgctgat cgaatccgca  12240
aagaatcccg gcaaccgccg gcagccggtg cgccgtcgat taggaagccg cccaagggcg  12300
acgagcaacc agatttttc gttccgatgc tctatgacgt gggcacccgc gatagtcgca  12360
gcatcatgga cgtggccgtt ttccgtctgt cgaagcgtga ccgacgagct ggcgaggtga  12420
tccgctacga gcttccagac gggcacgtag aggtttccgc agggccggcc ggcatggcca  12480
gtgtgtggga ttacgacctg gtactgatgg cggtttccca tctaaccgaa tccatgaacc  12540
gataccggga agggaaggga gacaagcccg gccgcgtgtt ccgtccacac gttgcggacg  12600
tactcaagtt ctgccggcga gccgatggcg gaaagcagaa agacgacctg gtagaaacct  12660
gcattcggtt aaacaccacg cacgttgcca tgcagcgtac gaagaaggcc aagaacggcc  12720
gcctggtgac ggtatccgag ggtgaagcct tgattagccg ctacaagatc gtaaagagcg  12780
aaaccgggcg gccggagtac atcgagatcg agctagctga ttggatgtac cgcgagatca  12840
cagaaggcaa gaacccggac gtgctgacgg ttcaccccga ttactttttg atcgatcccg  12900
gcatcggccg ttttctctac cgcctggcac gccgcgccgc aggcaaggca gaagccagat  12960
ggttgttcaa gacgatctac gaacgcagtg gcagcgccgg agagttcaag aagttctgtt  13020
tcaccgtgcg caagctgatc gggtcaaatg acctgccgga gtacgatttg aaggaggagg  13080
cggggcaggc tggcccgatc ctagtcatgc gctaccgcaa cctgatcgag ggcgaagcat  13140
ccgccggttc ctaatgtacg gagcagatgc tagggcaaat tgccctagca ggggaaaaag  13200
gtcgaaaagg tctctttcct gtggatagca cgtacattgg gaacccaaag ccgtacattg  13260
ggaaccggaa cccgtacatt gggaacccaa agccgtacat tgggaaccgg tcacacatgt  13320
aagtgactga tataaaagag aaaaaaggcg atttttccgc ctaaaactct ttaaaactta  13380
ttaaaactct taaaacccgc ctggcctgtg cataactgtc tggccagcgc acagccgaag  13440
agctgcaaaa agcgcctacc cttcggtcgc tgcgctccct acgccccgcc gcttcgcgtc  13500
ggcctatcgc ggccgctggc cgctcaaaaa tggctggcct acggccaggc aatctaccag  13560
ggcgcggaca agccgcgccg tcgccactcg accgccggcg ctgaggtctg cctcgtgaag  13620
aaggtgttgc tgactcatac caggcctgaa tcgccccatc atccagccag aaagtgaggg  13680
agccacggtt gatgagagct ttgttgtagg tggaccagtt ggtgattttg aacttttgct  13740
ttgccacgga acggtctgcg ttgtcgggaa gatgcgtgat ctgatccttc aactcagcaa  13800
aagttcgatt tattcaacaa agccgccgtc ccgtcaagtc agcgtaatgc tctgccagtg  13860
ttacaaccaa ttaaccaatt ctgattagaa aaactcatcg agcatcaaat gaaactgcaa  13920
tttattcata tcaggattat caataccata tttttgaaaa agccgtttct gtaatgaagg  13980
agaaaactca ccgaggcagt tccataggat ggcaagatcc tggtatcggt ctgcgattcc  14040
gactcgtcca acatcaatac aacctattaa tttcccctcg tcaaaaataa ggttatcaag  14100
```

```
tgagaaatca ccatgagtga cgactgaatc cggtgagaat ggcaaaagct ctgcattaat  14160

gaatcggcca acgcgcgggg agaggcggtt tgcgtattgg gcgctcttcc gcttcctcgc  14220

tcactgactc gctgcgctcg gtcgttcggc tgcggcgagc ggtatcagct cactcaaagg  14280

cggtaatacg gttatccaca gaatcagggg ataacgcagg aaagaacatg tgagcaaaag  14340

gccagcaaaa ggccaggaac cgtaaaaagg ccgcgttgct ggcgtttttc cataggctcc  14400

gcccccctga cgagcatcac aaaaatcgac gctcaagtca gaggtggcga aacccgacag  14460

gactataaag ataccaggcg tttccccctg gaagctccct cgtgcgctct cctgttccga  14520

ccctgccgct taccggatac ctgtccgcct ttctcccttc gggaagcgtg gcgctttctc  14580

atagctcacg ctgtaggtat ctcagttcgg tgtaggtcgt tcgctccaag ctgggctgtg  14640

tgcacgaacc ccccgttcag cccgaccgct gcgccttatc cggtaactat cgtcttgagt  14700

ccaacccggt aagacacgac ttatcgccac tggcagcagc cactggtaac aggattagca  14760

gagcgaggta tgtaggcggt gctacagagt tcttgaagtg gtggcctaac tacggctaca  14820

ctagaagaac agtatttggt atctgcgctc tgctgaagcc agttaccttc ggaaaaagag  14880

ttggtagctc ttgatccggc aaacaaacca ccgctggtag cggtggtttt tttgtttgca  14940

agcagcagat tacgcgcaga aaaaaaggat ctcaagaaga tcctttgatc ttttctacgg  15000

ggtctgacgc tcagtggaac gaaaactcac gttaagggat tttggtcatg agattatcaa  15060

aaaggatctt cacctagatc cttttgatcc ggaatta                           15097
```

<210> SEQ ID NO 83
<211> LENGTH: 35
<212> TYPE: DNA
<213> ORGANISM: Artificial sequence
<220> FEATURE:
<223> OTHER INFORMATION: 5' Bfr1 primer

<400> SEQUENCE: 83

```
cctggtggag tgcttaagcg acgagttctg cctgg                                35
```

<210> SEQ ID NO 84
<211> LENGTH: 36
<212> TYPE: DNA
<213> ORGANISM: Artificial sequence
<220> FEATURE:
<223> OTHER INFORMATION: 3'Xba1 primer

<400> SEQUENCE: 84

```
gggcttctcc tccaggaact ctagattgcc caggcg                               36
```

<210> SEQ ID NO 85
<211> LENGTH: 37
<212> TYPE: DNA
<213> ORGANISM: Artificial sequence
<220> FEATURE:
<223> OTHER INFORMATION: 5'Gfix primer

<400> SEQUENCE: 85

```
catcggcaag tgccaccaca gccaccactt cagcctg                              37
```

<210> SEQ ID NO 86
<211> LENGTH: 30
<212> TYPE: DNA
<213> ORGANISM: Artificial sequence
<220> FEATURE:
<223> OTHER INFORMATION: 3'Gfix primer -continued

<400> SEQUENCE: 86
gctgtggtgg cacttgccga tggggctggg 30

<210> SEQ ID NO 87
<211> LENGTH: 33
<212> TYPE: DNA
<213> ORGANISM: Artificial sequence
<220> FEATURE:
<223> OTHER INFORMATION: 5'1Ab5XbaI primer

<400> SEQUENCE: 87
gcccgcctgg gcaatctaga gttcctggag gag 33

<210> SEQ ID NO 88
<211> LENGTH: 37
<212> TYPE: DNA
<213> ORGANISM: Artificial sequence
<220> FEATURE:
<223> OTHER INFORMATION: 3'1Ab3d6 primer

<400> SEQUENCE: 88
gcgagctcct agatgcggcc ctcgagttcc tcgaaga 37

<210> SEQ ID NO 89
<211> LENGTH: 29
<212> TYPE: DNA
<213> ORGANISM: Artificial sequence
<220> FEATURE:
<223> OTHER INFORMATION: oligonucleotide cy2'

<400> SEQUENCE: 89
ccctgtacgg cacgatgggc aacgctgca 29

<210> SEQ ID NO 90
<211> LENGTH: 30
<212> TYPE: DNA
<213> ORGANISM: Artificial sequence
<220> FEATURE:
<223> OTHER INFORMATION: oligonucleotide cy1

<400> SEQUENCE: 90
atatatccac catggacaac aaccccaaca 30

<210> SEQ ID NO 91
<211> LENGTH: 31
<212> TYPE: DNA
<213> ORGANISM: Artificial sequence
<220> FEATURE:
<223> OTHER INFORMATION: oligonucleotide cy2

<400> SEQUENCE: 91
tatatagagc tcctagatgc ggccctcgag t 31